(12) United States Patent
Banz et al.

(10) Patent No.: US 7,875,275 B2
(45) Date of Patent: Jan. 25, 2011

(54) USE OF BRIDGE-1 AND ACTIVATORS AND INHIBITORS THEREOF IN THE TREATMENT OF INSULIN DEFICIENCY AND DIABETES

(75) Inventors: Constanze Banz, Lubeck (DE); Joel F. Habener, Newton, MA (US); Melissa K. Thomas, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 11/629,872

(22) PCT Filed: Jun. 16, 2005

(86) PCT No.: PCT/US2005/021181

§ 371 (c)(1),
(2), (4) Date: Jul. 28, 2008

(87) PCT Pub. No.: WO2006/007375

PCT Pub. Date: Jan. 19, 2006

(65) Prior Publication Data
US 2009/0138978 A1 May 28, 2009

Related U.S. Application Data

(60) Provisional application No. 60/579,668, filed on Jun. 16, 2004.

(51) Int. Cl.
*A01N 65/00* (2009.01)
(52) U.S. Cl. .................................. 424/93.7; 424/93.21
(58) Field of Classification Search ................. 424/93.7, 424/93.1
See application file for complete search history.

(56) References Cited

U.S. PATENT DOCUMENTS

| 4,690,918 A | 9/1987 | Beppu et al. |
| 5,328,470 A | 7/1994 | Nabel et al. |

FOREIGN PATENT DOCUMENTS

| WO | WO 93/25234 A1 | 12/1993 |
| WO | WO 94/06920 A1 | 3/1994 |
| WO | WO 0065052 A1 * | 11/2000 |

OTHER PUBLICATIONS

Thomas et al. Mol. & Cell. Bio., 19(12): 8492-8504, Dec. 1999.*
Thomas et al. Mol. And Cell. Bio., 19(12): 8492-8504, 1999.*
Ahlgren, U., et al., "β-Cell-specific inactivation of the mouse Ipf1/Pdxl gene results in loss of the β-cell phenotype and maturity onset diabetes," *Genes Dev* 12: 1763-1768, Cold Spring Harbor Laboratory Press, US (1998).
Alt, M. and Caselmann, W.H., "Liver-directed gene therapy: molecular tools and current preclinical and clinical studies," *J Hepatol* 23: 746-758, Elsevier, UK (1995).

Andreassen, O.A., et al., "Huntington's Disease of the Endocrine Pancreas: Insulin Deficiency and Diabetes Mellitus due to Impaired Insulin Gene Expression," *Neurobiol Dis* 11: 410-424, Elsevier Sience, US (2003).
Antinozzi, P.A., et al., "Metabolic Engineering with Recombinant Adenoviruses," *Annu Rev Nutr* 19: 511-544, Annual Reviews, US (1999).
Asahara, H., et al. "Pbx-Hox Heterodimers Recruit Coactivator-Corepressor Complexes in an Isoform-Specific Manner," *Mol Cell Biol* 19(12): 8219-8225, American Society for Microbiology, US (1999).
Berkner, K.L., "Development of Adenovirus Vectors for the Expression of Heterologous Genes," *Bio Techniques* 6(7): 616-629, Informa BioSciences, US (1988).
Ahlgren, U., et al., "β-Cell-specific inactivation of the mouse Ipf1/Pdx1 gene results in loss of the β-cell phenotype and maturity onset diabetes," *Genes Dev* 12: 1763-1768, Cold Spring Harbor Laboratory Press, US (1998).
Brody, S.L. and Crystal, R.G., "Adenovirus-Mediated in Vivo Gene Transfer," *Ann NY Acad Sci* 716: 90-101, New York Academy of Sciences, US (1994).
Brüning, J.C., et al., "Development of a Novel Polygenic Model of NIDDM in Mice Heterozygous for *IR* and *IRS-1* Null Alleles," *Cell* 88: 561-572, Cell Press, US (1997).
Butler, A.E., et al., "Increased β-Cell Apoptosis Prevents Adaptive Increase in β-Cell Mass in Mouse Model of Type 2 Diabetes," *Diabetes* 52: 2304-2314, American Diabetes Association, US (2003).
Chakrabarti, S.K., et al., "Covalent Histone Modifications Underlie the Developmental Regulation of Insulin Gene Transcription in Pancreatic β Cells," *J Biol Chem* 278(26): 23617-23623, The American Society for Biochemistry and Molecular Biology, US (2003).
Chan, H.M. and La Thangue, N.B., "p300/CBP proteins: HATs for transcriptional bridges and scaffolds," *J Cell Sci* 114: 2363-2373, The Company of Biologists Ltd, UK (2001).
Chen, J., et al., "Role of Akt/protein kinase B in the activity of transciptional coactivator p300," *Cell Mol Life Sci* 61: 1675-1683, Birkhäuser Verlag, DE (2004).
Chen, S., et al., "Gene therapy for brain tumors: Regression of experimental gliomas by adenovirus-mediated gene transfer in vivo," *Proc Natl Acad Sci USA* 91: 3054-3057, National Academy of Science, US (1994).
Conaway, R.C., et al., "Emerging Roles of Ubiquitin in Transcription Regulation," *Science* 296: 1254-1258, American Association for the Advancement of Science, US (2002).
Demartino, G.N., et al., "Identification, Purification, and Characterization of a PA700-dependent Activator of the Proteasome," *J Biol Chem* 271(6): 3112-3118, The American Socitey for Biochemistry and Molecular Biology, Inc., US (1996).

(Continued)

*Primary Examiner*—Thaian N Ton
(74) *Attorney, Agent, or Firm*—Sterne, Kessler, Goldstein & Fox P.L.L.C.

(57) ABSTRACT

The present invention is directed to the use of Bridge-1 polynucleotides and Bridge-1 polypeptides, as well as activators and inhibitors of Bridge-1 activity, in the treatment of Bridge-1 mediated disorders, including diabetes.

9 Claims, 40 Drawing Sheets

OTHER PUBLICATIONS

Figure 2:
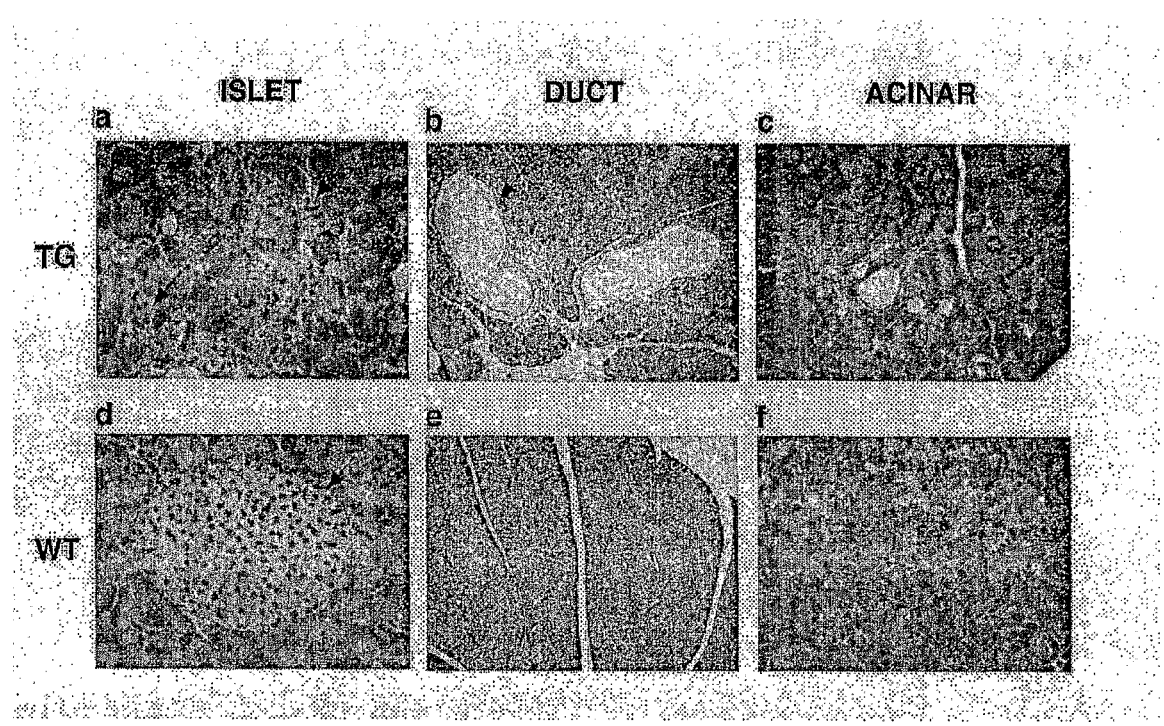

Donath, M.Y. And Halban, P.A., "Decreased beta-cell mass in diabetes: significance, mechanisms, and therapeutic implications," *Diabetologia* 47: 581-589, Springer-Verlag, DE (2004).

Dor, Y., et al., "Adult pancreatic β-cells are formed by self-duplication rather than stem-cell differentiation," *Nature* 429: 41-46, Nature Publishing Group, UK (2004).

Edgar, B.A., "From small flies come big discoveries about size control," *Nat Cell Biol* 7: E191-E193, Macmillan Magazines Ltd, UK (1999).

Eeckhoute, J., et al., "Maturity-Onset Diabetes of the Young Type 1 (MODY1)-Associated Mutations R154X and E276Q in Hepatocyte Nuclear Factor 4α (HNF4α) Gene Impair Recruitment of p300, a Key Transcriptional Coactivator," *Mol Endocrinol* 15(7): 1200-1210, The Endocrine Society, US (2001).

Ehm, M.G., et al., "Genomewide Search for Type 2 Diabetes Susceptibility Genes in Four American Populations," *Am J Hum Genet* 66: 1871-1881, The American Society of Human Genetics, US (2000).

Etienne-Julan, M., et al., "The efficiency of cell targeting by recombinant retroviruses depends on the nature of the receptor and the composition of the artificial cell-virus linker," *J Gen Virol* 73: 3251-3255, SGM, UK (1992).

Fajans, S.S., et al., "Molecular Mechanisms and Clinical Pathophysiology of Maturity-Onset Diabetes of the Young," *N Engl J Med* 345(13): 971-980, Massachusetts Medical Society, US (2001).

Ferry, N. and Heard, J.M., "Liver-Directed Gene Transfer Vectors," *Hum Gene Ther* 9: 1975-1981, Mary Ann Liebert, Inc., US (1998).

Flotte, T.R., et al., "Expression of the Cystic Fibrosis Transmembrane Conductance Regulator from a Novel Adeno-associated Virus Promoter," *J Biol Chem* 268(5): 3781-3790, The American Society for Biochemistry and Molecular Biology, Inc., US (1993).

Flotte, T.R., et al., "Gene Expression from Adeno-associated Virus Vectors in Airway Epithelial Cells," *Am J Respir Cell Mol Biol* 7: 349-356, American Thoratic Society, US (1992).

Frayling, T.M., et al., "A Genome-Wide Scan in Families With Maturity-Onset Diabetes of the Young," *Diabetes* 52: 872-881, American Diabetes Association, US (2003).

Gerich, J.E., "Contributions of Insulin-Resistance and Insulin-Secretory Defects to the Pathogenesis of Type 2 Diabetes Mellitus," *Mayo Clin Proc* 78: 447-456, Mayo Foundation for Medical Education and Research, US (2003).

Giles, R.H., et al., "Conjunction dysfunction: CBP/p300 in human disease," *TIG* 14(5): 178-83, Elsevier Science Ltd, UK (1998).

Gonzalez, F., et al., "Recruitment of a 19S Proteasome Subcomplex to an Activated Promoter," *Science* 296: 548-550, American Association for the Advancement of Science, US (2002).

Goud, B., et al., "Antibody-Mediated Binding of a Murine Ecotropic Moloney Retroviral Vector to Human Cells Allows Internalization But Not the Establishment of the Proviral State," *Virol* 163: 251-254, Academic Press, Inc., US (1988).

Graham, F.L. and Prevec, L., "Manipulation of Adenovirus Vectors," in *Methods in Molecular Biology*, E.J. Murray, Ed., vol. 7, pp. 109-127, Humana, Clifton N.J., 1991.

Grossman, S.R., et al., "p300/MDM2 Complexes Participate in MDM2-Mediated p53 Degradation," *Mol Cell* 2: 405-415, Cell Press, US (1998).

Grossman, S.R., et al., "Polyubiquination of p53 by a Ubiquitin Ligase Activity of p300," *Science* 300: 342-344, American Association for the Advancement of Science, US (2003).

Haj-Ahmad, Y., et al., "Development of a Helper-Independent Human Adenovirus Vector and Its Use in the Transfer of the Herpes Simplex Virus Thymidine Kinase Gene," *J Virol* 57(1): 267-274, American Society for Microbiology, US (1986).

Hara, K., et al., "A genetic variation in the *PGC-1* gene could confer insulin resistance and susceptibility to Type II diabetes," *Diabetologia* 45: 740-743, Springer-Verlag, DE (2002).

Hermonat, P.L., et al., "Use of adeno-associated virus as a mammalian DNA cloning vector: Transduction of neomycin resistance into mammalian tissue culture cells," *Proc Natl Acad Sci USA* 81: 6466-6470, National Academy of Science, US (1984).

Hussain, M.A., et al., "POU Domain Transcription Factor brain 4 Confers Pancreatic α-Cell-Specific Expression of the Proglucagon Gene through Interaction with a Novel Proximal Promoter G1 Element," *Mol Cell Biol* 17(12): 7186-7194, American Society for Microbiology, US (1997).

Iyer, N.G., et al., "p300/CBP and cancer," *Oncogene* 23: 4225-4231, Nature Publishing Group, UK (2004).

Jones, N. and Shenk, T., "Isolation of Adenovirus Type 5 Host Range Deletion Mutants Defective for Transformation of Rat Embryo Cells," *Cell* 17: 683-689, MIT, US (1979).

Kay, M.A., "Adenoviral Vectors for Hepatic Gene Transfer in Animals," *Chest* 111: 138S-142S, American College of Chest Physicians, US (1997).

Kitamura, T., et al., "The forkead transcription factor *Foxo1* links insulin signaling to *Pdx1* regulation of pancreatic β cell growth," *J Clin Invest* 110: 1839-1847, American Society for Clinical Investigation, US (2002).

Kubota, N., et al., "Disruption of Insulin Receptor Substrate 2 Causes Type 2 Diabetes Because of Liver Insulin Resistance and Lack of Compensatory β-Cell Hyperplasia," *Diabetes* 49: 1880-1889, American Diabetes Association, US (2000).

Kurihara, N., et al., "Paget's disease - A VDR coactivator disease?" *J Ster Biochem Mol Biol* 89-90: 321-325, Elsevier, UK (2004).

Kushner, J.A., et al., "Pdx1 restores β cell function in Irs2 knockout mice," *J Clin Invest* 109: 1193-1201, American Society for Clinical Investigation, US (2002).

Lee, H.C., et al., "Remission in models of type 1 diabetes by gene therapy using a single-chain insulin analogue," *Nature* 408: 483-488, Macmillan Magazines Ltd, UK (2000).

Li, Q., et al., "Attenuation of Glucocorticoid Signaling through Targeted Degradation of p300 via the 26S Proteasome Pathway," *Mol Endocrinol* 16(12): 2819-2827, The Endocrine Society, US (2002).

Lindgren, C.M., et al., "Genomewide Search for Type 2 Diabetes Mellitus Susceptibility Loci in Finnish Families: The Botnia Study," *Am J Hum Genet* 70: 509-516, The American Society of Human Genetics, US (2002).

Mahtani, M.M., et al., "Mapping of a gene for type 2 diabetes associated with an insulin secretion defect by a genome scan in Finnish families," *Nat Genet* 5(5): 1871-1881, Nature Publishing Group, UK (1996).

Malecki, M.T., et al., "Mutations in *NEUROD1* are associated with the development of type 2 diabetes mellitus," *Nat Genet* 23: 323-328, Nature America Inc., US (1999).

Marshak, S., et al., "Purification of the β-cell glucose-sensitive factor that transactivates the insulin gene differentially in normal and transformed islet cells," *Proc Natl Acad Sci USA* 93: 15057-15062, National Academy of Science, US (1996).

McLaughlin, S.K., et al., "Adeno-Associated Virus General Transduction Vectors: Analysis of Proviral Structures," *J Virol* 62(6): 1963-1973, American Society for Microbiology, US (1988).

Miller, A.D., "Progress Toward Human Genome Therapy," *Blood* 76(2): 271-287, The American Society of Hematology, US (1990).

Mosley, A.L., et al., "Glucose Regulation of Insulin Gene Expression Requires the Recruitment of p300 by the β-Cell-Specific Transcription Factor Pdx-1," *Mol Endocrinol* 18(9): 2279-2290, The Endocrine Society, US (2004).

Muzyczka, N., "Use of Adeno-Associated Virus as a General Transduction Vector for Mammalian Cells," *Curr Top Microbiol Immunol* 158: 97-129, Springer-Verlag, DE (1992).

Neda, H., et al., "Chemical Modification of an Ecotropic Murine Leukemia Virus . Results in Redirection of Its Target Cell Specificity," *J Biol Chem* 266(22): 14143-14146, The American Society for Biochemistry and Molecular Biology, Inc., US (1991).

Nieuwenhuizen, A.G., et al., "Progesterone stimulates pancreatic cell proliferation in vivo," *Eur J Endocrinol* 140: 256-263, BioScientifica Ltd, UK (1999).

Ohana, B., et al., "The type 1 human immunodeficiency virus Tat binding protein is a transcriptional activator belonging to an additional family of evolutionarily conserved genes," *Proc Natl Acad Sci USA* 90: 138-142, National Academy of Science, US (1993).

Ohneda, K., et al., "The Homeodomain of PDX-1 Mediates Multiple Protein-Protein Interactions in the Formation of a Transcriptional Activation Complex on the Insulin Promoter," *Mol Cell Biol* 20(3): 900-911, American Society for Microbiology, US (2000).

Oka, K., et al., "Recent advances in liver-directed gene therapy: implications for the treatment of dyslipidemia," *Curr Opin Lipidol* 11: 179-186, Lippincott Williams & Wilkins, US (2000).

Otani, K., et al., "Reduced β-cell mass and altered glucose sensing impair insulin-secretory function in βIRK0 mice," *Am J Physiol Endocrinol Metab* 286: E41-E49, American Physiological Society, US (2004).

Ottosen, S., et al., "Proteasome Parts at Gene Promoters," *Science* 296: 479-481, American Association for the Advancement of Science, US (2002).

Picard, F., et al., "SRC-1 and TIF2 Control Energy Balance between White and Brown Adipose Tissues," *Cell* 111: 931-941, Cell Press, US (2002).

Poizat, C., et al., "Proteasome-Mediated Degradation of the Coactivator p300 Impairs Cardiac Transcription," *Mol Cell Biol* 20(23): 8643-8654, American Society for Microbiology, US (2000).

Puigserver, P. and Spiegelman, B.M., "Peroxisome Proliferator-Activated Receptor-γ Coactivator 1α (PGC-1α): Transcriptional Coactivator and Metabolic Regulator," *Endo Rev* 24(1): 78-90, The Endocrine Society, US (2003).

Qiu, Y., et al., "Insulin Gene Transcription Is Mediated by Interactions between the p300 Coactivator and PCX-1, BETA2, and E47," *Mol Cell Biol* 22(2): 412-420, American Society for Microbiology, US (2002).

Qiu, Y., et al., "p300 Mediates Transcriptional Stimulation by the Basic Helix-Loop-Helix Activators of the Insulin Gene," *Mol Cell Biol* 18(5): 2957-2964, American Society for Microbiology, US (1998).

Roelfsema, J.H., et al., "Genetic Heterogeneity in Rubinstein-Taybi Syndrome: Mutations in Both the *CBP* and *EP300* Genes Cause Disease," *Am J Hum Genet* 76: 572-580, The American Society of Human Genetics, US (2005).

Rosenfeld, M.A., et al., "Adenovirus-Mediated Transfer of a Recombinant α1-Antitrypsin Gene to the Lung Epithelium in Vivo," *Science* 252: 431-434, American Association for the Advancement of Science, US (1991).

Rosenfeld, M.A., et al., "In Vivo Transfer of the Human Cystic Fibrosis Transmembrane Conductance Regulator Gene to the Airway Epithelium," *Cell* 68: 143-155, Cell Press, US (1992).

Roux, P., et al., "A versatile and potentially general approach to the targeting of specific cell types by retroviruses: Application to the infection of human cells by means of major histocompatibility complex class I and class II antigens by mouse ecotropic murine leukemia virus-derived viruses," *Proc Natl Acad Sci USA* 86: 9079-9083, National Academy of Science, US (1989).

Salghetti, S.E., et al., "Regulation of Transcriptional Activation Domain Function by Ubiquitin," *Science* 293: 1651-1653, American Association for the Advancement of Science, US (2001).

Samulski, R.J., et al., "Helper-Free Stocks of Recombinant Adeno-Associated Viruses: Normal Integration Does Not Require Viral Gene Expression," *J Virol* 63(9): 3822-3828, American Society for Microbiology, US (1989).

Sander, M.S., et al., "Homeobox gene *Nkx6.1* lies downstream of *Nkx2.2* in the major pathway of β-cell formation in the pancreas," *Development* 127: 5533-5540, The Company of Biologists Ltd, UK (2000).

Savkur, R.S., et al., "Pharmacology of Nuclear Receptor-Coregulator Recognition," *Vitamins and Hormones* 68: 145-183, Elsevier, UK (2004).

Seijffers, R., et al., "Increase in PDX-1 Levels Supresses Insulin Gene Expression in RIN 1046-38 Cells," *Endocrinol* 140(7): 3311-3317, The Endocrine Society, US (1999).

Shang, Y. and Brown, M., "Molecular Determinants for the Tissue Specificity of SERMs," *Science* 295: 2465-2468, American Association for the Advancement of Science, US (2002).

Sharma, A., et al., "The NeuroDl/BETA2 Sequences Essential for Insulin Gene Transcription Colocalize with Those Necessary for Neurogenesis and p300/CREB Binding Protein Binding," *Mol Cell Biol* 19(1): 704-713, American Society for Microbiology, US (1999).

Shaw, J.T.E., et al., "Novel Susceptibility Gene for Late-Onset NIDDM Is Localized to Human Chromosome 12q," *Diabetes* 47: 1793-1796, American Diabetes Association, US (1998).

Sheng, M. and Sala, C., "PDZ Domains and the Organization of Supramolecular Complexes," *Annu Rev Neurosci* 24: 1-29, Annual Reviews, US (2001).

Shiratori, Y., et al., "Strategy of liver-directed gene therapy: present status and future prospects," *Liver* 19: 265-274, Munksgaard, DK (1999).

Smith-Arica, J.R. and Bartlett, J.S., "Gene Therapy: Recombinant Adeno-associated Virus Vectors," *Curr Cardiol Rep* 3: 43-49, Springer-Verlag, DE (2001).

Stanojevic, V., et al., "Pancreas Duodenum Homeobox-1 Transcriptional Activation Requires Interactions with p300," *Endocrinology* 145(6): 2918-2928, The Endocrine Society, US (2004).

Stein, R.W., et al, "Analysis of E1A-Mediated Growth Regulation Fucntions: Binding of the 300-Kilodalton Cellular Product Correlates with E1A Enhancer Repression Function and DNA Synthesis-Inducing Activity," *J Virol* 64(9): 4421-4427, American Society for Microbiology, US (1990).

Steiner, D.F., et al., "Structure and Evolution of the Insulin Gene," *Ann Rev Genet* 19: 463-484, Annual Reviews Inc., US (1985).

Strayer, D.S., "Viral gene delivery," *Exp Opin Invest Drugs* 8(12): 2159-2172, Ashley Publications Ltd., US (1999).

Thomas, M.K., et al., "Development of diabetes mellitus in aging transgenic mice following suppression of pancreatic homeoprotein IDX-1," *J Clin Invest* 108: 319-329, American Society for Clinical Investigation, US (2001).

Thomas, M.K., et al.,"*IDX1* and Pancreatic Agenesis and Type 2 Diabetes," in *Molecular Basis Of Inborn Errors Of Development*, P. Erikson et al. Eds., pp. 552-556, Oxford University Press, UK 2004.

Thulé, P.M., et al., "Glucose regulated production of human insulin in rat hepatocytes," *Gene Ther* 7: 205-214, Macmillan Publishers Ltd, UK (2000).

Tratschin, J., et al., "A Human Parvovirus, Adeno-Associated Virus, as a Eucaryotic Vector: Transient Expression and Encapsidation of the Procaryotic Gene for Chloramphenicol Acetyltransferase," *Mol Cell Biol* 4(10): 2072-2081, American Society for Microbiology, US (1984).

Tratschin, J., et al., "Adeno-Associated Virus Vector for High-Frequency Integration, Expression, and Rescue of Genes in Mammalian Cells," *Mol Cell Biol* 5(11): 3251-3260, American Society for Microbiology, US (1985).

Tratschin, J., et al., "Genetic Analysis of Adeno-Associated Virus: Properties of Deletion Mutants Constructed in Vitro and Evidence for an Adeno-Associated Virus Replication Function," *J Virol* 51(3): 611-619, American Society for Microbiology, US (1984).

Tuttle, R.L., et al., "Regulation of pancreatic β-cell growth and survival by the serine/threonine protein kinase Akt1/PKBα," *Nat Med* 7(10): 1133-1137, Nature Publishing Group, UK (2001).

Vo, N., and Goodman, R.H.,."CREB-binding Protein and p300 in Transcriptional Regulation," *J Biol Chem* 276(17) 13505-13-508, The American Society for Biochemistry and Molecular Biology, US (2001).

Wiltschire, S., et al, "Evidence From a Large U.K. Family Collection That Genes Influencing Age of Onset of Type 2 Diabetes Map to Chromosome 12p and to the *MODY3/NIDDM2* Locus on 12q24," *Diabetes* 53: 855-860, American Diabetes Association, US (2004).

Withers, D.J., et al, "Disruption of IRS-2 causes type 2 diabetes in mice," *Nature* 391: 900-904, Nature Publishing Group, UK (1998).

Wondisford, F.E., et al., "Isolation and Characterization of the Human Thyrotropin β-Subunit Gene," *J Biol Chem* 263(25): 12538-12542, The American Society for Biochemistry and Molecular Biology, Inc., US (1988).

Yamauchi, T., et al., "Inhibition of Nucleotide Excision Repair by Fludarabine in Normal Lymphocytes in vitro, Measured by the Alkaline Single Cell Gel Electrophoresis (Comet) Assay," *Jpn J Cancer Res* 93: 567-573, Nihon Gan Gakkai, JP (2002).

Yang, N., "Gene Transfer into Mammalian Somatic Cells in Vivo," *Crit Rev Biotechnol* 12(4): 335-356, CRC Press, Inc., US (1992).

Yao, T., et al., "Gene Dosage-Dependent Embryonic Development and Proliferation Defects in Mice Lacking the Transcriptional Integrator p300," *Cell* 93: 361-372, Cell Press, US (1998).

Yoon, J.C., et al., "Suppression of β Cell Energy Metabolism and Insulin Release by PGC-1α," *Dev Cell* 5: 73-83, Cell Press, US (2003).

Yoon, K.H., et al., "Selective β-Cell Loss and α-Cell Expansion in Patients with Type 2 Diabetes Mellitus in Korea," *J Clin Endocrinol Metab* 88: 2300-2308, The Endocrine Society, US (2003).

* cited by examiner a
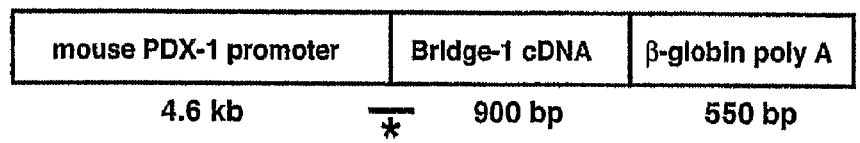
b
c
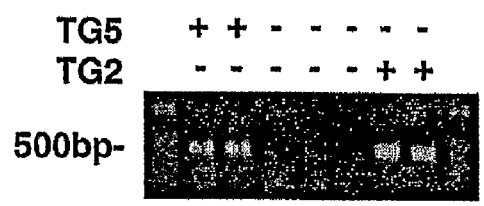
d
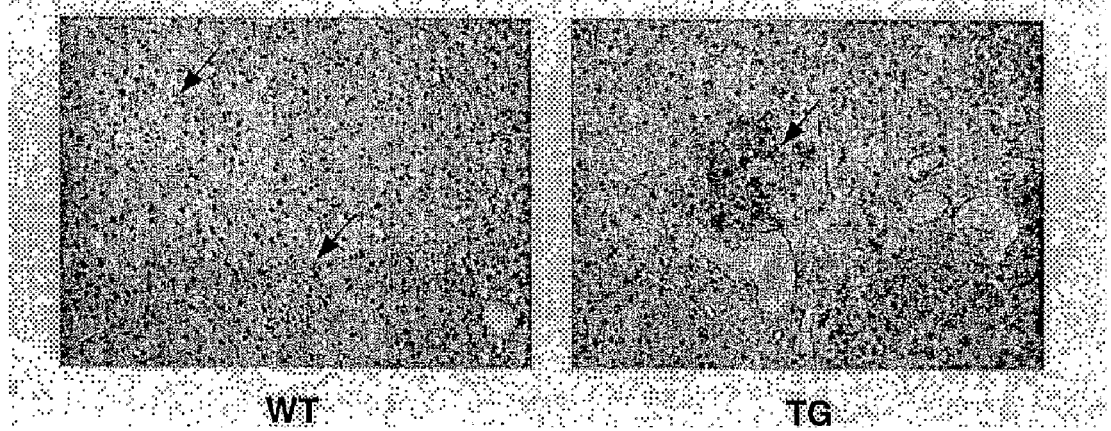
Figure 1

Figure 8
Pancreatic islets are enlarged in mutant Bridge-1 transgenic mice
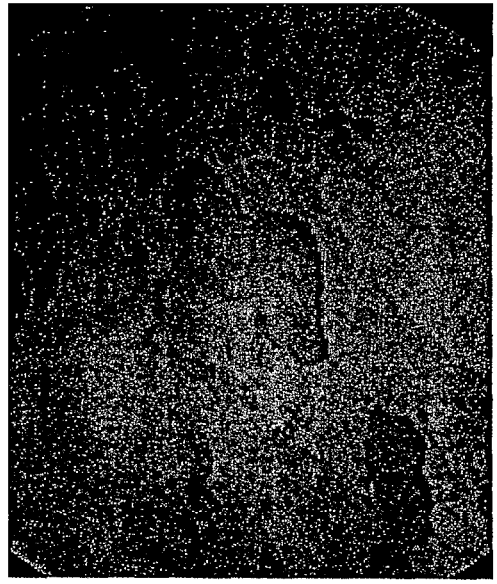
Transgenic
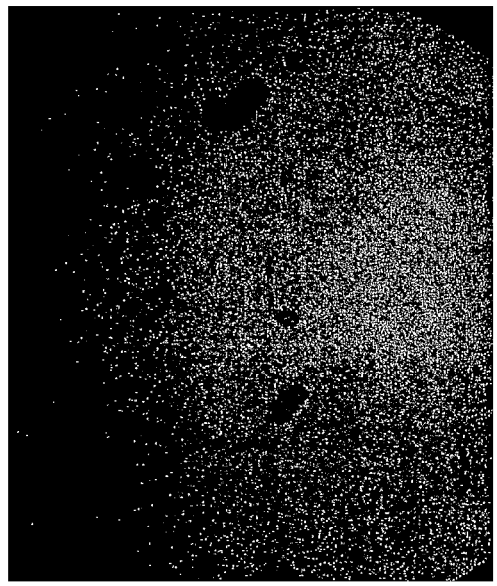
Wild type
Insulin immunostaining in brown pIDX-1-Bridge-1 Transgene
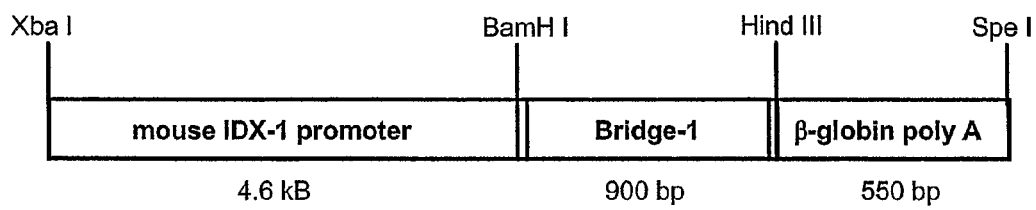
pIDX-1-Bridge-1(1-184) Transgene
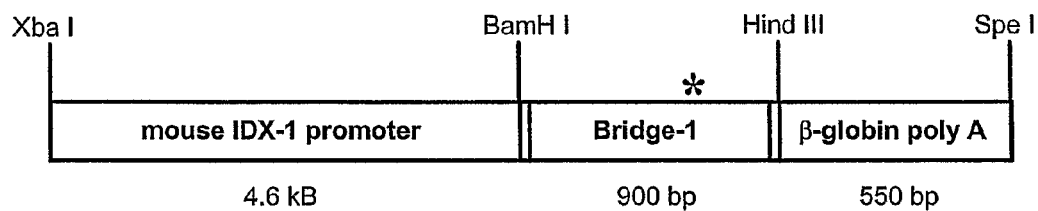
FIG. 12

```
   1 GAATTCGGCACGGCGTCGACCTCAACAGGAGGCACATAGAGAAACCCTATCTTGAAAAACAGGGGAGGGAGAAACAGGGGGAAGGAAGAAAGGAAGGAATG   120
 121 AGAAAGAAAAGTGGAAATAAGTCACGTATAAACGAGAGTTAAAGCCTAGTCATGGGGTTGGGGATTTAAGCTCAGTGGTAGAGGCCTTGCCTAGCAAGGCGCAAGGCCCTGGGTTCGGTC   240
                          *                                                                   *
 241 CCCAGCTCCGGGAAAAAAAAAAGAAAAAAAAAGCTACGTGATTCATCTGTCTCCACTTAGCTCTCGCCGGGTCTGAAGTATTTTGTCCCTTGGGAGGACCCGTGTCCGTAGCCGGGAAACCTGGGCGTCGGGGTGA   360
                                                                                                                                          *
 361 CCTCGCCCACCTTCAAACTCAGTACTGTTGCATTGGCTGAAGTATTTTGTCCCTTGGGAGGACCCGTGTCCGTAGCCGGGAAACCTGGGCGTCGGGGTTTTA   480
                                                                                                        >
 481 GGCTGAGGTCCGCGATGTCGAGTGAGGAAGTCCGGCACCGAGGTCCTCGAAGAGTCCGAGCCAGAGCATCCAGGAGTCGATGGACGCAAGAGGAGAAATCGAGGGGC   600
   1                 M  S  S  E  E  V  R  H  R  A  E  S  S  E  A  R  A  A  A  V  S  D  I  Q  E  L  M  R  R  K  E  E  I  E  A  Q    36
 601 AGATCAAGGCTAATTACGACGTGCTCGAGTCTCAGAAAGGAATTGGCATGAACGAGCCCTCAGTGGACTGCGAGGGCTACCCCCGGGCAGATGTGGATTTGTATCAGGTCCGAACAGCAA   720
  37  I  K  A  N  Y  D  V  L  E  S  Q  K  G  I  G  M  N  E  P  L  V  D  C  E  G  Y  P  R  A  D  V  D  L  Y  Q  V  R  T  A  R   76
 721 GGCACAACATCATCTGTCTCCAGAATGATCACAAGGCTCTGATGAAGCAGGTGGAGGAAGCACTCCATCAGCTACATGCTCGGGACAAAGAGAAGCAGGCTCGGGACATGGCTGAAGCC   840
  77  H  N  I  I  C  L  Q  N  D  H  K  A  L  M  K  Q  V  E  E  A  L  H  Q  L  H  A  R  D  K  E  K  Q  A  R  D  M  A  E  A  R  116
 841 GAGGAAGCCATGAACCGTCGCCTAGCCTCTGACAGCCCGGCACTCCCCAAGGCCTTTGCCCGGGTTAACAGTATCAGCCCAGGTTCCCCAGCCAGCATTGCGGGGCTGCAGGTGGATG   960
 117  E  E  A  M  N  R  R  L  A  S  D  S  P  A  L  P  K  A  F  A  R  V  N  S  I  S  P  G  S  P  A  S  I  A  G  L  Q  V  D  D  156
 961 ATGAAAATGTGGAGTTCGGCAGTGTCAACACTCAGAACTTCCAGTCTCTGCAGAACGTGGGTACGGTGGTCCAGCACAGCGAGGGGGAAGCCCCTGAATGTCATGGTGATCCGCAGAGGGG   1080
 157  E  I  V  E  F  G  S  V  N  T  Q  N  F  Q  S  L  Q  N  V  G  T  V  V  Q  H  S  E  G  K  P  L  N  V  M  V  I  R  R  G  E  196
1081 AGAAGACCACCAGCTCAGACTGACTCCCACGCGGTGGGCTGGGAAAGGCGGGCTGCTGGGCTGCAATATTACCCCTCTCCAAAGATCACCTGCTGCAGAGAGCTTCTTCAGCTG   1200
 197  K  H  Q  L  R  L  T  P  T  R  W  A  G  K  G  L  L  G  C  N  I  T  P  L  Q  R  *  (SEQ ID NO:2)                       222
1201 GGCCCGGGCTTGGCCGTGGGGGATTCCCTCATTCTCTGGGCTCCCTGCAAGTGTAGGGATCGAAGAGTGCCAAGAGTGGAAGAGACGGCTTTGGCTGCCTGATGT   1320
1321 AGTCTCTGGGTTGAGGCATTATTAAAAATGTGGTTTGTGCTTAAAAAAAAAAAAAAAAAAAAAAAAAAAAAAAAAAAAAAAAAAAAAAAAAAAAAAAAAA   1440
1441 AAAAAAAAGTCGAC (SEQ ID NO:1)                                                                          1454
```

Figure 16

A.
YEAST CELLS
B.
MAMMALIAN CELLS
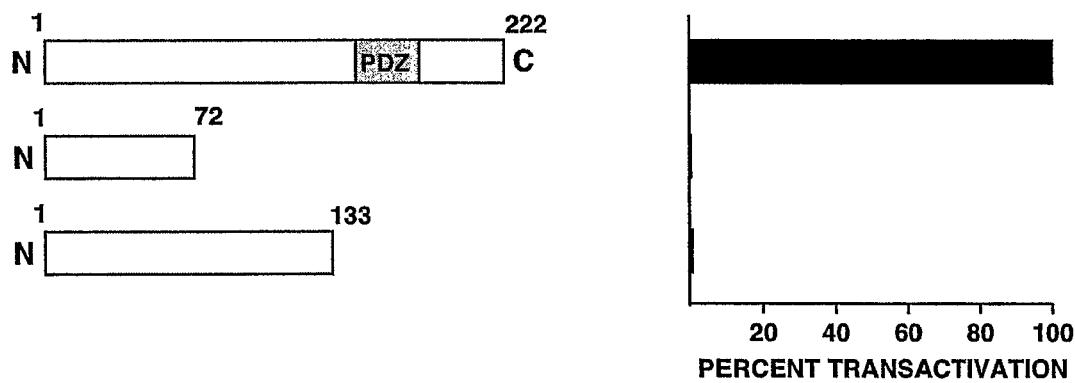
C.
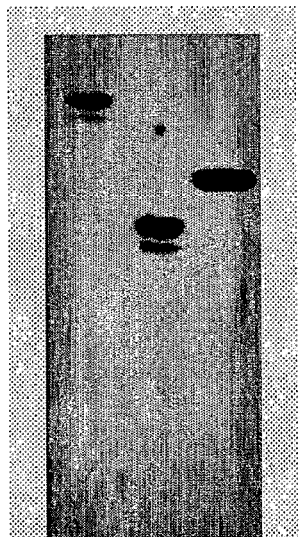
Gal4-Bridge-1        +   −   −
Gal4-Bridge-1        −   +   −
  (1-72)
Gal4-Bridge-1        −   −   +
  (1-133)
Figure 19

1) WT
2) G151P
3) D156P
4) V159P
5) V164P
6) V175P

1) GST-Bridge 1
2) GST
3) GST-Bridge-1 (1-72)
4) GST-Bridge-1 (1-133)

1) PDX-1 (1-143)
2) PDX-1 (143-283)
3) PDX-1 (1-206)
4) PDX-1 WT
5) Vector

Figure 27A

```
   1 cgcgttcgcg gacggctgtg gtgttttggc gcatgggcgg agccgtagtt acggtcgact
  61 ggggcgtcgt ccctagcccg ggagccgggt ctctggagtc gcggcccggg gttcacgatg
 121 tccgacgagg aagcgaggca gagcggaggc tcctcgcagg ccggcgtcgt gactgtcagc
 181 gacgtccagg agctgatgcg gcgcaaggag gagatagaag cgcagatcaa ggccaactat
 241 gacgtgctgg aaagccaaaa aggcattggg atgaacgagc cgctggtgga ctgtgagggc
 301 taccccggt cagacgtgga cctgtaccaa gtccgcaccg ccaggcacaa catcatatgc
 361 ctgcagaatg atcacaaggc agtgatgaag caggtggagg aggccctgca ccagctgcac
 421 gctcgcgaca aggagaagca ggcccgggac atggctgagg cccacaaaga ggccatgagc
 481 cgcaaactgg tcagagtga gagccagggc cctccacggg ccttcgccaa agtgaacagc
 541 atcagccccg ctccccagc cagcatcgcg ggtctgcaag tggatgatga gattgtggag
 601 ttcggctctg tgaacaccca gaacttccag tcactgcata acattggcag tgtggtgcag
 661 cacagtgagg ggaagcccct gaatgtgaca gtgatccgca gggggaaaa acaccagctt
 721 agacttgttc caacacgctg ggcaggaaaa ggactgctgg gctgcaacat tattcctctg
 781 caaagatgat tgtccctggg aacagtaac aggaaagcat cttcccttgc cctggacttg
 841 ggtctaggga tttccaactt gtcttctctc cctgaagcat aaggatctgg aagaggcttg
 901 taacctgaac ttctgtgtgg tggcagtact gtggcccacc agtgtaatct ccctggatta
 961 aggcattctt aaaaacttag gcttggcctc tttcacaaat taggccacgg ccctaaatag
 021 gaattccctg gattgtgggc aagtgggcgg aagttattct ggcaggtact ggtgtgatta
 081 ttattattat ttttaataaa gagttttaca gtgctgatat gaccctgttg tcaccccagc
 141 tgaatttctt atgaccctcc caaaccaaag ctcagatggg gtcagaagag cttcatagaa
 201 agttgggcaa acaggctag caattgcaaa gtcaggcttt gaccaacata tttctttgca
 261 ctgaggcctt gctgctgtgg atacggaaat ggttaagtac tgtgcttcct cagcagctgg
 321 gctgtcaggg ccatagtagc tcccttgga gaacagggaa agcctggagg cttcccaggt
 381 ggcccagcgt ggtgtcctgt cagcttcctc tttaggaacc caccagaggg cagcaagctc
 441 ctttcacttc gctagtaaga accctccgt ttttgtgtgt ttttgttttt gttttctgga
 501 gacaaggtct tgctttgtca cccaggctgg agtgcagtgt cgtgatcaag gttcactgaa
 561 gccttgacgc tgtgggcact gcctcagccg cccaagtatc tgggaccaca ggcgtgcacc
 621 accatgcata gctaatttat ttttgtaga gacagggtct ccctgtgttg accaggttgg
 681 tctcgaactc ctgggctcaa gcagtcctcc tgccttggcc tcctaaagtg ctgggatcac
 741 aggcgtgagc cactgcgccc agcccactgc tagtttgact ttttataatt gaacctcctg
 801 gctatgccct gagatcagcg ctatttgta aaccgctgag gtatggatag aacgagtag
 861 atcagacctc ttgaaaatgc ttattcttcc tcccttttat ttttttgtctc ttttaagatg
 921 gtaaaatggt tctcagggat tcctgccaat actttgaatt attttttcct ctccatggta
 981 tcagtgttca tttccccagt tcttgcacac cgctttctgt tttggcagtt ctgccaggca
 041 agccctgtgt tccttgggac tggttttgct gtggttggat acagatacca gcttgccttg
 101 atgggattgg tattgctgtg tgcttccagc cacaggttct cacactcaat tccaaagcct
 161 tcctattggg cgaattccct caaactctat ttgacctgac agccatacgt attccctct
 221 ggtagccaca gacatgctgt gtttaccaat gtttgctgtt taaattgcat gttctaattc
 281 cacgtatttt ccagtctctt ttataaagtc tcagactata ataaacacag cttgcccagt
 341 ttaaaaaaaa aaaaaaaaa (SEQ ID NO: 154)
```

Figure 27B

MSDEEARQSGGSSQAGVVTVSDVQELMRRKEEIEAQIKANYDVLESQKGIGMNEPLVDC
EGYPRSDVDLYQVRTARHNIICLQNDHKAVMKQVEEALHQLHARDKEKQARDMAEAHKE
AMSRKLGQSESQGPPRAFAKVNSISPGSPASIAGLQVDDEIVEFGSVNTQNFQSLHNIG
SVVQHSEGKPLNVTVIRRGEKHQLRLVPTRWAGKGLLGCNIIPLQR (SEQ ID
NO:155)

Figure 27C-1

THIS STYLE: Location of other exons
THIS STYLE: Location of selected exons
THIS STYLE: Location of SNPs
chromosome:NCBI35:12:120788766:120819090:1

```
   1 ACTGTTACCGTTATTATTATCACTACGATTTTTAGAGGCCTTAACAGGAACATCCAGCAC   60
  61 CTTCAACAGTATATGGCTCATAGGAATCATTCCATGAATATTTGTTAGCAGAAGGACAGC  120
 121 TCTATGAGATAGATTGCTATCAATTACTGCCCCATTTTACAGATGAGGAAACTGAGGCCC  180
 181 AGAGAAGCCAAGTAGTGACCTAGGGTCACACAGATTGCCGTTAAGTGGCAAGATACGGGG  240
 241 TGTGTACTCAGGCATATCGGATCTGTAAAGTGAGGGATAAGGAACCTTAATGTATTTTGT  300
 301 AAATCCTCCAGGGCTGTGTGGATGTGAAGAACTGAATTGGAGCGCCACGCAGCGGTTCTC  360
 361 TGGCGTACAGTATCCATCCATACAGTAGGCGCTCAATAAATGTCTGCTGCACGAATGAGA  420
 421 AAATGAGTCAGCTGGGGCGAGATCATCCCCTAGCGTTGGTGTGCAATTGCGTGGGGATCC  480
 481 ATTGCTTCCGACGCTACTCCTGCCGGGTCACCACAGGCGCACGTGTTCCGGCAGGGCGCG  540
 541 GCTTCCGGTGACCCAGCTCCGCCCTAAGCCCCATCCCAAGCCCCGCCCCTTGACTGTTCT  600
 601 CGCGTTCGCGGACGGCTGTGGTGTTTTGGCGCATGGGCGGAGCCGTAGTTACGGTCGACT  660
 661 GGGGCGTCGTCCCTAGCCCGGGAGCCGGGTCTCTGGAGTCGCGGCCCGGGGTTCACGATG  720
 721 TCCGACGAGGAAGCGAGGCAGAGCGGAGGCTCCTCGCAGGCCGGCGTCGTGACTGTCAGC  780
 781 GACGTCCAGGAGCTGATGCGGCGCAAGGAGGAGATAGAAGCGCAGATCAAGGCCAACTAT  840
 841 GACGTGCTGGAAAGCGTGAGTGTGGGTTCGGGGCGCCCCAAGTCGCCTAACCCGGCCCGG  900
 901 AGTCCCTGGGGTACTGGGATGCCAGGGCGGCCTCAGTTTGGGCGCTCCGCAACGGATCTC  960
 961 CCTGGGAGGCCCAAGGCGCCGCAAGTGCGGCCTCTGTCGGCACAAGAAGGCAGGCAAAGA 1020
1021 ACTTTAGCAACTGAAGAGTTAGCCATATTGATATCCAGCAAGAGTTTGTGGAGCCCTGCT 1080
1081 GTGTGCTAGGCGCTGGTTTAAGTGCTGTGCATTGTTGAGTTAATTTAATCTTTGCAACAA 1140
1141 CCCTTTGAGGTGGATGCTGTTACTCTTTCCATTTTAGGGAGGGGGAAACAGGTGTTACTT 1200
1201 GGTGATTAAACAGCTGTCATGTGCCTCGCTGACTGCCTTATCTTAATTTGTACTTTTTG 1260
1261 TAAAGACAGAGTCTCACTGTGTTGCCCAGGTTGGTATCGAACTCATGGCCTCAAGCGATC 1320
1321 CTTCCACCTCGGCCTTTCAAAGTGCTGGGATTACAGGCGTGAGCTACTGCACCCGGCATT 1380
1381 TGCTGATTGTATCGTGAATTCTTAAACTTCAGTGTGTATATGAATTACCTGGGGATCTTA 1440
1441 TTAAAATGCAGATTTTGTTTGAGGCAAGGGAGCAGATTCTGCATTTGTAGCAAACTCCCA 1500
1501 GCAATGCTGATGCTAGTGGTCTAAGGACCGAACTTTGAGTTACAAATAAGGCTCATCATC 1560
1561 CTTATTGCATAAGGAGGAAACTGAGGCCCAGAGTGGGCAAACGCCTATCTAAGGTCATG 1620
1621 TAGTTCGGAAGTGGCAGTGGTGGGTCTGGCTCAAAAGCTGATGCAGGTTTTCTTATGCCA 1680
1681 TCTAGTGTAAAATCACAGATCAGTTTGCAGAGGAAGATGCAATTAATTATGCCCAAGTAG 1740
1741 GGTGGGATGGAATGCATTTTAGGTGATGTAAGATGAAGTTTCTTTTTTTTTTGTCTGAGA 1800
1801 CGGAGTCTTGCTTTGTCACCCAGGCTGGAGTGCAGTGGCTCAATCTCGGCTCACTGCAGC 1860
1861 CTCTGCCTCCTGGGTTCAAGTGATTCTCCTGCCTCAGCCTCCCGAGTAGTAGGGATTACA 1920
1921 GGCGAGCGCCAGTACGCCAGGCTAATTTTTATTTTAAGTAAAAGCAGGGTTTCACCATG 1980
1981 TTGGTCAGGCCGGTGTTGGATTCCTGACCTCAGGTGATCCGCCCACCTTGGCCTCCCCAA 2040
2041 GTGCTGGGATTACAGGCGTGAGCCACCGCGTCCGGCCATAAGATGAAGTTTCATACGGAG 2100
2101 GGCCAGAGAACCATTTTACTGGGTGCTGACTATATGCTCAAAGTGGGATTCAGACTTCAG 2160
2161 GTCTGTTACATTCAGAACCTGTGCTTTCAAGCAAATTACCAGCAATTTCTCAAACTTTAG 2220
2221 TTTACTTTCTACCACATGCAGTATACTATATGCATATACCACTTGTGTTATTCCTTTGAT 2280
2281 ATTTTTATTTAAATAGATCTACTTTTAATCTTATATAAATGTATTATTATTGTTATTATT 2340
2341 ATTATTGAGACAGGGTCTCGCTCTGTTGCCCAGGCTGGAGTTCAGTGGCACCATCTTGGT 2400
2401 TCACTGCAGCCTCAATCTCCTGGTGTCAAGCAATCCTCCCACCTCAGCCTCCCAAGTAGC 2460
2461 TGAGACTGCAGGTACGTGCCACCACCCCCAGCTAATTTTTGTATTTTTTGTAGCTATGGG 2520
2521 GTCTCACTATGTTGCTTGCTCAGACTGGTCTGAAACTCCTGGGCTCAAGCAGTCCTCCTG 2580
2581 CCTCTGCCTCCCAAAGTGTTGGGGTTACAGGCATGAGCCACAGTGCCTTGCCCATAAATG 2640
2641 TATTTTAAAAGGAAATTTCAAAACTCCGCTGCATATGGAAAATGATAATCTCTTCTCTTA 2700
```

Figure 27C-2

```
2701 AATATAAGGTCAGATGCTTTGCATGTTGATACGGCATGTTGGTTGCTTCTGGCTAGCTGC 2760
2761 TGTTGCTTGCTGAAAGCTTTCAGCCTGAAACCGTGCTCTATATTTGTTTTAAAAAGTGG 2820
2821 GTTTGGGCCGGGCCTGGTGGCTCACGCCTGTAATCCCAGCACTTTGGGAGGCCAAGGTGG 2880
2881 GTGGATCACCTGAGGCCAGGATGGTCTCGATCTCCTGACCTCGTGATCCGCCCGCCTCGG 2940
2941 CCTCCCAAAGTGCTGGGATTACAGGCTTGAGCCACCGCGCCAGGCCTACAAAAAATTTTT 3000
3001 TTAAAAATTAGTTGGGCGTGGTGGTGCATGCCTGTAGTCCTAGCTACTTGGGAGGCTGAG 3060
3061 GCAGGAGGATTGCTTGAACCCTGAATGTTGAGGCTGCAGGGAGCTATAATTGCACCACTG 3120
3121 CACTCTCTTGTGGGTGACAGAGTGAGATGCTGTCTCTTTAAAAAAAAAAAAAAAAAAAAG 3180
3181 GCCGGGTGCGGTGGCTCATGCCTCTAATCCCAGCACTTTGGGAGGCCGAGGCGGGCGGAT 3240
3241 CACGAGGTCAGGAGATCGAGACCATCCTGGCTAACACAGTGAAACCCCGTCTCTACTAAA 3300
3301 AATACAAAAAATTAGCTGGACGTGGTGGCCAGCGCCTGTAGTCCCAGCTACTCTGGAGGC 3360
3361 TGAGGCAGGAGAATGGCCTGAACCCGGGATGTGGAGCTTGCAGTGAGCCAAGATTGCGCC 3420
3421 ACTGCACTTCAGCCTGGGTGACAGAGCGAGACTCCGTCTCAAGAAAAAGAAAAAAAAAA 3480
3481 AAAAGACTGGGCATGGTGGCTCACGTCTGTAATCCCAGCACTTTGGAAGGCCGAGGTGTG 3540
3541 TGGATCGCTTGAGGTCAGGAGTCCGAGACCAGCCTGGGCAACATGGTGAAACCCCGTCTC 3600
3601 AACGAAAAATACAAAAATTAGCCAGGTGTGGTGGTACACATCTATAATCCCAGCTACCCG 3660
3661 GGAGGCTGATGCAAGAGAATCACTTGAACCTGGGAGGCGGAGGTTGCAGTGAACCAAGAC 3720
3721 TGCACCACGACACTCCAGCCTGGGTGACAGAGATTCCATCTCAAAAAAAAAAAAAAAAAA 3780
3781 AAAAGAAGTGGACAGCTAAAACTATAAATCTCGTATAATAAAGCATAGGAGTAAATCTT 3840
3841 CATGACCTTGGATTAGGCAAAGCCTTTTAGATATGGCAGCAAAAACACAAGCTACAAAA 3900
3901 GAAAAAATGATAAGTTGGACTTCAACTTTAAAACTGTGTTTCAAAGGGCATAGTAAAATG 3960
3961 AAAAGATAAGCTCCAGAATGGGAGAAAATATTTGCATATCATTTCTCTGATAAGAGGATA 4020
4021 GTATCTAGACTATAATAAGAGCTCTTACAACTCAATAATAAAAAGACAGCCAATTAGAAG 4080
4081 ACAGGGAAAGGATCTGAATAAACATTTCTCCAAAGAAAATATGGTCAATACAAATGGTCA 4140
4141 ATGGCCAGGCGTGGTGGCTCATGCCTGTAATCCCAGGACTTTGGGAGTCTGAGGCAGGAG 4200
4201 GATCACTTGAGGCCAGGGGTTTGAGACTAGCCTGGGCAACACAGTAAGAGCCTATCTTTA 4260
4261 CAAAAAATTCAAAATTAAAGGCCGGGCATGGTGGCTCATGCCTGTAATCCCAGCACTTTG 4320
4321 GGAGGCCGAGGCTGGCAGATCACGAGGTCAGGAGATCGAGACCATCCTGGTTAACACGGT 4380
4381 GAAACCCCGTCTCTACTAAAAATACAAAAAAATTAGCCGGGTGTGGTGGCAGACGCCTGT 4440
4441 AGTCCCAGCTACTCGGGAGGCTGAGGCAGGAGAAGGGCCTGAACCCAGGAGGCGGAGCTT 4500
4501 GCAGTGAGCCAAGATCTCGCCACTGTACTCTAGCCTGGGCAACAGAGCGAGACTCTGTCT 4560
4561 TTAAAAAAAAAAAATTAAAAATTAAAAATTAGCCAGGTGTGATGACATGTGCCTGTGGTC 4620
4621 CCAGCTACTTAGGAGGCTGAGACAGATCGCTTGAACCCAGGAGTTTAAGGCGGCAGTGAG 4680
4681 CTATGAAGACACCACTGCACCCGATCCTGGGCAACAGAAGATCTTGTCTCAAACCAATAC 4740
4741 AAACACAAAAGCCATTACCTTTTACACTTTACATGGGTCAGTTATATGGTATCTGAATTA 4800
4801 TATCTCAATAAAACTGTTATAAAAACAGAGGGTACTAGAGATAGCAAGTAACTGGGGTGT 4860
4861 TGCAGAGACCAGCACCAAATGGACACTTTTGCCTTGACAATTGCAGGATTGTAGAGAATT 4920
4921 GGGAGAGGAATATGTATTTTTGATTCAGGGTTATTTAATGCCGTGTGTGTGAGCTGCTAG 4980
4981 TGTTATGGATCCCATCCTTTGAGAAGCATTATCCAATGTGATATTGATTCTCAAAGGCTG 5040
5041 GTCAACCCTTAACCACTGTGGGAAGGCAGGAGCAGATACAGGTTTTTAGCCCCTGGCGCA 5100
5101 TTTCTGCAGTGTCACGGCGAGTCCTGTGTTAGGGGAGTGTGGAGAACTATCTCCCTGCGC 5160
5161 AGTGGACAGTAGGTTTGGGTGTAACCCGGAGGCTTCCAGAGAGAAAGGGAGCAAAATGAA 5220
5221 TGGAATCCCTCTTCTCAGTGCCTGTGTACACTGGCAGCTTGTCCCTGGACTGACTAATCC 5280
5281 TTACAGCCACTATTTATGACTTCTGCGCGTAGTCGTTTTCTGAGGCCACCTTAACACCAC 5340
5341 AGAGTTGGTGACTTAAAACAGGAATTTACTTTGTCCCAGCTCTGGAGGCCAGAAGTCTGA 5400
5401 AATCAAGGTGTCAGCAGGGTTGGCTCCTTCTGCAGGCTCTGAGAGAGAAGCTCCCAAGCC 5460
5461 TTTCTCCTGGCCTCTGGTGACTGCTGGCGGTCCTTGGCCTACAGCTGTGTCACTTGAACC 5520
5521 TCTGCCTGCATCTTCATGTGGCCTTCCTCCTGTGTCTGTCCCACACCTACCTCTGCCTTT 5580
5581 CTTTTATGAGGACACCAGCCACCAGATGAGCTTATCTCGAGATCCTTAACATAATTACAT 5640
```

Figure 27C-3

```
5641 CTACAAAGACTCTTTTTCAAATAAAGTCATATTTACAGGTTCTGGGGGTTAGCTCGTGGT 5700
5701 TATCTGTTTTTGGGGGCCGCTCTTCAACCCACTATGCTGTGTATGCGCGTGGCATGTGCT 5760
5761 AAGTACTCTGCAGGTCAGCTCGTTAGTTCTTGCAGCAGGTAGGGAGGGAGGCGAGTGCTC 5820
5821 CTATTCCCATTTTATAATTGAGGAAGCTGAGGCTTAGAGAGGAGAAGGTCTCAGCTAAGG 5880
5881 ATGCCCAGCTTGTACATGGCAGAGTTGAGATTCAAATTAAAGTCTAACCAATTGCAAAGC 5940
5941 CCCTCCCCTGAACCATGTGACTGGTTTCACTGCTTTTGTGTACTCTCCTCTGACTCATGT 6000
6001 TAAAAAAAAAAAAAGTGTTGTTTTGAATAAAGAATACATTCCCATAGGCAAAATTCAAAA 6060
6061 CCTACAGAGGGGTATAAAATGGACTGTCTCTCTCCCTGCCCTGTCACCTAGCCACCCAGT 6120
6121 TCTTCTCCCCGGAGGCAGCTGGTGCTATCAGTTTCCTTCTTCAGATCTTTTTATTTTCAG 6180
6181 AAGAATCAAAGCCCTGCCACAGCTGGGTGCTGTCTGGCTTTTCACTCCCTCTAGCTTC 6240
6241 CAGGGCCAGCAGCCAGGTGTCAGCCACCTGTGGGAAGGAGGGTGTGAAGGAGTGGAGGAA 6300
6301 GAGGCTGGCCTTGGGGATGATGCTCAAAGGAGTCTTTGGTTTTATCGGCACTGTTTTAAC 6360
6361 TTCAAAAAAGAATGGATTCATGCATTACTTGCGTCGTTAAAAATAAAAAATGAAAAACAC 6420
6421 AGTGCCCACCCCAGGGTAGTTGTGAGGGCATGAGTAGAGCCCCTGGTGTAAGTGATCAGT 6480
6481 ATGTGGCAGTTTTCATTACTGTCACCTTTATTATGACTTCAGAGGAGAAGGGTCTGGGGA 6540
6541 AAGACATCCTGGGACATTACACCCATGAGCACCTTTTAACCACGTTTCTTTCCTCCAGC 6600
6601 AAAAAGGCATTGGGATGAACGAGCCGCTGGTGGACTGTGAGGGCTACCCCGGTCAGACG 6660
6661 TGGACCTGTACCAAGTCCGCACCGCCAGGCACAACATCATATGTGAGTGGCCCTCTTAGA 6720
6721 AGACTTTCCCCACCTTGTGGTGGGAAGGTGTTAAAGGCATACAAATAAAACCAACTATCT 6780
6781 GTATTATCTACTGCCTTCTCTTCTGCCTTGATGGGATTGTCTTGTCCCCATCCAAGGACT 6840
6841 GAGAACCAAGGGAATGGGCTAGACTCTAAGGTTCTATATTTCTGGTTTCATTTTCTCTCT 6900
6901 CTCTCTCTCTCTTTTTTTTTTGAGTCAGGGTCTTGCTCTGTCTTCCAGGCTGGAGTGC 6960
6961 AGTGGTGCTAACATGACTCACTGCAGTCTCAACCCCCCAGGCTCCAAGTGCTCCTTCTGC 7020
7021 CTCAGCCTCCCAAGTAGCTGGGACTATAGGCATGTGTCGCTGTGCCTGGCTAATTTTTTT 7080
7081 TAGTAGAGACGAGTCTCACTAAGTGGCCCAGGTGAGTCTTGAACTCCTGGACTCAAGTGG 7140
7141 TCCTCCTGCCTTGGCCTTCCAAGGTGCTGATTGTTTTAATTAAAGAGCTAGCAGAGAGT 7200
7201 ACAGATTGGATAGTATATTTGTTTTCTGTTTCTGCCATAACAAATGACGTGATTTGTTTT 7260
7261 TAATTAAAGAGCTAGCAGAGAGTACAGATTGGATAGTATATTTGTTTCTGTTTCTGCCAT 7320
7321 AACAAATGACCACAGACTTAGTAGCTGGAGATAAGAAGTCCAGATGGGTCTCACTGGACT 7380
7381 AAAATCAAGGTGTTGGCAGGGCTGGCTCCTTCTGGAGGATCTAGGGGAGAACCTGTTCCT 7440
7441 GGTCTTTTCTGGTTTCCAAAGGCTGCCCACCGTCCTTGGCTCATGGCTTCGTCCATCTAC 7500
7501 ACAGCCAGCAGTCGCATTTCCCTCCCTCTGATTCTGTCATAACATCTCTTTCTCTCACTC 7560
7561 TCCTGCCTCCCTCTTTCACCTATAAAGACCTCTGTGATGACACCAGGCCCACCTGGATAA 7620
7621 TCCAGGATCATGTCCGAATCTTAAGGTCCTTAATCACATCTGCAGAGCCTCTTTTGCCAT 7680
7681 GTAAGGTGGCATATTCCCAGCTTCTAGGGGCTAGGATGTGGATGTGTTGGGGGCCATTAT 7740
7741 CCACTCAGCCATAGGTAGGCAACCGTCTCCACCACAGAGTCCTATTAGCATTTATCCTCC 7800
7801 ACATTTTCACTTACTAACTCCTCTTTAATCTGTTTGAATCTTGATTCCATCTGCATCAC 7860
7861 ATCTTATTTATTTATTTATTTTTTGAGACGGAGTCTCGCTCTGTCACCCAGGTTGGAGTG 7920
7921 CAGTGGCACGATCTTGGCTCACTGCAACTTCCACCTCCCGAGTGACAGAGCAAGAGACCG 7980
7981 TCTCAAAAAAAAAAAAAAATCTGTTTGAGCAATTCCTTATTGGTCTTTTTTTGAAAAAT 8040
8041 CTGTTCTCGGCCGGGTGCGGTGGCTCATGCCTGTAATCCCAGCACTTTGGGAAGCCAAGG 8100
8101 CGGGCAGATCACCTGAGGTCAGGAGTTTGAGTCTAGCCTGACCAACATGGCAAATCCTG 8160
8161 TCTGTACTAAAAATAGAAAATTAACTGGATGTGGTGGCACATGCCTGTAATTCCAGCTA 8220
8221 CTTGGGAGGCTGAGACAGGAGAATCACTTGAACCCAGGAGGCAGAGGTTGCAAAGAGCCG 8280
8281 AGATTACACCACTGCACTCCACCCTGGGCGACAGAGCAAACAAAACTCTGTCTCAAAAAA 8340
8341 AAGAAAGAAAATCTATTCTCAAAACAGCCCTTTTAAAGAACAGTTATAGATTTACATAA 8400
8401 AAATTGGAAAATAATGGCTGGGTGCGGTGGCTCACGCCTGTAATCCCAGCACACTGGGAG 8460
8461 GCCGAGGTGGGCAGATCACCTGAGGTCGGGAGTTCGAGACCAGCCTGACCAACATGGAGA 8520
8521 AACCCTGTCTCTACTAAAAATACAAAATTAGCTGGGCATGGTGGCACGAACCTGTAATCC 8580
```

Figure 27C-4

```
 8581 CAGCTACTCAGGAGGTTGAGGCAGGAGAATCACTTGAACCCAGGAGGCGGAGGTTGCCGT  8640
 8641 GAGCCGAGATTGTGCCATTGCACTCCAGCCTGGGCAACAAGAGTGAAACTCTGTCTCAAA  8700
 8701 AAAAAAAAAAAAAGAAAAGAAAAAAAAATTGGAAAATAATGCATAGGTCCTTTGGCTTC   8760
 8761 TGTATGTAATCTCCCGTGTTGTTAACAGCATATATACACATACATGTGTATATATCTACA  8820
 8821 CATACATGTAAATATATACACACATACATGTGTATGTAAAATATACACATGCGTGTATAT  8880
 8881 ATGCAAATACACATATGAGTGAATGACTCAGGCTGGGTGTAACCAAGATTTCACTTTTC   8940
 8941 TCTGAAATCCTCTAGAAGGAAAAATGCTGCATAAGCTGGGCACAGAGGCTCATGCCTGTA  9000
 9001 ATCCCAGCACTTTGGGAGGCTGAGGCCTCCCAAATATATACACATGTGTATACACACAGG  9060
 9061 TTCAAGTGATTCTCCAGCCTTAGCTTCCCAAGTAGCTGGGATTACAGGTGCCCACCATCA  9120
 9121 CACCGGACTAATTTTTTTTTTTTTGAGATGGAATCTTGCTTAGCCACCTAGGCTGGA     9180
 9181 GTGCAGTGGCATGATCTCGGCTCACTCACTGCACTCACCATCTCCCGGGTTCAAGTGATT  9240
 9241 CTCCCATCTCAGCCTCCCAAGTAGCTGAGATTACAGGCATCCGCCATCGTGCCCGGCTAA  9300
 9301 TTTTTATATTTAGTAGAGACAGGGTTTCACCATGTTGGCCAGGCTGGTCTTGAACTCCT   9360
 9361 GACCTCAGGTGATCCGCCCGCCTCGGCCTCGACAGGCGTGAGCCACCATGCCTGGCCTAA  9420
 9421 TTTTTTAGTAGTATTTTTTAGTAGAGACGGGATTTCACCATGTTGGCCAGGCTGGTCTC   9480
 9481 GAACTCCTGACCTCAGGTGATCCGCCCGCCTCGGCCTCGACAGGCGTGAGCCACCATGCC  9540
 9541 TGGCCTAATTTTTAGTAGTATTTTTTAGTAGAGACGGGATTTCACCATGTTGGCCAGG    9600
 9601 CTGGTCTCGAACTCCTGACCTCAGGTGATCTGCCCGCCTCGGCCTCGCAAAGTGCTGGGA  9660
 9661 TTACAGGCATGAGCCACCGCGCCCAGCTAACAGCTTATGTTAATATGGTACGTTTGTTAT  9720
 9721 AATTGCAAATTTGTTTTTTGAAATACACTGCAGAAACATTTTGTACTGAAAAAAACCCTT  9780
 9781 TCAACATTTTGATTAGAATTGTAATATGTTGTAAATAGTCGTTCGTTCCATTCCCCAACA  9840
 9841 GCTGTGTATTGAGCACTTCCCTGTGCCAGGCATTGCAGAGTCTAGGGATGCTGTGGACCT  9900
 9901 CACTGGGGGAGGGCTTTTCTAGTGAAAGTGACCATGTATTATGTAAGTCTGCCTCCCAAG  9960
 9961 TGCATGTCTCCACTTGTTCAGATCTGGGTTCTTTTCCCACATCTGCTCCTGTGGGTTGAG 10020
10021 AACTTGAATCCCTTCATGACTGAGGGTCTTGCCTTTGCTCCAAAGTGACAGTGGCAGAGG 10080
10081 AGGCAGGTCAGGTAGTACCGCAATCCCACTGACAGGCACAAGGTATCAAAATACCAGCTG 10140
10141 CTGTGCTGGCGTGGCCTGCAGATTGCCATGGTGGTTCACAACATTTGAATTAGCTATCT  10200
10201 GTACTGAAAAATCAGAGAATTTCACTTCAAAGATCCCAATTTTCAGCTTTTCTGGAAAAA 10260
10261 TCAAAGATTTTGTAGCATTGGGTCTTCCTCCCAAACCCAGCCAATTGGCAAGAGCCCTGT 10320
10321 AGCAGGGGTGCCCTTTGGCCACCTCCCTGTGGACTCCCTCTCCTGGACTGAATGTCTCCA 10380
10381 GGATTACTAGGCTTATGCAGCACTTTTTTTTTTTTTTGAGACGAATTCTTGCTTTGT    10440
10441 CGCCAGGCTGGAGGGCAGTGGTGCGATCTCGGCTCACTGCAACCTCCACCTCCTGGGTTC 10500
10501 AAGTAATTCTCCTGCTTCAGCCTCCCAAGTAGCTGGGATTACAGGCACCCGCCACCACGC 10560
10561 CCAGCTAATTTTTGTTTTTGTTTTGTTTTGTTTTGAGACGGAGTCTTGCTCTGT       10620
10621 TGCCCAGGCTAGAGTGCAGTGGCGCGATCTCGGCTCACTGCAATCTCCGCCTCCCTGGTT 10680
10681 CACGCCAATCTCCTGCCTCAGCCTCCCGAGTAGCTGGGACTACAGGCGCCTGCCATCATG 10740
10741 CCCGGCTAATTTTTGTATTTTAGTAGAGACGGGGTTTCACCGTGTTAGCCAGGATGGTC  10800
10801 TCCATCTCCTGACCTCGTGATCCGGCCACCTTGACTTCCCAAAGTTCTGGGATTACAGGC 10860
10861 CTGAGCCACCACGCTCGGCCTAATTTTTGTATTTTTAGTAGAGACGGGGTTTCACCATG  10920
10921 TTGGCAAGGTGGTCGCGATCTCTTGACCTCGTGATCTGCCTGCCTCGGCCTCCCACAGTG 10980
10981 CTGGGATTACAGGCGTGAGCCTCTGTGCCCGGCTTATGCAGCATTTTTCCTTCTAGAGGA 11040
11041 TTTCAGAGAAAGTGAAATCTTGATTACACCCAGCCTGAGTCATTCATTCACATGATCAC  11100
11101 AGCGCTGGCCCCTCATACATATGCCTTTGAGTTCATGGCTGTGGATTCAGCTGGTTGTTA 11160
11161 CCTTCCTTCTGCTCACCTCTCAGGGCTCACCCGAGACAGCACTGCCTTCAGGAAGCCTTC 11220
11221 CCTCATATCCTAGACTAGCGAGGGCAGACTTTGCTGCTGGCCAGGCCTCCCTGCAGTCAT 11280
11281 CAGATGTTATTGTAATTACTTATTCTGGAGCTGCTCCTTGCAGGACTGAATGCTCCATGA 11340
11341 GGGAATGTCCTCTGTCTTGGTCAGAGACTCCTTCTCACCTCTAGCTCCACATCTGGCATG 11400
11401 TAATAAGCACTTGTTAACTCTTCAGTGAATAAATGTAGGAGTCTTGTGTCCTCCACTGTC 11460
11461 TTCCTTGGCCCCTGATGTGTGGTTCTCATCCCAGGCCTGCAGAATGATCACAAGGCAGTG 11520
```

Figure 27C-5

```
11521 ATGAAGCAGGTGGAGGAGGCCCTGCACCAGCTGCACGCTCGCGACAAGGAGAAGCAGGCC 11580
11581 CGGGACATGGCTGAGGCCCACAAAGAGGCCATGAGCCGCAAACTGGGTCAGAGTGAGAGC 11640
11641 CAGGGCCCTCCACGGGCCTTCGCCAAAGTGAACAGCATCAGCCCCGGCTCCCCAGCCAGC 11700
11701 ATCGCGGTAATCCAGGGGTTGGCCACTCAAGTCCATGCCCAGGGGACACGGTGGGTCAGG 11760
11761 TAGCCTTCGGGGATGTGGAAAGACAGACTAGTTCTCTCCGTGCTGCGGTGCTGAGTTCAG 11820
11821 TTACTCATTTAACAAACACTGACTGAGGCCTGTCGTGTATCCAGCCCTGTGCTGGGGCA 11880
11881 GAGTTTTAGAGAGGGGTCAGCCCCGGCTGCCCACTACATTGGTGGGGAGTGACCTCTTC 11940
11941 CCAGTGACAGAAGATGATAAATGTCCCAAGAGAGGGAGAGGATCTCTTCTTGGGGCTCAT 12000
12001 TTTAGCTGGGCACTGAATGATGAAAATGAGAATGGCATCTTGCCAAATGAGTTATGCATC 12060
12061 TTATGTGGTGTCTTAAAAAAAACATTAGGCTGGGCACAGTGGCTCATGCGTGTAATCCCA 12120
12121 GCACTTGAGAAGGCTGAGGCGACTTGGAAAGCTGAGATGGGAGGATCACTTGGGCTCAGG 12180
12181 AAGTCGAAGTTGCAGTGAGCTGTGACTGTGCCACTGCACTCCAGCCTGGGTGACAGAGTG 12240
12241 AGACCTTGTCTTAAAAAAAATTTTTTTTGACCGGGAGCATTGGCTCACGCCTGTAATCC 12300
12301 CAGCATGTTGGGAGGCCGAGGCCAGTGGATCACTTGAGGTCAGGAGTTCGAGACCAACCT 12360
12361 GGCCAACATGGCGAAACCCCGTCTCTACTAAAAATACGAAAATCATGCCACTGCACTCCA 12420
12421 GCCTGGGCAACAGAGTGAGACTCCGTCTCAAAAAAAAAAAAAAATTTACCCATTTAAAG 12480
12481 TCCGTATACAGTTTAGTGTCTTTTGGTGTATTCACAGAGCCATGCATTACCACAATCAAT 12540
12541 TTTCTTTCTATTTAAAAAATTTGCAGCCAGGTGCAGTGGCTCACGCCTGTAATCCCAGCA 12600
12601 CTTTGGGAGGCTTAGGTGGGCGATCACCTTATGTCAGGAGTTCAAGACCAGCCTGGCCAA 12660
12661 CATGGCGAAACCCCATCTGTACTAAAAATACAAACATTAGCCGGGTGTGGTGACATGTGC 12720
12721 CTGTAATCCCAGCTACTCGGGAGGCTGAGGCAGGAGAATCGCCTGAACCCAGGAGGTGGA 12780
12781 GGTTGCAGTGAGCGGAGATCGTGCCACTACACTCCAGAGCCTGGGCGACAGAGTGAGACT 12840
12841 CTGTCTAAAAAAAAAAAAAAAAAAAAAGGAGATGGGGTTTCGCTCTGTTGCGTAGGTTG 12900
12901 GTCTCCATCTCCTGGGCTCAAGTGATTCTACCACCTTGGCCTCCCAAAATGCTGGGATTA 12960
12961 TAGGCATGAGCCACCATGCCCAGCCATAATCAATTTCAGAACATTGTCATTGTCTTGTAA 13020
13021 AGAAACTCTGTAGTGATTTGCCATCACTTCCCAATCCCCCAGCTCCCCGCACCCAGTTAT 13080
13081 CTACTTTCTGTCTCTATGTATTTGTCTATTCTGGATATTTCCTATAAGTTGAATCATATA 13140
13141 ATATGTGACCTTTTATGACTGGCTTCTTTCACTTAGCAAATTTTCAAGTCATCTGTATTG 13200
13201 AGCATGGATCAGTGCTTCATTTGTTTACAGACAGGGTCTCACTCTCTCACCCAGACTTCA 13260
13261 GTGCCATGGTGCCATCATAGCTCACTGCAACCTCAAACTCGCAGAGTCAAGTGATCCTCC 13320
13321 TGTCTCAGCCTCCCAAGCAGCTAGGACTGTAGGCACATGTAACCATGCCTGGTTAATTTT 13380
13381 TTATTTCCTTTTTTTTTAGAGATGGGTTCTCACTATGTTGCCCAGGCTGGTCTTGAACT 13440
13441 CCTGGCCTCAAGCGATCCTTCTTCCTCGGCCTCCCAAAGTGCTAGAATTACAGGCATGAG 13500
13501 CTGTCATGCCTGGCCCTTCATTCCTTCTTTTTTTTTTTTTTTTTTTTTTGAGACG 13560
13561 GAGTCTCGCTCTGTCGCCCAGGCTGGAGTGCAGTGGCACGATCTCGGCTCACTGCAAGCT 13620
13621 CCGCCTCCCAGGTTCACGCCATTCTCCTGCCTCATCCTCCCGAGTAGCTGGGACTACAGG 13680
13681 CGCCTGCCATCACGTCCAGCTAATTTTATTTTTGTATTTTAGTAGAGACAGGGTTTC 13740
13741 ACTTTGTTAGCCAGGGTGGTCTCGATCTCCTGACCTCGTGATCCGCCCGCCTCAGCCTCC 13800
13801 CAAAGTGCTGGGATTACAGGCGTGAGCCACTGTGCCTGGCCCTTCATTCCTTTTTATGGC 13860
13861 CAAATAATATTCCACTGCCTGGATATATCATATTTTATTTATCCATTTGTCAGTTAATGG 13920
13921 ACATTTGAATTGTTACCACTTTTTGGCTATTACGAAGCATGTTGCTGCGAACATTCTTGT 13980
13981 ACAGTTTTTTGTGGAGATGTAGTTAAATTTAATTCCACAGCCACTTCTGGGATAGGTCC 14040
14041 TAATCTTTACTCATTTCATCCTCGAGGAAAAGCCTTGCAGACCTGAAGTAACTTATGTCA 14100
14101 GGACACATAGTTCCTGCCAGGTGGAATGGGGTCCTAAACCCTGGTCAGGACACATAGTTC 14160
14161 CTGCCAGGTGGAATGGGGTCCTAAACCCTGGTCAGGACACATAGTTCCTGCCAGGTGGAA 14220
14221 TGGGGTCCTAAACCCTGGTCCTACCAGTCTTCTTTAATGGTCACAAGTCTGTAAGTTACA 14280
14281 CAGAAGCTCCCTATCATTCACTACCCCATCTACTGCATCTAACCCAGTGCCAGTTGGCCC 14340
14341 ACAACAAATACTTGTTACAGGGGTGAATGAGTGGTGGTCTGTCTTCTTAGGACCTAGAAC 14400
14401 AAGAGCGTCACTCTAGTCTTGGATGCGCCGTGTGCCTGTGGCTGCTTGTCTGGGGGCTTC 14460
```

Figure 27C-6

```
14461 TAGGGCAAGTGTCTTGTCTAAATGTTGATCACTGAATAAAATGGGCCCAGCCTGGCTTGC 14520
14521 CTTCTCTTACCCTTGAACCTGGGTTAGGACCGCAGAGAGCAGCATTTGGCCTTTCCCATG 14580
14581 CTCCTCAAGGCCTTCACAGTGTCTGGTAACTGCCAGCTCTCAGACATTGGGCAGACCTGG 14640
14641 TCATCTTTACTAGAGCTGCCCTCAAAGGAACCCCAGGAGGAGGTGGCCCCGTTACCCACT 14700
14701 GCCCCTTCCTGCATGAGGTGTCTACATCCCTGACCTCTTTGTTCTGAGCCTACCCTGTAG 14760
14761 AAAACAAGCTCGTGACCTTGGCATTAAATTGGGTATTGAAGGTTAGAGACCACCAGGAGC 14820
14821 ACACTGAACCTCTAGCCTGATTTTCCATTTTTCCTTCCCTCTCCAGGGTCTGCAAGTGGA 14880
14881 TGATGAGATTGTGGAGTTCGGCTCTGTGAACACCCAGAACTTCCAGTCACTGCATAACAT 14940
14941 TGGCAGTGTGGTGCAGCACAGTGAGGGGGTGAGTGGGGCTACCTGGTGTCTCGGTCTGTT 15000
15001 TGGGTTTTTCTAACAGTATGCCATAGACTGCGTGGCTTACAAACAACAGAAGTTCATTTT 15060
15061 TCACAGCTCTGGAGGCAGGGAAGTCCAAGATCCAGGCACCAGCCAATTTGGTGTCTGGGG 15120
15121 AGGGCTTGCTTCCTAACTCCTAGGTGGTGCCTTCTTGCTGTGTCCTCACATGGCAGAAAG 15180
15181 GGGAGGAACCCTGGGAGCTCTTGTATAAGGGCACTAATCCCAGTGGGGGCGCCACCCCTC 15240
15241 ATGACCTAATCACCTTGCAGAGGCCCCACCCCTAATACCATCACATTGGTGGTTAGGATT 15300
15301 TCAACATATGAATTTCAGGGGGCCACAGACATTCAGGTCATAGCACTCGGCCTCTGGTCT 15360
15361 ATAGCCCTGGAGTTACTGGAAGTGTTGCTGAGGCCCTGGACTGCTGCCTTCATGGTGTTG 15420
15421 CTCAGCACAGCCCCATTCAAGGACTTGGCACCTGCTATTCCTTCTGTTTAGAATGCTCTT 15480
15481 CCTCTTCATCCTCCTTCTGTTTTACACTGGTGACATGCTCGCAGGGGCCTTTCCTGGCT 15540
15541 ACCCTAACCCAAATTCCCCTCTCCTCTGCCCTGTCTCTGTTTTCATTTAACAAGGTTTCT 15600
15601 TAGAGATCTTTTCTTTTTTTTTTTTTTTTTTTTTAAGACAGGGTCATGCTGTGTCACCCAG 15660
15661 GCTAGAGTGTGGTGGTGCTATCATAACTACCTCACGGCTAATTTTTTATATTTTGTGGA 15720
15721 GGCGGGGTCTTGCTATGTTGTCCAGGCTGGAATTTTGTTGTTGTTTTGTAGCAAAGATC 15780
15781 CACACTTTTCAGGAGTGATACTGTGGCAAAGCCCAGGAAAATTATTAACTAAAGTTTTTG 15840
15841 GTTCCCAAATGAAGTCTCCAGTTAACCCAACAGTTGTGGATTTTTTGACTCCTGCTTAGC 15900
15901 TGCACGGTTCATCTACTTGTAACCCATCAGTGCAGGCCAGGCCAGGTCAGGTCAGGAGAT 15960
15961 GGCTGGCAGTTGCCTATGCCCCTGCTAGTGGTCAGGCCATCGTTTCTGCACTGATACTGT 16020
16021 CATCAAATCTGTAACTTGTATGGACGTTTAAAATGATGATTTTGTGAAATTTATCAGTTT 16080
16081 TTTTGCTTATGGCTCTTGCATTTTGTGTCCATTTAAAGAAATTCTTTTTTTTTTTTTTAA 16140
16141 TTAAGAAATTCTTGGCTGGGCGTGGTGGCTCACTCCTGTAATCCCAGCACTTTAGGAGGG 16200
16201 CGAGGTGGGTGGATCACGAAGTCAGGAGTTGGAGACCATCCTGGCTAACACGGTGAAACC 16260
16261 CCGTCTCTACTAAAAATACAAAAAATTAGCCGGGTGTGGTGGCACACACTTGTAGTCCCA 16320
16321 GTTACTTGGGAGACTGAGGAAGGAGAATCGCTTGAACCCAGGAGGCAGAGCTTGCAGTGA 16380
16381 GCCGAGATCGCGCCATTGCACTCCAGCCTAGGCGACAGAGCAAGACTCTGTCTCAAAAAA 16440
16441 AGAAATTCTTTTAATTCTTTTATTGTTTTATTTCTGTTTTCCTTTAGTCCATCTGAAAT 16500
16501 TTATTATTATTATTATTATTATTATTATTTGAGATGGAGTCTCGCTCTGTCACC 16560
16561 CAGGCTGGAGTGCAGTGGTGCGATCTTGGCTCACTGCAACCTCCGCCTCCCAGGTTCAAG 16620
16621 TGATTCTCCTGCCTCAGCCTCCTGAGTAGCTGGGATTACAGGCGCCCACCACCATGCCTG 16680
16681 GCTAATTTTGTATTTTTAGTAGAGATGGGGTTTCGCTATGTTGGCCAGGCTGGTCTCAA 16740
16741 ACTGGCCTCCCAAAGTGCTGGGACTACAGATGTGAGCCACTGCGCCTGGTCTATTTTAT 16800
16801 TATTTTTACAACAGTTTTATTGAGATTTAATGCACATACTACACAGTTCACCCATTTAAA 16860
16861 GTGGTTTTAGTGTAGTCACAGAATTATGCAGCCATCACAATTGTACATTTTCATCACTT 16920
16921 CTCCTCCTGAGGCAGCCACTTTCCAGCCACATGTCCTTCAGAAAGACTGCTCATATACCA 16980
16981 GCACACAGAGCTGCCAGTTGATTTTATTTTATTAAGGTGTAATTTACCTGCACCAGATCC 17040
17041 ACCTTTTTCAGTGTACAGTCCCATGAGTTTTCTTCTTTTTCTTTCTTTTTTTTTTTTTA 17100
17101 GATGGAGTCTTGCTCTGTCGCCCAGGCTGGAGTGCAGTGGTGCAGTCTCGGGGGGCTAC 17160
17161 TGCAAGCTCTGCCTCCCAGGTTCACGCCATTCTCCTGCCTCAGCCTCCCGAGTAGCTGGG 17220
17221 ACTACAGGCATGTGCCACCATGCCCAGCTAATTTTTTGTATTTTTAGTAGAGATGGGGT 17280
17281 TTCACTGTGTTAGCCAGGATGGTCTCGATCTCCTGACCTCGTGATCCACCTGCCTTGGCC 17340
17341 TCCCAAAGTGCTGGGATTACAGGTGTGAGCCACCACACCCAGCCGAGTTTTCTTTTTTTT 17400
```

Figure 27C-7

```
17401 TTCTTTAAGATGGAGTTTTGCTCTTTTGCCCAGTCTGGAGTGCAGTGGCACGATCTCGGC 17460
17461 TCACTGCAACCTCTGCCTCCCAGGTTCAAGCGATTCTCCAGCCTCAGTCTCCCAAGTAGC 17520
17521 TGGGATTATAGGTGCCCACCACCACGCCCAGCTAATTTTTTTTGTATTTTTAGTAGAGA 17580
17581 CAGGGTTTCAGCATGTTGGCCAGGCTGGTCTCAAACTCCTAACCTCAGGTGATCCACCCA 17640
17641 CCTCAGCCTCCCAAAGTTCTGGGATTACAGGAGTGAGCCACTGTGGCCTGCCATTCCCGT 17700
17701 GAGTTTTCACAAATGTATGTAGTATGTCATTGCCACCACGATGAAGGTCAAGAGCATTCC 17760
17761 AACACCCCATAAAATTGCCTCAGGCTTCTTTGTAGTTAATCCCTCACCGTCAACTTCCAG 17820
17821 AATGTCATAGAGAGAAAAACCACACAATATATTGCCTTTTGAGTCTGGTGTTCTTCACTC 17880
17881 AGCCCAGTGGATTCTGAGACTTCTGTCTGTTGTGTGGATCTGTGAGAAGAGCTGCTGGTT 17940
17941 TTTAATCTGTTTTATCCAGTTAAATGTATTCTCAGCTTCCGTGTAGGCTTATAAATCCTT 18000
18001 CTTTATAAAGTAGTGATTCAATTTTAAGCAAAATGAATCTTTTCTTCATGTGAAATTTC 18060
18061 ACGGGGAATTCCAAGATGTCACTGGATAAAGGCTGAGCTGTCTTGGTGGGCTGGAGGATG 18120
18121 GAGAAGGTCGTGTGTTGTGAGTAGGGCCTTTCTGGCTTCAGCCTCATCCCCTCAGGGAC 18180
18181 CTGAGCTCAGCTGGAGAATCAAGAATCCGGGTTTGGTTGTCTGTTTTGTGAGTCAAGAAA 18240
18241 AAAAACCTTGCATAGCACAGTGGCTCACACCTGTAATCCCAGCACTTTGGGAGGCTGAGG 18300
18301 CGGGTGGATCACCTGAGGTCAGGAGTTCAAGACCAGCCTGGCCAACATGGTGAAACCCCA 18360
18361 TCTCTACTAAAAATAAGAAATTAGGCCTGGCACGGTGGCTCACACCTGTAATCCCAGCAC 18420
18421 TTTAAGAGGCCAAAGTGGGCAGATCACAAGGTCAAGAGATCGAGACCATCCTGCCCAACA 18480
18481 TGGTGAAAACCGGTCTCTACTAAAAATACAAAAAAAAAAAAAAAATTATCTGGGTGTGGT 18540
18541 GGTGTGTGCCTGTAGTCCCAGCTACTTGGGCTGCTGAGGCAGGAGAATCACTTGAACCTC 18600
18601 GGAGGCAGAGGTTGCAGTGAACCAAGATCACGCCACTGCACTCCAGCCTGGGCCGCACAG 18660
18661 CGAGACTCTCCCATCTCAAAAAAAAAAAATTAGGTGTGGTGGTACTCTCCAGCTACTTG 18720
18721 GGAGGCCGAGGCAGGAGAATTGCTTGAACCCGGGAGGCAGAGGTTGCAGTGAGCTTAGAT 18780
18781 CATGCCACTGCACCCTAGCCTGGGCGACAGAGTGAGGCTCTGTGTCAAAAAAAAAAAAA 18840
18841 AACCAAAAAACTCACAGTGTTCTATTGTGAGACATTTAGATAGTTTGCCATTTTGTGGAG 18900
18901 ATTAACACTCTTGCAGATGGATTTCTATTTCTTTTTTATTTTTTTGAGACGAAGTTTT 18960
18961 TCTCTTGTTGCCTAGGCTGGAGTGCAATGGCATGATCTCAGCTCACTGCAACCTCCGCCT 19020
19021 CACAGATTCAAGCGATTCTCCTGCCTCAGCCTCCCAAGTAGTTGGGACTACAGGCACCCG 19080
19081 CCACCACGCCCAGCTAATTTTTGTATTTTCAGTAGAGATGGGGTTTCACCATGTTGGCCA 19140
19141 GGCGGGTCTTGAACTCCTGACCTCAGGTGATCTGCCCGCCTCGGCCTCCCAAAGTGCTGG 19200
19201 GATTACAGGCGTGAGCCACTGTGCCCGGCCTTTCTTTGTTTTTTTTTTGTTTGTTTTTT 19260
19261 ATTTGAGATGGAGTCTTGCTCTGTCACCCAGGCTGGAGTGCAGTGGCATTATCTCAGCTC 19320
19321 ACTGCAACCTCTGCCTCCCGGCACCTGGCCTTTTTAGCGAACTTCCTACAGCTGGGATT 19380
19381 TCTAGATCAAATGCATACATTTTCAAGGGGAAAAGATCTTTAAAAAATTATAAATGACTG 19440
19441 CTGATGGATAATGGATTTCTTTTTGGGTGATGAAAATGATCCAGAATTAGATAGTGGTGG 19500
19501 TTGTTTATACTAAATACATTGAATATACTGAACTCTGAATATACTAAAACTCACTTAATT 19560
19561 GTATACTTTAAAATGGTGAATTTATTGTATGCAAATTATGTCTCAATGATAAAAATAGG 19620
19621 CTGGCTGCAGTGGCTCACGCCTGTGTTCCCAACACTTTGGGAGGCCAAGGCAGGAGGATC 19680
19681 ACTTGAGGCCAGGAGTTTGAGACCAGCCTGGGCAATATTGTGAGACTGTGTCTCTCCAAA 19740
19741 ATATTTTTTAAGAAATTGGCCAAGCATAGTGGCATGTGGCCAAGCTGCTCTGGAGGCTGA 19800
19801 GGCAGGAGGATCACTTGACCCTAGGAGTTCAAGGGTGCAGTAAGCCAAGGTCACACCACT 19860
19861 GCACTCCAGCCTGGATGACAGAGTGAAACCTGTCTCAAATAAATAAAATACATATTTAT 19920
19921 CCTTAAAATCACATAGTGCAATTGTATTTACAAACAAAGTCCTAGTGTTATAGCTCTAA 19980
19981 GAATTTGTCTACCAGGTTTTCTGGTCATCGCTGGAAACACCCTCTCCCCTCAAAATAAA 20040
20041 TTTTTTTTTTTTTTGAGACAGAGTTGTCGCTCTTGTTGCCCAGGCTGGAGTGCAGTGGC 20100
20101 GCGATCTTGGCTCACTGCAACCTCCGCCTCCCGGGTTCAAGCAATTCTCCTGCCTCAGCC 20160
20161 TCCTGAGTAGCTGGGATTACAGGCATGCACCACCAAGCCCGGCTAATTTTGTATTTTTAG 20220
20221 TAGAGATGGAGTTTCTCCATGTTGGTCAGGCTGGTCTCTTAATTCCTGACCTCAGATGAT 20280
20281 CTGCCCGCTTCGGCCTCCCAAAGTGCTGAGATTATAGGCGTGAGCCACTGTGCCTGGCCC 20340
```

Figure 27C-8

```
20341 CAAAATAATTTTTTAAAAAGTCCTGTGTCTCTCCCTTCCTTAGTGCCTCTTCCGCTGCAC 20400
20401 ATGCTGGGTCCTGGGCGAGGTACTGGGGCTGTAACGGGGAACGAAACAAACAGGGTCCTT 20460
20461 GCCTTGGGAGCACTTTGGTGGGGGAGCCAGGCCTTAATCAAATAATCTCAGCTGTATAAT 20520
20521 GATACACACTGATAAGTGTTATGAAGGAAGAGTGTTAAGAAGCTCAGAGAGTAAATCATG 20580
20581 GGGCCCTGATTTGGTTTGGGATTGAAGGAGTGTTCCTCAGGAAGTGACCTTCAGATGTGT 20640
20641 ATAGAAGTTTCTCTGGTCGAGGGGAAGCTGGCAGGGAGAAAAGCCTTCAAAGCAGGTTCA 20700
20701 TAGGCCCTGGGGTGGGAGGATCAAAGAACTCAAAGGAGGGTGGAGCCCAGAGCAGAATGG 20760
20761 AGAGAAGGGGAGGAGGTGAGGCCAGGAGGTGTTAAGGTCAGGCCTGTGGTCCTTAGTAAA 20820
20821 GATTGTGCTGTTTTTTTCCTGAGGTGCAGAAGGGAGCCACCGCACAGTTCCAGATTGGGG 20880
20881 TGTGACAGGGGTAAGAAGCCTTCTCTGGATGTTAGGTAGAGAACAGATTGGAGGGTGACA 20940
20941 GAGCTGTAGCAGTCAGTCAAGAGAGGATGGTGGCTGTGACAAATGGGGTGGAGGAAGGGG 21000
21001 TCAATCAAAGAGACATTTAGGGTGTAAAATCCATGGGCCTTAACCTGATGGAGTGTGTCA 21060
21061 AGGAGGCCTCCAGGTTTCCAGCCTGCCCAGGGCTGTCATTTATAGAACTGGAAGCACACA 21120
21121 AGTGTGTCCCTCACACAGTTTCCACACGTGGGTGCATGCGTCTACAGCCACTGCCTTTTT 21180
21181 TTTTTTTTTTAGGACAGGGTCTCTCGCTCTGCTGCCCAGGCTGGAGTGCAGTGGTGCAAT 21240
21241 CATAGCTCACTGCAGCCTCAAACTCCAGGGCTTGAGCAGTCCTCCTGCCTTGGCCTCCCA 21300
21301 GGTAGCTGGGACTACAGGTGTGCACCACCACACCTGGCTAATTTTTTTTTTTTCATTTT 21360
21361 TTGTAGAGACAGGGTCTTGCTATGTTGCCTAGGCCGGTCTAGAACTCCTGGGCTCAAGTG 21420
21421 AGCCTCCAGCCTCAGCCCCTCAAAACATTCAGATTATTAAGCATGAGCCACCACGCCTGG 21480
21481 CTGTGATTGCTTTTTGACAAAGATGACACAGAAAAGGCCTAATGTACATGTTACTCTGCA 21540
21541 TTTCCGCCCACTTCGAAGGGAATTCCTTGTCGGCACATTTGTATCTTCATTCCTTTGAAT 21600
21601 GATCCCACCATGTTCCATTGGTCGGTTCACCATCTTTTACTTAGCCAGCCTCCCATGTTC 21660
21661 GACATTTAGGTTGTTTCCAGTGTTTGGCCGTAACAAACAGTGGTGTAGCGAGTGTCCTTG 21720
21721 CCTGTGGGAGAATTTCTGCCATGTTGCTAGATGTGTCATTACTGAGTTAAAGGCAGTGCA 21780
21781 CATTTACCCTTCATAGATCTTGTCAAGGTGTCCTCCAAGAAGCTTGTGCCAGTGCACCTT 21840
21841 CTCTCAAGTAGCACCTGTGAGTGCGTCTGTTTCTAGCTTTCCCAACTATGTTACAGTCTT 21900
21901 TGGCAATAACATAGATATTCTTTGACAATCTGGTAGGAAATGACTTTTTTTTTTTTTTT 21960
21961 TTTTTGAGATGGAGTCTCGCTCTATAGCCAGGCTGGAGTGCAGCGGCATGATCTCAGCTC 22020
22021 ACTGCAGCCTCCGCCTCCCAGGTTCAAGCGATTCTCCTGCCTCAGCCTCCCAAGTAGCTG 22080
22081 GGACTACAGGTGCCTGCCACCATGCCCAGCTAATGTTTGTATTTTAGTAGAGATGGGTT 22140
22141 TTCACTATGTTGGCCAGGATGGTCTCTATCTCTTGACCTCATGATCCGCCTGCCTTGGCC 22200
22201 TCCCAAGGTGCTGGGATTACAGGTGTGAGCTACCATGCCCGGCCTATGCTGTATTTTCTT 22260
22261 AGATTTAGAGATTCCATTGATAGACCTGACATATTTATTTTTTGTGGTAAATATACATA 22320
22321 ATATAAAAATTACCATTTTAGGCCGGGCGCGGTGGCTCACGCCTATAATCCCAGCACTTT 22380
22381 GGGAGGCCAAGGTGGGCGGATCACCTGAGGTCAGGAGCTGGAGACCAGCCTGCCAGCGTG 22440
22441 GTGAAACCCTATCTCTACTAAAAATACAAAATTAGCCGGGCGTGGTGGTGGGCGCCTGTA 22500
22501 ATCCCAGTTACTCGGGAGGCTGAGGCAGGAGAATTGCCTGAACCCGGGAGGCAGAGGTTG 22560
22561 CAGTGAGCCGAGATCACGCCACTGCACTCTGGCCTGGGTGACAAGAGTGAAACTTTGTCT 22620
22621 CAAAAAAAAAAAAATTACCATTTTAACCATTAAAAAATCTACACTTTAGTGGCATTAAGT 22680
22681 ACATTCACATTATTTTGCAAATATCACCCCTACCCATCTCCCATCTCCAAAACTTTTTCA 22740
22741 CCCTCCTAAACTGAAACCCAAATCTCCATTAAACACTAACTCTCCATTCCCACTTTCCGC 22800
22801 AGGCCCTGGCACCCACCATCCTACTTTCTGTCTCTATGAATTTGACTACTCCAGGGACCT 22860
22861 CATCTAGGTGAAATCTTACATACTGTGTAGTTTTTTGTTTTGTTTGTTTTGTTTTGA 22920
22921 GATGGTGTCTCGCTCTGTTGCCCAGGCTGGAGTGCAGTGGCTCAATCTCCACTCACTGCA 22980
22981 CCCTCCACCTCCCAGGTTTGAGCCATTCTTCTATCTCAGCCTCCTGAGTAGCTGGGACTA 23040
23041 CAGGCGTATGCCACCAGGCATGGCTAATTTTTGTATTTTAGTAGAGATGGGGTTTTGCC 23100
23101 ATGTTGGCCAGGCTGGTCTTAAACTCCTTATCTCAGATGATCTGCCTGCCTCTGCCTCCC 23160
23161 AAAGTGCTGGGATTACAGGACACTGTATAGTTTTTGTCTGGCTTATTTCACTTAGCATAA 23220
23221 TGTCCTCAAGGTTCATCCATGTTACAGCATGTGTCAGAATTTCCTTCCTTTTAAAGGCTG 23280
```

Figure 27C-9

```
23281 TATAATATTCGACTGTATGTATACACCACATTATTTTTATCCATTCATTAGTCAATGGAC 23340
23341 ACTAGGATTGCTTCCACCTTTTTGTTGTGAACAATGCTGCTTTGAACATGGTTGTAGCAA 23400
23401 TATCTGTTCAAATCTCTGCTTTCATTTCTTTGTATATATGCCCAGAAATTTAATTGCTGC 23460
23461 ATCATGTGGTCATTCTATGTTTAAAGTTTCTAAAATTTTTTTTAACTTCAATATATGAAC 23520
23521 TTTTTTTTTTTTTGAGATGGAGTCTTGCTCTCACCCAGGCTGGAGTGCAGTGGTGCAA 23580
23581 TCTCAGCTCACTGCAACCTCCGCCTCCCAGGTTAGTGATTCTCCTGTCTTAGCCTCCTGA 23640
23641 GTAGCTGGGATTACAGGCACCCACCACCACTCCCAGCTAATTTTTGTATTTTTAGTAGAG 23700
23701 ACTGGGTTTCACCATGTTGACCAGGCTCGCCTCGAACTCCTGACCTCAAGTAATCCACCT 23760
23761 GCCTTGGCCTCCCAAAGTGCTGGGATTGCAGGCGTGAACCACCACACCTGGCCTATGAAC 23820
23821 ATTTTAAAATGTCAAAGATGACTTCCAGGTTTCTGGAATGAGCTTGCTTATTTATTTATT 23880
23881 TATTTATTTATTTATTTATTTATTTATTTATTTATTTTGAGACAGGTTCTCTGTTG 23940
23941 CCAAGGCTGGAGTGCAGTGGTGTGATCTTGGCTCACTGCAATCTGGACTTCCCAGGCTCA 24000
24001 AGCAATCCTCCCACCTCAGCCTTGAGAGTAGCTGGGACTACAGGCATGTGCCACCATGCC 24060
24061 CAGCTAATTTTTGCATTTTGTGGTTTTGCCGTGTTGCCCAGGCTGGTCTTGAATTCCTGG 24120
24121 GCTCAAGCGATCCCACCCGTCTTGGCCTCCCAAAGTGCTGCTATTATAGGCGTGAGCCAC 24180
24181 CGTGCCCGGCGCTTTGTTTAGGTTTTGGAGGACCCTCCATTACTGTTTTCCACTGCCGTG 24240
24241 CACCGTTTCACATTCCCACCAGTGGTGCACAGGGCTCCATTTTCCCCGCTTCCTCGCCAG 24300
24301 CACTTGTTTTCTGTTTCATAATCAGTGTGTGGTAGAATCTCATTGTGGTTTTGATTTTCA 24360
24361 TTTCTCTTATGATTAGTGACATGGAGCATCTTTTCCTGTGCTTTTTGATCATTTGTATAT 24420
24421 CTTCTTTGAAGAAATGTCTATTTAGGCTGGGCGCTGTGTCTCATGCCTGTAATCCCAGTG 24480
24481 CTTTGGGAGGCTGAGGCGGGCGGATCACTCGAGCTCAGGAGTTTGAGACCAGCCTGGGGA 24540
24541 TCATGGTGAAACCTGTCTCTGGAAAAAAATACAAAAATTAGCCAGGTGTGGAGGATTGTG 24600
24601 CCTGTAGTCACAGCTACTCAGGAGGCTGAGGCAGGAGAATCGCTTGAGCCCAGGAGGCAG 24660
24661 AGGTTGCAGTGAGCTAAGGGATTGCATCACTACACTCCAGCCTGGGCAACAGGAGTGAAA 24720
24721 CCCTGTCTCAAAAAAAAAAAAAAAAAAAAGAAAGAAAAGAAAGGTCTATTCAAGTCCTTT 24780
24781 GCTCATTTTCTTTTCTTTTCTTTTTTTTTTTTGAGACGGAGTCTCGCTCTGTCACCC 24840
24841 AGGCTGGAGTGCAGTGGCACAATCTCGGCTCACTGCAAACTCCGCCTCCTGGGTTGACGC 24900
24901 CATTCTCCTGCCTCAGCCTCCCGAGTAGCTGGGACTACAGGCGTCCACCACCAAGCCTGG 24960
24961 CTAATTTTTTTGTGTGTGTATTTTTAGTAGAGATAGGGTTTCACTGTGTTAGCCACGAT 25020
25021 GGTGTCAATCTCCTGACTTTGTGATCTGCCCACCTTGGCCTCCCAAAGTGCTGGGATTAC 25080
25081 AGGCGTGAGCCACCGCGCCTGGCCTTTTTTTTGTATTTTTAGTAGAGACGGGGTTTCAC 25140
25141 CGTGTTAGCCAGGATGGTCTTGATCTCCTGACCTCATGATCCGCCTGCCTTGGCCTCCCA 25200
25201 AAGTGTTGGGATTACAGGCGTGAGCCACCACACCCAGCCCTTTGCTCATATTCTAATCAG 25260
25261 ATTTTTTGTTGATGTTGAGGTATAGGAGTTCTTTATATGTTCTGGATGTTAAATCCTTA 25320
25321 TTAGATATATGATTTGCATGTATTTCTTTTTCTTTTTTTTTTTTTAAGACAGAAT 25380
25381 CTCACTCTGTCACCCAGGCTGGAGTGCAGTGGCACATTCATGGCTCACTGCAGCCTTGAG 25440
25441 CTTCTGGGCTCAAGTGATCCTCCCACCTCAGCCTCCCAAGTAGCTGGGACTACAGATGTG 25500
25501 CGTCATCAAGCCTGGCTAATTAAAAAAAATATATGTTTTTTGTAAAGACGAGATCTCTCT 25560
25561 TTGTTGCCGGGCTGGTCTTGAACTTTTGAGCTGAGGCAGTCCTCCTGCCTGGGCCTCTGA 25620
25621 ATGTGTTGGGATTACAGGCATGAGCCACCGTACCCAGCATGTATGTATTTCTCCTATCA 25680
25681 TGTGGGTTGCCTTTTCACTCTGTTAATAGTGTCATTTGATACATAGAAGTTTTAGATTTT 25740
25741 GATGGCATCTTGTTTTATTTATTTATTTTTATTTTTTTGAGACAGGGTCTCACTCTGTTG 25800
25801 CCCAGGCTGGAGTGCAGTGGTGCAGTCACAGCTCACTGCAGCCTTGACCTCCCTTGAGCA 25860
25861 ATCCTCCTGCCTCAGCCTCCCGAGTAGCTGGGACTATAGGTGCACACCACCATGCCTCGC 25920
25921 TAATTTTTATACTTTTTGTAGAGTCAGGGTTTCACCATGCCCAGCCTGGTCTTCAACTCC 25980
25981 TGGGCTCAAGTGATCTTCCTGCCTCCCAAAGTGCTGGGATTACTGGCGTGAGCCACCGTG 26040
26041 CCTGGATATCGTATTTTAATTTGTAATTTTTTGGTATGTACTCCCCCTGCTTTAATTTT 26100
26101 AATTTTTTAAATTAAAGTACTATATACAGGCTGGGTGTGGTGGCTCATGCCTGTAATCCC 26160
26161 AGCACTTTGGGAGGCTGAGGTGGGTGGATCACCTGAGATCAGGAGTTCAAGACCAGCCTG 26220
```

Figure 27C-10

```
26221 GCCAACATGGCGAAACCCCATCTCTATTAAAAATACAAAAATTATCTGGGCATGGTGGCA 26280
26281 CGTGCCTGTAATCCCAGTTGCTCAGGAGGCTGAGGCAGGAGAATTGCTTGAACCGGGGAG 26340
26341 GCGGAGGTTGCAGTGAGCCGAGATTGTGCCACTGTACTCCAGCCTGCGCGACAGAGAACC 26400
26401 CATCTCAAAAAAAGAAAGTAATACATACATGCCAGGTGTGGTGGCACATGCCCAAAATC 26460
26461 CCAGCACTTTGGGATGCTGAGGTGGGCAGATCACTTGAGCCCAGGAGTTTGAGACCAGGC 26520
26521 TGGCCAGTATGGTGAAACCCTGTCTCTACTAAATATACAGAAACATTAGCTGAGCATGGT 26580
26581 GCTGCATGCCTCTAGTCCCAGCTACTCAGGAGGCTGAGGCACGAGAATTGCTTGAACCTA 26640
26641 GGAGGCTGAGGTTGCGGTGAGCTGAGATTGCACCACTACACTCCAGCCTGGGCAACAGAG 26700
26701 CAAGACTCTGTCTCAGAAAAATAAAGCAATACATACGCATGGTTAAAAAATTAATGATAT 26760
26761 GGAAATATATAAAAGTAAACATCTTCTTTTTCCAAAGGACTAGTCCTCTCTGGAAGTAAC 26820
26821 CACTCTTAACAAGTTTTTCCATGTTCTTCCAGAAAACTTCGCACACTAGAGCAACACAGG 26880
26881 TGTCCTTTTAGAAAATATTATCGGCCGGGCACGGTGGCTCACACCTGTAATCCCAGCACT 26940
26941 TTGGGAGGCTGAGGTGGGTGGATCACCTGAGATCAGGAGTTCTGAGACCAGCCTGGCCAA 27000
27001 CATGGCGAAACCCTGTCTCTACTAAAAATACTAAAATTAGGCGGGTGTGGTGGCGGGCAC 27060
27061 CTGTAGTCCCAGCTACTCAGGAGGCTGGGGCATGAGAATTGCTAGAACCTGGGAAGCAGA 27120
27121 GGTTGCAGTGAGCCAAGATTGTGCCACTGCACTCCAGCCTGGGTGACAGAGTGAGACTGT 27180
27181 GTCTCAAAAAAAAAAAAAAAGAAAGAAAATATTATCAAATAGGTTCATACTTTGGTGGGG 27240
27241 TTTTGGTTTGTTTTGACTAAAACCCTTCATTCTCTGTACTGTATTTGAACAATACCTATT 27300
27301 GATGGACATTTCTGGTGTTTTCAGTTTTTGAATTTCTACACAGTCCTGGAATGAACATTT 27360
27361 CATTTGTATGTCTCGCTAATTTTTATACTTTTTGTAGAGTGCTGGGATTACAGGCATTTG 27420
27421 TATGTCTTGTAATTTGTATGTCATCTTGCAATTGTGTACTATGTACCTTGGATGTACCTT 27480
27481 TTAAAGATCGTTGGTGGTGGGACACGTGTTTTTTGAGGAAGATGGTACTGAGGTCAGCAC 27540
27541 CCTGGCTGCCCTGAGAGTGCAGTGCCACGTTCCCCACCCTCTCGCCAACCACAGGATTAT 27600
27601 GCTGCAAATGTAAATCTTTACCAATTTGATAGGCAAAAATGGGATCTCAGCATTTTAGC 27660
27661 CTGCATCTCTGAGTACTAACGAGGCTGAACACGAAATGAGCTTATTTTCTTTTCAGAAGC 27720
27721 CCTGAATGTGACAGTGATCCGCAGGGGGAAAAACACCAGCTTAGACTTGTTCCAACAC 27780
27781 GCTGGGCAGGAAAAGGACTGCTGGGGTAAAGTATCTGTTTCTGTTCATTCTCACTGGGGC 27840
27841 ATCATTTGAGTGTTTGTTAAACATGAAGCTGGAGGGGAAGGCTGGGGAGACATTGGGGAA 27900
27901 TAATGGGAATCCCCAGTTTGCATGGAAACTGCAGATAAATCCTCGTGGTAGGAACGAGAC 27960
27961 TACAGCTCTAGAAGCAGAGGGAGCCCCAGAGTCTCTCCTGGGAGTCTCTCCAGTTCATTC 28020
28021 ATGCACTAGGCATTTGCTTTAAAAGAATGAAAGAACATTGGTGAAAAGGTCAGAAGGGCT 28080
28081 CAGCCTCTGACCTTCCTGAAGGGAGCCTCCAAACTTACGCCATTCCTTTTCTTCTTTCTT 28140
28141 CCAGCTGCAACATTATTCCTCTGCAAAGATGATTGTCCCTGGGGAACAGTAACAGGAAAG 28200
28201 CATCTTCCCTTGCCCTGGACTTGGGTCTAGGGATTTCCAACTTGTCTTCTCTCCCTGAAG 28260
28261 CATAAGGATCTGGAAGAGGCTTGTAACCTGAACTTCTGTGTGGTGGCAGTACTGTGGCCC 28320
28321 ACCAGTGTAATCTCCCTGGATTAAGGCATTCTTAAAAACTTAGGCTTGGCCTCTTTCACA 28380
28381 AATTAGGCCACGGCCCTAAATAGGAATTCCCTGGATTGTGGGCAAGTGGGCGGAAGTTAT 28440
28441 TCTGGCAGGTACTGGTGTGATTATTATTATTTTTAATAAAGAGTTTTACAGTGCTGA 28500
28501 TATGACCCTGTTGTCACCCCAGCTGAATTTCTTATGACCCTCCCAAACCAAAGCTCAGAT 28560
28561 GGGGTCAGAAGAGCTTCATAGAAAGTTGGGCAAAACAGGCTAGCAATTGCAAAGTCAGGC 28620
28621 TTTGACCAACATATTTCTTTGCACTGAGGCCTTGCTGCTGTGGATACGGAAATGGTTAAG 28680
28681 TACTGTGCTTCCTCAGCAGCTGGGCTGTCAGGGCCATAGTAGCTCCCTTTGGAGAACAGG 28740
28741 GAAAGCCTGGAGGCTTCCAGGTGGCCCAGCGTGGTGTCCTGTCAGCTTCCTCTTTAGGA 28800
28801 ACCCACCAGAGGGCAGCAAGCTCCTTTCACTTCGCTAGTAAGAACCCCTCCGTTTTTGTG 28860
28861 TGTTTTTGTTTTTGTTTTCTGGAGACAAGGTCTTGCTTTGTCACCCAGGCTGGAGTGCAG 28920
28921 TGTCGTGATCAAGGTTCACTGAAGCCTTGACGCTGTGGGCACTGCCTCAGCCGCCCAAGT 28980
28981 ATCTGGGACCACAGGCGTGCACCACCATGCATAGCTAATTTATTTTTTGTAGAGACAGGG 29040
29041 TCTCCCTGTGTTGACCAGGTTGGTCTCGAACTCCTGGGCTCAAGCAGTCCTCCTGCCTTG 29100
29101 GCCTCCTAAAGTGCTGGGATCACAGGCGTGAGCCACTGCGCCCAGCCCACTGCTAGTTTG 29160
```

Figure 27C-11

```
29161 ACTTTTTATAATTGAACCTCCTGGCTATGCCCTGAGATCAGCGCTATTTTGTAAACCGCT 29220
29221 GAGGTATGGATAGGAACGAGTAGATCAGACCTCTTGAAAATGCTTATTCTTCCTCCCTTT 29280
29281 TATTTTTTGTCTCTTTTAAGATGGTAAAATGGTTCTCAGGGATTCCTGCCAATACTTTGA 29340
29341 ATTATTTTTCCTCTCCATGGTATCAGTGTTCATTTCCCCAGTTCTTGCACACCGCTTTC 29400
29401 TGTTTTGGCAGTTCTGCCAGGCAAGCCCTGTGTTCCTTGGGACTGGTTTTGCTGTGGTTG 29460
29461 GATACAGATACCAGCTTGCCTTGATGGGATTGGTATTGCTGTGTGCTTCCAGCCACAGGT 29520
29521 TCTCACACTCAATTCCAAAGCCTTCCTATTGGGCGAATTCCCTCAAACTCTATTTGACCT 29580
29581 GACAGCCATACGTATTCCCCTCTGGTAGCCACAGACATGCTGTGTTTACCAATGTTTGCT 29640
29641 GTTTAAATTGCATGTTCTAATTCCACGTATCTTCCAGTCTCTTTTATAAAGTCTCAGACT 29700
29701 ATAATAAACACAGCTTGCCCAGTTTATCCTTTCTTTTTATTTTAAGATGTATGCATATT 29760
29761 AATCAATTTACCATCACTGGGGCATGGCAGTGTGGGCGGGGAGAATTATTCACATTCTCC 29820
29821 TAAAATGACAGCAGCAGAGAGCCTTCTGCCTCAGTGGCTCTGGCTGGTTTCCTGCAGGGG 29880
29881 TCCCAGTGGAAACCCGTGTGGCCACCTGTTGCCGTCTTCCATGAGATGTTAGTGGAGAGC 29940
29941 CACTTTGACGTGGAATGATCCTAATAGATATAGCCAGACCGGTTTTGCGGAAACGCTTTG 30000
30001 TGCTGAGAACCGCAAGCTGGTGCACCCTGTGTCATATCTGCCCCCAGCCAGCTGGAATTG 30060
30061 TCTGCAACACGCGGTGCCCGGTGAGGAGGCAGGCAGGACGGTTGTGTGCTGCATCCATGA 30120
30121 GACCTGGAAATTCAGTTTGCTTTTGGAAAAGAGCATTGTATCCGAGTTCATACTTCTCCA 30180
30181 CCCCATCTTGCCAAGGTTGCGGAAAGTAAAAATTGGCAGTATTGGCCGCTGCAGCTTCTT 30240
30241 AGGGGACGGGACCATGTGAAAAGGTGGGATCGTGCGAGCGGAGGAAGGACAGAAAAGCGA 30300
30301 GGAAAGTCTATGCCGCCAGCGACCG    (SEQ ID NO: 164)           30325
```

NGN-3

SEQUENCE LISTING

```
<160> NUMBER OF SEQ ID NOS: 164

<210> SEQ ID NO 1
<211> LENGTH: 1454
<212> TYPE: DNA
<213> ORGANISM: Rattus sp.
<220> FEATURE:
<221> NAME/KEY: CDS
```

<222> LOCATION: (495)..(1160)

<400> SEQUENCE: 1

| | |
|---|---:|
| gaattcgcgg cgcgtcgacc tcaagaggca gaggcacata gagaaaccct atcttgaaaa | 60 |
| acggggagg gagaaacagg ggcagaatga aaaagggagg aaggaagaaa ggaaggaatg | 120 |
| agaaagaaaa gtggaaataa gtcacgtata aaacgagagt taaagcctac gtcatggggt | 180 |
| tggggattta gctcagtggt agagcgcttg cctagcaagc gcaggccct gggttcggtc | 240 |
| cccagctccg gaaaaaaaaa aaaaaagaa aaaaaaaaa gcctacgtca tcctgtctcc | 300 |
| acttagctct gccgggtcat ctgaaaacca cgtggtctat ttagctggag tttccggtga | 360 |
| cctcgcccca ccttcaaact cagtacttgt gcattggctg aagtattttg tcccttggga | 420 |
| ggacccgtag ctccagcctc ccggtgtccg tagccgggaa acctggcgtc cggcgtttta | 480 |
| ggctgaggtc cgcg atg tcg agt gag gaa gtc cgg cac cgg gca gag tcc | 530 |
|                Met Ser Ser Glu Glu Val Arg His Arg Ala Glu Ser | |
|                 1              5                  10 | |
| tct gag gcc cgt gcg gcc gcg gtc agc gac atc cag gag ctg atg cga | 578 |
| Ser Glu Ala Arg Ala Ala Ala Val Ser Asp Ile Gln Glu Leu Met Arg | |
|      15                      20                   25 | |
| cgc aag gag gaa atc gag gcg cag atc aag gct aat tac gac gtc ctc | 626 |
| Arg Lys Glu Glu Ile Glu Ala Gln Ile Lys Ala Asn Tyr Asp Val Leu | |
|  30                   35                   40 | |
| gag agc caa aaa gga att ggc atg aac gag cct cta gtg gac tgc gag | 674 |
| Glu Ser Gln Lys Gly Ile Gly Met Asn Glu Pro Leu Val Asp Cys Glu | |
| 45                    50                   55                  60 | |
| ggc tac ccc cgg gca gat gtg gat ttg tat cag gtc cga aca gca agg | 722 |
| Gly Tyr Pro Arg Ala Asp Val Asp Leu Tyr Gln Val Arg Thr Ala Arg | |
|                65                   70                   75 | |
| cac aac atc atc tgt ctc cag aat gat cac aag gca ctg atg aag cag | 770 |
| His Asn Ile Ile Cys Leu Gln Asn Asp His Lys Ala Leu Met Lys Gln | |
|                   80                   85                  90 | |
| gtg gag gag gcc cta cac cag cta cat gct cgg gac aaa gag aag cag | 818 |
| Val Glu Glu Ala Leu His Gln Leu His Ala Arg Asp Lys Glu Lys Gln | |
|      95                   100                 105 | |
| gct cgg gac atg gct gaa gcc cga gaa gag gcc atg aac cgt agg ctg | 866 |
| Ala Arg Asp Met Ala Glu Ala Arg Glu Glu Ala Met Asn Arg Arg Leu | |
| 110                  115                 120 | |
| gcc tcg gac agt ccc gcc cta ccc aag gcc ttt gcc aga gtg aac agt | 914 |
| Ala Ser Asp Ser Pro Ala Leu Pro Lys Ala Phe Ala Arg Val Asn Ser | |
| 125                  130                 135                 140 | |
| atc agc cct ggt tcc cca gcc agt att gcg ggc ctg caa gtg gat gat | 962 |
| Ile Ser Pro Gly Ser Pro Ala Ser Ile Ala Gly Leu Gln Val Asp Asp | |
|                   145                 150                 155 | |
| gaa att gtg gag ttc ggc tct gtg aac acc caa aac ttc cag tct ctg | 1010 |
| Glu Ile Val Glu Phe Gly Ser Val Asn Thr Gln Asn Phe Gln Ser Leu | |
|                      160                 165                 170 | |
| cag aac gtg ggc act gtg gtg cag cac agc gag ggg aag ccc ctg aat | 1058 |
| Gln Asn Val Gly Thr Val Val Gln His Ser Glu Gly Lys Pro Leu Asn | |
|                   175                 180                 185 | |
| gtc atg gtg atc cgc aga ggg gag aag cac cag ctc aga ctg act ccc | 1106 |
| Val Met Val Ile Arg Arg Gly Glu Lys His Gln Leu Arg Leu Thr Pro | |
|                190                 195                 200 | |
| acc cgc tgg gca gga aaa gga ctg ctg ggc tgc aat att acc cct ctc | 1154 |
| Thr Arg Trp Ala Gly Lys Gly Leu Leu Gly Cys Asn Ile Thr Pro Leu | |
| 205                  210                 215                 220 | |
| caa aga tgactgcttc ctgggagctg caggagagct tcttcagctg ggcccgcgct | 1210 |
| Gln Arg | |

-continued

```
tggcctgggg gatttcctca ttctctcggc tccctcaagt gtaaggatct ggaagagagt    1270
ggcggacgcc tgagcgtcga ggtggaagag acgctttggc tgcctgatgt agtctctggg    1330
ttgaggcatt attaaaaatg tggtttgtgc ttaaaaaaaa aaaaaaaaaa aaaaaaaaaa    1390
aaaaaaaaaa aaaaaaaaaa aaaaaaaaaa aaaaaaaaaa aaaaaaaaaa aaaaaaaagt    1450
cgac                                                                 1454
```

<210> SEQ ID NO 2
<211> LENGTH: 222
<212> TYPE: PRT
<213> ORGANISM: Rattus sp.

<400> SEQUENCE: 2

```
Met Ser Ser Glu Glu Val Arg His Arg Ala Glu Ser Ser Glu Ala Arg
  1               5                  10                  15

Ala Ala Ala Val Ser Asp Ile Gln Glu Leu Met Arg Arg Lys Glu Glu
                 20                  25                  30

Ile Glu Ala Gln Ile Lys Ala Asn Tyr Asp Val Leu Glu Ser Gln Lys
             35                  40                  45

Gly Ile Gly Met Asn Glu Pro Leu Val Asp Cys Glu Gly Tyr Pro Arg
         50                  55                  60

Ala Asp Val Asp Leu Tyr Gln Val Arg Thr Ala Arg His Asn Ile Ile
 65                  70                  75                  80

Cys Leu Gln Asn Asp His Lys Ala Leu Met Lys Gln Val Glu Glu Ala
                     85                  90                  95

Leu His Gln Leu His Ala Arg Asp Lys Glu Lys Gln Ala Arg Asp Met
                100                 105                 110

Ala Glu Ala Arg Glu Glu Ala Met Asn Arg Arg Leu Ala Ser Asp Ser
            115                 120                 125

Pro Ala Leu Pro Lys Ala Phe Ala Arg Val Asn Ser Ile Ser Pro Gly
        130                 135                 140

Ser Pro Ala Ser Ile Ala Gly Leu Gln Val Asp Asp Glu Ile Val Glu
145                 150                 155                 160

Phe Gly Ser Val Asn Thr Gln Asn Phe Gln Ser Leu Gln Asn Val Gly
                165                 170                 175

Thr Val Val Gln His Ser Glu Gly Lys Pro Leu Asn Val Met Val Ile
            180                 185                 190

Arg Arg Gly Glu Lys His Gln Leu Arg Leu Thr Pro Thr Arg Trp Ala
        195                 200                 205

Gly Lys Gly Leu Leu Gly Cys Asn Ile Thr Pro Leu Gln Arg
    210                 215                 220
```

<210> SEQ ID NO 3

<400> SEQUENCE: 3

000

<210> SEQ ID NO 4

<400> SEQUENCE: 4

000

<210> SEQ ID NO 5

<400> SEQUENCE: 5

000

<210> SEQ ID NO 6
<400> SEQUENCE: 6
000

<210> SEQ ID NO 7
<400> SEQUENCE: 7
000

<210> SEQ ID NO 8
<400> SEQUENCE: 8
000

<210> SEQ ID NO 9
<400> SEQUENCE: 9
000

<210> SEQ ID NO 10
<400> SEQUENCE: 10
000

<210> SEQ ID NO 11
<400> SEQUENCE: 11
000

<210> SEQ ID NO 12
<400> SEQUENCE: 12
000

<210> SEQ ID NO 13
<400> SEQUENCE: 13
000

<210> SEQ ID NO 14
<400> SEQUENCE: 14
000

<210> SEQ ID NO 15
<400> SEQUENCE: 15
000

<210> SEQ ID NO 16
<400> SEQUENCE: 16
000

-continued

<210> SEQ ID NO 17
<400> SEQUENCE: 17
000

<210> SEQ ID NO 18
<400> SEQUENCE: 18
000

<210> SEQ ID NO 19
<400> SEQUENCE: 19
000

<210> SEQ ID NO 20
<400> SEQUENCE: 20
000

<210> SEQ ID NO 21
<400> SEQUENCE: 21
000

<210> SEQ ID NO 22
<400> SEQUENCE: 22
000

<210> SEQ ID NO 23
<400> SEQUENCE: 23
000

<210> SEQ ID NO 24
<400> SEQUENCE: 24
000

<210> SEQ ID NO 25
<400> SEQUENCE: 25
000

<210> SEQ ID NO 26
<400> SEQUENCE: 26
000

<210> SEQ ID NO 27
<400> SEQUENCE: 27
000

<210> SEQ ID NO 28

<400> SEQUENCE: 28

000

<210> SEQ ID NO 29
<211> LENGTH: 495
<212> TYPE: DNA
<213> ORGANISM: Rattus sp.

<400> SEQUENCE: 29

| cagctacatg | ctcgggacaa | agagaagcag | gctcgggaca | tggctgaagc | ccgagaagag | 60 |
| gccatgaacc | gtaggctggc | ctcggacagt | cccgccctac | ccaaggcctt | tgccagagtg | 120 |
| aacagtatca | gccctggttc | cccagccagt | attgcgggcc | tgcaagtgga | tgatgaaatt | 180 |
| gtggagttcg | gctctgtgaa | cacccaaaac | ttccagtctc | tgcagaacgt | gggctctgtg | 240 |
| gtgcagcaca | gcgaggggaa | gcccctgaat | gtcatggtga | tccgcagagg | ggagaagcac | 300 |
| cagctcagac | tgactcccac | ccgctgggca | ggaaaaggac | tgctgggctg | caatattacc | 360 |
| cctctccaaa | gatgactgct | tcctgggagc | tgcaggagag | cttcttcagc | tgggcccgcg | 420 |
| cttggcctgg | gggatttcct | cattctctcg | gctccctcaa | gtgtaaggat | ctggaagaga | 480 |
| gtggcggacg | cctga | | | | | 495 |

<210> SEQ ID NO 30
<211> LENGTH: 574
<212> TYPE: DNA
<213> ORGANISM: Rattus sp.

<400> SEQUENCE: 30

| aagcacaaac | cacatttta | ataatgcctc | aacccagaga | ctacatcagg | cagccaaagc | 60 |
| gtctcttcca | cctcgacgct | caggcgtccg | ccactctctt | ccagatcctt | acacttgagg | 120 |
| gagccgagag | aatgaggaaa | tcccccaggc | caagcgcggg | cccagctgaa | gaagctctcc | 180 |
| tgcagctccc | aggaagcagt | catctttgga | gagggtaat | attgcagccc | agcagtcctt | 240 |
| ttcctgccca | gcgggtggga | gtcagtctga | gctggtgctt | ctcccctctg | cggatcacca | 300 |
| tgacattcag | gggcttcccc | tcgctgtgct | gcaccacaga | gcccacgttc | tgcagagact | 360 |
| ggaagttttg | ggtgttcaca | gagccgaact | ccacaatttc | atcatccact | tgcaggcccg | 420 |
| caatactggc | tggggaacca | gggctgatac | tgttcactct | ggcaaaggcc | ttgggtaggg | 480 |
| cgggactgtc | cgaggccagc | ctacggttca | tggcctcttc | tcgggcttca | gccatgtccc | 540 |
| gagcctgctt | ctctttgtcc | cgagcatgta | gctg | | | 574 |

<210> SEQ ID NO 31
<211> LENGTH: 469
<212> TYPE: DNA
<213> ORGANISM: Rattus norvegicus

<400> SEQUENCE: 31

| cggccgcggt | cagcgacatc | caggagctga | tgcgacgcaa | ggaggaaatc | gaggcgcaga | 60 |
| tcaaggctaa | ttacgacgtc | ctcgagagcc | aaaaaggaat | tggcatgaac | gagcctctag | 120 |
| tggactgcga | gggctacccc | cgggcagatg | tggatttgta | tcaggtccga | acagcaaggc | 180 |
| acaacatcat | ctgtctccag | aatgatcaca | aggcactgat | gaagcaggtg | gaggaggccc | 240 |
| tacaccagct | acatgctcgg | gacaaagaga | agcaggctcg | ggacatggct | gaagcccgag | 300 |
| aagaggccat | gaaccgtagg | ctggcctcgg | acagtcccgc | cctacccaag | gcctttgcca | 360 |

```
gagtgaacag tatcagccct ggttccccag ccagtattgc gggcctgcaa gtggatgatg    420
aaattgtgga gttcggctct gtgaacaccc aaaacttcca gtctctgca               469
```

<210> SEQ ID NO 32
<211> LENGTH: 332
<212> TYPE: DNA
<213> ORGANISM: Rattus sp.

<400> SEQUENCE: 32

```
aagcacaaac cacattttta ataatgcctc aacccagaga ctacatcagg cagccaaagc    60
gtctcttcca cctcgacgct caggcgtccg ccactctctt ccagatcctt acacttgagg   120
gagccgagag aatgaggaaa tcccccaggc caagcgcggg cccagctgaa gaagctctcc   180
tgcagctccc aggaagcagt catctttgga gaggggtaat attgcagccc agcagtcctt   240
ttcctgccca gcgggtggga gtcagtctga gctggtgctt ctcccctctg cggatcacca   300
tgacattcag gggcttcccc tcgctgtgct gc                                 332
```

<210> SEQ ID NO 33
<211> LENGTH: 534
<212> TYPE: DNA
<213> ORGANISM: Rattus sp.

<400> SEQUENCE: 33

```
ttatagaggc tggaaaatac ttggacttct agcctacaac gggaacagca aacacaagta    60
aacatagcaa gtctggctac aagagaggga tgcgtgnggc tgtctggatg aagcagcctg   120
ggggaggctt tcaagtccag tgtgaatagt caaagcagga agcacgcatc agtactgact   180
gccatcagag aaagctggtc tctgcctcca tcctgagcaa atccaatcca aggacacaag   240
cttccttgta gaaagtgcca gacatccaaa acagaaacgg gtggcaactg gggaatgaac   300
ttgagggagc cgagagaatg aggaaatccc ccaggccaag cgcgggccca gctgaagaag   360
ctctcctgca gctcccagga agcagtcatc tttggagagg ggtaatattg cagcccagca   420
gtccttttcc tgcccagcgg gtgggagtca gtctgagctg gtgcttctcc cctctgcgga   480
tcaccatgac attcaggggc ttccccctcg ctgtgctgca cacagcctcg tgcc         534
```

<210> SEQ ID NO 34
<211> LENGTH: 249
<212> TYPE: DNA
<213> ORGANISM: Rattus sp.

<400> SEQUENCE: 34

```
aagcacaaac cacattttta ataatgcctc aacccagaga ctacatcagg cagccaaagc    60
gtctcttcca cctcgacgct caggcgtccg ccactctctt ccagatcctt acacttgagg   120
gagccgagag aatgaggaaa tcccccaggc caagcgcggg cccagctgaa gaagctctcc   180
tgcagctccc aggaagcagt catctttgga gagggtaat attgcatccc aacagacctt    240
ttcctgccc                                                          249
```

<210> SEQ ID NO 35
<211> LENGTH: 277
<212> TYPE: DNA
<213> ORGANISM: Rattus sp.

<400> SEQUENCE: 35

```
gaggctggaa aatacttgga cttctagcct acaacgggaa cagcaaacac aagtaaacat    60
agcaagtctg gctacaagag agggatgcgt ggggctgtat ggatgaagca ccctgggga   120
```

```
ggctttcaag tccagtgtga atagtcaaag caggaagcac gcatcagtac tgactgccat      180
cagagaaagc tggtctctgc ctccatcctg agcaaatcca atccaaggac acaagcttcc      240
ttgtagaaag tgccagacat ccaaaacaga aacgggt                               277

<210> SEQ ID NO 36
<211> LENGTH: 337
<212> TYPE: DNA
<213> ORGANISM: Rattus norvegicus

<400> SEQUENCE: 36
tttttttttt ggatgtctgg cactttctac aaggaagctt gtgtccttgg attggatttg       60
ctcaggatgg aggcagagac cagctttctc tgatggcagt cagtactgat gcgtgcttcc      120
tgctttgact attcacactg gacttgaaag cctcccccag gctgcttcat ccagacagcc      180
ccacgcatcc ctctcttgta gccagacttg ctatgtttac ttgtgtttgc tgttcccgtt      240
gtaggctaga agtccaagta ttttccagcc tctataataa aacgcagctt gtaccaacaa      300
aaaaaaaaaa aaaaaaccct tgcggccct cgtgccg                                337

<210> SEQ ID NO 37
<211> LENGTH: 304
<212> TYPE: DNA
<213> ORGANISM: Rattus norvegicus

<400> SEQUENCE: 37
cggccgcggt cagcgacatc caggagctga tgcgacgcaa ggaggaaatc gaggcgcaga       60
tcaaggctaa ttacgacgtc ctcgagagcc aaaaaggaat tggcatgaac gagcctctag      120
tggactgcga gggctacccc cgggcagatg tggatttgta tcaggtccga acagcaaggc      180
acaacatcat ctgtctccag aatgatcaca aggcactgat gaagcaggtg gaggaggccc      240
tacaccagct acatgctcgg gacaaagaga agcaggctcg ggacatggct gaagcccgag      300
aaga                                                                   304

<210> SEQ ID NO 38
<211> LENGTH: 211
<212> TYPE: DNA
<213> ORGANISM: Rattus norvegicus

<400> SEQUENCE: 38
cggccgcggt cagcgacatc caggagctga tgcgacgcaa ggaggaaatc gaggcgcaga       60
tcaaggctaa ttacgacgtc ctcgagagcc aaaaaggaat tggcatgaac gagcctctag      120
tggactgcga gggctacccc cgggcagatg tggatttgta tcaggtccga acaagcaagg      180
cacaacatca tctgtctcca gaatgatcac a                                     211

<210> SEQ ID NO 39
<211> LENGTH: 433
<212> TYPE: DNA
<213> ORGANISM: Mus musculus

<400> SEQUENCE: 39
aattcggcac tagggccgcg gaatttttt tttttttttt tttttttttt cttagtaggt       60
tatttattta aaagaaaaa aaacaaaaga gggcaagaac ctgggaagtg ggtacgaggg      120
gaggtctgag agggacttga gatgacagga aatatagaaa tgtactatgt gcatgtacga      180
aattctcaaa aataagtata aattatatat gtataataca tattcctcag agtctagcca      240
```

```
gccatgtcag tatatgcctc tcatcccaat actaatgagg cagaggcagg gggatctctg      300
tcagctcaag gccagcctgg tctacacagg gaattccagg atagtcagga ttacacactg      360
agtccgtctc caaaaggaaa atgacatcaa atcattactc gccagagtca tccccactca      420
ctggctcata atc                                                         433

<210> SEQ ID NO 40
<211> LENGTH: 460
<212> TYPE: DNA
<213> ORGANISM: Mus musculus

<400> SEQUENCE: 40
cacttagtag gttatttatt taaaaagaaa aaaacaaaa gagggcaaga acctgggaag        60
tgggtacgag gggaggtctg agagggactt gagatgacag gaaatataga aatgtactat     120
gtgcatgtac gaaattctca aaaataagta taaattatat atgtataata catattcctc     180
agagtctagc cagccatgtc agtatatgcc tctcatccca atactaatga ggcagaggca     240
gggggatctc tgtcagctca aggccagcct ggtctacaca gggaattcca ggatagtcag     300
gattacacac tgagtccgtc tccaaaagga aatgacatc aaatcattac tcgccagagt     360
catccccact cactggctca atctagag aattcccaga caggctatgg cctaatttgc     420
acaagacgta gctaggcaca atcacactt ttaataatgc                            460

<210> SEQ ID NO 41
<211> LENGTH: 389
<212> TYPE: DNA
<213> ORGANISM: Mus musculus

<400> SEQUENCE: 41 tttttttggca cttagtaggt tatttattta aaagaaaaa aacaaaaga gggcaagaac       60 ctggaagtg ggtacgaggg gaggtctgag agggacttga gatgacagga aatatagaaa     120
tgtactatgt gcatgtacga aattctcaaa ataagtata aattatatat gtataataca     180
tattcctcag agtctagcca gccatgtcag tatatgcctc tcatcccaat actaatgagg     240
cagaggcagg gggatctctg tcagctcaag gccagcctgg tctacacagg gaattccagg     300
atagtcagga ttacacactg agtccgtctc caaaaggaaa atgacatcaa atcattactc     360
gccagagtca tccccactca ctggctcat                                       389

<210> SEQ ID NO 42
<211> LENGTH: 312
<212> TYPE: DNA
<213> ORGANISM: Mus musculus

<400> SEQUENCE: 42
ggtgtaatcc tgaatatctt ggaattccct gtgtagacca ggctggcctt gagctgacag       60
aaatccccct gcctttgcct cattagtatt gggatgagag gcatatactg acatggctgg     120
ctagattctg aggaatatgt attatacata tataatttat acttattttt gagaatttcg     180
tacatgcaca tagtacattt ctatatttcc tgtcatttca agtcccttc agacctcccc       240 tcgtacccac ttcccaggtt cttgccctct tttgttttt tctttttaa ataaataacc       300 tactaagtgc ct                                                          312

<210> SEQ ID NO 43
<211> LENGTH: 323
<212> TYPE: DNA
<213> ORGANISM: Mus musculus
```

<400> SEQUENCE: 43

| taaaaagaaa aaaaacaaaa gagggcaaga acctgggaag tgggtacgag gggaggtctg | 60 |
| agagggactt gagatgacag gaaatataga aatgtactat gtgcatgtac gaaattctca | 120 |
| aaaataagta taaattatat atgtataata catattcctc agagtctagc cagccatgtc | 180 |
| agtatatgcc tctcatccca atactaatga ggcagaggca gggggatctc tgtcagctca | 240 |
| aggccagcct ggtctacaca gggaattcca ggatagtcag gattacacac tgagtccgtc | 300 |
| tccaaaagga aaatgacatc aaa | 323 |

<210> SEQ ID NO 44
<211> LENGTH: 374
<212> TYPE: DNA
<213> ORGANISM: Mus musculus

<400> SEQUENCE: 44

| taaaaagaaa aaaacaaaa gagggcaaga acctgggaag tgggtacgag gggaggtctg | 60 |
| agagggactt gagatgacag gaaatataga aatgtactat gtgcatgtac gaaattctca | 120 |
| aaaataagta taaattatat atgtataata catattcctc agagtctagc cagccatgtc | 180 |
| agtatatgcc tctcatccca atactaatga ggcagaggca gggggatctc tgtcagctca | 240 |
| aggccagcct ggtctacaca gggaattcca ggatagtcag gattacacac tgagtccgtc | 300 |
| tccaaaagga aaatgacatc aaatcattac tcgccagagt catccccact cactggctca | 360 |
| taatctagag aatt | 374 |

<210> SEQ ID NO 45
<211> LENGTH: 404
<212> TYPE: DNA
<213> ORGANISM: Mus musculus

<400> SEQUENCE: 45

| gcctgtctgg gaattctcta gattatgagc cagtgagtgg ggatgactct ggcgagtaat | 60 |
| gatttgatgt cattttcctt ttggagacgg actcagtgtg taatcctgac tatcctggaa | 120 |
| ttccctgtgt agaccaggct ggccttgagc tgacagagat cccctgcct ctgcctcatt | 180 |
| agtattggga tgagaggcat atactgacat ggctggctag actctgagga atatgtatta | 240 |
| tacatatata atttatactt attttgaga atttcgtaca tgcacatagt acatttctat | 300 |
| atttcctgtc atctcaagtc cctctcagac ctcccctcgt acccacttcc caggttcttg | 360 |
| ccctcttttg ttttttttct ttttaaataa ataacctact aagt | 404 |

<210> SEQ ID NO 46
<211> LENGTH: 442
<212> TYPE: DNA
<213> ORGANISM: Mus musculus

<400> SEQUENCE: 46

| cttagtaggt tatttattta aaagaaaaaa aaacaaaaga gggcaagaac ctgggaagtg | 60 |
| ggtacgaggg gaggtctgag agggacttga gatgacagga aatatagaaa tgtactatgt | 120 |
| gcatgtacga aattctcaaa aataagtata aattatatat gtaataca tattcctcag | 180 |
| agtctagcca gccatgtcag tatatgcctc tcatcccaat actaatgagg cagaggcagg | 240 |
| gggatctctg tcagctcaag gccagcctgg tctacacagg gaattccagg atagtcagga | 300 |
| ttacacactg agtccgtctc caaaaggaaa atgacatcaa atcattactc gccagaggca | 360 |

```
tccccactca ctggctcata atctagagaa ttcccagaca ggctatggcc taatttgcac    420
aagacgtagc taggcacaaa tc                                             442
```

<210> SEQ ID NO 47
<211> LENGTH: 263
<212> TYPE: DNA
<213> ORGANISM: Mus musculus

<400> SEQUENCE: 47

```
attcggatcc ttcgcctcat tagtattggg atgagaggca tatactgaca tggctggcta     60
gactctgagg aatatgtatt atacatatat aatttatact tattttttgag aatttcgtac   120 atgcacatag tacatttcta tatttcctgt catctcaagt ccctctcaga cctcccgctc   180
gtacccactt cctcaggttc ttgccctctt ttgtttttt tcttttttaaa taaataaacct   240 actaagtgag aaacaaaaag aaa                                            263
```

<210> SEQ ID NO 48
<211> LENGTH: 497
<212> TYPE: DNA
<213> ORGANISM: Mus musculus
<220> FEATURE:
<221> NAME/KEY: misc_feature
<222> LOCATION: (360)..(360)
<223> OTHER INFORMATION: n can be any nucleotide

<400> SEQUENCE: 48

```
cgaggggaag ccctgaatgt gacggtgatc cgcagaggag agaagcacca gctcagactg     60
attccaaccc gctggcagga aaaggactgc tgggctgcaa cattattcct ctccagagat   120
gactgtttcc tgggatctgc ctgcaggaag ctgcctcagc tggccccgtg cttgggcctg   180
gaggcgtttc ctcgttctct aggctccctt aagtgtaagg atctggagaa gaatggtcga   240
agcctgggca tcgaggtgga agagacgctt tggctgcctg atgtaatctc tctgggttga   300
ggcattatta aaagtgtgat ttgtgcctag ctacgtcttg tgcaaattag gccatagctn   360
gtctgggaat tctctagatt atgagccagt gagtggggat gactctggcg agtaatgatt   420
tgatgtcata ttccttttgg agacggactc agtgtgtaat cctgactatc ctggaattcc   480
ctgtgtagac caggctg                                                  497
```

<210> SEQ ID NO 49
<211> LENGTH: 301
<212> TYPE: DNA
<213> ORGANISM: Mus musculus

<400> SEQUENCE: 49

```
tgattatcct ggaattccct gtgtagacca ggctggcctt gagctgacag agatccccct     60
gcctctgcct cattagtatt gggatgagag gcatatactg acatggctgg ctagactttg   120
aggaatatgt attatacata taaatttat acttatttt gagaatttcg tacatgcaca    180
tagtacattt ctatatttcc tgtcatctca agtccctctc agacctccct tcgtacccac   240
ttcccaggtt cttgccctct tttgttttt ttcttttaa ataaataacc tactaagtgc   300
c                                                                    301
```

<210> SEQ ID NO 50
<211> LENGTH: 451
<212> TYPE: DNA
<213> ORGANISM: Mus musculus

<400> SEQUENCE: 50

```
acagccccgt cctgccccag gccttttgcca gagtgaacag tatcagcccc ggttccccag      60
ccagtattgc gggcctgcaa gtggatgacg aaattgtgga gttcggctcc gtgaacaccc     120
aaaacttcca gtcagtgcag aacgtgggca ctgtggtcag catagcgagg ggaagcccct     180
gaatgtgacg gtgatccgca gaggagagaa gcaccagctc agactgattc caacccgctg     240
ggcaggaaaa ggactgctgg gctgcaacat tattcctctc cagagatgac tgtttcctgg     300
gatctgcctg caggaagctg cctcagctgg ccccgtgctt gggcctggag gcgtttcctc     360
gttctctagg ctcccttaag tgtaaggatc tggagaagaa tggtcgaagc ctgggcatcg     420
aggtggaaga gacgctttgg ctgcctgatg t                                    451

<210> SEQ ID NO 51
<211> LENGTH: 497
<212> TYPE: DNA
<213> ORGANISM: Mus musculus

<400> SEQUENCE: 51
cttcagaagc ccctgaatgt gacggtgatc cgcagaggag agaagcacca gctcagactg      60
attccaaccc gctggcagga aaaggactgc tgggctgcaa cattattcct ctccagagat     120
gactgtttcc tgggatctgc ctgcaggaag ctgcctcagc tggccccgtg cttgggcctg     180
gagggtttcc tcgttctcta ggctccctta agtgtaagga tctggagaag aatggtcgaa     240
gcctgggcat cgaggtggaa gagacgcttt ggctgcctga tgtaatctct ctgggttgag     300
gcattattaa aagtgtgatt tgtgcctagc tacgtcttgt gcaaattagg ccatagcctg     360
tctgggaatt ctctagatta tgagccagtg agtagggatg actctggcga gtaatgattt     420
gatgtcattt tccttttgga gacggactca gtgtgtaatc ctgactatcc tggaattccc     480
tgtgtagacc aggctgg                                                    497

<210> SEQ ID NO 52
<211> LENGTH: 437
<212> TYPE: DNA
<213> ORGANISM: Mus musculus

<400> SEQUENCE: 52
gcttagtatt tcttttgcaa acagctctta acttattcgg atatttatta aattatgagt      60
tattaagttg gaagactacg gtgagtaata aattaatgtc attttcctat tggagacgga     120
ctcagtgagt aatcctgact atcctggaat tccctgcgta gaccaggctg gccttgagtt     180
gacagagatc cccctgcctc tgcctcgatt agtattggga tgagaggcat atactgacat     240
ggctggctag actctgagga atatgtatta tacatatata atttatactt atttttgaga     300
atttcgtaca tgcacatagt acatttctat atttcctgtc atctcaagtc cctctcagac     360
ctcccctcgt acccacttcc caggttcttg ccctcttttg ttttttttct ttttaaataa     420
ataacctact aagtgcc                                                    437

<210> SEQ ID NO 53
<211> LENGTH: 425
<212> TYPE: DNA
<213> ORGANISM: Mus musculus

<400> SEQUENCE: 53
aacacccaaa acttccagtc agtgcagaac gtgggcactg tggtgagcat agcgagggga      60
agcccctgaa tgtgacggtg atccgcagag gagagaagca ccagctcaga ctgattccaa     120
```

| | |
|---|---|
| cccgctgggc aggaaaagga ctgctgggct gcaacattat tcctctccag agatgactgt | 180 |
| ttcctgggat ccgcctgcag gaagctgcct cagctggccc cgtgcttggg cctggaggcg | 240 |
| tttcctcgtt ctctaggctc ccttaagtgt aaggatctgg agaagaatgg tcgaagcctg | 300 |
| ggcatcgagg tggaagagac gctttggctg cctgatgtaa tctctctggg ttgaggcatt | 360 |
| attaaaagtg tgatttgtgc ctaaaaaaaa aaaaaaaaa aaaaaaaaaa aaaaaaaaaa | 420 |
| aaaaa | 425 |

<210> SEQ ID NO 54
<211> LENGTH: 414
<212> TYPE: DNA
<213> ORGANISM: Mus musculus

<400> SEQUENCE: 54

| | |
|---|---|
| tttttttttt tttttttttt tttttttttt ttttaggca caaatcacac ttttaataat | 60 |
| gcctcaaccc agagagatta catcaggcag ccaaagcgtc tcttccacct cgatgcccag | 120 |
| gcttcgacca ttcttctcca gatccttaca cttaagggag cctagagaac gaggaaacgc | 180 |
| ctccaggccc aagcacgggg ccagctgagg cagcttcctg caggcagatc ccaggaaaca | 240 |
| gtcatctctg gagaggaata atgttgcagc ccagcagtcc ttttcctgcc cagcgggttg | 300 |
| gaatcagtct gagctggtgc ttctctcctc tgcggatcac cgtcacattc aggggcttcc | 360 |
| ctcgctatgc tgcaccacag tgccacgttc tgcactgact ggaagttttg ggtg | 414 |

<210> SEQ ID NO 55
<211> LENGTH: 264
<212> TYPE: DNA
<213> ORGANISM: Mus musculus

<400> SEQUENCE: 55

| | |
|---|---|
| ggcacttggg aggttattta tttaaaaaga aaaaaacaa aagagggcaa gaacctggga | 60 |
| agtgggtacg aggggaggtc tgagagggac ttgagatgac aggaaatata gaaatgtact | 120 |
| atgtgcatgt acgaaattct caaaaataag tataaattat atatgtataa tacatattcc | 180 |
| tcagagtcta gccagccatg tcagtatatg cctctcatcc aatactaat gaggcagagg | 240 |
| caggggggat ctctgtcagc tcaa | 264 |

<210> SEQ ID NO 56
<211> LENGTH: 234
<212> TYPE: DNA
<213> ORGANISM: Mus musculus

<400> SEQUENCE: 56

| | |
|---|---|
| cccattaagt attgggatga gaggcatata ctgaaatggc tggctagact ctgaggaata | 60 |
| tgtattatac atatataatt tatacttatt tttgagaatt tcgtacatgc acatagtaca | 120 |
| tttctatatt tcctttcttc tcaagtccct ctcagacctc ccctcgtacc cacttcccag | 180 |
| gttttttgccc tcttttgttt ttttttctttt taaataaata acctactaag tgcc | 234 |

<210> SEQ ID NO 57
<211> LENGTH: 315
<212> TYPE: DNA
<213> ORGANISM: Mus musculus

<400> SEQUENCE: 57

| | |
|---|---|
| tttttttttt ttttggagac ggactcagtg tgtaatcctg actatcctgg aattccctgt | 60 |
| gtagaccagg ctggccttga gctgacagag atcccctgc ctctgcctca ttagtattgg | 120 |

```
gatgagaggc atatactgac atggctggct agactctgag gaatatgtat tatacatata    180
taatttatac ttatttttga gaatttcgta catgcacata gtacatttct atatttcctg    240
tcatctcaag tccctctcag acctcccctc gtatccactt cccaggttct tgccctcttt    300 tgttttttt cttt                                                        315

<210> SEQ ID NO 58
<211> LENGTH: 430
<212> TYPE: DNA
<213> ORGANISM: Mus musculus

<400> SEQUENCE: 58
gcggaaattt ttttttttt tttaggcaca aatcacactt ttaataatgc                  60
ctcaacccag agagattaca tcaggcagcc aaagcgtctc ttccacctcg atgcccaggc    120
ttcgaccatt cttctccaga tccttacact taagggagcc tagagaacga ggaaacgcct    180
ccaggcccaa gcacggggcc agctgaggca gcttcctgca ggcagatccc aggaaacagt    240
catctctgga gaggaataat gttgcagccc agcagtcctt ttcctgccca gcggttgga     300 atcagtctga gctggtgctt ctctcctctg cggatcaccg tcacattcag gggcccctcg    360
ctatgctgca ccacagtgcc cacgttctgc actgactgga agttttgggt gttcacggag    420
ccgaactcca                                                            430

<210> SEQ ID NO 59
<211> LENGTH: 286
<212> TYPE: DNA
<213> ORGANISM: Mus musculus

<400> SEQUENCE: 59
ctggaatttc ctgtgtagac caggctggcc ttgagctgac agagatcccc ctgcctttgc     60
ctcattagta tttgggatgag aggcatatac tgacatggct ggttagactt tgaggaatat   120
gtattataca tataatttt atacttattt ttgagaattt tgtacatgca catagtacat    180
ttctatattt cctgtcattt caagtccctt tcagacctcc ccttgtaccc acttcccagg    240
ttcttgccct cttttgtttt ttttcttttt aaataaataa cctact                   286

<210> SEQ ID NO 60
<211> LENGTH: 320
<212> TYPE: DNA
<213> ORGANISM: Mus musculus

<400> SEQUENCE: 60
ctgaatgtga cggtgatccg cagaggagag aagcaccagc tcagactgat tccaacccgc     60
tgggcaggaa aaggactgct gggctgcaac attattcctc tccagagatg actgtttcct   120
gggatctgcc tgcaggaagc tgcctcagct ggccccgtgc ttgggcctgg aggcgtttcc   180
tcgttctcta ggctccctta agtgtaagga tctgagaag aatggtcgaa gcctgggcat    240
cgaggtggaa gagacgcttt ggctgcctga tgtaatctct ctgggttgag gcattattaa    300
aagtgtgatt tgtgcctagc                                                320

<210> SEQ ID NO 61
<211> LENGTH: 424
<212> TYPE: DNA
<213> ORGANISM: Mus musculus
<220> FEATURE:
<221> NAME/KEY: misc_feature
<222> LOCATION: (7)..(7)
```

<223> OTHER INFORMATION: n can be any nucleotide

<400> SEQUENCE: 61

```
cagaggnctc cgtgaaaacc caaaacttcc agtcagtgca gaacgtgggc actgtggctg     60
gacatagcgc ggggaagccc tgaagtgtga cggtgatccg cagaggagag aagcaccagc    120
tcagactgat tccaacccgc tggcaggaaa aggactgctg gctgcaaca ttattcctct     180
ccagagatga ctgtttcctg ggatctgcct gcaggaagct gcctcagctg gccccgtgct    240
tgggcctgga gggtttcctc gttctctagg ctcccttaag tgtaaggatc tggagaagaa    300
tggtcgaagc ctgggcatcg aggtggaaga acgctttgg ctgcctgatg taatctctct     360
gggttgaggc attattaaaa gtgtgatttg tgcctagcta cgtcttgtgc aaattaggcc    420
atag                                                                 424
```

<210> SEQ ID NO 62
<211> LENGTH: 438
<212> TYPE: DNA
<213> ORGANISM: Mus musculus

<400> SEQUENCE: 62

```
ctcagactga ttccaacccg ctgggcagga aaaggactgc tgggctgcaa cattattcct     60
ctccagagat gactgtttcc tgggatctgc ctgcaggaag ctgcctcagc tggccccgtg    120
cttgggcctg gaggcgtttc ctcgttctct aggctcccctt aagtgtaagg atctggagaa   180
gaatggtcga agcctgggca tcgaggtgga agagacgctt tggctgcctg atgtaatctc    240
tctgggttga ggcattatta aaagtgtgat ttgtgcctag ctacgtcttg tgcaaattag    300
gccatagcct gtctgggaat tctctagatt atgagccagt gagtggggat gactctggcg    360
agtaatgatt tgatgtcatt ttccttttgg agacggactc agtgtgtaat cctgactatc    420
ctggaattcc ctgtgtag                                                  438
```

<210> SEQ ID NO 63
<211> LENGTH: 668
<212> TYPE: DNA
<213> ORGANISM: Mus musculus
<220> FEATURE:
<221> NAME/KEY: misc_feature
<222> LOCATION: (442)..(442)
<223> OTHER INFORMATION: n can be any nucleotide

<400> SEQUENCE: 63

```
ctcttccacc tcgatgccca ggcttcgacc attcttctcc agatccttac acttaaggga     60
gcctagagaa cgaggaaacg cctccaggcc caagcacggg gcagtctgag gcagcttcct    120
gcaggcagat cccaggaaac agtcatctct ggagaggaat aatgttgcag cccagcagtc    180
cttttcctgc ccagcggtgt ggaatcagtc tgagctggtg cttctctcct ctgcggatca    240
ccgtcacatt caggggcttc cctcgctatg ctgcaccaca gtgccacgtt ctgcactgac    300
tggaagtttt gggtgtcacg gagccgaact ccacaatttc gtcatccact gcaggccgc     360
aatactggct ggggaaccgg ggctgatact gttcactctg gcaaagggct ggggcagga    420
cggggcgtgt tggaggccag cntgcggttc atggcctcat ctcgggcttc agcaatgtcc    480
cggagctgct tctccttgtt ccgaacgtgc acgtggtgca gggcgtcctc acttgcttca    540
tcagtgcctt gtgatcattc tggagaaaga gtgatgttgt gccttgtgtt cgggactggt    600
acaggtcaca tccgccgggg gatagcctca cagttcacca ggcggtcggt taagcaaatc    660
cttttttg                                                             668
```

<210> SEQ ID NO 64
<211> LENGTH: 447
<212> TYPE: DNA
<213> ORGANISM: Mus musculus
<220> FEATURE:
<221> NAME/KEY: misc_feature
<222> LOCATION: (427)..(427)
<223> OTHER INFORMATION: n can be any nucleotide

<400> SEQUENCE: 64

```
ccaaagcttt tcttccacct cgatgcccag gcttcgacca ttcttctcca gatccttaca      60
cttaagggag cctagagaac gaggaaacgc ctccaggccc aagcacgggg ccagctgagg     120
cagcttcctg caggcagatc ccaggaaaca gtcatctctg gagaggaata atgttgcagc     180
ccagcagtcc tttcctgcc cagcgggttg gaatcagtct gagctggtgc ttctctcctc      240
tgcggatcac cgtcacattc aggggcttcc cctcgctatg ctgcaccaca gtgcccacgt     300
tctgcactga ctggaagttt tgggtgttta tccacccgcc actccacacc cctcatcatc     360
cacttgcagg cccgcaatac tggctgggga accggggctg atactgttta ttttggcaaa     420
ggcctgnggc acggcccgc tgctgga                                          447
```

<210> SEQ ID NO 65
<211> LENGTH: 436
<212> TYPE: DNA
<213> ORGANISM: Mus musculus

<400> SEQUENCE: 65

```
aattttgctt gcaaacatag gcaataacct gtttggggat tatctttatt atgagcaaat      60
ggagtggaga tgactgttgg actttatttg attagaagtt atttctttt tggggacgga      120
gtcagggtct agtcctgact atcctggaat tccgagtgta gatcagggtg gccttgagct     180
gacagagatc ccctgcttt tgcctcatta gtattgggat gagaggcata tactgacatg     240
gctgggtaga ctctgaggga tatgtattat acatatataa tttatactta ttttgagaa      300
tttcgtacat gcacatagta catttctata tttcctgtca tctcaagtcc ctctcagacc     360
tcccctcgta cccacttccc aggttcttgc cctctttttgt tttttttctt tttaaataaa    420
taacctacta agtgcc                                                     436
```

<210> SEQ ID NO 66
<211> LENGTH: 484
<212> TYPE: DNA
<213> ORGANISM: Mus musculus

<400> SEQUENCE: 66

```
cggccgcggt cagcgacatc caggatctga tgcgacgcaa ggaggagatc gaggcggaga      60
tcaaggctaa ttcgacgtc ctggagagcc aaaaaggaat tggcatgaac gaaccgctgg      120
tggactgtga gggctatccc cggcggatg tggacttgta ccaggtccga acagcaaggc      180
acaacatcat ctgtctccag aatgaccaca aggcactgat gaagcaagtg gaggaggccc     240
tgcaccagct gcacgctcgg gacaaagaga agcaggctcg ggacatggct gaagcccgag     300
aagaggccat gaaccgcagg ctggcctcca acagccccgt cctgcccag gcctttgcca      360
gagtgaacag tatcagcccc ggttccccag ccagtattgc gggcctgcaa gtggatgacg     420
aaattgtgga gttcggctcc gtgaacaccc aaaacttcca gtcagtgcag aacgtgggca     480
ctgt                                                                  484
```

<210> SEQ ID NO 67
<211> LENGTH: 494
<212> TYPE: DNA
<213> ORGANISM: Mus musculus

<400> SEQUENCE: 67

```
caaggaggag atcgaggcgg agatcaaggc taattacgac gtcctggaga gccaaaaagg      60
aattggcatg aacgaaccgc tggtggactg tgagggctat ccccgggcgg atgtggactt     120
gtaccaggtc cgaacagcaa ggcacaacat catctgtctc cagaatgatc acaaggcact     180
gatgaagcaa gtggaggagg ccctgcacca gctgcacgct cgggacaaag agaagcatgc     240
tcgggacatg gctgaagccc gagaagaggc catgaaccgc aggctggcct ccaacagccc     300
cgccctgccc caggcctttg ccagagtgaa cagtatcagc cccggttccc cagccagtat     360
tgcgggcctg caagtggatg acgaaattgt ggagttcggc tccgtgaaca cccaaaactt     420
gcagtcagtg cagaacgtgg gcactgtggt gcagcatagc gaggggaagc ccctgaatgt     480
gacggtgatc cgca                                                       494
```

<210> SEQ ID NO 68
<211> LENGTH: 288
<212> TYPE: DNA
<213> ORGANISM: Mus musculus

<400> SEQUENCE: 68

```
gttcggcact atggggagcg ccgtcacatt caggggcttc ccctcgctat gctgcaccac      60
agtcccacgt tctgcactga ctggaagttt tgggtgttca cggagccgaa ctccacaatt     120
tcgtcatcca cttgcaggcc cgcaatactg gctggggaac cggggctgat actgttcact     180
ctggcaaagg cctgggctag gacggggctg ttggaggcca gcctgcggtt catggcctct     240
tctcgggctt cagcatggtc ccgagcctgc ttctctttgt cccgagcg                  288
```

<210> SEQ ID NO 69
<211> LENGTH: 455
<212> TYPE: DNA
<213> ORGANISM: Mus musculus
<220> FEATURE:
<221> NAME/KEY: misc_feature
<222> LOCATION: (44)..(44)
<223> OTHER INFORMATION: n can be any nucleotide

<400> SEQUENCE: 69

```
cgggcccgtg cggcgcggtc aggacatcca ggatctgatg cgancaagga ggagatcgag      60
gcggagatca aggctaatta cgacgtcctg gagagccaaa aaggaattgg catgaacgaa     120
ccgctggtgg actgtgaggg ctatccccgg gcggatgtgg acttgtacca ggtccgaaca     180
gcaaggcaca acatcatctg tctccagaat gatcacaagg cactgatgaa gcaagtggag     240
gaggccctgc accagctgca cgctcgggac aaagagaagc aggctcggga catggctgaa     300
gcccgagaag aggccatgaa ccgcaggctg cctccaaca gccccgccct gccccaggcc     360
tttgccagag tgaacagtat cagccccggt tccccagcca gtattgcggg cctgcaagtg     420
gatgacgaaa ttgtggagtt cggctccgtg aacac                                455
```

<210> SEQ ID NO 70
<211> LENGTH: 320
<212> TYPE: DNA
<213> ORGANISM: Mus musculus

<400> SEQUENCE: 70

```
cggattcagt gtttaatcct gaatatactg gaattccctg tctagaccag gctgcccttg    60
agctgacaga gatcccctg catttgcctc attagtattg ggatgagagg catatactga   120
catggctggc tagactctga ggaatatgta ttatacatat ataatttata tttattttg   180 agaattttgt acatgcacat agtacatttc tatatttcct ttcatctcaa ttccctttca   240
gacctccctt cgtacccact tcccaggttc ttgccctctt ttgttttttt tcttttaaa    300 taaataacct actaagtttc                                              320

<210> SEQ ID NO 71
<211> LENGTH: 277
<212> TYPE: DNA
<213> ORGANISM: Mus musculus

<400> SEQUENCE: 71
agagcaggct gcccttgagc tgacagagat ccccctgctt ctgcctcatt agtattggga    60 tgagggcat atactgacat ggctggctag actttgaggg atatgtatta tacatatata   120
atttatactt attttgaga atttcgtaca tgcacatagt acatttctat atttcctttc   180
atctcaactc cttctcagac ttcccttcgt acccacttcc caggttcttg ccctcttttg   240 tttttttct ttttaaataa ataacctact aagtgcc                              277

<210> SEQ ID NO 72
<211> LENGTH: 307
<212> TYPE: DNA
<213> ORGANISM: Mus musculus

<400> SEQUENCE: 72
cagtgcgcaa tcctcacaat tctggaattc cccgactaga ccaccctgcc cccgacctca    60
cagaaatccc cctccctctg cctcattagt atcgggatga gagccatata ctgacatggc   120
tggctagact ctgaggaata tgtattatac atatataatt tatacttatt tttgagaatt   180
tcgtacatgc acatagtaca tttctatatt tcctgtcatc tcaattccct ttcagacctc   240
ccctcgtacc cacttcccag gttcttgccc tcttttgttt ttttcttttt aaataaata    300 acctact                                                            307

<210> SEQ ID NO 73
<211> LENGTH: 308
<212> TYPE: DNA
<213> ORGANISM: Mus musculus

<400> SEQUENCE: 73
gtaatcctga ttatcttggt attccctcct tagaccagct cggccttgag ctgacagaga    60
tcccccttcc tttgcttcat tagtattcgg atgagaggca tatactgaca tggctggcta   120
gaatatgagg aatatgtatt atacatatat aatttatact tattttttgag aatttcgtac   180 atgcacatag tacatttcta tatttcctgt cttttcaatt ccctttcaga cctcccttcg   240
tacccacttc ccaggttctt gccctctttt gttttttttc ttttaaata aataacctac   300 taagtgcc                                                           308

<210> SEQ ID NO 74
<211> LENGTH: 295
<212> TYPE: DNA
<213> ORGANISM: Mus musculus

<400> SEQUENCE: 74
```

-continued catccggaat tcccccccac acaccaggcc ccctagagcc gacagagatc cccacccctc     60
tccctcatta atactgggat gagacgcata taccgacatg gctggttaga ctctgaggaa    120
tatgtattat acataaataa tttatactta tttttgagaa tttcgtacat gcacatagta    180
catttctata tttcctgtca tctcaagtcc ctctcagacc tcccttcgta cccacttccc    240
aggttcttgc cctcttttgt ttttttcctt tttaaataaa taacctacta agtgc         295

<210> SEQ ID NO 75
<211> LENGTH: 271
<212> TYPE: DNA
<213> ORGANISM: Mus musculus

<400> SEQUENCE: 75
aaatttattt ttctctcccc ctcccccccc cttcctctgc ctcattagta tccgcatgag     60
aggcatatac tgacatcctg gctagacttt gaggaatatt tattatacat atataattta    120
tacttatttt cgagaatttc gtacatgcac atagtacatt tctatatttc ctgtcatttc    180
aagtccctct cagacctccc ctcgtaccca cttcccaggt tcttgccctc ttttgttttt    240
tttcttttta aataaataac ctactaagtg c                                   271

<210> SEQ ID NO 76
<211> LENGTH: 244
<212> TYPE: DNA
<213> ORGANISM: Mus musculus

<400> SEQUENCE: 76
cctccctcta ctttattact attgggatga gaggcacata ctgacatgcc aggctagaat     60
ctgagggata tgtattatac atatataatt tatacttatt tttgaggatt ttgtacatgc    120
acatagtaca tttttatatt cctttattt tcaattccct ttcagacctc ccctcgtacc    180
cacttcccag gttcttgccc tttttgtttt ttttctttt taaataaata acctactaag    240
tgcc                                                                 244

<210> SEQ ID NO 77
<211> LENGTH: 210
<212> TYPE: DNA
<213> ORGANISM: Mus musculus

<400> SEQUENCE: 77
cacatactga aatggccggt tagattctga ggaatattta ttatacataa ataattcata     60 cttattttg aggattcgt acatgaacat agtacatttc tatatttcct gttatttcaa     120 gtcccttca gacctcccct tgtacccact tcccaggttc ttgcccttt ttgtttttt     180 tcttttaaa taataacct actaagtgcc                                       210

<210> SEQ ID NO 78
<211> LENGTH: 261
<212> TYPE: DNA
<213> ORGANISM: Mus musculus
<220> FEATURE:
<221> NAME/KEY: misc_feature
<222> LOCATION: (143)..(143)
<223> OTHER INFORMATION: n can be any nucleotide

<400> SEQUENCE: 78
ctctccagag atgactgttt cctgggattt gcctgcagga agctgcctca gctggccacg     60
tgcttgggcc tggaggcgtt tccttcgttt tttcttaggt tccccccccc ccctcccctc    120
cccccccccc ccccccccctt ctnaagtgta aggatttgga gaagaatggt cgaagcctgg   180

```
gcatcgaggt ggaagagacg ctttggctgc ctgatgtaat ttatttgggt tgaggcatta    240
ttcaaagtgt gatttgtgcc t                                              261
```

<210> SEQ ID NO 79
<211> LENGTH: 72
<212> TYPE: DNA
<213> ORGANISM: Mus musculus

<400> SEQUENCE: 79

```
ttttggcact tagtaggtta tttatttaaa aagaaaaaaa acaaaagagg gcaagaacct    60
gggaagtggg ta                                                        72
```

<210> SEQ ID NO 80
<211> LENGTH: 208
<212> TYPE: DNA
<213> ORGANISM: Mus musculus
<220> FEATURE:
<221> NAME/KEY: misc_feature
<222> LOCATION: (4)..(4)
<223> OTHER INFORMATION: n can be any nucleotide
<220> FEATURE:
<221> NAME/KEY: misc_feature
<222> LOCATION: (26)..(26)
<223> OTHER INFORMATION: n can be any nucleotide
<220> FEATURE:
<221> NAME/KEY: misc_feature
<222> LOCATION: (31)..(31)
<223> OTHER INFORMATION: n can be any nucleotide
<220> FEATURE:
<221> NAME/KEY: misc_feature
<222> LOCATION: (35)..(35)
<223> OTHER INFORMATION: n can be any nucleotide
<220> FEATURE:
<221> NAME/KEY: misc_feature
<222> LOCATION: (51)..(51)
<223> OTHER INFORMATION: n can be any nucleotide
<220> FEATURE:
<221> NAME/KEY: misc_feature
<222> LOCATION: (73)..(73)
<223> OTHER INFORMATION: n can be any nucleotide
<220> FEATURE:
<221> NAME/KEY: misc_feature
<222> LOCATION: (79)..(79)
<223> OTHER INFORMATION: n can be any nucleotide
<220> FEATURE:
<221> NAME/KEY: misc_feature
<222> LOCATION: (108)..(108)
<223> OTHER INFORMATION: n can be any nucleotide
<220> FEATURE:
<221> NAME/KEY: misc_feature
<222> LOCATION: (141)..(141)
<223> OTHER INFORMATION: n can be any nucleotide

<400> SEQUENCE: 80

```
gacngtttcc tcggatggcg tggagnaagg ntgcntcagc gggcccaaag ntttcgcctg    60
gaggcgtttc ctngttgtnt aggctcccct aagtgtaagg atctgganaa gaatggtcga    120
agcctgggca tcgaggtgga ngagactctt tggctgcctg atgtaatctc tctgggttga    180
ggcattatta aaagtgtgat ttgtgccc                                       208
```

<210> SEQ ID NO 81
<211> LENGTH: 253
<212> TYPE: DNA
<213> ORGANISM: Mus musculus

<400> SEQUENCE: 81

```
cacaaagatt cccttccct cttcttcatt atatcggggc gagcgcattc tgacacgccc    60
```

```
ggctagattc cgaggcacat gtattataca tctataattt atacttattt ttgagaattt    120
cgtacatgca catagtacat ttctattttt cctgtcatct caattccctc tcagacctcc    180
cctcgtaccc acttcccagg ttcttgccct cttttgtttt ttttcttttt aaataaataa    240
cctactaagt gcc                                                       253

<210> SEQ ID NO 82
<211> LENGTH: 378
<212> TYPE: DNA
<213> ORGANISM: Homo sapiens

<400> SEQUENCE: 82
atatcagcac tgtaaaactc tttattaaaa ataataataa taatcacacc agtacctgcc     60
agaataactt ccgcccactt gcccacaatc cagggaattc ctatttaggg ccgtggctag    120
atttgtgaaa gaggccaagc ctaagttttt aagaatgcct taatccaggg agattacact    180
ggtgggccac agtactgcca ccacacagaa gtctcaggtt acaagcctct tccagatcct    240
tatgcttcag ggagagaaga caagttggaa atccctagac ccaagtccag ggcaagggaa    300
gatgctttcc tgttactgtt ccccagggac aatcatcttt gcagaggaat aatgttgcag    360
cccagcagtc cttttcct                                                  378

<210> SEQ ID NO 83
<211> LENGTH: 379
<212> TYPE: DNA
<213> ORGANISM: Homo sapiens

<400> SEQUENCE: 83
catatcagca ctgtaaaact ctttattaaa aataataata ataatcacac cagtacctgc     60
cagaataact tccgcccact tgcccacaat ccagggaatt cctatttagg gccgtggcct    120
aatttgtgaa agaggccaag cctaagtttt taagaatgcc ttaatccagg gagattacac    180
tggtgggcca cagtactgcc accacacaga agttcaggtt acaagcctct tccagatcct    240
tatgcttcag ggagagaaga caagttggaa atccctagac ccaagtccag ggcaagggaa    300
gatgctttcc tgttactgtt ccccagggac aatcatcttt gcagaggaat aatgttgcag    360
cccagcagtc cttttcctg                                                 379

<210> SEQ ID NO 84
<211> LENGTH: 442
<212> TYPE: DNA
<213> ORGANISM: Homo sapiens

<400> SEQUENCE: 84
catatcagca ctgtaaaact ctttattaaa aataataata ataatcacac cagtacctgc     60
cagaataact tccgcccact tgcccacaat ccagggaatt cctatttagg gccgtggcct    120
aatttgtgaa agaggccaag cctaagtttt taagaatgcc ttaatccagg gagattacac    180
tggtgggcca cagtactgcc accacacaga agttcaggtt acaagcctct tccagatcct    240
tatgcttcag ggagagaaga caagttggaa atccctagac ccaagtccag ggcaagggaa    300
gatgctttcc tgttactgtt ccccagggac aatcatcttt gcagaggaat aatgttgcag    360
cccagcagtc cttttcctgc ccagcggttg gaacaagtct aaagctgtgt ttttccccc    420 ctgcgatcac tgtcacattc ag                                             442

<210> SEQ ID NO 85
<211> LENGTH: 300
```

```
<212> TYPE: DNA
<213> ORGANISM: Homo sapiens

<400> SEQUENCE: 85
ttcatatcag cactgtaaaa ctctttatta aaaataataa taataatcac accagtacct      60
gccagaataa cttccgccca cttgcccaca atccagggaa ttcctattta gggccgtggc     120
ctaatttgtg aaagaggcca agcctaagtt tttaagaatg ccttaatcca gggagattac     180
actggtgggc cacagtactg ccaccacaca gaagttcagg ttacaagcct cttccagatc     240
cttatgcttc agggagagaa gacaagttgg aaatccctag acccaagtcc agggcaaggg     300

<210> SEQ ID NO 86
<211> LENGTH: 632
<212> TYPE: DNA
<213> ORGANISM: Homo sapiens
<220> FEATURE:
<221> NAME/KEY: misc_feature
<222> LOCATION: (383)..(383)
<223> OTHER INFORMATION: n can be any nucleotide
<220> FEATURE:
<221> NAME/KEY: misc_feature
<222> LOCATION: (481)..(481)
<223> OTHER INFORMATION: n can be any nucleotide
<220> FEATURE:
<221> NAME/KEY: misc_feature
<222> LOCATION: (493)..(493)
<223> OTHER INFORMATION: n can be any nucleotide
<220> FEATURE:
<221> NAME/KEY: misc_feature
<222> LOCATION: (578)..(578)
<223> OTHER INFORMATION: n can be any nucleotide

<400> SEQUENCE: 86
catatcagca ctgtaaaact ctttattaaa aataataata ataatcacac cagtacctgc      60
cagaataact tccgcccact tgcccacaat ccagggaatt cctatttagg gccgtggcct     120
aatttgtgaa agaggccaag cctaagtttt taagaatgcc ttaatccagg gagattacac     180
tggtgggcca cagtactgcc accacacaga agttcaggtt acaagcctct tccagatcct     240
tatgcttcag ggagagaaga caagttggaa atccctagac ccaagtccag ggcaaggaa     300 gatgctttcc tgttactgtt ccccagggac aatcatcttt gcagaggaat aatgttgcag     360
cccagcagtc ctttctgcc agncgtgttg gaacaagtct agctttggtg ttttccccc     420 ctggcggatc actgtcacat tcaggggccc ctcactgtgc tgcaccacct gcccaatgta     480
nttcagtggt tgngaagtct tgggggtgtt cacagagccg aactccacaa tctatcattc     540
acttgcagac cccggatgct gcttgggagc cgggctgnag gctgtttact ttggcgaaag     600
gcccctggag gggccttgct tctacttggt cc                                   632

<210> SEQ ID NO 87
<211> LENGTH: 673
<212> TYPE: DNA
<213> ORGANISM: Homo sapiens
<220> FEATURE:
<221> NAME/KEY: misc_feature
<222> LOCATION: (497)..(497)
<223> OTHER INFORMATION: n can be any nucleotide
<220> FEATURE:
<221> NAME/KEY: misc_feature
<222> LOCATION: (505)..(505)
<223> OTHER INFORMATION: n can be any nucleotide
<220> FEATURE:
<221> NAME/KEY: misc_feature
<222> LOCATION: (576)..(576)
<223> OTHER INFORMATION: n can be any nucleotide
<220> FEATURE:
```

<221> NAME/KEY: misc_feature
<222> LOCATION: (633)..(633)
<223> OTHER INFORMATION: n can be any nucleotide
<220> FEATURE:
<221> NAME/KEY: misc_feature
<222> LOCATION: (641)..(641)
<223> OTHER INFORMATION: n can be any nucleotide
<220> FEATURE:
<221> NAME/KEY: misc_feature
<222> LOCATION: (646)..(646)
<223> OTHER INFORMATION: n can be any nucleotide

<400> SEQUENCE: 87

```
tttttcatat cagcactgta aaactctttta ttaaaaataa taataataat cacaccagta    60
cctgccagaa taacttccgc ccacttgccc acaatccagg gaattcctat ttagggccgt   120
ggcctaattt gtgaaagagg ccaagcctaa gtttttaaga atgccttaat ccagggagat   180
tacactggtg ggccacagta ctgccaccac acagaagttc aggttacaag cctcttccag   240
atccttatgc ttcagggaga gaagacaagt tggaaatccc tagacccaag tccagggcaa   300
gggaagatgc tttcctgtta ctgttcccca gggacaatca tctttgcaga ggaataatgt   360
tgcagcccag cagtcctttt cctgcccagc gtgttggaac aagtctaagc tggtgttttc   420
cccccctgcg gatcactgtc acattcaggg gcttcccctc actgtgctgc accacactgc   480
caatgttatg cagtganctg aagtntctgg tgttcacaga gccgaactcc acaatctcat   540
catccacttg cagacccgcg atgctggctg gggagnccgg gctgatgctg ttcactttgg   600
cgaaggcccg tggagggccc tggctctcac tcntgaccag nttgcngctc atgggcctct   660
tgtgggcctc acc                                                     673
```

<210> SEQ ID NO 88
<211> LENGTH: 666
<212> TYPE: DNA
<213> ORGANISM: Homo sapiens

<400> SEQUENCE: 88

```
tttttttttt tcatatcagc actgtaaaac tctttattaa aaataataat aataatcaca    60
ccagtacctg ccaaaataac ttccgcccac ttgcccacaa tccagggaat tcctatttag   120
gccgtggcc taatttgtga aagaggccaa gcctaagttt ttaaaaatgc cttaatccag   180
ggagattaca ctggtgggcc acagtactgc caccacacag aagttcaggt tacaagcctc   240
ttccaaatcc ttatgcttca gggagagaag acaagttgga aatccctaga cccaagtcca   300
gggcaaggga agatgctttc ctgttactgt tccccaggga caatcatctt tgcagaggaa   360
taatgttgca gcccagcagt cctttttcctg cccagcgtgt tggaacaagt ctaagctggg   420
tgtttttccc ccctgcggat cactgtcaca ttcaggggc ttcccctcac tgtgctgcac   480
cacactgcca atgttatgca gtgattggaa gtcttgggtg ttcacaagac cgaactccac   540
aatctcatta tccacttgca gaccccgat gcttgctggg gagccgggc tgatgctttt   600
cactttgccg aggccccttg ggaggccctg gctctcactc tgaccaattt gccggtcaag   660
ccctc                                                              666
```

<210> SEQ ID NO 89
<211> LENGTH: 311
<212> TYPE: DNA
<213> ORGANISM: Homo sapiens
<220> FEATURE:
<221> NAME/KEY: misc_feature
<222> LOCATION: (162)..(162)
<223> OTHER INFORMATION: n can be any nucleotide

```
<220> FEATURE:
<221> NAME/KEY: misc_feature
<222> LOCATION: (180)..(180)
<223> OTHER INFORMATION: n can be any nucleotide
<220> FEATURE:
<221> NAME/KEY: misc_feature
<222> LOCATION: (248)..(248)
<223> OTHER INFORMATION: n can be any nucleotide
<220> FEATURE:
<221> NAME/KEY: misc_feature
<222> LOCATION: (254)..(254)
<223> OTHER INFORMATION: n can be any nucleotide
<220> FEATURE:
<221> NAME/KEY: misc_feature
<222> LOCATION: (280)..(280)
<223> OTHER INFORMATION: n can be any nucleotide

<400> SEQUENCE: 89
tccccaggga caatcatctt tgcagaggaa taatgttgca gcccagcagt ccttttcctg    60
cccagcgtgt tggaacaagt ctaagctggt gttttccccc cctgcggatc actgtcacat   120
tcagggcttc ccctcactg tgctgcacca cactgccaat gnttatgcag tgactgaagn    180
ttctggtgtt cacagagccg aactccacaa tctcatcatc cacttgcaga cccgcgatgc   240
tggctggnga gccnggggctg atgctgtcac tttggcgaan gcccgtgagg gcccctgctc   300
tcactctgac c                                                         311

<210> SEQ ID NO 90
<211> LENGTH: 192
<212> TYPE: DNA
<213> ORGANISM: Homo sapiens

<400> SEQUENCE: 90
tttttttttt ttttttttt ttttttcag cactgtaaaa ctctttatta aaataataa      60 taataatcac cccagtccct gccaaaataa cttccgccca cttgcccaca atccagggaa   120
ttcctattta gggccggggc ctaatttggg aagaggcca acctaagttt ttaaaaatgc    180
cttaatccag gg                                                       192

<210> SEQ ID NO 91
<211> LENGTH: 304
<212> TYPE: DNA
<213> ORGANISM: Homo sapiens

<400> SEQUENCE: 91 tttttttcata tcagcactgt aaaactcttt attaaaaata ataataataa tcacaccagt   60
acctgccaga ataacttccg cccacttgcc cacaatccag ggaattccta tttagggccg   120
tggcctaatt tgtgaaagag gccaagccta agtttttaag aatgccttaa tccagggaga   180
ttacactggt gggccacagt actgccacca cacagaagtt caggttacaa gcctcttcca   240
gatccttatg cttcagggag agaagacaag ttggaaatcc ctagacccaa gtccagggca   300
aggg                                                                304

<210> SEQ ID NO 92
<211> LENGTH: 421
<212> TYPE: DNA
<213> ORGANISM: Homo sapiens

<400> SEQUENCE: 92
tttagcactg taaaactctt tattaaaaat aataataata atcacaccag tacctgccag    60
aataacttcc gcccacttgc ccacaatcca gggaattcct atttagggcc gtggcctaat   120
```

| | |
|---|---:|
| ttgtgaaaga ggccaagcct aagtttttaa gaatgcctta atccagggag attacactgg | 180 |
| tgggccacag tactgccacc acacagaagt tcaggttaca agcctcttcc agatccttat | 240 |
| gcttcaggga gagaagacaa gttggaaatc cctagaccca agtccagggc aagggaagat | 300 |
| gctttcctgt tactgttccc cagggacaat catctttgca gaggaataat gttgcagccc | 360 |
| agcagtcctt ttcctgccca gcgtgttgga acaagtctaa gctggtgttt ttccccctg | 420 |
| c | 421 |

<210> SEQ ID NO 93
<211> LENGTH: 461
<212> TYPE: DNA
<213> ORGANISM: Homo sapiens

<400> SEQUENCE: 93

| | |
|---|---:|
| atcagcactg taaaactctt tattaaaaat aataataata atcacaccag tacctgccag | 60 |
| aataacttcc gcccacttgc ccacaatcca gggaattcct atttagggcc gtggcctaat | 120 |
| ttgtgaaaga ggccaagcct aagtttttaa gaatgcctta atccagggag attacactgg | 180 |
| tgggccacag tactgccacc acacagaagt tcaggttaca agcctcttcc agatccttat | 240 |
| gcttcaggga gagaagacaa gttggaaatc cctagaccca agtccagggc aagggaagat | 300 |
| gctttcctgt tactgttccc cagggacaat catctttgca gaggaataat gttgcagccc | 360 |
| agcagtcctt ttcctgccca gcgtgttgga acaagtctaa ggctgtgttt ttcccccct | 420 |
| gcggatcact gtcacattca agggcttccc ctcactgtgc t | 461 |

<210> SEQ ID NO 94
<211> LENGTH: 555
<212> TYPE: DNA
<213> ORGANISM: Homo sapiens
<220> FEATURE:
<221> NAME/KEY: misc_feature
<222> LOCATION: (308)..(308)
<223> OTHER INFORMATION: n can be any nucleotide
<220> FEATURE:
<221> NAME/KEY: misc_feature
<222> LOCATION: (391)..(391)
<223> OTHER INFORMATION: n can be any nucleotide
<220> FEATURE:
<221> NAME/KEY: misc_feature
<222> LOCATION: (397)..(397)
<223> OTHER INFORMATION: n can be any nucleotide

<400> SEQUENCE: 94

| | |
|---|---:|
| catatcagca ctgtaaaact ctttattaaa aataataata ataatcacac cagtacctgc | 60 |
| cagaataact tccgcccact tgcccacaat ccagggaatt cctatttagg gccgtggcct | 120 |
| aatttgtgaa agaggccaag cctaagtttt taagaatgcc ttaatccagg gagattacac | 180 |
| tggtgggcca cagtactgcc accacacaag aagtttcagg ttacaagcct cttccagatc | 240 |
| cttatgcttc agggagagaa gaacaagttg gaaatcccta acccaagtca gggcagggaa | 300 |
| gatgttntct gttacctgtt cccagggaca atattttgca gagaataatg ttgcaccaac | 360 |
| agtctttctg ccaagcggtg aacaagtact nggggngtt tccctgcggg atcatggaca | 420 |
| tcagggcttc cttcactggt gacatgccat gtttcagtat gggatttttg ggggggggtc | 480 |
| acaaccactc acatctatat cactgcaccc gatctgctgg accggcctat ttctttactt | 540 |
| gcaaacccc tgagg | 555 |

<210> SEQ ID NO 95
<211> LENGTH: 750

```
<212> TYPE: DNA
<213> ORGANISM: Homo sapiens
<220> FEATURE:
<221> NAME/KEY: misc_feature
<222> LOCATION: (633)..(633)
<223> OTHER INFORMATION: n can be any nucleotide

<400> SEQUENCE: 95
ttcatatcag cactgtaaaa ctctttatta aaataataa taataatcac accagtacct      60
gccagaataa cttccgccca cttgcccaca atccaggaa ttcctattta gggccgtggc     120
ctaatttgtg aaagaggcca agcctaagtt tttaagaatg ccttaatcca gggagattac    180
actggtgggc cacagtactg ccaccacaca gaagttcagg ttacaagcct cttccagatc    240
cttatgcttc agggagagaa gacaagttgg aaatccctag acccaagtcc agggcaaggg    300
aagatgcttt cctgttactg ttccccaggg acaatcatct tttgcagagg aataatgttg    360
cagcccagca ggtccttttc ctgcccagcg tgttggaaca agtctaagct ggtgttttc     420 cccctgcgg atcactgtca cattcagggg cttcccctca ctgtgctgca ccacactgcc     480
aatgttatgc agtgactgga agttctgggt gttcacagag ccgaactcca caatctcatc    540
atccacttgc agacccgcga tgctggctgg ggagccgggg ctgatgctgt tcactttggc    600
gaaggcccgt ggagggccct ggctctcact ctngaccagt ttgcgggtca tggcctcttg    660
tgggcctcag ccatgtcccg ggcctggctt cttcttgtcg cgagcgtgca agtggtgcag    720
ggcctccttc acctgcttta tcactgccct                                     750

<210> SEQ ID NO 96
<211> LENGTH: 376
<212> TYPE: DNA
<213> ORGANISM: Homo sapiens
<220> FEATURE:
<221> NAME/KEY: misc_feature
<222> LOCATION: (180)..(180)
<223> OTHER INFORMATION: n can be any nucleotide
<220> FEATURE:
<221> NAME/KEY: misc_feature
<222> LOCATION: (218)..(218)
<223> OTHER INFORMATION: n can be any nucleotide
<220> FEATURE:
<221> NAME/KEY: misc_feature
<222> LOCATION: (272)..(272)
<223> OTHER INFORMATION: n can be any nucleotide
<220> FEATURE:
<221> NAME/KEY: misc_feature
<222> LOCATION: (279)..(279)
<223> OTHER INFORMATION: n can be any nucleotide
<220> FEATURE:
<221> NAME/KEY: misc_feature
<222> LOCATION: (344)..(344)
<223> OTHER INFORMATION: n can be any nucleotide
<220> FEATURE:
<221> NAME/KEY: misc_feature
<222> LOCATION: (370)..(370)
<223> OTHER INFORMATION: n can be any nucleotide

<400> SEQUENCE: 96
cgctggtgga ctgtgagggc taccccggt cagacgtgga cctgtaccaa gtccgcaccg       60
ccagcacaac atcatatgcc tgcagaatga tcacaaggca gtgatgaagc aggtggagga    120
ggccctgcac cagctgcacg ctcgcgacaa ggagaagcag gcccgggaca tggctgaggn    180
ccacaaagag gccatgagcc gcaaactggg tcagagtnag agccagggcc ctccacgggc    240
tttcgccaaa gtgaacagca tcagccccgg gntccccanc cagcattcgc gtggtctgca    300
agtggatgat tgagattgtg ggagtttcgg gctctgtgga acanccccaga attttcagtt    360
```

```
caattgcatn aacttt                                                      376
```

<210> SEQ ID NO 97
<211> LENGTH: 225
<212> TYPE: DNA
<213> ORGANISM: Homo sapiens
<220> FEATURE:
<221> NAME/KEY: misc_feature
<222> LOCATION: (198)..(198)
<223> OTHER INFORMATION: n can be any nucleotide
<220> FEATURE:
<221> NAME/KEY: misc_feature
<222> LOCATION: (220)..(220)
<223> OTHER INFORMATION: n can be any nucleotide

<400> SEQUENCE: 97

```
tatcagcact gtaaaactct ttattaaaaa taataataat aatcacacca gtacctgcca        60
gaataacttc cgcccacttg cccacaatcc agggaattcc tatttagggc cgtggctaat       120
tttgtgaaag aggccaagcc taagttttta agaatgcctt aatccgggga gattacactg       180
ggtggggccc caggtacngc ccccccacag gagttcaggn tacaa                      225
```

<210> SEQ ID NO 98
<211> LENGTH: 654
<212> TYPE: DNA
<213> ORGANISM: Homo sapiens

<400> SEQUENCE: 98

```
tttttttatca gcactgtaaa actctttatt aaaataata ataataatca caccagtacc        60
tgccagaata acttccgccc acttgcccac aatccaggga attcctattt agggccgtgg       120
ctcaatttgt gaaagaggcc aagcctaagt ttttaagaat gccttaatcc agggagatta       180
cactggtggg ccacagtact gccaccacac agaagttcag gttacaagcc tcttccagat       240
ccttatgctt cagggagaga agacaagttg gaaatcccta gacccaagtc cagggcaagg       300
gaagatgctt tcctgttact gttccccagg gacaatcatc tttgcagagg aataatgttg       360
cagcccagca gtccttttcc tgcccagcgt gttggaacaa gtctaagctg gtgttttccc       420
cccctgcgga tcactgtcac attcagggtg cttccctcac tgtgctgcac cacactgcca       480
atgttatgca gtgactggaa gttctgggtg ttcacagagc cgagattccc aatctcatca       540
tcaacttgca gacccgcgat gctggctggg ggagccgggg ctcgatgtgg ttcattttgg       600
cgaaggccgt ggaatgcctc ggctctcaat ctgatccagt ttgcggctca tggc            654
```

<210> SEQ ID NO 99
<211> LENGTH: 749
<212> TYPE: DNA
<213> ORGANISM: Homo sapiens
<220> FEATURE:
<221> NAME/KEY: misc_feature
<222> LOCATION: (642)..(642)
<223> OTHER INFORMATION: n can be any nucleotide
<220> FEATURE:
<221> NAME/KEY: misc_feature
<222> LOCATION: (625)..(625)
<223> OTHER INFORMATION: n can be any nucleotide

<400> SEQUENCE: 99

```
ttttcatatt tgcactgtaa aactctttat taaaaggggg aataataatc acaccagtac        60
ctgccagaat aacttccgcc cacttgccca atccaggg aattcctatt tagggccgtg        120
gcctaatttg tgaaagaggc caagcctaag ttttaagaa tgccttaatc cagggagatt       180
acactggtgg gccacagtac tgccaccaca cagaagttca ggttacaagc ctcttccaga       240
```

-continued

```
tccttatgct tcagggagag aagacaagtt ggaaatccct agacccaagt ccagggcaag    300
ggaagatgct ttcctgttac tgttccccag ggacaatcat ctttgcagag aataatgtt    360 gcagcccagc agtccttttc ctgcccagcg tgttggaaca agtctaagct ggtgtttttc    420 cccctgcgg atcactgtca cattcagggg cttcccctca ctgtgctgca ccacactgcc    480
aatgttatgc agtgactgga agttctgggt gttcacagag ccgaactcca caatcttatc    540
atccacttgc agacccgcga tgctggctgg ggagcctggg ctgatgctgt tcactatggc    600
gaaggcccgt ggagggccct gactctcact ctgacccagt tngcggctca tggcctcttt    660
gtggcctcag ccatgtcccg ggcctgcttc tccttgacgc gagcgtgcag ctggtgcagg    720
gcctncctca cttggcttat cactgcctt                                      749
```

<210> SEQ ID NO 100
<211> LENGTH: 502
<212> TYPE: DNA
<213> ORGANISM: Homo sapiens

<400> SEQUENCE: 100

```
ttcatatcag cactgtaaaa ctctttatta aaaataataa taataatcac accagtacct    60
gccagaataa cttccgccca cttgcccaca atccagggaa ttcctattta gggccgtggc    120
ctaatttgtg aaagaggcca agcctaagtt tttaagaatg ccttaatcca gggagattac    180
actggtgggc cacagtactg ccaccacaca gaagttcagg ttacaagcct cttccagatc    240
cttatgcttc agggagagaa gacaagttgg aaatccctag acccaagtcc agggcaaggg    300
aagatgcttt cctgttactg ttccccaggg acaatcatct tgcagagga ataatgttgc    360 agcccagcag tccttttcct gcccagcgtg ttggaacaag tctaagctgg tgttttccc    420 ccctgcggat cactgtcaca ttcaggggct tcccctcact gtgctgcacc acactgccaa    480
tgttatgcag tgactggaag tt                                             502
```

<210> SEQ ID NO 101
<211> LENGTH: 587
<212> TYPE: DNA
<213> ORGANISM: Homo sapiens

<400> SEQUENCE: 101

```
catatcagca ctgtaaaact ctttattaaa aataataata ataatcacac cagtacctgc    60
cagaataact tccgcccact tgcccacaat ccagggaatt cctatttagg gccgtggcct    120
aatttgtgaa agaggccaag cctaagtttt taagaatgcc ttaatccagg gagattacac    180
tggtgggcca cagtactgcc accacacaga agttcaggtt acaagcctct tccagatcct    240
tatgcttcag ggagagaaga caagttggaa atccctagac ccaagtccag ggcaagggaa    300
gatgctttcc tgttactgtt ccccaggac aatcatcttt gcagaggaat aatgttgcag    360
cccagcagtc cttttcctgc ccagcgtgtt ggaacaagtc taagctggtg ttttccccc    420 ctgcggatca ctgtcacatt caggggcttc ccctcactgt gctgcaccac actgccaatg    480
ttatgcaggg acctgaaagt tctggtgttc acagagccga actccacatt ctcatcatcc    540
actggcagac cctgtcata tgttggcgag gtgggacaac tggactc                   587
```

<210> SEQ ID NO 102
<211> LENGTH: 354
<212> TYPE: DNA
<213> ORGANISM: Homo sapiens

```
<400> SEQUENCE: 102
gtggagttcg gctctgtgaa cacccagaac ttccagtcac tgcataacat tggcagtgtg      60
gtgcagcaca gtgagggaa gccctgaat gtgacagtga tccgcagggg gaaaaacacc       120
agcttagact tgttccaaca cgctgggcag gaaaaggact gctgggctgc aacattattc     180
ctctgcaaag atgattgtcc ctggggaaca gtaacaggaa agcatcttcc cttgccctgg     240
gacttgggtc tagggatttc caacttgtct tctctccctg aagcataagg atctgggaag    300
aggcttgtta acctggaact tctgtgtggt ggccagtact gtgggcccac cagt          354

<210> SEQ ID NO 103
<211> LENGTH: 568
<212> TYPE: DNA
<213> ORGANISM: Homo sapiens
<220> FEATURE:
<221> NAME/KEY: misc_feature
<222> LOCATION: (7)..(7)
<223> OTHER INFORMATION: n can be any nucleotide
<220> FEATURE:
<221> NAME/KEY: misc_feature
<222> LOCATION: (12)..(12)
<223> OTHER INFORMATION: n can be any nucleotide
<220> FEATURE:
<221> NAME/KEY: misc_feature
<222> LOCATION: (14)..(14)
<223> OTHER INFORMATION: n can be any nucleotide
<220> FEATURE:
<221> NAME/KEY: misc_feature
<222> LOCATION: (350)..(350)
<223> OTHER INFORMATION: n can be any nucleotide
<220> FEATURE:
<221> NAME/KEY: misc_feature
<222> LOCATION: (422)..(422)
<223> OTHER INFORMATION: n can be any nucleotide
<220> FEATURE:
<221> NAME/KEY: misc_feature
<222> LOCATION: (432)..(432)
<223> OTHER INFORMATION: n can be any nucleotide
<220> FEATURE:
<221> NAME/KEY: misc_feature
<222> LOCATION: (509)..(509)
<223> OTHER INFORMATION: n can be any nucleotide
<220> FEATURE:
<221> NAME/KEY: misc_feature
<222> LOCATION: (525)..(525)
<223> OTHER INFORMATION: n can be any nucleotide
<220> FEATURE:
<221> NAME/KEY: misc_feature
<222> LOCATION: (533)..(533)
<223> OTHER INFORMATION: n can be any nucleotide

<400> SEQUENCE: 103
tcatatnagc antntaaaac tctttattaa aaataataat aataatcaca ccagtacctg      60
ccagaataac ttccgcccac ttgcccacaa tccagggaat tcctatttag ggccgtggct     120
aattttgtga agaggccaa gcctaagttt ttaagaatgc cttaatccag ggagattaca     180
ctggtgggcc acagtactgc caccacacag aagttcaggt tacaagcctc ttccagatcc     240
ttatgcttca gggagagaag acaagttgga aatccctaga cccaagtcca gggcaaggga    300
agatgctttc ctgttactgt tcccaggga caatcatctt tgcagaggan taatgttgca     360
gcccagcagt cctttcctg cccagcgtgt tggaacaagt ttaaggtggt gttttcccc      420 cntgcggatc antgttcaca tttcaggggt tcccctcact gtgctgcacc acattgccat    480
tgttattgca gtgactggag ttttgggtnt tcacagaggc cgaantccac ctngtggcca   540
ttttttgggc tcgagggcaa atttccct                                      568
```

<210> SEQ ID NO 104
<211> LENGTH: 301
<212> TYPE: DNA
<213> ORGANISM: Homo sapiens

<400> SEQUENCE: 104

| | | |
|---|---|---|
| attgtggagt tcggctctgt gaacacccag aacttccagt cactgcataa cattggcagt | 60 |
| gtggtgcagc acagtgaggg gaagcccctg aatgtgacag tgatccgcag ggggaaaaac | 120 |
| accagcttag acttgttcca acacgctggg caggaaaagg actgctgggc tgcaacatta | 180 |
| ttcctctgca aagatgattg tccctgggga acagtaacag gaaagcatct tcccttgccc | 240 |
| tggacttggg tctagggatt ccaacttgt cttctctccc tgaaagcata aaggatctgg | 300 |
| g | 301 |

<210> SEQ ID NO 105
<211> LENGTH: 265
<212> TYPE: DNA
<213> ORGANISM: Homo sapiens

<400> SEQUENCE: 105

| | | |
|---|---|---|
| catatcagca ctgtaaaact ctttattaaa aataataata ataatcacac cagtacctgc | 60 |
| cagaataact tccgcccact tgcccacaat ccagggaatt cctatttagg gccgtggcta | 120 |
| atttgtgaaa gaggccaagc ctaagttttt aagaatgcct taatccaggg agattacact | 180 |
| ggtgggccac agtactgcca ccacacagaa gttcaggtta caagcctctt ccagatcctt | 240 |
| atgcttcagg gagagaagac aagtt | 265 |

<210> SEQ ID NO 106
<211> LENGTH: 398
<212> TYPE: DNA
<213> ORGANISM: Homo sapiens
<220> FEATURE:
<221> NAME/KEY: misc_feature
<222> LOCATION: (96)..(96)
<223> OTHER INFORMATION: n can be any nucleotide
<220> FEATURE:
<221> NAME/KEY: misc_feature
<222> LOCATION: (310)..(310)
<223> OTHER INFORMATION: n can be any nucleotide
<220> FEATURE:
<221> NAME/KEY: misc_feature
<222> LOCATION: (359)..(359)
<223> OTHER INFORMATION: n can be any nucleotide
<220> FEATURE:
<221> NAME/KEY: misc_feature
<222> LOCATION: (386)..(386)
<223> OTHER INFORMATION: n can be any nucleotide
<220> FEATURE:
<221> NAME/KEY: misc_feature
<222> LOCATION: (395)..(395)
<223> OTHER INFORMATION: n can be any nucleotide

<400> SEQUENCE: 106

| | | |
|---|---|---|
| tgagccgcaa actgggtcag agtgagagcc agggccctcc acgggctttc gccaaagtga | 60 |
| acagcatcag ccccggctcc ccagccagca tcgcgngtct gcaagtggat gatgagattg | 120 |
| tggagttcgt ctctgtgaac acccagaact tccagtcact gcataacatt ggcagtgtgg | 180 |
| tgcagcacag tgagggggccc ctgaatgtga cagtgatccg cagggggaaa aacaccagct | 240 |
| tagacttgtt ccaacacgct gggcaggaaa aggactgctg ggctgcaaca ttattcctct | 300 |
| tgcaaagatn gattgtccct ggggaacag ttaacaggga aagctttttc cctttgccng | 360 |
| ggatttgggt ctaggggttt tccaanttgt ttttnttt | 398 |

```
<210> SEQ ID NO 107
<211> LENGTH: 354
<212> TYPE: DNA
<213> ORGANISM: Homo sapiens
<220> FEATURE:
<221> NAME/KEY: misc_feature
<222> LOCATION: (65)..(65)
<223> OTHER INFORMATION: n can be any nucleotide
<220> FEATURE:
<221> NAME/KEY: misc_feature
<222> LOCATION: (155)..(155)
<223> OTHER INFORMATION: n can be any nucleotide
<220> FEATURE:
<221> NAME/KEY: misc_feature
<222> LOCATION: (230)..(230)
<223> OTHER INFORMATION: n can be any nucleotide
<220> FEATURE:
<221> NAME/KEY: misc_feature
<222> LOCATION: (274)..(274)
<223> OTHER INFORMATION: n can be any nucleotide
<220> FEATURE:
<221> NAME/KEY: misc_feature
<222> LOCATION: (282)..(282)
<223> OTHER INFORMATION: n can be any nucleotide
<220> FEATURE:
<221> NAME/KEY: misc_feature
<222> LOCATION: (297)..(297)
<223> OTHER INFORMATION: n can be any nucleotide

<400> SEQUENCE: 107
catatcagca ctgtaaaact ctttattaaa aataataata ataatcacac cagtacctgc      60
cagantaact tccgcccact tgcccacaat ccagggaatt cctatttagg gccgtggcta     120
aatttgtgaa agaggcaagc ctaagttttt aagantgcct taatccaggg gagattacac     180
tggtggggcc acagtactgc caccacacag aagttcaggt tacaagcctn ttccagatcc     240
ttatgcttca ggggagagaa gacaagttgg gaantcccta gncccaagtc cgggggnaag     300
gggaggatgc ttttcctgtt tacttttttcc ccgggggaca atcatctttt gcag           354

<210> SEQ ID NO 108
<211> LENGTH: 614
<212> TYPE: DNA
<213> ORGANISM: Homo sapiens
<220> FEATURE:
<221> NAME/KEY: misc_feature
<222> LOCATION: (447)..(447)
<223> OTHER INFORMATION: n can be any nucleotide

<400> SEQUENCE: 108
catatcagca ctgtaaaact ctttattaaa aataataata ataatcacac cagtacctgc      60
cagaataact tccgcccact tgcccacaat ccagggaatt cctatttagg gccgtggcct     120
aatttgtgaa agaggccaag cctaagtttt taagaatgcc ttaatccagg gagattacac     180
tggtgggcca cagtactgcc accacacaga agttcaggtt acaagcctct tccagatcct     240
tatgcttcag ggagagaaga caagttggaa atccctagac ccaagtccag ggcaaggaa      300 gatgctttcc tgttactgtt ccccagggac aatcatcttt gcagaggaat aatgttgcag     360
cccagcagtc cttttcctgc ccagcgtgtt ggaacaagtc taagctgggt gttttttcccc    420 ccttgcggat cactgtcaca ttcaggnggc ttcccctcac ttgtgctgca ccacactgcc     480
aatgttatgc agtgatggga agttctgggg tgttcacaga gccgaactcc acaatctcat     540
catccacttg cagacccgcg atgctggctg gggagccggg gctgatgcct gttcactttg     600
gcgaaggccc gtgg                                                       614
```

```
<210> SEQ ID NO 109
<211> LENGTH: 308
<212> TYPE: DNA
<213> ORGANISM: Homo sapiens

<400> SEQUENCE: 109
tttttttttt ttttttttta tcagcactgg aaaactcttt attaaaaata ataataataa      60
tcacaccagt acctgccaga ataacttccg cccacttgcc cacaatccag ggaattccta     120
tttagggccg gggcctaatt tgtgaaagag gccaagccta agttttttaag aatgccttaa    180 tccagggaga ttacactggt gggccacagt actgccacca cacagaagtt caggttacaa    240
gcctcttcca gatccttatg cttcagggag agaagacaag ttggaaatcc ctagacccaa    300
gtccaggg                                                              308

<210> SEQ ID NO 110
<211> LENGTH: 379
<212> TYPE: DNA
<213> ORGANISM: Homo sapiens
<220> FEATURE:
<221> NAME/KEY: misc_feature
<222> LOCATION: (121)..(121)
<223> OTHER INFORMATION: n can be any nucleotide
<220> FEATURE:
<221> NAME/KEY: misc_feature
<222> LOCATION: (260)..(260)
<223> OTHER INFORMATION: n can be any nucleotide
<220> FEATURE:
<221> NAME/KEY: misc_feature
<222> LOCATION: (341)..(341)
<223> OTHER INFORMATION: n can be any nucleotide
<220> FEATURE:
<221> NAME/KEY: misc_feature
<222> LOCATION: (356)..(356)
<223> OTHER INFORMATION: n can be any nucleotide

<400> SEQUENCE: 110
catatcagca ctgtaaaact ctttattaaa aataataata ataatcacac cagtacctgc      60
cagaataact tccgcccact tgcccacaat ccagggaatt cctatttagg gccgtggcta     120
natttgtgaa agaggccaag cctaagtttt taagaatgcc ttaatccagg gagattacac    180
tggtgggcca cagtactgcc accacacaga agttcaggtt acaagcctct tccagatcct    240
tatgcttcag ggagagaagn cgagttggaa acccctagac ccaagtccag ggcaagggaa    300
gatgctttcc tgttactgtt ccccagggac aatcatcttt ngcagaggga ttaatngttg    360
cagcccagca gtcctttc                                                  379

<210> SEQ ID NO 111
<211> LENGTH: 533
<212> TYPE: DNA
<213> ORGANISM: Homo sapiens
<220> FEATURE:
<221> NAME/KEY: misc_feature
<222> LOCATION: (383)..(383)
<223> OTHER INFORMATION: n can be any nucleotide
<220> FEATURE:
<221> NAME/KEY: misc_feature
<222> LOCATION: (494)..(494)
<223> OTHER INFORMATION: n can be any nucleotide
<220> FEATURE:
<221> NAME/KEY: misc_feature
<222> LOCATION: (495)..(495)
<223> OTHER INFORMATION: n can be any nucleotide

<400> SEQUENCE: 111
ttttcagcac tgtaaaactc tttattaaaa ataataataa taatcacacc agtacctgcc      60
```

```
agaataactt ccgcccactt gcccacaatc cagggaattc ctatttaggg ccgtggccta    120
atttgtgaaa gaggccaagc ctaagttttt aagaatgcct taatccaggg agattacact    180
ggtgggccac agtactgcca ccacacagaa gttcaggtta caagcctctt ccagatcctt    240
atgcttcagg gagagaagac aagttggaaa tccctagacc caagtccagg gcaagggaag    300
atgctttcct gttactgttc ccagggaca atcatctttg cagaggaata atgttgcagc     360
ccagcagtcc ttttcctgcc agncgtgttg gaacaagtct agcttggtgt ttcccccct    420 ggcggatcac tgtcacattc aggggctttc tcactgtgc tgaccacact gccatgtatg     480
catggctggg agtnntgggg tgttcacaga gccgaactcc acaatctcat cat           533

<210> SEQ ID NO 112
<211> LENGTH: 314
<212> TYPE: DNA
<213> ORGANISM: Homo sapiens

<400> SEQUENCE: 112
tttttttttt tttttttta tcagcactgg aaaactcttt attaaaaata ataataataa     60
tcacaccagt acctgccaga ataacttccg cccacttgcc cacaatccag ggaattccta    120
tttagggccg tggcctaatt tgtgaaagag gccaagccta agttttttaag aatgccttaa   180 tccagggaga ttacactggt gggccacagt actgccacca cacagaagtt caggttacaa    240
gcctcttcca gatccttatg cttcagggag agaagacaag ttggaaatcc ctagacccaa    300
gtccagggca aggg                                                      314

<210> SEQ ID NO 113
<211> LENGTH: 578
<212> TYPE: DNA
<213> ORGANISM: Homo sapiens

<400> SEQUENCE: 113
tttttttttt ttttttcag cactgtaaaa ctctttatta aaataataa taataatcac      60 accagtacct gccaaaataa cttccgccca cttgcccaca atccagggaa ttcctattta    120
gggccggggc ctaatttggg aaagaggcca agcctaagtt tttaagaatg ccttaatcca    180
gggagattac actggtgggc cacagtactg ccaccacaca gaagttcagg ttacaagcct    240
tttccagatc cttatgcttc agggagagaa gacaagttgg aaatccctag acccaagtcc    300
agggcaaggg aagatgcttt cctgttactg ttccccaggg acaatcatct ttgcagagga    360
ataatgttgc agcccagcag tccttttcct gcccagcgtg ttggaacaag tctaagctgg    420
tgttttcccc cctgcggat cactgtcaca ttcaggggct tccctcact gtgctgcacc     480 acactgccaa tgttatgcag tgactggaaa gtctgggtgg tcacagagcc gaacttcaca    540
atctcatcat ccacttgcag acccgcgatg ctggtggg                            578

<210> SEQ ID NO 114
<211> LENGTH: 408
<212> TYPE: DNA
<213> ORGANISM: Homo sapiens
<220> FEATURE:
<221> NAME/KEY: misc_feature
<222> LOCATION: (374)..(374)
<223> OTHER INFORMATION: n can be any nucleotide
<220> FEATURE:
<221> NAME/KEY: misc_feature
<222> LOCATION: (400)..(400)
<223> OTHER INFORMATION: n can be any nucleotide

<400> SEQUENCE: 114
```

```
ataatgggaa tccccagttt gcatggaaac tgcagataaa tcctcgtggt aggaacgaga      60
ctacagctct agaagcagag ggagcccag agtctctcct gggagtctct ccagttcatt     120
catgcactag gcatttgctt taaaagaatg aaagaacatt ggtgaaaagg tcagaagggc     180
tcagcctctg accttcctga agggagcctc caaacttacg ccattccttt tcttctttct     240
tccagctgca acattattcc tctgcaaaga tgattgtccc gggggaacag taacaggaaa     300
gcatcttccc ttgccctggg acttgggtct agggatttcc aacttgtctt ctctccctga     360
agcattaagg attntgggaa ggaggctttg taacctgaan ttctgtgt                  408

<210> SEQ ID NO 115
<211> LENGTH: 576
<212> TYPE: DNA
<213> ORGANISM: Homo sapiens

<400> SEQUENCE: 115
tcatatcagc actgtaaaac tctttattaa aaataataat aataatcaca ccagtacctg      60
ccagaataac ttccgcccac ttgcccacaa tccagggaat tcctatttag ggccgtggct     120
aatttgtgaa agaggccaag cctaagtttt taagaatgcc ttaatccagg gagattacac     180
tggtgggcca cagtactgcc accacacaga agttcaggtt acaagcctct tccagatcct     240
tatgcttcag ggagagaaga caagttggaa atccctagac ccagtccag ggcaaggaa      300 gatgctttcc tgttactgtt ccccaggac aatcatcttt gcaggaat aatgttgcag       360 cccagcagtc cttgtcatgc ccagcgtgtt ggaacaagtc taagctggtg ttttccccc     420 tgcggatcac tgtcacattc aggggcttcc ctcactgtgc tgcaccacac tgccaatgtt     480
atgcagtgac tggaagttct gggtgttcac agagccgaac tccacaatct catcatccac     540
ttgcagaccc gcgatgctgg gctgtggagc gggggc                               576

<210> SEQ ID NO 116
<211> LENGTH: 549
<212> TYPE: DNA
<213> ORGANISM: Homo sapiens
<220> FEATURE:
<221> NAME/KEY: misc_feature
<222> LOCATION: (21)..(21)
<223> OTHER INFORMATION: n can be any nucleotide
<220> FEATURE:
<221> NAME/KEY: misc_feature
<222> LOCATION: (23)..(23)
<223> OTHER INFORMATION: n can be any nucleotide
<220> FEATURE:
<221> NAME/KEY: misc_feature
<222> LOCATION: (29)..(29)
<223> OTHER INFORMATION: n can be any nucleotide
<220> FEATURE:
<221> NAME/KEY: misc_feature
<222> LOCATION: (33)..(33)
<223> OTHER INFORMATION: n can be any nucleotide
<220> FEATURE:
<221> NAME/KEY: misc_feature
<222> LOCATION: (73)..(73)
<223> OTHER INFORMATION: n can be any nucleotide
<220> FEATURE:
<221> NAME/KEY: misc_feature
<222> LOCATION: (75)..(75)
<223> OTHER INFORMATION: n can be any nucleotide
<220> FEATURE:
<221> NAME/KEY: misc_feature
<222> LOCATION: (93)..(93)
<223> OTHER INFORMATION: n can be any nucleotide
<220> FEATURE:
<221> NAME/KEY: misc_feature
<222> LOCATION: (106)..(106)
```

```
<223> OTHER INFORMATION: n can be any nucleotide
<220> FEATURE:
<221> NAME/KEY: misc_feature
<222> LOCATION: (134)..(134)
<223> OTHER INFORMATION: n can be any nucleotide
<220> FEATURE:
<221> NAME/KEY: misc_feature
<222> LOCATION: (142)..(142)
<223> OTHER INFORMATION: n can be any nucleotide
<220> FEATURE:
<221> NAME/KEY: misc_feature
<222> LOCATION: (158)..(158)
<223> OTHER INFORMATION: n can be any nucleotide
<220> FEATURE:
<221> NAME/KEY: misc_feature
<222> LOCATION: (159)..(159)
<223> OTHER INFORMATION: n can be any nucleotide
<220> FEATURE:
<221> NAME/KEY: misc_feature
<222> LOCATION: (160)..(160)
<223> OTHER INFORMATION: n can be any nucleotide
<220> FEATURE:
<221> NAME/KEY: misc_feature
<222> LOCATION: (198)..(198)
<223> OTHER INFORMATION: n can be any nucleotide
<220> FEATURE:
<221> NAME/KEY: misc_feature
<222> LOCATION: (264)..(264)
<223> OTHER INFORMATION: n can be any nucleotide
<220> FEATURE:
<221> NAME/KEY: misc_feature
<222> LOCATION: (352)..(352)
<223> OTHER INFORMATION: n can be any nucleotide
<220> FEATURE:
<221> NAME/KEY: misc_feature
<222> LOCATION: (382)..(382)
<223> OTHER INFORMATION: n can be any nucleotide
<220> FEATURE:
<221> NAME/KEY: misc_feature
<222> LOCATION: (416)..(416)
<223> OTHER INFORMATION: n can be any nucleotide
<220> FEATURE:
<221> NAME/KEY: misc_feature
<222> LOCATION: (426)..(426)
<223> OTHER INFORMATION: n can be any nucleotide
<220> FEATURE:
<221> NAME/KEY: misc_feature
<222> LOCATION: (461)..(461)
<223> OTHER INFORMATION: n can be any nucleotide
<220> FEATURE:
<221> NAME/KEY: misc_feature
<222> LOCATION: (472)..(472)
<223> OTHER INFORMATION: n can be any nucleotide
<220> FEATURE:
<221> NAME/KEY: misc_feature
<222> LOCATION: (483)..(483)
<223> OTHER INFORMATION: n can be any nucleotide
<220> FEATURE:
<221> NAME/KEY: misc_feature
<222> LOCATION: (496)..(496)
<223> OTHER INFORMATION: n can be any nucleotide
<220> FEATURE:
<221> NAME/KEY: misc_feature
<222> LOCATION: (515)..(515)
<223> OTHER INFORMATION: n can be any nucleotide
<220> FEATURE:
<221> NAME/KEY: misc_feature
<222> LOCATION: (522)..(522)
<223> OTHER INFORMATION: n can be any nucleotide

<400> SEQUENCE: 116
ggctccccag ccagcatcgg ngntttgcna gtngatgatg agattgtgga gttcggctct     60
gtgaacaccc agnanttcca gtcactgcat aanattggca gtgtgntgca gcacagtgag    120
gggtagcccc tgantgtgac antgatccgc aggggganrn acaccagctt agacttgttc    180
caacacgctg ggcagganaa ggactgctgg gctgcaacat tattcctctg caaagatgat    240
```

```
tgtccctggg gaacagtaac aggnaagcat cttcccttgc cctggacttg ggtctaggga      300
tttccaactt gtcttctctc cctgaagcat aaggttctgg aagaggcttg tnacctgaac      360
ttctgtgtgg tggcagtact gnggcccacc agtgtaatct ccctggatta aggcantctt      420
aaaacntagg cttggctctt tcacaaatta ggccacggcc naaataggaa tnccctggat      480
tgngggcaag tgggcngaag tagctggcag ggacnggggg anatatatat tttataaaga      540
gttacaggc                                                              549

<210> SEQ ID NO 117
<211> LENGTH: 550
<212> TYPE: DNA
<213> ORGANISM: Homo sapiens
<220> FEATURE:
<221> NAME/KEY: misc_feature
<222> LOCATION: (474)..(474)
<223> OTHER INFORMATION: n can be any nucleotide
<220> FEATURE:
<221> NAME/KEY: misc_feature
<222> LOCATION: (480)..(480)
<223> OTHER INFORMATION: n can be any nucleotide
<220> FEATURE:
<221> NAME/KEY: misc_feature
<222> LOCATION: (525)..(525)
<223> OTHER INFORMATION: n can be any nucleotide
<220> FEATURE:
<221> NAME/KEY: misc_feature
<222> LOCATION: (532)..(532)
<223> OTHER INFORMATION: n can be any nucleotide
<220> FEATURE:
<221> NAME/KEY: misc_feature
<222> LOCATION: (533)..(533)
<223> OTHER INFORMATION: n can be any nucleotide
<220> FEATURE:
<221> NAME/KEY: misc_feature
<222> LOCATION: (543)..(543)
<223> OTHER INFORMATION: n can be any nucleotide
<220> FEATURE:
<221> NAME/KEY: misc_feature
<222> LOCATION: (544)..(544)
<223> OTHER INFORMATION: n can be any nucleotide

<400> SEQUENCE: 117
catatcagca ctgtaaaact ctttattaaa aataataata ataatcacac cagtacctgc      60
cagaataact tccgcccact tgcccacaat ccagggaatt cctatttagg gccgtggcta     120
atttgtgaaa gaggccaagc ctaagttttt aagaatgcct taatccaggg agattacact     180
ggtgggccac agtactgcca ccacacagaa gttcaggtta caagcctctt ccagatcctt     240
atgcttcagg gagagaagac aagttggaaa tccctagacc caagtccagg gcaagggaag     300
atgctttcct gttactgttc cccagggaca atcatctttg cagaggaata atgttgcagc     360
ccagcagtcc ttttcctgcc cagcgtgttg gaacaagtct aagctggtgt ttttccccc      420 tgcggatcac tgtcacattc agggcttcc cctcactgtg gctgcaccaa ctgncaatgn      480
tatgcagtga ctggaaattc tgggtgtcaa agggcccgaa tccanaattt annatcccct    540 tgnngaaccc                                                            550

<210> SEQ ID NO 118
<211> LENGTH: 366
<212> TYPE: DNA
<213> ORGANISM: Homo sapiens

<400> SEQUENCE: 118
caacacgctg ggcaggaaaa ggactgctgg gctgcaacat tattcctctg caaagatgat      60
```

```
tgtccctggg gaacagtaac aggaaagcat cttcccttgc cctggacttg ggtctaggga    120
tttccaactt gtcttctctc cctgaagcat aaggatctgg aagaggcttg taacctgaac    180
ttctgtgtgg tggcagtact gtggcccacc agtgtaatct ccctggatta aggcattctt    240
aaaaacttag gcttggctct ttcacaaatt aggccacggc ctaaatagga attccctgga    300
ttgtgggcaa gtgggcggaa gttattctgg caggtactgg tgtgattagt attattattt    360
ttaata                                                                366
```

<210> SEQ ID NO 119
<211> LENGTH: 504
<212> TYPE: DNA
<213> ORGANISM: Homo sapiens
<220> FEATURE:
<221> NAME/KEY: misc_feature
<222> LOCATION: (454)..(454)
<223> OTHER INFORMATION: n can be any nucleotide
<220> FEATURE:
<221> NAME/KEY: misc_feature
<222> LOCATION: (481)..(481)
<223> OTHER INFORMATION: n can be any nucleotide

<400> SEQUENCE: 119

```
ttttcatatc agcactgtaa aactctttat taaaaataat aataataatc acaccagtac    60
ctgccagaat aacttccgcc cacttgccca caatccaggg aattcctatt tagggccgtg   120
gcctaatttg tgaaagaggc caagcctaag ttttttaagaa tgccttaatc cagggagatt   180
acactggtgg gccacagtac tgccaccaca cagaagttca ggttacaagc ctcttccaga   240
tccttatgct tcagggagag aagacaagtt ggaaatccct agacccaagt ccagggcaag   300
ggaagatgct ttcctgttac tgttccccag ggacaatcat ctttgcagag gaataatgtt   360
gcagcccagc agtccttttc ctgccagccg tgttggaaca agtctagctg ggtgttttcc   420
cccctggcgg atcactgtca cattcagggg cttnccctca ctgtgctgca ccacactgcc   480
natgtattgc agtattggga agtc                                          504
```

<210> SEQ ID NO 120
<211> LENGTH: 417
<212> TYPE: DNA
<213> ORGANISM: Homo sapiens
<220> FEATURE:
<221> NAME/KEY: misc_feature
<222> LOCATION: (341)..(341)
<223> OTHER INFORMATION: n can be any nucleotide
<220> FEATURE:
<221> NAME/KEY: misc_feature
<222> LOCATION: (407)..(407)
<223> OTHER INFORMATION: n can be any nucleotide

<400> SEQUENCE: 120

```
gtggagttcg gctctgtgaa cacccagaac ttccagtcac tgcataacat tggcagtgtg    60
gtgcagcaca gtgaggggaa gcccctgaat gtgacgtga tccgcagggg gaaaaacacc    120
agcttagact tgttccaaca cgctgggcag gaaaaggact gctgggctgc aacattattc    180
ctctgcaaag atgattgtcc ctggggaaca gtaacaggaa agcatcttcc cttgccctgg    240
gacttgggtc tagggattt ccaacttgtc tttctctccc tggaaggcat taaggatctg    300
ggaaggaggg tttgttaacc tggaactttc ttgtgtgggt nggcagttac tgtgggcccc    360
accagtgtta attttccctg ggggtttaag ggcattttttt aaaaaantta gggtttg     417
```

<210> SEQ ID NO 121
<211> LENGTH: 370

```
<212> TYPE: DNA
<213> ORGANISM: Homo sapiens
<220> FEATURE:
<221> NAME/KEY: misc_feature
<222> LOCATION: (99)..(99)
<223> OTHER INFORMATION: n can be any nucleotide
<220> FEATURE:
<221> NAME/KEY: misc_feature
<222> LOCATION: (122)..(122)
<223> OTHER INFORMATION: n can be any nucleotide
<220> FEATURE:
<221> NAME/KEY: misc_feature
<222> LOCATION: (123)..(123)
<223> OTHER INFORMATION: n can be any nucleotide
<220> FEATURE:
<221> NAME/KEY: misc_feature
<222> LOCATION: (157)..(157)
<223> OTHER INFORMATION: n can be any nucleotide

<400> SEQUENCE: 121
tcatatcagc actgtaaaac tctttattaa aaataataat aataatcaca ccagtacctg      60
ccagaataac ttccgcccac ttgcccacaa tccagggant tcctatttag ggccgtggct     120
anntttgtga aagaggccaa gcctaagttt ttaagantgc cttaatccag gggagattac     180
actgggtggg gccacagtac tgccaccaca caggaagttc agggttacaa ggcctcttcc     240
agatccttat gcttcagggg agaggaagga caagttggga aatccctagg acccaagtcc     300
gggggcaagg ggaaggatgc ttttcctgtt tactgtttcc ccgggggac aattcatctt      360 ttggcaggag                                                             370

<210> SEQ ID NO 122
<211> LENGTH: 303
<212> TYPE: DNA
<213> ORGANISM: Homo sapiens

<400> SEQUENCE: 122 ttttcatat cagcactgta aaactcttta ttaaaataa taataataat cacaccagta        60
cctgccagaa taacttccgc ccacttgccc acaatccagg gaattcctat ttagggccgt     120
ggcataattt gtgaaagagg ccaagcctaa gttttttaaga atgccttaat ccagggagat    180
tacactggtg ggccacagta ctgccaccac acagaagttc aggttacaag cctcttccag     240
atccttatgc ttcagggaga agacaagt tggaaatccc tagacccaag tccagggcaa       300
ggg                                                                    303

<210> SEQ ID NO 123
<211> LENGTH: 286
<212> TYPE: DNA
<213> ORGANISM: Homo sapiens

<400> SEQUENCE: 123
catatcagca ctgtaaaact ctttattaaa aataataata ataatcacac cagtacctgc      60
cagaataact tccgcccact tgcccacaat ccagggaatt cctatttagg gccgtggcct     120
aatttgtgaa agaggccaag cctaagtttt taagaatgcc ttaatccagg gagattacac     180
tggtgggcca cagtactgcc accacacaga agttcaggtt acaagcctct tccagatcct     240
tatgcttcag ggagagaaga caagttggaa atccctaacc caagtc                    286

<210> SEQ ID NO 124
<211> LENGTH: 411
<212> TYPE: DNA
<213> ORGANISM: Homo sapiens
<220> FEATURE:
```

```
<221> NAME/KEY: misc_feature
<222> LOCATION: (18)..(18)
<223> OTHER INFORMATION: n can be any nucleotide

<400> SEQUENCE: 124 ttttttttttt tttttttncc aaatcagcac tgtaaaactc tttattaaaa ataataataa      60
taatcacacc agtacctgcc agaataactt ccgcccactt gcccacaatc cagggaattc      120
ctatttaggg ccgtggccta atttgtgaaa gaggccaagc ctaagttttt aagaatgcct      180
taatccaggg agattacact ggtgggccac agtactgcca ccacacagaa gttcaggtta      240
caagcctctt ccagatcctt atgcttcagg gagagaagac aagttggaaa tccctagacc      300
caagtccagg gcaagggaag atgctttcct gttactgttc cccagggaca atcatctttg      360
cagaggaata atgttgcagc ccagcagtcc ttttcctgcc cagcgtgttg g                411

<210> SEQ ID NO 125
<211> LENGTH: 398
<212> TYPE: DNA
<213> ORGANISM: Homo sapiens

<400> SEQUENCE: 125
tttttttcat atcagcactg taaaactctt tattaaaaat aataataata atcacaccag      60
tacctgccag aataacttcc gcccacttgc ccacaatcca gggaattcct atttagggcc      120
gtggctcaat ttgtgaaaga ggccaagcct aagttttaa gaatgcctta atccagggag      180
attacactgg tgggccacag tactgccacc acacagaagt tcaggttaca agcctcttcc      240
agatccttat gcttcaggga gaagacaa gttggaaatc cctagaccca gtccagggc      300 aagggaagat gctttcctgt tactgttccc agggacaatc atctttgcag aggaataatg      360
ttgcagccca gcagtccttt tcctgcccag cgtgttgg                              398

<210> SEQ ID NO 126
<211> LENGTH: 597
<212> TYPE: DNA
<213> ORGANISM: Homo sapiens
<220> FEATURE:
<221> NAME/KEY: misc_feature
<222> LOCATION: (573)..(573)
<223> OTHER INFORMATION: n can be any nucleotide
<220> FEATURE:
<221> NAME/KEY: misc_feature
<222> LOCATION: (584)..(584)
<223> OTHER INFORMATION: n can be any nucleotide
<220> FEATURE:
<221> NAME/KEY: misc_feature
<222> LOCATION: (591)..(591)
<223> OTHER INFORMATION: n can be any nucleotide

<400> SEQUENCE: 126
tcagcactgt taaactctt tattaaaaat aataataatg tatcacacca gtacctgcca      60
gaataacttc cgcccacttg cccacaatcc agggaattcc tatttagggc cgtggctaa      120 tttgtgaaaa aggccaagcc taagttttta aaatgcctt aatccaggga gattacactg      180
gtgggccaca gtactgccac cacacagaag ttcaggttac aagcctcttc cagatcctta      240
tgctttaggg agagaagaca agttggaaat ccctagaccc aagtccaggg caagggaaga      300
tgctttcctg ttactgttcc ccaggacaa tcatctttgc agaggaataa tgttgcagcc      360
cagcagtcct tttcctgccc agcgtgttgg aacaagtcta agctggtgtt ttcccccct       420 gcggatcact gtcacattca ggggcttccc ctcactgtgc tgcaccacac tgccaatgtt      480
atgcagtgac tggaagttct gggtgttcac agagccgaac tccacaatct catcatccac      540
```
ttgcagaccc gcgatgcttg cttgggagcc ggngctgatg ctgntcactt ntgcgaa        597

<210> SEQ ID NO 127
<211> LENGTH: 448
<212> TYPE: DNA
<213> ORGANISM: Homo sapiens
<220> FEATURE:
<221> NAME/KEY: misc_feature
<222> LOCATION: (137)..(137)
<223> OTHER INFORMATION: n can be any nucleotide
<220> FEATURE:
<221> NAME/KEY: misc_feature
<222> LOCATION: (402)..(402)
<223> OTHER INFORMATION: n can be any nucleotide
<220> FEATURE:
<221> NAME/KEY: misc_feature
<222> LOCATION: (438)..(438)
<223> OTHER INFORMATION: n can be any nucleotide
<220> FEATURE:
<221> NAME/KEY: misc_feature
<222> LOCATION: (447)..(447)
<223> OTHER INFORMATION: n can be any nucleotide

<400> SEQUENCE: 127
tttttttttt tttttttttt atcagcactg taaaactctt tattaaaaat aataataata     60
atcacaccag tacctgccag ataaacttcc gcccacttgc ccacaatcca gggaattcct    120
atttagggcc gtggctnaat ttgtgaaaga ggccaagcct aagttttaa gaatgcctta    180 atccagggag attacactgg tgggccacag tactgccacc acacaggaag ttcaggttac    240
aagcctcttc cagatcctta tgcttcaggg agagaagaca agttgggaaa tccctaggac    300
ccaagtccag gggcaaggga agatgctttc ctgttactgt ttccccgggg acaatcatct    360
ttgcagaggg aataatgttg gcagcccagc agttcctttt tnctggccca gcgttttgg    420 gaacaagttt aaggtggngt tttttcnc                                      448

<210> SEQ ID NO 128
<211> LENGTH: 323
<212> TYPE: DNA
<213> ORGANISM: Homo sapiens

<400> SEQUENCE: 128
tgaacaccca gaacttccag tcactgcata acattggcag tgtggtgcag cacagtgagg     60
ggaagcccct gaatgtgaca gtgatccgca gggggaaaaa caccagctta gacttgttcc    120
aacacgctgg gcaggaaaag gactgctggg ctgcaacatt attcctctgc aaagatgatt    180
gtccctgggg aacagtaaca ggaaagcatc ttcccttgcc ctggacttgg gtctagggat    240
ttccaacttg tcttctctcc ctgaagcata aggatctgga agaggcttgt aacctgaact    300
tctgtgtggt ggcagtactg tgg                                           323

<210> SEQ ID NO 129
<211> LENGTH: 484
<212> TYPE: DNA
<213> ORGANISM: Homo sapiens

<400> SEQUENCE: 129
tttttttttt ttttttttta tatcagcact gtaaaactct ttattaaaaa taataataat     60
aatcacacca gtacctgcca gaataacttc cgcccacttg cccacaatcc agggaattcc    120
tatttagggc cgtggcctaa tttgtgaaag aggccaagcc taagtttta agaatgcctt    180 aatccaggga gattacactg gtgggccaca gtactgccac cacacagaag ttcaggttac    240

```
aagcctcttc cagatcctta tgcttcaggg agagaagaca agttggaaat ccctagaccc    300
aagtccaggg caagggaaga tgctttcctg ttactgttcc ccaggacaa  tcatctttgc    360 agaggaataa tgttgcagcc cagcagtcct tttcctgccc agcgtgttgg aacaagtcta    420
agctggtgtt tttcccccct gcggatcact gtcacattca ggggcttccc ctcactgtgc    480
tgca                                                                 484
```

<210> SEQ ID NO 130
<211> LENGTH: 628
<212> TYPE: DNA
<213> ORGANISM: Homo sapiens

<400> SEQUENCE: 130

```
tattaaaata taacataatc atacagtact gcagaataac ttccgcccac tgccacaatc     60
caggaattcc tatttagggc cgtgcgctaa tttgtgaaag aggccaagcc taagcttta    120 agaatgcctt aatccaggga gattacactg gtgggccaca gtactgccac cacacagaag   180
ttcaggttac aagcctcttc cagatcctta tgcttcaggg agagaagaca agttggaaat   240
ccctagaccc aagtccaggg caagggaaga tgctttcctg ttactgttcc ccaggacaa    300 tcatctttgc agaggaataa tgttgcagcc cagcagtcct tttcctgccc agcgtgttgg   360
aacaagtcta agctggtgtt tttcccccct gcggatcact gtcacattca ggggcttccc   420
ctcactgtgc tgcaccacac tgccaatgtt atgcagtgac tggaagttct gggtgttcac   480
agagccgaac tccacaatct catcatccac ttgcagaccc gcgatgctgg ctggggagcc   540
ggggctgatg ctgttcactt tggcgaaggc ccgtggaggg cccggttctc attctgacac   600
gtttgcgtgg aaggggatct ctagagtg                                      628
```

<210> SEQ ID NO 131
<211> LENGTH: 314
<212> TYPE: DNA
<213> ORGANISM: Homo sapiens

<400> SEQUENCE: 131

```
tttttttttt ttttttttta tcagcactgg aaaactcttt attaaaaata ataataataa    60
tcacaccagg acctgccaga ataacttccg cccacttgcc cacaatccag ggaattccta   120
tttagggccg tggcctaatt tgtgaaagag gccaagccta agttttttaag aatgccttaa  180 tccagggaga ttacactggt gggccacagt actgccacca cacagaagtt caggttacaa   240
gcctcttcca gatccttatg cttcagggag agaagacaag ttggaaatcc ctagacccaa   300
gtccagggca aggg                                                     314
```

<210> SEQ ID NO 132
<211> LENGTH: 461
<212> TYPE: DNA
<213> ORGANISM: Homo sapiens
<220> FEATURE:
<221> NAME/KEY: misc_feature
<222> LOCATION: (16)..(16)
<223> OTHER INFORMATION: n can be any nucleotide
<220> FEATURE:
<221> NAME/KEY: misc_feature
<222> LOCATION: (56)..(56)
<223> OTHER INFORMATION: n can be any nucleotide
<220> FEATURE:
<221> NAME/KEY: misc_feature
<222> LOCATION: (129)..(129)
<223> OTHER INFORMATION: n can be any nucleotide
<220> FEATURE:
<221> NAME/KEY: misc_feature
<222> LOCATION: (149)..(149)
<223> OTHER INFORMATION: n can be any nucleotide
<220> FEATURE:
<221> NAME/KEY: misc_feature
<222> LOCATION: (174)..(174)
<223> OTHER INFORMATION: n can be any nucleotide
<220> FEATURE:
<221> NAME/KEY: misc_feature
<222> LOCATION: (185)..(185)
<223> OTHER INFORMATION: n can be any nucleotide
<220> FEATURE:
<221> NAME/KEY: misc_feature
<222> LOCATION: (392)..(392)
<223> OTHER INFORMATION: n can be any nucleotide
<220> FEATURE:
<221> NAME/KEY: misc_feature
<222> LOCATION: (430)..(430)
<223> OTHER INFORMATION: n can be any nucleotide
<220> FEATURE:
<221> NAME/KEY: misc_feature
<222> LOCATION: (452)..(452)
<223> OTHER INFORMATION: n can be any nucleotide
<220> FEATURE:
<221> NAME/KEY: misc_feature
<222> LOCATION: (460)..(460)
<223> OTHER INFORMATION: n can be any nucleotide

<400> SEQUENCE: 132

| | | | | | |
|---|---|---|---|---|---|
| tttcatatca | gcactntaaa | actctttatt | aaaaataata | ataataatca | caccantacc | 60 |
| tgccagaata | acttccgccc | acttgcccac | aatccaggga | attcctattt | agggccgtgg | 120 |
| ctaaattnt | gaaagaggcc | aagcctaant | ttttaagaat | gccttaatcc | aggnagatta | 180 |
| cactngtggg | ccacagtact | gccaccacac | agaagttcag | gttacaagcc | tcttccagat | 240 |
| ccttatgctt | cagggagaga | agacaagttg | gaaatcccta | gacccaagtc | cagggcaagg | 300 |
| gaagatgctt | tcctgttact | tgttccccag | ggacaatcat | ctttgcagag | gaataatgtt | 360 |
| gcagcccagc | agtccttttc | ctgcccagct | tnttggaaca | agtctaagct | ggtgttttc | 420 |
| ccccctgcgn | atcactgtca | cattcagggg | cntccctcan | a | | 461 |

<210> SEQ ID NO 133
<211> LENGTH: 325
<212> TYPE: DNA
<213> ORGANISM: Homo sapiens

<400> SEQUENCE: 133

| | | | | | |
|---|---|---|---|---|---|
| catatcagca | ctgtaaaact | ctttattaaa | aataataata | ataatcacac | cagtacctgc | 60 |
| cagaataact | tccgcccact | tgcccacaat | ccagggaatt | cctatttagg | ccgtggcct | 120 |
| aatttgtgaa | agaggccaag | cctaagtttt | taagaatgcc | ttaatccagg | gagattacac | 180 |
| tggtgggcca | cagtactgcc | accacacaga | agttcaggtt | acaagcctct | tccagatcct | 240 |
| tatgcttcag | ggagagaaga | caagttggaa | atccctagac | ccaagtccag | ggcaagggaa | 300 |
| gatgctttcc | tgttactgtt | cccca | | | | 325 |

<210> SEQ ID NO 134
<211> LENGTH: 295
<212> TYPE: DNA
<213> ORGANISM: Homo sapiens

<400> SEQUENCE: 134

| | | | | | |
|---|---|---|---|---|---|
| tttttttttt | tttccatat | cagcactgta | aaactcttta | ttaaaaataa | taataataat | 60 |
| cacaccagta | cctgccaaaa | taacttccgc | ccacttgccc | acaatccagg | gaattcctat | 120 |
| ttagggccgg | ggcctaattt | gggaaagagg | ccaagcctaa | gttttaaga | atgccttaat | 180 |

```
ccagggagat tacactgggg ggccacagta ctgccaccac acaaaagttc aggttacaag    240
cctcttccag atccttatgc ttcagggaga aagacaagt tggaaatccc tagac          295

<210> SEQ ID NO 135
<211> LENGTH: 527
<212> TYPE: DNA
<213> ORGANISM: Homo sapiens

<400> SEQUENCE: 135
ggggtctaca agtggatgat gagattgtgg agtccggctc tgtgaacaac cagaacttcc     60
agtcactgca ttacattggc agtgtggtgc agcacagtga ggggaagccc ctgaatgtga   120
cagtgatccg caggggggaa aaacaccagc ttagacttgt tccaacacgc cgggcaggaa   180
aaggactgct gggctgcaac attattcctc tgcaaagatg attggccctg ggaacagta    240 acaggaaagc atcttccctt gccctggact tgggtctagg gatttccaac ttgtcttctc   300
tccctgaagc ataaggatct ggaagaggct tggtaactga acttctgtgt ggtggcagta   360
ctgtggccca ccagtgtaat ctccctggat taaggcattc ttaaaaactt aggcttggcc   420
tctttcacaa attaggccac ggccctaaat aggaattccc tggattgtgg gcaagtgggc   480
ggaagttata ctggcaggta ctggtgtgat tattattatt atgttca                 527

<210> SEQ ID NO 136
<211> LENGTH: 159
<212> TYPE: DNA
<213> ORGANISM: Homo sapiens
<220> FEATURE:
<221> NAME/KEY: misc_feature
<222> LOCATION: (32)..(32)
<223> OTHER INFORMATION: n can be any nucleotide
<220> FEATURE:
<221> NAME/KEY: misc_feature
<222> LOCATION: (63)..(63)
<223> OTHER INFORMATION: n can be any nucleotide
<220> FEATURE:
<221> NAME/KEY: misc_feature
<222> LOCATION: (79)..(79)
<223> OTHER INFORMATION: n can be any nucleotide

<400> SEQUENCE: 136
ttgttccaac acgctgggca ggaaaaggac tnctgggctg caacattatt cctctgcaaa    60
gangattgtc cctggggganc agtaacagga aagcatcttc ccttgccctg gacttgggtc  120
tagggatttc caacttgtct tctctcccctt aagcataag                          159

<210> SEQ ID NO 137
<211> LENGTH: 641
<212> TYPE: DNA
<213> ORGANISM: Homo sapiens

<400> SEQUENCE: 137
gggtcagagt gagagccagg ccctcgaggg ccttcgccaa agtgaacagc atcagccccg     60
gctccccagc cagcatcgcg ggtctgcaag tggatgatga gattgtggag ttcggctctg   120
tgaacaccca gaacttccag tcactgcata acattggcag tgtggtgcag cacagggagg   180
ggaagcccct gaatgtgaca gtgatccgca gggggggaaa acaccagctt agacttgttc   240
caacacgctg gcaggaaaaa ggactgctgg gctgcaacat tattcctctg caaagatgat   300
tgtccctggg gaacagtaac aggaaagcat cttcccttgc cctggacttg gtctaggga   360 tttccaactt gtcttctctc cctgaagcat aaggatctgg aagaggcttg taacctgaac   420
ttctgtgtgg tggcagtact gtggcccacc agtgtaatct ccctggatta aggcattctt   480
```

```
aaaaacttag gcttggcctc tttcacaaat taggccacgg cctaaatagg aatccctgga    540
ttgtgggcaa gtgggcggaa gtatcctggc aggtacggtg tgatatcatc atcatcttaa    600
taagaagttg gtgcatgaac cgattccaca actggcgccg t                         641

<210> SEQ ID NO 138
<211> LENGTH: 586
<212> TYPE: DNA
<213> ORGANISM: Homo sapiens

<400> SEQUENCE: 138
gaaccagtac ctgccagaat aacttccgcc cacgtgccca caatccagga attcctattt     60
agggccgtgg cctaatgtgt gaaagaggcc aagcctaagt ttttaagaat gccttaatcc    120
agtgagatta cactggtggg ccacagtact gccaccacac agaagttcag gttacaagcc    180
tcttccagat cctatgcttc agggagaga agacaagttg gaaatcccta gacccaagtc     240
cagggcaagg gaagatgctt tcctgttact gttccccagg acaatcatc tttgcagagg      300 aataatgttg cagcccagca gtccttttcc tgcccagcgt gttggaacaa gtctaagctg    360 gtgttttttcc cccctgcgga tcactgtcac attcaggggc ttcccctcac tgtgctgcac    420
cacactgcca atgttatgca gtgactggaa gttctgggtg ttcacagagc cgaactccac    480
aatctcatca tccacttgca gacccgcgat gctggctggg gagccggggc tgatgctgtt    540
cactttggcg aaggcccgtg gagggccctg gctctcactc tgaccc                    586

<210> SEQ ID NO 139
<211> LENGTH: 116
<212> TYPE: DNA
<213> ORGANISM: Homo sapiens

<400> SEQUENCE: 139
atatcagcac tgtaaaactc tttattaaaa ataataataa taatcacacc agtacctgcc     60
agaataactt ccgcccactt gcccacaatc cagggaattc ctatttaggg ccgtgg         116

<210> SEQ ID NO 140
<211> LENGTH: 283
<212> TYPE: DNA
<213> ORGANISM: Homo sapiens

<400> SEQUENCE: 140
tcatatcagc actgtaaaac tctttattaa aaataataat aataatcaca ccagtacctg     60
ccagaataac ttccgcccac ttgcccacaa tccagggaat tcctatttag gccgtggcc     120 taatttgtga agaggccaa gcctaagttt ttaagaatgc cttaatccag ggagattaca     180
ctggtgggcc acagtactgc caccacacag aagttcaggt tacaagcctc ttccagatcc    240
ttatgcttca gggagagaag acaagttgga aatccctaga ccc                       283

<210> SEQ ID NO 141
<211> LENGTH: 332
<212> TYPE: DNA
<213> ORGANISM: Homo sapiens

<400> SEQUENCE: 141
catatcagca ctgtaaaact ctttattaaa aataataata ataatcacac cagtacctgc     60
cagaataact tccgcccact tgcccacaat ccagggaatt cctatttagg gccgtggcct    120
aatttgtgaa agaggccaag cctaagtttt taagaatgcc ttaatccagg gagattacac    180
```

```
tggtgggcca cagtactgcc accacacaga agttcaggtt acaagcctct tccagatcct    240
tatgcttcag ggagagaaga caagttggaa atccctagac ccaagtccag ggcaagggaa    300
gatgctttcc tgttactgtt ccccagggac aa                                  332
```

<210> SEQ ID NO 142
<211> LENGTH: 456
<212> TYPE: DNA
<213> ORGANISM: Homo sapiens
<220> FEATURE:
<221> NAME/KEY: misc_feature
<222> LOCATION: (1)..(1)
<223> OTHER INFORMATION: n can be any nucleotide

<400> SEQUENCE: 142

```
ncatatcagc actgtaaaac tctttattaa aaataataat aataatcaca ccagtacctg     60
ccagaataac ttccgcccac ttgcccacaa tccagggaat tcctatttag ggccgtggct    120
aatttgtgaa agaggccaag cctaagtttt taagaatcgc cttaatccag ggagattaca    180
ctggtgggcc acagtactgc caccacacag aagttcaggt tacaagcctc ttccagatcc    240
ttatgcttca gggagagaag acaagttgga aatccctaga cccaagtcca gggcaaggga    300
agatgctttc ctgttactgt tccccaggga caatcatctt tggcagagga ataatgttgc    360
agcccagcag tccttttcct ggcccagcgt gttggaacaa gtctaagctg gtgttttccc    420
cccctggcgg atcactggtc acattcaggg ggcttc                              456
```

<210> SEQ ID NO 143
<211> LENGTH: 493
<212> TYPE: DNA
<213> ORGANISM: Homo sapiens

<400> SEQUENCE: 143

```
cccagaactt ccagtcactg cataacattg gcagtgtggt gcagcacagt gaggggaagc     60
ccctgaatgt gacagtgatc cgcagggcgg aaaaacacca gcttagactt gttccaacac    120
gctgggcagg aaaaggactg ctgggctgca acattattcc tctgcaaaga tgattgtccc    180
tggggaacag taacaggaaa gcatcttccc ttgccctgga cttgggtcta gggatttcca    240
acttgtcttc tctccctgaa gcataaggat ctggaagagg cttgtaacct gaacttctgt    300
gtggtggcag tactgtggcc caccagtgta atctccctgg attaaggcat tcttaaaaac    360
ttaggcttgg cctctttcac aaattaggcc acggctctaa ataggaattc cctggattgt    420
gggcaagtgg gcggaagtta ttctggcagg tactggtgtg attattatta ttatttttaa    480
taaagagttt tac                                                       493
```

<210> SEQ ID NO 144
<211> LENGTH: 598
<212> TYPE: DNA
<213> ORGANISM: Homo sapiens

<400> SEQUENCE: 144

```
cctggtggcg aattcggcac gaggcatggg cggagccgta gttacggtcg actgggcgt      60 cgtccctatc ccgggagccg ggtctctgga gtcgcggccc ggggttcacg atgtccgacg    120
aggaagcgag gcagagcgga ggctcctcgc aggccgcgct cgtgactgtc agcgacgtcc    180
aggagctgat gcggcgcaag gaggagatag aagcgcagat caaggccaac tatgacgtgc    240
tggaaagcca aaaaggcatt gggatgaacg agccgctggt ggactgtgag ggctacccccc   300 ggtcagacgt ggacctgtac caagtccgca ccgccaggca caacatcata tgcctgcaga    360
```

```
atgatcacaa ggcagtgatg aagcaggtgg aggaggccct gcaccagctg cacgctcgcg    420
acaaggagaa gcaggcccgg acatggctg aggcccacaa agaggccatg agccgcaaac    480
tgggtcagag tgagagccag ggccctccac ggtccttcgc caaagtgaac agcatcagcc    540
ccggctcccc agccagcatc gcgggtctgc aagtggatga tgagattgtg gagttcgg     598
```

<210> SEQ ID NO 145
<211> LENGTH: 539
<212> TYPE: DNA
<213> ORGANISM: Homo sapiens
<220> FEATURE:
<221> NAME/KEY: misc_feature
<222> LOCATION: (354)..(354)
<223> OTHER INFORMATION: n can be any nucleotide
<220> FEATURE:
<221> NAME/KEY: misc_feature
<222> LOCATION: (474)..(474)
<223> OTHER INFORMATION: n can be any nucleotide
<220> FEATURE:
<221> NAME/KEY: misc_feature
<222> LOCATION: (536)..(536)
<223> OTHER INFORMATION: n can be any nucleotide

<400> SEQUENCE: 145

```
gaagcgcaga tcaaggccaa ctatgacgtg ctggaaacca aaaaggcatt gggatgaacg     60
agccgctggt ggactgtgag ggctaccccc ggtcagacgt ggacctgtac caagtccgca    120
ccgccaggca acatcata tgcctgcaga atgatcacaa ggcagtgatg aagcaggtgg     180
aggaggccct gcaccagctg cacgctcgcg acaaggagaa gcaggcccgg acatggctg    240 aggcccacaa agaggccatg agccgcaaac tgggtcagag tgagagccag ggccctccac    300
gggccttcgc caaagtgaac agcatcagcc ccggctcccc agccagcatc gcgngtctgc    360
aagtggatga tgagattgtg gagttcggct ctgtgaacac ccagaacttc cagtcactgc    420
ataacattgg cagtgtggtg cagcacagtg aaggggaagc ccctgaatgt gacnagtgat    480
tccgcagggg ggaaaaaaca ccagctttag acttggttcc aaaaacgctt gggcanttg    539
```

<210> SEQ ID NO 146
<211> LENGTH: 293
<212> TYPE: DNA
<213> ORGANISM: Homo sapiens

<400> SEQUENCE: 146

```
gcggctacgc gtgactgtca gcgacgtcca ggagctgatg cggcgcaagg aggagataga     60
agcgcagatc aaggccaact atgacgtgct ggaaagccaa aaaggcattg ggatgaacga    120
gccgctggtg gactgtgagg gctaccccg gtcagacgtg gacctgtacc aagtccgcac    180
cgccaggcac aacatcatat gcctgcagaa tgctcacaag gcagtgatga attaggtgga    240
ggaggccctg cacccagctg cacgctcgcg acaaggagaa cgcgtcaaaa tcg           293
```

<210> SEQ ID NO 147
<211> LENGTH: 438
<212> TYPE: DNA
<213> ORGANISM: Homo sapiens

<400> SEQUENCE: 147

```
catatcagca ctgtaaaaact ctttattaaa aataataata ataatcacac cagtacctgc     60
cagaataact tccgcccact tgcccacaat ccagggaatt cctatttagg gccgtggcta    120
atttgtgaaa gaggccaagc ctaagttttt aagaatgcct taatccaggg agattacact    180
```

```
ggtgggccac agtactgcca ccacacagaa gttcaggtta caagcctctt ccagatcctt      240
atgcttcagg gagagaagac aagttggaaa tccctagacc caagtccagg gcaagggaag      300
atgctttcct gttacttgtt ccccaggac aatcatcttt gcagaggaat aatgttgcag       360
cccagcagtc cttttcctgc ccagcgtgtt ggaacaagtc taagctggtg ttttccccc      420 ctggggatca ctgtcaca                                                    438

<210> SEQ ID NO 148
<211> LENGTH: 531
<212> TYPE: DNA
<213> ORGANISM: Homo sapiens

<400> SEQUENCE: 148
gtcaaacagg ggtccgagtg ataaaccagg cccctcgatt gacctgcgcc aaagtgaaca       60
gcatcagccc cggatcacca gccagcatcg cgagtctgca agtggataat gagatggtgg      120
agttcggctc agtgaacacc cagaactacc agtcactgaa taacattggc agtgtggtgc      180
agcacagtga ggggaagccc ctgaatgtga cagtgatccg caggggggaa aaacaccagc      240
ttagacttgt cccaagaggc tgggcaggac aaggactgct gggctgcaac attattcctc      300
tgcaaagatg attgtcccta gggaacagta acaggaaagc atcttccctt gcccaggact      360
tgggtctagg gattaccaac ttgtctactc tccctgaagc ataaggatct ggaagaggct      420
tgtaacctga acttctagtg tggtggcaga actgtggccc accagtgtaa tctccctgga      480
ttaaggcatt cttaacaaac ttaggcttgg cctctttcaa caaactaggc c              531

<210> SEQ ID NO 149
<211> LENGTH: 615
<212> TYPE: DNA
<213> ORGANISM: Homo sapiens

<400> SEQUENCE: 149
gggtcagagt gagagccagg ccctccacgg gccttcgcca aagtgaacag catcagcccc       60
ggctccccag ccagcatcgc gggtctgcaa gtggatgatg agattgtgga gttcggctct      120
gtgaacaccc agaacttcca gtcactgcat aacattggca gtgtggtgca gcacagtgag      180
gggaagcccc tgaatgtgac agtgatccgc aggggggaaa acaccagct tagacttgtt      240 ccaacacgct gggcaggaaa aggactgctg ggctgcaaca ttattcctct gcaaagatga      300
ttgtccctgg gaacagtaa caggaaagca tcttcccttg ccctggactt gggtctaggg      360
atttccaact tgtcttctct ccctgaagca taaggatctg gaagaggctt gtaacctgaa      420
cttctgtgtg gtggcagtac tgtgcccac cagtgtaatc tccctggatt aaggcattct      480
taaaaactta ggcttggcct ctttcgcaaa ttaggccacg ccctaaata ggaattccct      540 ggattgtggg caagtgggcg gaagttattc tggcaggtac tggtgtgatt atcatcatca      600
tctttaataa agagt                                                       615

<210> SEQ ID NO 150
<211> LENGTH: 558
<212> TYPE: DNA
<213> ORGANISM: Homo sapiens
<220> FEATURE:
<221> NAME/KEY: misc_feature
<222> LOCATION: (19)..(19)
<223> OTHER INFORMATION: n can be any nucleotide
<220> FEATURE:
<221> NAME/KEY: misc_feature
<222> LOCATION: (24)..(24)
<223> OTHER INFORMATION: n can be any nucleotide
```

```
<220> FEATURE:
<221> NAME/KEY: misc_feature
<222> LOCATION: (377)..(377)
<223> OTHER INFORMATION: n can be any nucleotide
<220> FEATURE:
<221> NAME/KEY: misc_feature
<222> LOCATION: (404)..(404)
<223> OTHER INFORMATION: n can be any nucleotide
<220> FEATURE:
<221> NAME/KEY: misc_feature
<222> LOCATION: (473)..(473)
<223> OTHER INFORMATION: n can be any nucleotide
<220> FEATURE:
<221> NAME/KEY: misc_feature
<222> LOCATION: (484)..(484)
<223> OTHER INFORMATION: n can be any nucleotide
<220> FEATURE:
<221> NAME/KEY: misc_feature
<222> LOCATION: (513)..(513)
<223> OTHER INFORMATION: n can be any nucleotide
<220> FEATURE:
<221> NAME/KEY: misc_feature
<222> LOCATION: (550)..(550)
<223> OTHER INFORMATION: n can be any nucleotide
<220> FEATURE:
<221> NAME/KEY: misc_feature
<222> LOCATION: (557)..(557)
<223> OTHER INFORMATION: n can be any nucleotide

<400> SEQUENCE: 150
tgttttggcg catgggcgnc gtangtttac ggtcgactgg ggcgtcgtcc ctagcccggg       60
agccggtact ctggagtcgc ggcccggggt tcacgatgtc cgacgaggaa gcgaggcaga      120
gcggaggctc ctcgcaggcc ggcgccgtga ctgtcagcga cgtccaggag ctgatgcggc      180
gcaaggagga gatagaagcg cagatcaagg ccaactatga cgtgctggaa agccaaaaag      240
gcattgggat gaacgagccg ctggtggact gtgaggcta ccccccggtca gacgtggacc      300 tgtaccaagt ccgcaccgcc aggcacaaca ttcatatgcc tgcagaatga ttcacaaggc      360
agtgatggaa gcaggtngga ggaggccttg caccagttgc acgnttcgcg aacaaggaga      420
agcaggcccg ggacttggtt gaggcccaca agaggccttt gagccgcaaa ttnggttcag      480
attnagagcc agggcctttc acgggttttt cgncaaattg aacagctttta gccccgtttc      540 cccagccagn tttgggnt                                                    558

<210> SEQ ID NO 151
<211> LENGTH: 170
<212> TYPE: DNA
<213> ORGANISM: Homo sapiens
<220> FEATURE:
<221> NAME/KEY: misc_feature
<222> LOCATION: (19)..(19)
<223> OTHER INFORMATION: n can be any nucleotide
<220> FEATURE:
<221> NAME/KEY: misc_feature
<222> LOCATION: (87)..(87)
<223> OTHER INFORMATION: n can be any nucleotide
<220> FEATURE:
<221> NAME/KEY: misc_feature
<222> LOCATION: (92)..(92)
<223> OTHER INFORMATION: n can be any nucleotide
<220> FEATURE:
<221> NAME/KEY: misc_feature
<222> LOCATION: (118)..(118)
<223> OTHER INFORMATION: n can be any nucleotide
<220> FEATURE:
<221> NAME/KEY: misc_feature
<222> LOCATION: (141)..(141)
<223> OTHER INFORMATION: n can be any nucleotide
<220> FEATURE:
<221> NAME/KEY: misc_feature
<222> LOCATION: (156)..(156)
```

```
<223> OTHER INFORMATION: n can be any nucleotide
<220> FEATURE:
<221> NAME/KEY: misc_feature
<222> LOCATION: (158)..(158)
<223> OTHER INFORMATION: n can be any nucleotide
<220> FEATURE:
<221> NAME/KEY: misc_feature
<222> LOCATION: (166)..(166)
<223> OTHER INFORMATION: n can be any nucleotide

<400> SEQUENCE: 151
gatctggaag aggcttgtna cctgaacttc tgtgtggtgg cagtactgtg gcccaccagt      60
gtaatctccc tggattaagg cattctnaaa ancttaggct tggcctcttt cacaaatnag    120
gccacggcct aaataggaat nccctggatt gtgggnangt gggcgnaagt                170

<210> SEQ ID NO 152
<211> LENGTH: 587
<212> TYPE: DNA
<213> ORGANISM: Homo sapiens

<400> SEQUENCE: 152
atcagcactg taaaactctt tattaaaaat aataataata atcacaccag tacctgccag      60
aataacttcc gcccacttgc ccacaatcca gggaattcct atttagggcc gtggcctaat    120
ttgtgaaaga ggccaagcct aagttttttaa gaatgcctta atccagggag attacactgg    180
tgggccacag tactgccacc acacagaagt tcaggttaca agcctcttcc agatccttat    240
gcttcaggga gagaagacaa gttggaaatc cctagaccca agtccagggc aagggaagat    300
gctttcctgt tactgttccc cagggacaat catctttgca gaggaataat gttgcagccc    360
agcagtcctt ttcctgccca gcgtgttgga acaagtctaa gctggtgttt ttccccctg     420 cggatcactg tcacattcag gggcttcccc tcactgtgct gcaccacact gccaatgtta    480
tgcagtgact ggaagttctg ggtgttcaca gagccgaact ccacaatctc atcatccact    540
tgcagacccg cgatgctggc tggggagccc gggctgatgc tgttcac                    587

<210> SEQ ID NO 153
<211> LENGTH: 477
<212> TYPE: DNA
<213> ORGANISM: Homo sapiens

<400> SEQUENCE: 153 ttttttcat atcagcactg taaaactctt tattaaaaat aataataata atcacaccag      60
tacctgccag aataacttcc gcccacttgc ccacaatcca gggaattcct atttagggcc    120
gtggctaatt tgtgaaaga ggccaagcct aagttttttaa gaatgcctta atccagggag    180
attacactgg tgggccacag tactgccacc acacagaagt tcaggttaca agcctcttcc    240
agatccttat gcttcaggga gagaagacaa gttggaaatc cctagaccca agtccagggc    300
aagggaagat gctttcctgt tactgttccc cagggacaat catctttgca gaggaataat    360
gttgcagccc agcagtcctt ttcctgccca gcgtgttgga acaagtctaa gctggtgttt    420 ttccccctg cggatcactg tcacattcag gggcttcccc tcactgtgct gcaccac        477

<210> SEQ ID NO 154
<211> LENGTH: 2360
<212> TYPE: DNA
<213> ORGANISM: Homo sapiens
<220> FEATURE:
<221> NAME/KEY: CDS
<222> LOCATION: (118)..(789)
```

<400> SEQUENCE: 154

```
cgcgttcgcg gacggctgtg gtgttttggc gcatgggcgg agccgtagtt acggtcgact      60
ggggcgtcgt ccctagcccg ggagccgggt ctctggagtc gcggcccggg gttcacg        117
```

| | | | | | | | | | | | | | | | | |
|---|---|---|---|---|---|---|---|---|---|---|---|---|---|---|---|---|
| atg | tcc | gac | gag | gaa | gcg | agg | cag | agc | gga | ggc | tcc | tcg | cag | gcc | ggc | 165 |
| Met | Ser | Asp | Glu | Glu | Ala | Arg | Gln | Ser | Gly | Gly | Ser | Ser | Gln | Ala | Gly | |
| 1 | | | | 5 | | | | | 10 | | | | | 15 | | |
| gtc | gtg | act | gtc | agc | gac | gtc | cag | gag | ctg | atg | cgg | cgc | aag | gag | gag | 213 |
| Val | Val | Thr | Val | Ser | Asp | Val | Gln | Glu | Leu | Met | Arg | Arg | Lys | Glu | Glu | |
| | | | 20 | | | | | 25 | | | | | 30 | | | |
| ata | gaa | gcg | cag | atc | aag | gcc | aac | tat | gac | gtg | ctg | gaa | agc | caa | aaa | 261 |
| Ile | Glu | Ala | Gln | Ile | Lys | Ala | Asn | Tyr | Asp | Val | Leu | Glu | Ser | Gln | Lys | |
| | 35 | | | | | 40 | | | | | 45 | | | | | |
| ggc | att | ggg | atg | aac | gag | ccg | ctg | gtg | gac | tgt | gag | ggc | tac | ccc | cgg | 309 |
| Gly | Ile | Gly | Met | Asn | Glu | Pro | Leu | Val | Asp | Cys | Glu | Gly | Tyr | Pro | Arg | |
| 50 | | | | | 55 | | | | | 60 | | | | | | |
| tca | gac | gtg | gac | ctg | tac | caa | gtc | cgc | acc | gcc | agg | cac | aac | atc | ata | 357 |
| Ser | Asp | Val | Asp | Leu | Tyr | Gln | Val | Arg | Thr | Ala | Arg | His | Asn | Ile | Ile | |
| 65 | | | | | 70 | | | | | 75 | | | | | 80 | |
| tgc | ctg | cag | aat | gat | cac | aag | gca | gtg | atg | aag | cag | gtg | gag | gag | gcc | 405 |
| Cys | Leu | Gln | Asn | Asp | His | Lys | Ala | Val | Met | Lys | Gln | Val | Glu | Glu | Ala | |
| | | | | 85 | | | | | 90 | | | | | 95 | | |
| ctg | cac | cag | ctg | cac | gct | cgc | gac | aag | gag | aag | cag | gcc | cgg | gac | atg | 453 |
| Leu | His | Gln | Leu | His | Ala | Arg | Asp | Lys | Glu | Lys | Gln | Ala | Arg | Asp | Met | |
| | | 100 | | | | | 105 | | | | | 110 | | | | |
| gct | gag | gcc | cac | aaa | gag | gcc | atg | agc | cgc | aaa | ctg | ggt | cag | agt | gag | 501 |
| Ala | Glu | Ala | His | Lys | Glu | Ala | Met | Ser | Arg | Lys | Leu | Gly | Gln | Ser | Glu | |
| | | | 115 | | | | | 120 | | | | | 125 | | | |
| agc | cag | ggc | cct | cca | cgg | gcc | ttc | gcc | aaa | gtg | aac | agc | atc | agc | ccc | 549 |
| Ser | Gln | Gly | Pro | Pro | Arg | Ala | Phe | Ala | Lys | Val | Asn | Ser | Ile | Ser | Pro | |
| | 130 | | | | | 135 | | | | | 140 | | | | | |
| ggc | tcc | cca | gcc | agc | atc | gcg | ggt | ctg | caa | gtg | gat | gat | gag | att | gtg | 597 |
| Gly | Ser | Pro | Ala | Ser | Ile | Ala | Gly | Leu | Gln | Val | Asp | Asp | Glu | Ile | Val | |
| 145 | | | | | 150 | | | | | 155 | | | | | 160 | |
| gag | ttc | ggc | tct | gtg | aac | acc | cag | aac | ttc | cag | tca | ctg | cat | aac | att | 645 |
| Glu | Phe | Gly | Ser | Val | Asn | Thr | Gln | Asn | Phe | Gln | Ser | Leu | His | Asn | Ile | |
| | | | | 165 | | | | | 170 | | | | | 175 | | |
| ggc | agt | gtg | gtg | cag | cac | agt | gag | ggg | aag | ccc | ctg | aat | gtg | aca | gtg | 693 |
| Gly | Ser | Val | Val | Gln | His | Ser | Glu | Gly | Lys | Pro | Leu | Asn | Val | Thr | Val | |
| | | | 180 | | | | | 185 | | | | | 190 | | | |
| atc | cgc | agg | ggg | gaa | aaa | cac | cag | ctt | aga | ctt | gtt | cca | aca | cgc | tgg | 741 |
| Ile | Arg | Arg | Gly | Glu | Lys | His | Gln | Leu | Arg | Leu | Val | Pro | Thr | Arg | Trp | |
| | 195 | | | | | 200 | | | | | 205 | | | | | |
| gca | gga | aaa | gga | ctg | ctg | ggc | tgc | aac | att | att | cct | ctg | caa | aga | tga | 789 |
| Ala | Gly | Lys | Gly | Leu | Leu | Gly | Cys | Asn | Ile | Ile | Pro | Leu | Gln | Arg | | |
| 210 | | | | | 215 | | | | | 220 | | | | | | |

```
ttgtccctgg ggaacagtaa caggaaagca tcttcccttg ccctggactt gggtctaggg      849
atttccaact tgtcttctct ccctgaagca taaggatctg gaagaggctt gtaacctgaa      909
cttctgtgtg gtggcagtac tgtggcccac cagtgtaatc tccctggatt aaggcattct      969
taaaaactta ggcttggcct ctttcacaaa ttaggccacg gccctaaata ggaattcccct     1029 ggattgtggg caagtgggcg gaagttattc tggcaggtac tggtgtgatt attattatta     1089
tttttaataa agagttttac agtgctgata tgaccctgtt gtcacccag ctgaatttct      1149 tatgacccctc ccaaaccaaa gctcagatgg ggtcagaaga gcttcataga aagttgggca     1209
aaacaggcta gcaattgcaa agtcaggctt tgaccaacat atttctttgc actgaggcct     1269
tgctgctgtg gatacggaaa tggttaagta ctgtgcttcc tcagcagctg ggctgtcagg     1329
```

-continued

```
gccatagtag ctcccttttgg agaacaggga aagcctggag gcttcccagg tggcccagcg   1389
tggtgtcctg tcagcttcct ctttaggaac ccaccagagg gcagcaagct cctttcactt   1449
cgctagtaag aacccctccg tttttgtgtg ttttttgttt tgttttctgg agacaaggtc   1509
ttgctttgtc acccaggctg gagtgcagtg tcgtgatcaa ggttcactga agccttgacg   1569
ctgtgggcac tgcctcagcc gcccaagtat ctgggaccac aggcgtgcac caccatgcat   1629
agctaattta ttttttgtag agacagggtc tccctgtgtt gaccaggttg gtctcgaact   1689
cctgggctca agcagtcctc ctgccttggc ctcctaaagt gctgggatca caggcgtgag   1749
ccactgcgcc cagcccactg ctagtttgac tttttataat tgaacctcct ggctatgccc   1809
tgagatcagc gctattttgt aaaccgctga ggtatggata ggaacgagta gatcagacct   1869
cttgaaaatg cttattcttc ctccctttta tttttttgtct cttttaagat ggtaaaatgg   1929
ttctcaggga ttcctgccaa tactttgaat tatttttttcc tctccatggt atcagtgttc   1989
atttccccag ttcttgcaca ccgctttctg ttttggcagt tctgccaggc aagccctgtg   2049
ttccttggga ctggttttgc tgtggttgga tacagatacc agcttgcctt gatgggattg   2109
gtattgctgt gtgcttccag ccacaggttc tcacactcaa ttccaaagcc ttcctattgg   2169
gcgaattccc tcaaactcta tttgacctga cagccatacg tattcccctc tggtagccac   2229
agacatgctg tgtttaccaa tgtttgctgt ttaaattgca tgttctaatt ccacgtattt   2289
tccagtctct tttataaagt ctcagactat aataaacaca gcttgcccag tttaaaaaaa   2349
aaaaaaaaaa a                                                        2360
```

<210> SEQ ID NO 155
<211> LENGTH: 223
<212> TYPE: PRT
<213> ORGANISM: Homo sapiens

<400> SEQUENCE: 155

```
Met Ser Asp Glu Glu Ala Arg Gln Ser Gly Gly Ser Ser Gln Ala Gly
1               5                   10                  15

Val Val Thr Val Ser Asp Val Gln Glu Leu Met Arg Arg Lys Glu Glu
            20                  25                  30

Ile Glu Ala Gln Ile Lys Ala Asn Tyr Asp Val Leu Glu Ser Gln Lys
        35                  40                  45

Gly Ile Gly Met Asn Glu Pro Leu Val Asp Cys Glu Gly Tyr Pro Arg
    50                  55                  60

Ser Asp Val Asp Leu Tyr Gln Val Arg Thr Ala Arg His Asn Ile Ile
65                  70                  75                  80

Cys Leu Gln Asn Asp His Lys Ala Val Met Lys Gln Val Glu Glu Ala
                85                  90                  95

Leu His Gln Leu His Ala Arg Asp Lys Glu Lys Gln Ala Arg Asp Met
            100                 105                 110

Ala Glu Ala His Lys Glu Ala Met Ser Arg Lys Leu Gly Gln Ser Glu
        115                 120                 125

Ser Gln Gly Pro Pro Arg Ala Phe Ala Lys Val Asn Ser Ile Ser Pro
    130                 135                 140

Gly Ser Pro Ala Ser Ile Ala Gly Leu Gln Val Asp Asp Glu Ile Val
145                 150                 155                 160

Glu Phe Gly Ser Val Asn Thr Gln Asn Phe Gln Ser Leu His Asn Ile
                165                 170                 175

Gly Ser Val Val Gln His Ser Glu Gly Lys Pro Leu Asn Val Thr Val
```

```
                180             185             190
Ile Arg Arg Gly Glu Lys His Gln Leu Arg Leu Val Pro Thr Arg Trp
        195                 200                 205
Ala Gly Lys Gly Leu Leu Gly Cys Asn Ile Ile Pro Leu Gln Arg
    210                 215                 220
```

<210> SEQ ID NO 156
<211> LENGTH: 31
<212> TYPE: DNA
<213> ORGANISM: Rattus sp.

<400> SEQUENCE: 156
tggatgatga aattccggag ttcggctctg t            31

<210> SEQ ID NO 157
<211> LENGTH: 31
<212> TYPE: DNA
<213> ORGANISM: Rattus sp.

<400> SEQUENCE: 157
tggagttcgg ctctccgaac acccaaaact t            31

<210> SEQ ID NO 158
<211> LENGTH: 31
<212> TYPE: DNA
<213> ORGANISM: Rattus sp.

<400> SEQUENCE: 158
agtctctgca gaacccgggc actgtggtgc a            31

<210> SEQ ID NO 159
<211> LENGTH: 30
<212> TYPE: DNA
<213> ORGANISM: Rattus sp.

<400> SEQUENCE: 159
cctgcaagtg gatcctgaaa ttgtggagtt              30

<210> SEQ ID NO 160
<211> LENGTH: 31
<212> TYPE: DNA
<213> ORGANISM: Rattus sp.

<400> SEQUENCE: 160
agccagtatt gcgcccctgc aagtggatga t            31

<210> SEQ ID NO 161
<211> LENGTH: 31
<212> TYPE: DNA
<213> ORGANISM: Rattus sp.

<400> SEQUENCE: 161
ggatttgtat caggtctgaa cagcaaggca c            31

<210> SEQ ID NO 162
<211> LENGTH: 32
<212> TYPE: DNA
<213> ORGANISM: Rattus sp.

<400> SEQUENCE: 162
cagtcccgcc ctaccctagg cctttgccag ag           32

```
<210> SEQ ID NO 163
<211> LENGTH: 30
<212> TYPE: DNA
<213> ORGANISM: Rattus sp.

<400> SEQUENCE: 163
cctgcaagtg gatcctgaaa ttgtggagtt                                      30

<210> SEQ ID NO 164
<211> LENGTH: 30325
<212> TYPE: DNA
<213> ORGANISM: Homo sapiens

<400> SEQUENCE: 164
actgttaccg ttattattat cactacgatt tttagaggcc ttaacaggaa catccagcac     60
cttcaacagt atatggctca taggaatcat tccatgaata tttgttagca gaaggacagc    120
tctatgagat agattgctat caattactgc cccattttac agatgaggaa actgaggccc    180
agagaagcca agtagtgacc tagggtcaca cagattgccg ttaagtggca agatacgggg    240
tgtgtactca ggcatatcgg atctgtaaag tgagggataa ggaaccttaa tgtattttgt    300
aaatcctcca gggctgtgtg gatgtgaaga actgaattgg agcgccacgc agcggttctc    360
tggcgtacag tatccatcca tacagtaggc gctcaataaa tgtctgctgc acgaatgaga    420
aaatgagtca gctggggcga gatcatcccc tagcgttggt gtgcaattgc gtggggatcc    480
attgcttccg acgctactcc tgccgggtca ccacaggcgc acgtgttccg gcagggcgcg    540
gcttccggtg acccagctcc gccctaagcc ccatcccaag ccccgcccct tgactgttct    600
cgcgttcgcg gacggctgtg gtgttttggc gcatgggcgg agccgtagtt acggtcgact    660
ggggcgtcgt ccctagcccg ggagccgggt ctctggagtc gcggcccggg gttcacgatg    720
tccgacgagg aagcgaggca gagcggaggc tcctcgcagg ccggcgtcgt gactgtcagc    780
gacgtccagg agctgatgcg gcgcaaggag gagatagaag cgcagatcaa ggccaactat    840
gacgtgctgg aaagcgtgag tgtgggttcg gggcgcccca agtcgcctaa cccggcccgg    900
agtccctggg gtactgggat gccagggcgg cctcagtttg ggcgctccgc aacggatctc    960
cctgggaggc ccaaggcgcc gcaagtgcgg cctctgtcgg cacaagaagg caggcaaaga   1020
actttagcaa ctgaagagtt agccatattg atatccagca agagtttgtg gagccctgct   1080
gtgtgctagg cgctggttta agtgctgtgc attgttgagt taatttaatc tttgcaacaa   1140 cccttttgagg tggatgctgt tactctttcc attttaggga gggggaaaca ggtgttactt   1200
ggtgattaaa cagctgtcat gtgcctcgct gactgcctta tcttaatttt gtacttttg    1260 taaagacaga gtctcactgt gttgcccagg ttggtatcga actcatggcc tcaagcgatc   1320
cttccacctc ggcctttcaa agtgctggga ttacaggcgt gagctactgc acccggcatt   1380
tgctgattgt atcgtgaatt cttaaacttc agtgtgtata tgaattacct ggggatctta   1440
ttaaaatgca gattttgttt gaggcaaggg agcagattct gcatttgtag caaactccca   1500
gcaatgctga tgctagtggt ctaaggaccg aactttgagt tacaaataag gctcatcatc   1560
cttattgcat aaggaggaaa ctgaggccca gagtggggca aacgcctatc taaggtcatg   1620
tagttcggaa gtgcagtggt gggtctggc tcaaaagctg atgcaggttt tcttatgcca    1680
tctagtgtaa aatcacagat cagtttgcag aggaagatgc aattaattat gcccaagtag   1740
ggtgggatgg aatgcatttt aggtgatgta agatgaagtt tcttttttttt ttgtctgaga   1800 cggagtcttg ctttgtcacc caggctggag tgcagtggct caatctcggc tcactgcagc   1860
```

```
ctctgcctcc tgggttcaag tgattctcct gcctcagcct cccgagtagt agggattaca    1920
ggcgagcgcc agtacgccag gctaattttt tattttaagt aaaagcaggg tttcaccatg    1980
ttggtcaggc cggtgttgga ttcctgacct caggtgatcc gcccaccttg gcctccccaa    2040
gtgctgggat tacaggcgtg agccaccgcg tccggccata agatgaagtt tcatacggag    2100
ggccagagaa ccattttact gggtgctgac tatatgctca aagtgggatt cagacttcag    2160
gtctgttaca ttcagaacct gtgctttcaa gcaaattacc agcaatttct caaactttag    2220
tttactttct accacatgca gtatactata tgcatatacc acttgtgtta ttcctttgat    2280
atttttattt aaatagatct acttttaatc ttatataaat gtattattat tgttattatt    2340
attattgaga cagggtctcg ctctgttgcc caggctggag ttcagtggca ccatcttggt    2400
tcactgcagc ctcaatctcc tggtgtcaag caatcctccc acctcagcct cccaagtagc    2460
tgagactgca ggtacgtgcc accacgccca gctaattttt gtattttttg tagctatggg    2520
gtctcactat gttgcttgct cagactggtc tgaaactcct gggctcaagc agtcctcctg    2580
cctctgcctc ccaaagtgtt ggggttacag gcatgagcca cagtgccttg cccataaatg    2640
tattttaaaa ggaaatttca aaactccgct gcatatggaa aatgataatc tcttctctta    2700
aatataaggt cagatgcttt gcatgttgat acggcatgtt ggttgcttct ggctagctgc    2760
tgttgcttgc tgaaagcttt cagcctgaaa ccgtgctcta tatttgtttt taaaaagtgg    2820
gtttgggccg ggctggtgg ctcacgcctg taatcccagc actttgggag gccaaggtgg    2880
gtggatcacc tgaggccagg atggtctcga tctcctgacc tcgtgatccg cccgcctcgg    2940
cctcccaaag tgctgggatt acaggcttga gccaccgcgc aggcctaca aaaattttt    3000 ttaaaaatta gttgggcgtg gtggtgcatg cctgtagtcc tagctacttg ggaggctgag    3060
gcaggaggat tgcttgaacc ctgaatgttg aggctgcagg gagctataat tgcaccactg    3120
cactctcttg tgggtgacag agtgagatgc tgtctcttta aaaaaaaaaa aaaaaaaaag    3180
gccgggtgcg gtggctcatg cctctaatcc cagcactttg ggaggccgag gcgggcggat    3240
cacgaggtca ggagatcgag accatcctgg ctaacacagt gaaacccgt ctctactaaa    3300 aatacaaaaa attagctgga cgtggtggcc agcgcctgta gtcccagcta ctctggaggc    3360
tgaggcagga gaatggcctg aacccgggat gtggagcttg cagtgagcca agattgcgcc    3420
actgcacttc agcctgggtg acagagcgag actccgtctc aagaaaaaag aaaaaaaaaa    3480
aaaagactgg gcatggtggc tcacgtctgt aatcccagca ctttggaagg ccgaggtgtg    3540
tggatcgctt gaggtcagga gtccgagacc agcctggcca acatggtgaa accccgtctc    3600
aacgaaaaat acaaaaatta gccaggtgtg gtggtacaca tctataatcc cagctacccg    3660
ggaggctgat gcaagagaat cacttgaacc tgggaggcgg aggttgcagt gaaccaagac    3720
tgcaccacga cactccagcc tgggtgacag agattccatc tcaaaaaaaa aaaaaaaaaa    3780
aaaaagaagt ggacagctaa aactataaat ctcgtataat aaagcatagg agtaaatctt    3840
catgaccttg gattaggcaa agcctttta gatatggcac caaaacaca agctacaaaa    3900 gaaaaaatga taagttggac ttcaacttta aaactgtgtt tcaagggca tagtaaaatg    3960 aaaagataag ctccagaatg ggagaaaata tttgcatatc atttctctga taagaggata    4020
gtatctagac tataataaga gctcttacaa ctcaataata aaaagacagc caattagaag    4080
acagggaaag gatctgaata aacatttctc caaagaaaat atggtcaata caaatggtca    4140
atggccaggc gtggtggctc atgcctgtaa tcccaggact tgggagtct gaggcaggag    4200 gatcacttga ggccaggggt ttgagactag cctgggcaac acagtaagag cctatcttta    4260
```

```
caaaaaattc aaaattaaag gccgggcatg gtggctcatg cctgtaatcc cagcactttg    4320
ggaggccgag gctggcagat cacgaggtca ggagatcgag accatcctgg ttaacacggt    4380 gaaacccgt ctctactaaa aatacaaaaa aattagccgg gtgtggtggc agacgcctgt    4440
agtcccagct actcgggagg ctgaggcagg agaagggcct gaacccagga ggcggagctt    4500
gcagtgagcc aagatctcgc cactgtactc tagcctgggc aacagagcga gactctgtct    4560
ttaaaaaaaa aaaattaaaa attaaaaatt agccaggtgt gatgacatgt gcctgtggtc    4620
ccagctactt aggaggctga gacagatcgc ttgaacccag gagtttaagg cggcagtgag    4680
ctatgaacac accactgcac ccgatcctgg gcaacagaag atcttgtctc aaaccaatac    4740
aaacacaaaa gccattacct tttacacttt acatgggtca gttatatggt atctgaatta    4800
tatctcaata aaactgttat aaaaacagag ggtactagag atagcaagta actggggtgt    4860
tgcagagacc agcaccaaat ggacactttt gccttgacaa ttgcaggatt gtagagaatt    4920
gggagaggaa tatgtatttt tgattcaggg ttatttaatg ccgtgtgtgt gagctgctag    4980
tgttatggat cccatccttt gagaagcatt atccaatgtg atattgattc tcaaaggctg    5040 gtcaacccctt aaccactgtg ggaaggcagg agcagataca ggttttttagc ccctggcgca    5100 tttctgcagt gtcacggcga gtcctgtgtt aggggagtgt ggagaactat ctccctgcgc    5160
agtggacagt aggtttgggt gtaacccgga ggcttccaga gagaaaggga gcaaaatgaa    5220
tggaatccct cttctcagtg cctgtgtaca ctggcagctt gtccctggac tgactaatcc    5280
ttacagccac tatttatgac ttctgcgcgt agtcgttttc tgaggccacc ttaacaccac    5340
agagttggtg acttaaaaca ggaatttact ttgtcccagc tctggaggcc agaagtctga    5400
aatcaaggtg tcagcagggt tggctccttc tgcaggctct gagagagaag ctcccaagcc    5460
tttctcctgg cctctggtga ctgctggcgg tccttggcct acagctgtgt cacttgaacc    5520
tctgcctgca tcttcatgtg gccttcctcc tgtgtctgtc ccacacctac ctctgccttt    5580
cttttatgag gacaccagcc accagatgag cttatctcga gatccttaac ataattacat    5640
ctacaaagac tcttttttcaa ataaagtcat atttacaggt tctgggggtt agctcgtggt    5700 tatctgttttt tgggggccgc tcttcaaccc actatgctgt gtatgcgcgt ggcatgtgct    5760
aagtactctg caggtcagct cgttagttct tgcagcaggt agggagggag gcgagtgctc    5820
ctattcccat tttataattg aggaagctga ggcttagaga ggagaaggtc tcagctaagg    5880
atgcccagct tgtacatggc agagttgaga ttcaaattaa agtctaacca attgcaaagc    5940
ccctcccctg aaccatgtga ctggtttcac tgcttttgtg tactctcctc tgactcatgt    6000 taaaaaaaa aaagtgttg ttttgaataa agaatacatt cccataggca aaattcaaaa    6060
cctacagagg ggtataaaat ggactgtctc tctccctgcc ctgtcaccta gccacccagt    6120
tcttctcccc ggaggcagct ggtgctatca gtttccttct tcagatcttt ttattttcag    6180
aagaatcaaa gccctgccac agctgggtgc tgtctgggct tttcactccc ctctagcttc    6240
cagggccagc agccaggtgt cagccacctg tgggaaggag ggtgtgaagg agtggaggaa    6300
gaggctggcc ttggggatga tgctcaaagg agtctttggt tttatcggca ctgttttaac    6360
ttcaaaaaag aatggattca tgcattactt gcgtcgttaa aaataaaaaa tgaaaaacac    6420
agtgcccacc ccagggtagt tgtgagggca tgagtagagc ccctggtgta agtgatcagt    6480
atgtggcagt tttcattact gtcaccttta ttatgacttc agaggagaag ggtctgggga    6540
aagacatcct ggggacatta cacccatgag caccttttaa ccacgtttct ttcctccagc    6600
```

```
aaaaaggcat tgggatgaac gagccgctgg tggactgtga gggctacccc cggtcagacg    6660
tggacctgta ccaagtccgc accgccaggc acaacatcat atgtgagtgg ccctcttaga    6720
agactttccc caccttgtgg tgggaaggtg ttaaaggcat acaaataaaa ccaactatct    6780
gtattatcta ctgccttctc ttctgccttg atgggattgt cttgtcccca tccaaggact    6840
gagaaccaag ggaatgggct agactctaag gttctatatt tctggtttca ttttctctct    6900
ctctctctct ctcttttttt tttgagtcag ggtcttgctc tgtcttccag gctggagtgc    6960
agtggtgcta acatgactca ctgcagtctc aacccccag gctccaagtg ctccttctgc      7020
ctcagcctcc caagtagctg ggactatagg catgtgtcgc tgtgcctggc taatttttt      7080 tagtagagac gagtctcact aagtggccca ggtgagtctt gaactcctgg actcaagtgg    7140
tcctcctgcc ttggccttcc aaggtgctga ttgtttttaa ttaaagagct agcagagagt    7200
acagattgga tagtatattt gttttctgtt tctgccataa caaatgacgt gatttgtttt    7260
taattaaaga gctagcagag agtacagatt ggatagtata tttgtttctg tttctgccat    7320
aacaaatgac cacagactta gtagctggag ataagaagtc cagatgggtc tcactggact    7380
aaaatcaagg tgttggcagg gctggctcct tctggaggat ctaggggaga acctgttcct    7440
ggtcttttct ggtttccaaa ggctgcccac cgtccttggc tcatggcttc gtccatctac    7500
acagccagca gtcgcatttc cctccctctg attctgtcat aacatctctt tctctcactc    7560
tcctgcctcc ctctttcacc tataaagacc tctgtgatga caccaggccc acctggataa    7620
tccaggatca tgtccgaatc ttaaggtcct taatcacatc tgcagagcct cttttgccat    7680
gtaaggtggc atattcccag cttctagggg ctaggatgtg gatgtgttgg gggccattat    7740
ccactcagcc ataggtaggc aaccgtctcc accacagagt cctattagca tttatcctcc    7800
acatttttca cttactaact cctctttaat ctgtttgaat cttgattcca tctgcatcac    7860
atcttattta tttatttatt ttttgagacg gagtctcgct ctgtcaccca ggttggagtg    7920
cagtggcacg atcttggctc actgcaactt ccacctcccg agtgacagag caagagaccg    7980
tctcaaaaaa aaaaaaaaaa tctgtttgag caattcctta ttggtctttt tttgaaaaat    8040
ctgttctcgg ccgggtgcgg tggctcatgc ctgtaatccc agcactttgg gaagccaagg    8100
cgggcagatc acctgaggtc aggagtttga gtctagcctg accaacatgg caaaatcctg    8160
tctgtactaa aaatagaaaa attaactgga tgtggtggca catgcctgta attccagcta    8220
cttgggaggc tgagacagga gaatcacttg aacccaggag gcagaggttg caaagagccg    8280
agattacacc actgcactcc accctgggcg acagagcaaa caaaactctg tctcaaaaaa    8340
aagaaagaaa atctattctc aaaacagccc ttttaaaga acagttatag atttacataa     8400
aaattggaaa ataatggctg ggtgcggtgg ctcacgcctg taatcccagc acactgggag    8460
gccgaggtgg gcagatcacc tgaggtcggg agttcgagac cagcctgacc aacatggaga    8520
aaccctgtct ctactaaaaa tacaaaatta gctgggcatg gtggcacgaa cctgtaatcc    8580
cagctactca ggaggttgag gcaggagaat cacttgaacc caggaggcgg aggttgccgt    8640
gagccgagat tgtgccattg cactccagcc tgggcaacaa gagtgaaact ctgtctcaaa    8700
aaaaaaaaaa aaaagaaaag aaaaaaaaat tggaaaataa tgcataggtc ctttggcttc    8760
tgtatgtaat ctcccgtgtt gttaacagca tatatacaca tacatgtgta tatatctaca    8820
catacatgta aatatataca cacatacatg tgtatgtaaa atatacacat gcgtgtatat    8880
atgcaaaata cacatatgag tgaatgactc aggctgggtg taaccaagat ttcactttc     8940 tctgaaatcc tctagaagga aaaatgctgc ataagctggg cacagaggct catgcctgta    9000
```

```
atcccagcac tttgggaggc tgaggcctcc caaatatata cacatgtgta tacacacagg   9060
ttcaagtgat tctccagcct tagcttccca agtagctggg attacaggtg cccaccatca   9120
caccggacta attttttttt tttttttgag atggaatctt gcttagccac ctaggctgga   9180
gtgcagtggc atgatctcgg ctcactcact gcactcacca tctcccgggt tcaagtgatt   9240
ctcccatctc agcctcccaa gtagctgaga ttacaggcat ccgccatcgt gcccggctaa   9300 ttttttatatt ttagtagaga cagggtttca ccatgttggc caggctggtc ttgaactcct   9360
gacctcaggt gatccgcccg cctcggcctc gacaggcgtg agccaccatg cctggcctaa   9420 tttttttagta gtattttttt agtagagacg ggatttcacc atgttggcca ggctggtctc   9480
caactcctga cctcaggtga tccgcccgcc tcggcctcga caggcgtgag ccaccatgcc   9540
tggcctaatt ttttagtagt atttttttag tagagacggg atttcaccat gttggccagg   9600
ctggtctcga actcctgacc tcaggtgatc tgcccgcctc ggcctcgcaa agtgctggga   9660
ttacaggcat gagccaccgc gcccagctaa cagcttatgt taatatggta cgtttgttat   9720
aattgcaaat ttgttttttg aaatacactg cagaaacatt ttgtactgaa aaaaacccctt   9780 tcaacatttt gattagaatt gtaatatgtt gtaaatagtc gttcgttcca ttccccaaca   9840
gctgtgtatt gagcacttcc ctgtgccagg cattgcagag tctaggatg ctgtggacct     9900 cactggggga gggcttttct agtgaaagtg accatgtatt atgtaagtct gcctcccaag   9960
tgcatgtctc cacttgttca gatctgggtt cttttcccac atctgctcct gtgggttgag  10020
aacttgaatc ccttcatgac tgagggtctt gcctttgctc caaagtgaca gtggcagagg  10080
aggcaggtca ggtagtaccg caatcccact gacaggcaca aggtatcaaa ataccagctg  10140
ctgtgctggc gtggcctgca gattgccatg gtggttcaca acatttttgaa ttagctatct  10200 gtactgaaaa atcagagaat ttcacttcaa agatcccaat tttcagcttt ctggaaaaa   10260 tcaaagattt gtagcattg gtcttcctc ccaaacccag ccaattggca agagccctgt    10320
agcaggggtg ccctttggcc acctccctgt ggactccctc tcctggactg aatgtctcca  10380
ggattactag gcttatgcag cacttttttt ttttttttt gagacgaatt cttgctttgt   10440
cgccaggctg gagggcagtg gtgcgatctc ggctcactgc aacctccacc tcctgggttc   10500
aagtaattct cctgcttcag cctcccaagt agctgggatt acaggcaccc gccaccacgc   10560
ccagctaatt tttgtttttg ttttgtttg ttttgttttt gagacggagt cttgctctgt    10620
tgcccaggct agagtgcagt ggcgcgatct cggctcactg caatctccgc ctccctggtt   10680
cacgccaatc tcctgcctca gcctcccgag tagctgggac tacaggcgcc tgccatcatg   10740
cccggctaat ttttgtattt ttagtagaga cggggtttca ccgtgttagc caggatggtc   10800
tccatctcct gacctcgtga tccggccacc ttgacttccc aaagttctgg gattacaggc   10860
ctgagccacc acgctcggcc taatttttgt atttttagt agagacgggg tttcaccatg    10920
ttggcaaggt ggtcgcgatc tcttgacctc gtgatctgcc tgcctcggcc tcccacagtg   10980 ctggattac aggcgtgagc ctctgtgccc ggcttatgca gcattttcc ttctagagga     11040 tttcagagaa aagtgaaatc ttgattacac ccagcctgag tcattcattc acatgatcac  11100
agcgctggcc cctcatacat atgcctttga gttcatggct gtggattcag ctggttgtta   11160
ccttccttct gctcacctct cagggctcac ccgagacagc actgccttca ggaagccttc  11220
cctcatatcc tagactagcg agggcagact ttgctgctgg ccaggcctcc ctgcagtcat   11280
cagatgttat tgtaattact tattctggag ctgctccttg caggactgaa tgctccatga  11340
```

-continued

```
gggaatgtcc tctgtcttgg tcagagactc cttctcacct ctagctccac atctggcatg    11400
taataagcac ttgttaactc ttcagtgaat aaatgtagga gtcttgtgtc ctccactgtc    11460
ttccttggcc cctgatgtgt ggttctcatc ccaggcctgc agaatgatca caaggcagtg    11520
atgaagcagg tggaggaggc cctgcaccag ctgcacgctc gcgacaagga gaagcaggcc    11580
cgggacatgg ctgaggccca caaagaggcc atgagccgca aactgggtca gagtgagagc    11640
cagggccctc cacgggcctt cgccaaagtg aacagcatca gccccggctc cccagccagc    11700
atcgcggtaa tccaggggtt ggccactcaa gtccatgccc aggggacacg gtgggtcagg    11760
tagccttcgg ggatgtggaa agacagacta gttctctccg tgctgcggtg ctgagttcag    11820
ttactcattt aacaaacact gactgaggcc tgtcgtgtat ccagccctgt gctgggggca    11880
gagttttaga gaggggtcag ccccggctgc ccactacatt ggtggggggag tgacctcttc    11940 ccagtgacag aagatgataa atgtcccaag agagggagag gatctcttct tggggctcat    12000
tttagctggg cactgaatga tgaaaatgag aatggcatct tgccaaatga gttatgcatc    12060
ttatgtggtg tcttaaaaaa aacattaggc tgggcacagt ggctcatgcg tgtaatccca    12120
gcacttgaga aggctgaggc gacttggaaa gctgagatgg gaggatcact tgggctcagg    12180
aagtcgaagt tgcagtgagc tgtgactgtg ccactgcact ccagcctggg tgacagagtg    12240
agaccttgtc ttaaaaaaaa tttttttttg accgggagca ttggctcacg cctgtaatcc    12300
cagcatgttg ggaggccgag gccagtggat cacttgaggt caggagttcg agaccaacct    12360
ggccaacatg gcgaaacccc gtctctacta aaaatacgaa aatcatgcca ctgcactcca    12420
gcctgggcaa cagagtgaga ctccgtctca aaaaaaaaa aaaaatttac ccatttaaag    12480
tccgtataca gtttagtgtc ttttggtgta ttcacagagc catgcattac cacaatcaat    12540
tttctttcta tttaaaaaat ttgcagccag gtgcagtggc tcacgcctgt aatcccagca    12600 cttttgggagg cttaggtggg cgatcacctt atgtcaggag ttcaagacca gcctggccaa    12660
catggcgaaa ccccatctct actaaaaata caaacattag ccgggtgtgg tgacatgtgc    12720
ctgtaatccc agctactcgg gaggctgagg caggagaatc gcctgaaccc aggaggtgga    12780
ggttgcagtg agcggagatc gtgccactac actccagagc ctgggcgaca gagtgagact    12840
ctgtctaaaa aaaaaaaaaa aaaaaaagg agatgggggtt tcgctctgtt gcgtaggttg    12900
gtctccatct cctgggctca agtgattcta ccaccttggc ctcccaaaat gctgggatta    12960
taggcatgag ccaccatgcc cagccataat caatttcaga acattgtcat tgtcttgtaa    13020
agaaactctg tagtgatttg ccatcacttc ccaatccccc agctccccgc acccagttat    13080
ctactttctg tctctatgta tttgtctatt ctggatattt cctataagtt gaatcatata    13140
atatgtgacc ttttatgact ggcttctttc acttagcaaa ttttcaagtc atctgtattg    13200
agcatggatc agtgcttcat ttgtttacag acagggtctc actctctcac ccagacttca    13260
gtgccatggt gccatcatag ctcactgcaa cctcaaactc gcagagtcaa gtgatcctcc    13320
tgtctcagcc tcccaagcag ctaggactgt aggcacatgt aaccatgcct ggttaatttt    13380
ttatttcctt tttttttttag agatgggttc tcactatgtt gcccaggctg gtcttgaact    13440
cctggcctca agcgatcctt cttcctcggc ctcccaaagt gctagaatta caggcatgag    13500
ctgtcatgcc tggcccttca ttccttcttt tttttttttt ttttttttt ttttgagacg    13560 gagtctcgct ctgtcgccca ggctggagtg cagtggcacg atctcggctc actgcaagct    13620
ccgcctccca ggttcacgcc attcctctgc ctcatcctcc cgagtagctg ggactacagg    13680
cgcctgccat cacgtccagc taattttttat ttttttgtatt tttagtagag acagggtttc    13740
```

```
actttgttag ccagggtggt ctcgatctcc tgacctcgtg atccgcccgc ctcagcctcc   13800
caaagtgctg ggattacagg cgtgagccac tgtgcctggc ccttcattcc tttttatggc   13860
caaataatat tccactgcct ggatatatca tattttattt atccatttgt cagttaatgg   13920
acatttgaat tgttaccact ttttggctat tacgaagcat gttgctgcga acattcttgt   13980 acagttttt tgtggagatg tagttaaatt taattccaca gccacttctg ggataggtcc   14040
taatctttac tcatttcatc ctcgaggaaa agccttgcag acctgaagta acttatgtca   14100
ggacacatag ttcctgccag gtggaatggg gtcctaaacc ctggtcagga cacatagttc   14160
ctgccaggtg gaatggggtc ctaaaccctg gtcaggacac atagttcctg ccaggtggaa   14220
tggggtccta aaccctggtc ctaccagtct tctttaatgg tcacaagtct gtaagttaca   14280
cagaagctcc ctatcattca ctaccccatc tactgcatct aacccagtgc cagttggccc   14340
acaacaaata cttgttacag gggtgaatga gtggtggtct gtcttcttag gacctagaac   14400
aagagcgtca ctctagtctt ggatgcgccc tgtgcctgtg gctgcttgtc tgggggcttc   14460
tagggcaagt gtcttgtcta aatgttgatc actgaataaa atgggcccag cctggcttgc   14520
cttctcttac ccttgaacct gggttaggac cgcagagagc agcatttggc ctttcccatg   14580
ctcctcaagg ccttcacagt gtctggtaac tgccagctct cagacattgg gcagacctgg   14640
tcatctttac tagagctgcc ctcaaaggaa ccccaggagg aggtggcccc gttaccccact   14700 gccccttcct gcatgaggtg tctacatccc tgacctcttt gttctgagcc taccctgtag   14760
aaaacaagct cgtgaccttg gcattaaatt gggtattgaa ggttagagac caccaggagc   14820
acactgaacc tctagcctga ttttccattt ttccttccct ctccagggtc tgcaagtgga   14880
tgatgagatt gtggagttcg gctctgtgaa cacccagaac ttccagtcac tgcataacat   14940
tggcagtgtg gtgcagcaca gtgagggggt gagtggggct acctggtgtc tcggtctgtt   15000
tgggtttttc taacagtatg ccatagactg cgtggcttac aaacaacaga agttcatttt   15060
tcacagctct ggaggcaggg aagtccaaga tccaggcacc agccaatttg gtgtctgggg   15120
agggcttgct tcctaactcc taggtggtgc cttcttgctg tgtcctcaca tggcagaaag   15180
gggaggaacc ctgggagctc ttgtataagg gcactaatcc cagtgggggc gccaccctc   15240 atgacctaat caccttgcag aggccccacc cctaatacca tcacattggt ggttaggatt   15300
tcaacatatg aatttcaggg ggccacagac attcaggtca tagcactcgg cctctggtct   15360
atagccctgg agttactgga agtgttgctg aggccctgga ctgctgcctt catggtgttg   15420
ctcagcacag ccccattcaa ggacttggca cctgctattc cttctgttta gaatgctctt   15480
cctcttcatc ctccttctgt tttacactgg tgacatgctc gcaggggcc tttcctggct   15540 accctaaccc aaattcccct ctcctctgcc ctgtctctgt tttcatttaa caaggtttct   15600
tagagatctt ttcttttttt ttttttttt tttaagacag ggtcatgctg tgtcacccag   15660
gctagagtgt ggtggtgcta tcataactac ctcacggcta attttttat attttgtgga   15720 ggcgggtct tgctatgttg tccaggctgg aattttgtt gttgttttgt agcaaagatc   15780 cacactttc aggagtgata ctgtggcaaa gcccaggaaa attattaact aaagtttttg   15840
gttcccaaat gaagtctcca gttaacccaa cagttgtgga ttttttgact cctgcttagc   15900
tgcacggttc atctacttgt aacccatcag tgcaggccag gccaggtcag gtcaggagat   15960
ggctggcagt tgcctatgcc cctgctagtg gtcaggccat cgtttctgca ctgatactgt   16020
catcaaatct gtaacttgta tggacgttta aaatgatgat tttgtgaaat ttatcagttt   16080
```

```
ttttgcttat ggctcttgca ttttgtgtcc atttaaagaa attctttttt ttttttttaa   16140
ttaagaaatt cttggctggg cgtggtggct cactcctgta atcccagcac tttaggaggg   16200
cgaggtgggt ggatcacgaa gtcaggagtt ggagaccatc ctggctaaca cggtgaaacc   16260
ccgtctctac taaaaataca aaaaattagc cgggtgtggt ggcacacact tgtagtccca   16320
gttacttggg agactgagga aggagaatcg cttgaaccca ggaggcagag cttgcagtga   16380
gccgagatcg cgccattgca ctccagccta ggcgacagag caagactctg tctcaaaaaa   16440
agaaattctt ttaattcttt tattgtttta tttctgtttt tcctttagtc catctgaaat   16500
ttattattat tattattatt attattatta ttatttgaga tggagtctcg ctctgtcacc   16560
caggctggag tgcagtggtg cgatcttggc tcactgcaac ctccgcctcc caggttcaag   16620
tgattctcct gcctcagcct cctgagtagc tgggattaca ggcgcccacc accatgcctg   16680
gctaattttt gtattttttag tagagatggg gtttcgctat gttggccagg ctggtctcaa   16740
actggcctcc caaagtgctg ggactacaga tgtgagccac tgcgcctggt ctattttat   16800 tattttaca acagttttat tgagatttaa tgcacatact acacagttca cccatttaaa   16860
gtggttttta gtgtagtcac agaattatgc agccatcaca attgtacatt ttcatcactt   16920
ctcctcctga ggcagccact ttccagccac atgtccttca gaaagactgc tcatatacca   16980
gcacacagag ctgccagttg atttatttt attaaggtgt aatttacctg caccagatcc   17040 accttttca gtgtacagtc ccatgagttt tcttcttttt cttttctttt tttttttta    17100 gatggagtct tgctctgtcg cccaggctgg agtgcagtgg tgcagtctcg gggggctac    17160 tgcaagctct gcctcccagg ttcacgccat tctcctgcct cagcctcccg agtagctggg   17220
actacaggca tgtgccacca tgcccagcta attttttgt attttagta gagatggggt     17280 ttcactgtgt tagccaggat ggtctcgatc tcctgacctc gtgatccacc tgccttggcc   17340
tcccaaagtg ctgggattac aggtgtgagc caccacaccc agccgagttt cttttttttt   17400
ttctttaaga tggagttttg ctcttttgcc cagtctggag tgcagtggca cgatctcggc   17460
tcactgcaac ctctgcctcc caggttcaag cgattctcca gcctcagtct cccaagtagc   17520
tgggattata ggtgcccacc accacgccca gctaattttt ttttgtattt ttagtagaga   17580
cagggtttca gcatgttggc caggctggtc tcaaactcct aacctcaggt gatccaccca   17640
cctcagcctc ccaaagttct gggattacag gagtgagcca ctgtggcctg ccattcccgt   17700
gagttttcac aaatgtatgt agtatgtcat tgccaccacg atgaaggtca agagcattcc   17760 aacacccat aaaattgcct caggcttctt tgtagttaat ccctcaccgt caacttccag    17820
aatgtcatag agagaaaaac cacacaatat attgccttt gagtctggtg ttcttcactc    17880
agcccagtgg attctgagac ttctgtctgt tgtgtggatc tgtgagaaga gctgctggtt   17940
tttaatctgt tttatccagt taaatgtatt ctcagcttcc gtgtaggctt ataaatcctt   18000
ctttataaaa gtagtgattc aatttaagc aaaatgaatc ttttcttcat gtgaaatttc     18060
acggggaatt ccaagatgtc actggataaa ggctgagctg tcttggtggg ctggaggatg   18120
gagaaggtcg tgtgttgtga gtagggcctt tctggcttca gcctcatccc ctcagggac    18180 ctgagctcag ctggagaatc aagaatccgg gtttggttgt ctgttttgtg agtcaagaaa   18240
aaaaaccttg catagcacag tggctcacac ctgtaatccc agcactttgg gaggctgagg   18300
cgggtggatc acctgaggtc aggagttcaa gaccagcctg gccaacatgg tgaaacccca   18360
tctctactaa aaataagaaa ttaggcctgg cacggtggct cacacctgta atcccagcac   18420
tttaagaggc caaagtgggc agatcacaag gtcaagagat cgagaccatc ctgcccaaca   18480
```

```
tggtgaaaac cggtctctac taaaaataca aaaaaaaaaa aaaaattatc tgggtgtggt    18540
ggtgtgtgcc tgtagtccca gctacttggg ctgctgaggc aggagaatca cttgaacctc    18600
ggaggcagag gttgcagtga accaagatca cgccactgca ctccagcctg gccgcacag     18660 cgagactctc ccatctcaaa aaaaaaaaaa ttaggtgtgg tggtactctc cagctacttg    18720
ggaggccgag gcaggagaat tgcttgaacc cgggaggcag aggttgcagt gagcttagat    18780
catgccactg caccctagcc tgggcgacag agtgaggctc tgtgtcaaaa aaaaaaaaaa    18840
aaccaaaaaa ctcacagtgt tctattgtga gacatttaga tagtttgcca tttttgtggag   18900 attaacactc ttgcagatgg atttctattt cttttttat ttttttgag acgaagtttt      18960 tctcttgttg cctaggctgg agtgcaatgg catgatctca gctcactgca acctccgcct    19020
cacagattca agcgattctc ctgcctcagc ctcccaagta gttgggacta caggcacccg    19080
ccaccacgcc cagctaattt ttgtattttc agtagagatg gggtttcacc atgttggcca    19140
ggcgggtctt gaactcctga cctcaggtga tctgcccgcc tcggcctccc aaagtgctgg    19200
gattacaggc gtgagccact gtgcccggcc tttctttgtt tttttttttg tttgttttt     19260 atttgagatg gagtcttgct ctgtcaccca ggctggagtg cagtggcatt atctcagctc    19320
actgcaacct ctgcctcccg gcacctggcc ttttttagcg aacttcctac agctgggatt    19380
tctagatcaa atgcatacat tttcaagggg aaaagatctt taaaaaatta taaatgactg    19440
ctgatggata atggatttct ttttgggtga tgaaaatgat ccagaattag atagtggtgg    19500
ttgtttatac taaatacatt gaatatactg aactctgaat atactaaaac tcacttaatt    19560
gtatacttta aaatggtgaa ttttattgta tgcaaattat gtctcaatga taaaaatagg    19620
ctggctgcag tggctcacgc ctgtgttccc aacactttgg gaggccaagg caggaggatc    19680
acttgaggcc aggagtttga gaccagcctg gcaatattg tgagactgtg tctctccaaa     19740
atatttttta agaaattggc caagcatagt ggcatgtggc caagctgctc tggaggctga    19800
ggcaggagga tcacttgacc ctaggagttc aagggtgcag taagccaagg tcacaccact    19860
gcactccagc ctggatgaca gagtgaaacc ctgtctcaaa taaataaaat acatatttat    19920
ccttaaaatc acatagtgca attgtattta caaacaaaag tcctagtgtt atagctctaa    19980
gaatttgtct accaggtttt ctggtcatcg ctggaaacac cctctcccct caaaaataaa    20040
tttttttttt tttttgagac agagttgtcg ctcttgttgc ccaggctgga gtgcagtggc    20100
gcgatcttgg ctcactgcaa cctccgcctc ccgggttcaa gcaattctcc tgcctcagcc    20160
tcctgagtag ctgggattac aggcatgcac caccaagccc ggctaatttt gtatttttag    20220
tagagatgga gtttctccat gttggtcagg ctggtctctt aattcctgac ctcagatgat    20280
ctgcccgctt cggcctccca aagtgctgag attataggcg tgagccactg tgcctggccc    20340
caaaataatt ttttaaaaag tcctgtgtct ctcccttcct tagtgcctct tccgctgcac    20400
atgctgggtc ctgggcgagg tactggggct gtaacgggga acgaaacaaa cagggtcctt    20460
gccttgggag cactttggtg ggggagccag gccttaatca aataatctca gctgtataat    20520
gatacacact gataagtgtt atgaaggaag agtgttaaga agctcagaga gtaaatcatg    20580
gggccctgat ttggtttggg attgaaggag tgttcctcag gaagtgacct tcagatgtgt    20640
atagaagttt ctctggtcga ggggaagctg gcagggagaa aagccttcaa agcaggttca    20700
taggccctgg ggtgggagga tcaaagaact caaaggaggg tggagcccag agcagaatgg    20760
agagaagggg aggaggtgag gccaggaggt gttaaggtca ggcctgtggt ccttagtaaa    20820
```

```
gattgtgctg ttttttttcct gaggtgcaga agggagccac cgcacagttc cagattgggg   20880
tgtgacaggg gtaagaagcc ttctctggat gttaggtaga gaacagattg gagggtgaca   20940
gagctgtagc agtcagtcaa gagaggatgg tggctgtgac aaatggggtg gaggaagggg   21000
tcaatcaaag agacatttag ggtgtaaaat ccatgggcct taacctgatg gagtgtgtca   21060
aggaggcctc caggttttcca gcctgcccag ggctgtcatt tatagaactg gaagcacaca   21120
agtgtgtccc tcacacagtt tccacacgtg ggtgcatgcg tctacagcca ctgcctttt    21180
tttttttttt aggacagggt ctctcgctct gctgcccagg ctggagtgca gtggtgcaat   21240
catagctcac tgcagcctca aactccaggg cttgagcagt cctcctgcct tggcctccca   21300
ggtagctggg actacaggtg tgcaccacca cacctggcta atttttttt ttttcatttt    21360
ttgtagagac agggtcttgc tatgttgcct aggccggtct agaactcctg ggctcaagtg   21420
agcctccagc ctcagcccct caaaacattc agattattaa gcatgagcca ccacgcctgg   21480
ctgtgattgc ttttttgacaa agatgacaca gaaaaggcct aatgtacatg ttactctgca   21540
tttccgccca cttcgaaggg aattccttgt cggcacattt gtatcttcat tcctttgaat   21600
gatcccacca tgttccattg gtcggttcac catcttttac ttagccagcc tcccatgttc   21660
gacatttagg ttgtttccag tgtttggccg taacaaacag tggtgtagcg agtgtccttg   21720
cctgtgggag aatttctgcc atgttgctag atgtgtcatt actgagttaa aggcagtgca   21780
catttaccct tcatagatct tgtcaaggtg tcctccaaga agcttgtgcc agtgcacctt   21840
ctctcaagta gcacctgtga gtgcgtctgt ttctagcttt cccaactatg ttacagtctt   21900
tggcaataac atagatattc tttgacaatc tggtaggaaa tgactttttt tttttttttt   21960
tttttgagat ggagtctcgc tctatagcca ggctggagtg cagcggcatg atctcagctc   22020
actgcagcct ccgcctccca ggttcaagcg attctcctgc ctcagcctcc caagtagctg   22080
ggactacagg tgcctgccac catgcccagc taatgtttgt attttagta gagatggggtt   22140
ttcactatgt tggccaggat ggtctctatc tcttgacctc atgatccgcc tgccttggcc   22200
tcccaaggtg ctgggattac aggtgtgagc taccatgccc ggcctatgct gtattttctt   22260
agatttagag attccattga tagacctgac atatttatt ttttgtggta aatatacata    22320
atataaaaat taccatttta ggccgggcgc ggtggctcac gcctataatc ccagcacttt   22380
gggaggccaa ggtgggcgga tcacctgagg tcaggagctg gagaccagcc tgccagcgtg   22440
gtgaaaccct atctctacta aaaatacaaa attagccggg cgtcgtggtg ggcgcctgta   22500
atcccagtta ctctggaggc tgaggcagga gaattgcctg aacccgggag gcagaggttg   22560
cagtgagccg agatcacgcc actgcactct ggcctgggtg acaagagtga aactttgtct   22620
caaaaaaaaa aaaattacca ttttaaccat taaaaatct acactttagt ggcattaagt    22680
acattcacat tattttgcaa atatcacccc tacccatctc ccatctccaa aacttttca    22740
ccctcctaaa ctgaaaccca aatctccatt aaacactaac tctccattcc cactttccgc   22800
aggccctggc acccaccatc ctactttctg tctctatgaa tttgactact ccagggacct   22860
catctaggtg aaatcttaca tactgtgtag ttttttttgtt ttgttttgtt ttgttttga    22920
gatggtgtct cgctctgttg cccaggctgg agtgcagtgg ctcaatctcc actcactgca   22980
ccctccacct cccaggttg agccattctt ctatctcagc ctcctgagta gctgggacta    23040
caggcgtatg ccaccaggca tggctaattt ttgtattttt agtagagatg gggttttgcc   23100
atgttggcca ggctggtctt aaactcctta tctcagatga tctgcctgcc tctgcctccc   23160
aaagtgctgg gattacagga cactgtatag ttttttgtctg gcttatttca cttagcataa   23220
```

```
tgtcctcaag gttcatccat gttacagcat gtgtcagaat ttccttcctt ttaaaggctg    23280
tataatattc gactgtatgt atacaccaca ttatttttat ccattcatta gtcaatggac    23340
actaggattg cttccacctt tttgttgtga acaatgctgc tttgaacatg gttgtagcaa    23400
tatctgttca aatctctgct ttcatttctt tgtatatatg cccagaaatt taattgctgc    23460
atcatgtggt cattctatgt ttaaagtttc taaaattttt tttaacttca atatatgaac    23520
tttttttttt tttttgagat ggagtcttgc tctcacccag gctggagtgc agtggtgcaa    23580
tctcagctca ctgcaacctc cgcctcccag gttagtgatt ctcctgtctt agcctcctga    23640
gtagctggga ttacaggcac ccaccaccac tcccagctaa ttttttgtatt tttagtagag    23700 actgggtttc accatgttga ccaggctcgc ctcgaactcc tgacctcaag taatccacct    23760
gccttggcct cccaaagtgc tgggattgca ggcgtgaacc accacacctg gcctatgaac    23820
attttaaaat gtcaaagatg acttccaggt ttctggaatg agcttgctta tttatttatt    23880
tatttattta tttatttatt tatttattta tttatttatt ttgagacagg ttctctgttg    23940
ccaaggctgg agtgcagtgg tgtgatcttg gctcactgca atctggactt cccaggctca    24000
agcaatcctc ccacctcagc cttgagagta gctgggacta caggcatgtg ccaccatgcc    24060
cagctaattt ttgcattttg tggttttgcc gtgttgccca ggctggtctt gaattcctgg    24120
gctcaagcga tcccacccgt cttggcctcc caaagtgctg ctattatagg cgtgagccac    24180
cgtgcccggc gctttgttta ggttttggag gaccctccat tactgttttc cactgccgtg    24240
caccgtttca cattcccacc agtggtgcac agggctccat tttccccgct tcctcgccag    24300 cacttgttttt ctgtttcata atcagtgtgt ggtagaatct cattgtggtt ttgattttca    24360
tttctcttat gattagtgac atggagcatc ttttcctgtg cttttttgatc atttgtatat    24420 cttctttgaa gaaatgtcta tttaggctgg gcgctgtgtc tcatgcctgt aatcccagtg    24480 cttttgggagg ctgaggcggg cggatcactc gagctcagga gtttgagacc agcctgggga    24540
tcatggtgaa acctgtctct ggaaaaaaat acaaaaatta gccaggtgtg gaggattgtg    24600
cctgtagtca cagctactca ggaggctgag gcaggagaat cgcttgagcc caggaggcag    24660
aggttgcagt gagctaaggg attgcatcac tacactccag cctgggcaac aggagtgaaa    24720
ccctgtctca aaaaaaaaaa aaaaaaaga aagaaaaaga aaggtctatt caagtccttt    24780
gctcattttc ttttctttttc tttttttttt ttttttgagac ggagtctcgc tctgtcaccc    24840
aggctggagt gcagtggcac aatctcggct cactgcaaac tccgcctcct gggttgacgc    24900
cattctcctg cctcagcctc ccgagtagct gggactacag gcgtccacca ccaagcctgg    24960 ctaattttttt ttgtgtgtgt atttttagta gagatagggt ttcactgtgt tagccacgat    25020
ggtgtcaatc tcctgacttt gtgatctgcc caccttggcc tcccaaagtg ctgggattac    25080
aggcgtgagc caccgcgcct ggcctttttt tttgtatttt tagtagagac ggggtttcac    25140
cgtgttagcc aggatggtct tgatctcctg acctcatgat ccgcctgcct tggcctccca    25200
aagtgttggg attacaggcg tgagccacca cacccagccc tttgctcata ttctaatcag    25260
atttttttgt tgatgttgag gtataggagt tctttatatg ttctggatgt taaatcctta    25320
ttagatatat gatttgcatg tatttttcttt tttcttttttt tttttttttt aagacagaat    25380
ctcactctgt cacccaggct ggagtgcagt ggcacattca tggctcactg cagccttgag    25440
cttctgggct caagtgatcc tcccacctca gcctcccaag tagctgggac tacagatgtg    25500
cgtcatcaag cctggctaat taaaaaaaat atatgttttt tgtaaagacg agatctctct    25560
```

```
ttgttgccgg gctggtcttg aacttttgag ctgaggcagt cctcctgcct gggcctctga   25620
atgtgttggg attacaggca tgagccaccg tacccagcat gtatgtattt tctcctatca   25680
tgtgggttgc cttttcactc tgttaatagt gtcatttgat acatagaagt tttagatttt   25740
gatggcatct tgttttattt atttattttt atttttttga cagggtct cactctgttg    25800 cccaggctgg agtgcagtgg tgcagtcaca gctcactgca gccttgacct cccttgagca   25860
atcctcctgc ctcagcctcc cgagtagctg ggactatagg tgcacaccac catgcctcgc   25920
taatttttat acttttgta gagtcagggt ttcaccatgc ccagcctggt cttcaactcc    25980
tgggctcaag tgatcttcct gcctcccaaa gtgctgggat tactggcgtg agccaccgtg   26040
cctggatatc gtattttaat ttgtaatttt tttggtatgt actcccctg ctttaatttt    26100 aattttttaa attaaagtac tatatacagg ctgggtgtgg tggctcatgc ctgtaatccc   26160
agcactttgg gaggctgagg tgggtggatc acctgagatc aggagttcaa gaccagcctg   26220
gccaacatgc gaaaccccca tctctattaa aaatacaaaa attatctggg catggtggca   26280
cgtgcctgta atcccagttg ctcaggaggc tgaggcagga gaattgcttg aaccggggag   26340
gcggaggttg cagtgagccg agattgtgcc actgtactcc agcctgcgcg acagagaacc   26400
catctcaaaa aaagaaagt aatacataca tgccaggtgt ggtggcacat gcccaaaatc    26460
ccagcacttt gggatgctga ggtgggcaga tcacttgagc ccaggagttt gagaccaggc   26520
tggccagtat ggtgaaaccc tgtctctact aaatatacag aaacattagc tgagcatggt   26580
gctgcatgcc tgtagtccca gctactcagg aggctgaggc acgagaattg cttgaaccta   26640
ggaggctgag gttgcggtga gctgagattg caccactaca ctccagcctg gcaacagag    26700 caagactctg tctcagaaaa ataaagcaat acatacgcat ggttaaaaaa ttaatgatat   26760
ggaaatatat aaaagtaaac atcttctttt tccaaaggac tagtcctctc tggaagtaac   26820
cactcttaac aagttttttcc atgttcttcc agaaaacttc gcacactaga caacacagg    26880 tgtccttta gaaaatatta tcggccgggc acggtggctc acacctgtaa tcccagcact   26940
ttgggaggct gaggtgggtg gatcacctga gatcaggagt tctgagacca gcctggccaa   27000
catggcgaaa ccctgtctct actaaaaata ctaaaattag gcgggtgtgg tggcgggcac   27060
ctgtagtccc agctactcag gaggctgggg catgagaatt gctagaacct gggaagcaga   27120
ggttgcagtg agccaagatt gtgccactgc actccagcct gggtgacaga gtgagactgt   27180
gtctcaaaaa aaaaaaaaa gaaagaaaat attatcaaat aggttcatac tttggtgggg    27240
ttttggtttg ttttgactaa aacccttcat tctctgtact gtatttgaac aatacctatt   27300
gatggacatt tctggtgttt tcagtttttg aatttctaca cagtcctgga atgaacattt   27360
catttgtatg tctcgctaat ttttatactt tttgtagagt gctgggatta caggcatttg   27420
tatgtcttgt aattgtatg tcatcttgca attgtgtact atgtaccttg gatgtacctt     27480
ttaaagatcg ttggtggtgg gacacgtgtt ttttgaggaa gatggtactg aggtcagcac   27540
cctggctgcc ctgagagtgc agtgccacgt tccccaccct ctcgccaacc acaggattat   27600
gctgcaaatg taaatcttta ccaatttgat aggcaaaaaa tgggatctca gcattttagc   27660
ctgcatctct gagtactaac gaggctgaac acgaaatgag cttatttttct tttcagaagc   27720 ccctgaatgt gacagtgatc cgcagggggg aaaaacacca gcttagactt gttccaacac   27780
```

```
gctgggcagg aaaaggactg ctggggtaaa gtatctgttt ctgttcattc tcactggggc  27840
atcatttgag tgtttgttaa acatgaagct ggaggggaag gctggggaga cattggggaa  27900
taatgggaat ccccagtttg catggaaact gcagataaat cctcgtggta ggaacgagac  27960
tacagctcta gaagcagagg gagccccaga gtctctcctg ggagtctctc cagttcattc  28020
atgcactagg catttgcttt aaaagaatga aagaacattg gtgaaaaggt cagaagggct  28080
cagcctctga ccttcctgaa gggagcctcc aaacttacgc cattccttt cttctttctt  28140
ccagctgcaa cattattcct ctgcaaagat gattgtccct ggggaacagt aacaggaaag  28200
catcttccct tgccctggac ttgggtctag ggatttccaa cttgtcttct ctccctgaag  28260
cataaggatc tggaagaggc ttgtaacctg aacttctgtg tggtggcagt actgtggccc  28320
accagtgtaa tctccctgga ttaaggcatt cttaaaaact taggcttggc ctctttcaca  28380
aattaggcca cggccctaaa taggaattcc ctggattgtg ggcaagtggg cggaagttat  28440
tctggcaggt actggtgtga ttattattat tattttaat aaagagtttt acagtgctga  28500
tatgaccctg ttgtcacccc agctgaattt cttatgaccc tcccaaacca aagctcagat  28560
ggggtcagaa gagcttcata gaaagttggg caaaacaggc tagcaattgc aaagtcaggc  28620
tttgaccaac atatttcttt gcactgaggc cttgctgctg tggatacgga aatggttaag  28680
tactgtgctt cctcagcagc tgggctgtca gggccatagt agctcccttt ggagaacagg  28740
gaaagcctgg aggcttccca ggtggcccag cgtggtgtcc tgtcagcttc ctctttagga  28800
acccaccaga gggcagcaag ctcctttcac ttcgctagta agaacccctc cgttttgtg   28860
tgttttgtt tttgttttct ggagacaagg tcttgctttg tcacccaggc tggagtgcag  28920
tgtcgtgatc aaggttcact gaagccttga cgctgtgggc actgcctcag ccgcccaagt  28980
atctgggacc acaggcgtgc accaccatgc atagctaatt tatttttgt agagacaggg  29040
tctccctgtg ttgaccaggt tggtctcgaa ctcctgggct caagcagtcc tcctgccttg  29100
gcctcctaaa gtgctgggat cacaggcgtg agccactgcg cccagcccac tgctagtttg  29160
acttttata attgaacctc ctggctatgc cctgagatca gcgctatttt gtaaaccgct  29220
gaggtatgga taggaacgag tagatcagac ctcttgaaaa tgcttattct tcctcccttt  29280
tattttttgt ctcttttaag atggtaaaat ggttctcagg gattcctgcc aatactttga  29340
attattttt cctctccatg gtatcagtgt tcatttcccc agttcttgca caccgctttc  29400
tgttttggca gttctgccag gcaagccctg tgttccttgg gactggtttt gctgtggttg  29460
gatacagata ccagcttgcc ttgatgggat tggtattgct gtgtgcttcc agccacaggt  29520
tctcacactc aattccaaag ccttcctatt gggcgaattc cctcaaactc tatttgacct  29580
gacagccata cgtattcccc tctggtagcc acagacatgc tgtgtttacc aatgtttgct  29640
gtttaaattg catgttctaa ttccacgtat cttccagtct cttttataaa gtctcagact  29700
ataataaaca cagcttgccc agtttatcct ttctttttta ttttaagatg tatgcatatt  29760
aatcaattta ccatcactgg ggcatggcag tgtgggcggg gagaattatt cacattctcc  29820
taaaatgaca gcagcagaga gccttctgcc tcagtggctc tggctggttt cctgcagggg  29880
tcccagtgga aacccgtgtg gccacctgtt gccgtcttcc atgagatgtt agtggagagc  29940
cacttttgacg tggaatgatc ctaatagata tagccagacc ggttttgcgg aaacgctttg  30000
tgctgagaac cgcaagctgg tgcaccctgt gtcatatctg cccccagcca gctggaattg  30060
```

-continued

```
tctgcaacac gcggtgcccg gtgaggaggc aggcaggacg gttgtgtgct gcatccatga    30120
gacctggaaa ttcagtttgc ttttggaaaa gagcattgta tccgagttca tacttctcca    30180
ccccatcttg ccaaggttgc ggaaagtaaa aattggcagt attggccgct gcagcttctt    30240
aggggacggg accatgtgaa aaggtgggat cgtgcgagcg gaggaaggac agaaaagcga    30300
ggaaagtcta tgccgccagc gaccg                                          30325
```

USE OF BRIDGE-1 AND ACTIVATORS AND INHIBITORS THEREOF IN THE TREATMENT OF INSULIN DEFICIENCY AND DIABETES

CROSS-REFERENCE TO RELATED APPLICATIONS

This application is the National Stage of International Application No. PCT/US2005/021181, filed Jun. 16, 2005, which claims the benefit of U.S. Provisional Application No. 60/579,668, filed Jun. 16, 2004.

FIELD OF THE INVENTION

The present invention relates to the field of transcription factors. More specifically, the present invention relates to a mammalian transcription factor, Bridge-1, to nucleotide and amino acid sequences thereof, and to the use of Bridge-1 in the treatment of developmental and acquired disorders including diabetes.

BACKGROUND OF THE INVENTION

Diabetes mellitus results from an absolute or relative deficiency of the hormone insulin. Although absolute deficits in the numbers of insulin-producing pancreatic β cells are seen in Type 1 diabetes, Type 2 diabetes often is accompanied by relative deficits in pancreatic β-cell mass and insulin production in the setting of insulin resistance (Butler, A. E., et al., *Diabetes* 52:102-110 (2003); Gerich, J. E., *Mayo Clin. Proc* 78:447-456 (2003); Yoon, K. H., et al., *J Clin Endocrinol Metab* 88:2300-2308 (2003)). Monogenic heritable forms of insulin-deficient, early-onset diabetes are associated with mutations in genes encoding factors essential for the transcriptional regulation of insulin production in pancreatic β cells (Fajans, S. S., et al., *N Engl J Med* 345:971-980 (2001)). Five of the six genes linked to maturity-onset diabetes of the young (MODY), hnf-4α/MODYI, hnf-1α/MODY3. ipf-1 (pdx-1)/ MODY4, hnf-1β/MODY5, and neuroDl/MODY6, are transcription factors known to regulate endocrine cell development and/or the glucose-responsive expression of the insulin gene in pancreatic β-cells. Thus transcriptional regulators of pancreatic β-cell mass and insulin production represent an important pool of candidate diabetes genes.

Glucose-responsive regulatory regions that are highly conserved in the insulin promoters of multiple species serve as convergence points for β-cell transcription factors of the homeodomain and basic helix-loop-helix (bHLH) classes including several of the designated MODY genes (Steiner, D. F., et al., *Annu Rev Genet.* 19:463-484 (1985); German, M. S., et al, *Genes Dev* 6:2165-2176 (1992)). The physiologic regulation of insulin gene expression is dependent on the precise assembly of transcription factors and coactivators within specific concentration ranges. Multiple protein-protein interactions generate functional regulatory complexes that couple with the coactivators Creb-binding protein (CBP) or p300 in the transcriptional activation of the insulin gene (Ohneda, K., et al., *Mol Cell Biol* 20:900-911 (2000); Asahara, H., et al., *Mol Cell Biol* 19:8219-8225 (1999); Qiu, Y., et al., *Mol Cell Biol* 22:412-420 (2002); Stanojevic, V., et al., *Endocrinology* p. 300 145:918-928 (June 2004).

Bridge-1. By screening for novel interaction partners for the bHLH transcription factor E12 in a clonal β-cell line the present inventors previously identified Bridge-1 as a PDZ-domain coactivator of the insulin gene (Thomas M. K., et al., *Mol Cell Biol* 19:8492-8404 (1999)). Bridge-1 contains a highly conserved PDZ protein-protein interaction domain and is part of the large family of PDZ-domain proteins that facilitate the assembly of supramolecular protein complexes on PDZ-based scaffolds to transduce localized intracellular signals (Sheng, M., and Sala, C., *Annu Rev Neurosci* 24:1-29 (2001)). Rat Bridge-1 is a highly conserved, widely expressed protein with substantial homology to the human proteasomal modulator protein PSMD9 (Thomas, M. K., et al., *Mol Cell Biol* 19:8492-8404 (1999); Watanabe, T. K., et al., *Genomics* 50:241-250 (1998)). In the adult pancreas Bridge-1 is expressed predominantly in the insulin-expressing pancreatic βcells of the endocrine compartment. Bridge-1 interacts with E12 and E47 to coactivate glucose-responsive enhancers within the insulin promoter, and Bridge-1 antisense constructs substantially reduce insulin promoter activation in insulin-producing cells in vitro (Thomas, M. K., et al., *Mol Cell Biol* 19:8492-8404 (1999)). Therefore, the present inventors hypothesized that endogenous Bridge-1 signaling regulates insulin production in pancreatic β cells.

P300. Transcriptional coregulators provide important regulatory flexibility in the cellular responsiveness to hormones and extracellular signals. The physiologic importance of coregulator function is highlighted by the association of coactivator dysfunction with multiple human disease states including neurodegeneration, malignancies and metabolic disorders. The nuclear receptor coactivator p300 functions to assemble multimolecular transcriptional regulatory protein complexes through interactions with a large repertoire of transcription factors and components of basal transcription machinery (Vo, N. and Goodman, R. H., *J. Biol. Chem.* 276: 13505-13508 (2001); Chan, H. M. and La Thangue, N. B., *J. Cell. Sci.* 114:2363-2373 (2001)). The intrinsic acetyltransferase activity of p300 augments the activation of gene transcription through acetylation of histones and transcription factors (Vo, N. and Goodman, R. H., supra). Mutations in the human p300 gene, like those in the related Creb-binding protein (CBP) gene, result in heritable tumors in the Rubinstein-Taybi syndrome (Roelfsema, J. H., et al., *Am. J. Hum. Genet.* 76:572-580 (2005); Giles, R. H., et al., *Trends Genet.* 14:178-183 (1998)). Somatic mutations in p300 also occur in sporadic tumors, consistent with the demonstrated function of this coactivator as a tumor suppressor in mouse models (Chan, H. M. and La Thangue, N. B., supra; Iyer, N. G., et al., *Oncogene* 23:4225-4231 (2004)). Altered levels of expression of p300 modify embryonic development, cellular functions, and responsiveness to extracellular signals (Yao, T. P., et al., *Cell* 93:361-372 (1998)). For example, in the case of Paget's disease, the hyperresponsiveness of osteoclast precursors to vitamin D is associated with increased expression levels of coactivators including p300 (Kurihara, N., et al., *J. Ster. Biochem. Molec. Biol.* 89-90:321-325 (2004)). In a mouse model of Huntington's disease, progressive deficits in insulin production are correlated with decreased expression levels of p300 and other transcription factors in insulin-expressing cells (Andreassen, O. A., et al., *Neurobiol. Dis.* 11:410-424 (2002)).

In early-onset autosomal-dominant heritable forms of diabetes known as maturity-onset diabetes of the young (MODY), abnormal interactions between mutant MODY transcription factors and p300 may contribute to deficits in insulin production and the pathogenesis of disease. p300 recruitment to the proximal insulin promoter in insulin-producing pancreatic beta cells is associated with hyperacetylation and transcriptional activation (Chakrabarti, S. K., et al.,*J. Biol. Chem.* 278:23617-23623 (2003)), and p300 interactions with the transcriptional regulators PDX-1, NeuroD1, and E47 enhance insulin gene transcription (Qiu,Y., et al., *Molec. Cell.*

*Biol.* 18:2957-2964 (1998)); Sharna, A., et al., *Molec. Cell. Biol.* 19:704-713 (1999); Qiu, Y., et al., *Molec. Cell. Biol.* 22:412-420 (2002); Mosley, A. L., et al., *Molec. Endocrinol.* 18:2279-2290 (2004); Stanojevic, V., et al., *Endocrinol.* 145:2918-2928 (2004)). Five direct or indirect transcriptional regulators of insulin gene transcription are encoded by genes associated with MODY (Fajans, S. S., et al., *New Engl. J. Med.* 345:971-980 (2001)). MODY1 mutations R154X and E276Q in the HNF-4α gene interfere with p300 recruitment and transcriptional activation (Eeckhoute, J., et al., *Molec. Endocrinol.* 15:1200-1210 (2001)), the MODY4 mutation P63fsdelC results in a truncated cytoplasmic PDX-1 protein with the capacity to sequester p300 (Stanojevic, V., et al., supra), and the MODY6 mutation 206+C disrupts NeuroD1 binding to p300 (Malecki, M. T., et al., *Nat. Genet.* 23:323-328 (1999)).

PDX-1. The homeodomain transcription factor pancreas duodenum homeobox-1 (PDX-1) is an important regulator of both the embryonic development of the pancreas as well as the function and mass of insulin-expressing pancreatic beta cells (Thomas et al., 2004). PDX-1 has also been referred to as IPF-1, STF-1, IUF-1, GSF, and IDX-1. Homozygous or compound heterozygous disruption of pdx-1 gene expression in mice or in humans results in a common phenotype of pancreatic agenesis (Jonsson et al., 1994; Offield et al., 1996; Schwitzgebel et al., 2003; Stoffers et al., 1997a). Partial reductions of PDX-1 expression levels in genetically-modified mouse models disrupt glucose homeostasis by reducing insulin expression, insulin secretion, and pancreatic beta-cell mass, in part via accelerated apoptosis of insulin-producing pancreatic beta cells (Ahlgren et al., 1998; Brissova et al., 2002; Dutta et al., 1998; Holland et al., 2002; Johnson et al., 2003; Thomas et al., 2001).

In humans, pdx-1 (ipf-1, insulin promoter factor-1) is a diabetes gene. Heterozygous inheritance of an inactivating mutation in pdx-1 results in autosomal-dominant maturity-onset diabetes of the young (MODY4) (Stoffers et al., 1997b) while heterozygous missense mutations in pdx-1 confer an increased risk of early- or late-onset type 2 diabetes in selected populations, often in combination with other diabetogenic genotypes (Cockburn et al., 2004; Elbein et al., 2004; Hani et al., 1999; Hansen et al., 2000; Macfarlane et al., 1999; Owen et al., 2004; Waeber et al., 2000; Weng et al., 2001; Weng et al., 2002).

PDX-1 is implicated in the transcriptional regulation of a large number of pancreatic islet genes, including insulin and somatostatin (Leonard et al., 1993; Miller et al., 1994; Ohlsson et al., 1993). Nutrient-dependent regulation of insulin gene expression is mediated in part through the regulation of PDX-1 nuclear translocation, DNA-binding and transcriptional activation by glucose (MacFarlane et al., 1994; MacFarlane et al., 1997; Melloul et al., 1993; Petersen et al., 1998; Rafiq et al., 1998; Shushan et al., 1999). PDX-1 participates in the synergistic activation of glucose-responsive enhancers with basic helix-loop-helix transcription factors, such as E12 and E47 (Massari et al., 2000), via its amino-terminal domain (German et al., 1992; Johnson et al., 1997; Peers et al., 1994).

The regulation of PDX-1 target genes also is governed by the interactions of PDX-1 proteins with other transcription factors and coactivators. Nuclear translocation of PDX-1 is regulated by interaction of the PDX-1 homeodomain with the nuclear import receptor importin beta1 (Guillemain et al., 2004). PDX-1 cooperatively activates the somatostatin promoter in conjunction with PBX and the PBX regulating protein-1 (Prep1) (Goudet et al., 1999). Interactions between PBX and a conserved amino acid motif (FPWMK) within PDX-1 are necessary for the proliferation of differentiated pancreatic cells during embryonic pancreas development (Dutta et al., 2001). PDX-1 recruits E47, Beta2/NeuroD1, and the high-mobility group protein HMG(Y) to the insulin promoter (Ohneda et al., 2000). The amino-terminal transactivation domain of PDX-1 (Lu et al., 1996; Peers et al., 1994) interacts with the coactivators Creb-binding protein (CBP) and p300 (Asahara et al., 1999; Qiu et al., 2002; Stanojevic et al., 2004). In contrast, the carboxy-terminal domain of PDX-1 serves as an interaction domain for transcriptional repressors, including phosphorylated carboxy-terminal domain interacting factor 1 (PCIF1) and the histone deacetylases HDAC1 and 2 (Liu et al., 2004; Mosley et al., 2004).

BRIEF SUMMARY OF THE INVENTION

To further investigate the function of the coactivator Bridge-1 in the regulation of glucose homeostasis in vivo, the present inventors generated a transgenic mouse model in which Bridge-1 is overexpressed in the pancreas. The inventors hypothesized that the overexpression of this scaffolding protein would interrupt the balance of coactivator and transcription factor interactions to disrupt the regulation of Bridge-1 target genes. It was discovered that dysregulation of Bridge-1 signaling represses insulin gene expression, increases pancreatic apoptosis, and reduces the number of insulin producing cells to result in severe, early-onset, insulin-deficient diabetes. These studies indicate that signals mediated by Bridge-1 regulate glucose homeostasis and contribute to the pathogenesis of diabetes mellitus.

Thus, in one aspect, the present invention is directed to a method for modulating Bridge-1 activity in a cell comprising contacting said cell with a modulator of Bridge-1 activity. Bridge-1 activity may either be increased or decreased. In one embodiment, the modulator of Bridge-1 activity increases or, alternatively, decreases expression of Bridge-1 in said cell. In another embodiment, expression of a Bridge-1 target gene is increased or, alternatively, decreased. In a preferred embodiment, the modulator of Bridge-1 activity is a peptide, small molecule, or anti-Bridge-1 antibody. In one embodiment, the modulator may be selected from the group consisting of: Activin A, Trichostatin A, or Progesterone.

In another aspect, the present invention is directed to a method for modulating apoptosis in a cell or cells comprising modulating Bridge-1 activity in said cell or cells. Bridge-1 activity may either be increased or decreased. In one embodiment, the modulator increases or, alternatively, decreases expression of Bridge-1 in said cell. In a preferred embodiment, apoptosis is increased and the cells are tumor cells. Modulation of apoptosis may also be the result of modulation of a Bridge-1 target gene, for example, by increasing or decreasing target gene expression. Particularly preferred are methods for modulating apoptosis in a cell or cells comprising treating said cells with a Bridge-1 polypeptide, a polynucleotide encoding Bridge-1, or a compound that activates or inhibits expression of Bridge-1 or of a Bridge-1 target gene. Suitable polynucleotides include naked DNA or vectors encoding Bridge-1. Preferably, the apoptosis is modulated in pancreatic βcells.

The invention is further directed to method for modulating islet cell apoptosis in a mammal, such as a human, comprising administering to said mammal a Bridge-1 polypeptide, a polynucleotide encoding Bridge-1, or a compound that activates or inhibits expression of Bridge-1 or of a Bridge-1 target gene.

In another aspect, the invention is directed to a method for modulating cellular replication in a cell or cells comprising modulating Bridge-1 activity in said cell or cells. Bridge-1 activity may be increased or, alternatively, decreased as a result of said modulation. Likewise, replication may either be increased or decreased. In one embodiment, said Bridge-1 activity is expression of Bridge-1. In another embodiment, said Bridge-1 activity is expression of a Bridge-1 target gene. In a preferred embodiment, the invention is directed to a method for modulating replication in a cell or cells comprising treating said cells with a Bridge-1 polypeptide, a polynucleotide encoding Bridge-1, or a compound that activates or inhibits expression of Bridge-1 or of a Bridge-1 target gene. Preferably, said polynucleotides are DNA or vectors encoding Bridge-1. In preferred embodiments, the cells are pancreatic β cells. The invention is also directed to a method for modulating replication of pancreatic β cells in a mammal, such as a human, comprising administering to said mammal a Bridge-1 polypeptide, a polynucleotide encoding Bridge-1, or a compound that activates or inhibits expression of Bridge-1 or of a Bridge-1 target gene.

In another aspect, the present invention is directed to a method for modulating the mass of a cell or cells comprising modulating Bridge-1 activity in said cell or cells. In such methods, Bridge-1 activity may be increased or, alternatively, decreased. Likewise, cell mass may be either increased or decreased. In one embodiment, said Bridge-1 activity is expression of Bridge-1. In another embodiment, said Bridge-1 activity is expression of a Bridge-1 target gene. In a preferred embodiment, the invention is directed to a method for modulating the mass of a cell or cells comprising treating said cells with a Bridge-1 polypeptide, a polynucleotide encoding Bridge-1, or a compound that activates or inhibits expression of Bridge-1 or of a Bridge-1 gene. In these methods, said polynucleotide may be DNA, such as a vector, encoding Bridge-1. Preferably, the cells are are pancreatic β cells. In a particularly preferred embodiment, the invention is directed to a method for modulating pancreatic β cell mass in a mammal comprising administering to said mammal a Bridge-1 polypeptide, a polynucleotide encoding Bridge-1, or a compound that activates or inhibits expression of Bridge-1 or of a Bridge-1 target gene.

In another aspect, the present invention is directed to a method for modulating insulin production in a cell or cells comprising modulating Bridge-1 activity in said cell or cells. In such methods, Bridge-1 activity may either be increased or decreased. Likewise, insulin production may be increased or decreased as a result of said modulation. In one embodiment, said Bridge-1 activity is expression of Bridge-1. In another embodiment, said Bridge-1 activity is expression of a Bridge-1 target gene. A preferred embodiment of the invention is directed to a method for modulating insulin production in a cell or cell comprising treating said cells with a Bridge-1 polypeptide, a polynucleotide encoding Bridge-1, or a compound that activates or inhibits expression of Bridge-1 or of a Bridge-1 gene. Such polynucleotides can be DNA, such as a vector, encoding Bridge-1. Preferably, the cells are pancreatic β cells. In a particularly preferred embodiment, the present invention is directed to a method for modulating insulin production in a mammal, such as a human, comprising administering to said mammal a Bridge-1 polypeptide, a polynucleotide encoding Bridge-1, or a compound that activates or inhibits expression of Bridge-1 or of a Bridge-1 target gene.

In another aspect, the invention is directed to a method for modulating blood glucose levels in a mammal, such as a human, comprising administering to said mammal a Bridge-1 polypeptide, a polynucleotide encoding Bridge-1, or a compound that activates or inhibits expression of Bridge-1 or of a Bridge-1 target gene.

In yet another aspect, the invention is directed to a method for treating a Bridge-1 mediated disorder in a mammal, such as a human, comprising administering to said mammal a Bridge-1 polypeptide, a polynucleotide encoding Bridge-1, or a compound that activates or inhibits expression of Bridge-1 or of a Bridge-1 gene in said mammal. In a preferred embodiment, the mammal is a human. In another embodiment, the disorder is caused by a mutation in the endogenous Bridge-1 gene. In a preferred embodiment, the disorder is diabetes, such as Type II diabetes mellitus.

In another aspect, the invention is directed to a method for modulating insulin secretion from a cell or cells, comprising modulating Bridge-1 activity in the cells or cells. In such methods, Bridge-1 activity may either be increased or decreased. Likewise, insulin secretion may be increased or decreased as a result of such modulation. In one embodiment, expression of Bridge-1 is increased. In another embodiment, the Briedge-1 activity is expression of Breidge-1 or of a Breidge-1 target gene.

In another aspect, the invention is directed to a method for regulating glucose homeostasis in a cell or cells, comprising modulating Bridge-1 activity in the cell or cells. In such methods, Bridge-1 activity may either be increased or decreased. In one embodiment, expression of Bridge-1 is increased. In another embodiment, the Briedge-1 activity is expression of Breidge-1 or of a Breidge-1 target gene.

In another aspect, the invention is directed to a method for modulating survival of a cell or cells comprising treating the cell or cells with a Bridge-1 polypeptide, a polynucleotide encoding Bridge-1, or a compound that activates or inhibits expression of Bridge-1 or of a Bridge-1 target gene. In a preferred embodiment, the cell or cells are pancreatic β cells.

In another aspect, the invention is directed to a method for treating hyperglycemia in an animal, comprising administering to the animal a Bridge-1 polypeptide, a polynucleotide encoding Bridge-1, or a compound that activates or inhibits expression of Bridge-1 or of a Bridge-1 target gene.

In another aspect, the invention is directed to a method for treating insulin deficiency in an animal, comprising administering to the animal a Bridge-1 polypeptide, a polynucleotide encoding Bridge-1, or a compound that activates or inhibits expression of Bridge-1 or of a Bridge-1 target gene.

In another aspect, the invention is directed to a method for modulating expression of a nucleic acid sequence in a cell or cells, wherein the nucleic acid sequence is operably linked to an insulin promoter enhancer or a somatostatin promoter enhancer, the method comprising treating the cell or cells with a Bridge-1 polypeptide, a polynucleotide encoding Bridge-1, or a compound that activates or inhibits expression of Bridge-1 or of a Bridge-1 target gene. In a preferred embodiment, the cell or cells are pancreatic islet cells, such as α cells, β cells, δ cells, or PP cells. In various embodiments, the nucleic acid sequence may be an insulin gene or a somatostatin gene.

In another aspect, the invention is directed to a non-human transgenic mammal whose somatic and germ cells contain a transgene construct, the transgene construct comprising all or a portion of a nucleotide sequence encoding Bridge-1. Preferably, the transgene construct is expressed in the somatic and germ cells of the transgenic, e.g., in the pancreas of the transgenic mammal. In a preferred embodiment, the expression of an insulin gene in the transgenic mammal is decreased relative to a mammal lacking the transgene construct. In another embodiment, the expression of a glucagon gene in the transgenic mammal is increased relative to a mammal lacking the transgene construct. In yet another embodiment, the expression of a pancreas duodenum homeobox-1 (PDX-1)

gene in the transgenic mammal is decreased relative to a mammal lacking the transgene construct. In one embodiment, expression of an Nkx 6.1 gene in the transgenic mammal is decreased relative to a mammal lacking the transgene construct. In another embodiment, expression of a Brain-4 gene is increased in the transgenic mammal relative to a mammal lacking the transgene construct. In another embodiment, apoptosis of pancreatic cells in the transgenic mammal is increased relative to a mammal lacking the transgene construct. In yet another embodiment, the number of insulin-producing cells in the transgenic mammal is decreased relative to a mammal lacking the transgene construct. In various embodiments, the transgenic mammal is diabetic, hyperglycemic, and/or insulin-deficient. In another embodiment, expression of pancreatic preproinsulin in the transgenic mammal is decreased relative to a mammal lacking the transgene construct. In yet another embodiment, the transgene construct encodes a polypeptide consisting of amino acids 1 to 184 of Bridge-1. Preferably, the nucleotide sequence encoding amino acids 1 to 184 of Bridge-1 is expressed in the pancreas of the transgenic mammal. In one embodiment, the number of insulin-producing cells in a transgenic mammal expressing a polypeptide consisting of amino acids 1-184 of Bridge-1 is increased relative to a mammal lacking the transgene. In various embodiments, the transgenic mammal is a rodent (e.g., a mouse or a rat), a pig, a rabbit, a goat, a cow, a horse, or a sheep. Such transgenic mammals (e.g., a mouse, a rat, a pig, a rabbit, a goat, a cow, a horse, or a sheep can be used, for example, in methods for determining whether a test compound administered to the mammal (i) modulates insulin gene expression or insulin activity, (ii) modulates glucagon gene expression or glucagon activity, (iii) modulates PDX-1 gene expression or PDX-1 activity, (iv) modulates Nkx 6.1 gene expression or Nkx 6.1 activity, (v) modulates Brain-4 gene expression or Brain-4 activity, (vi) modulates apoptosis of pancreatic cells, (vii) affects the number of insulin-producing cells, (viii) modulates, mediates, ameliorates, or treats diabetes, hyperglycemia, and/or insulin deficiency, and/or (ix) modulates expression of pancreatic preproinsulin. The test compound can be administered by any of various methods, e.g., orally, intravenously, intraperitoneally, by nasal administration, topically, etc.

In a preferred embodiment, the modulation is Bridge-1 activity is determined by analyzing the ability of Bridge-1 to stimulate transcription of a reporter gene. A preferred assay is the Gal4-Bridge-1 transactivation assay in BHK cells.

In various embodiments of each of the methods of the invention described herein, the method may further comprise contacting a cell or cells with a p300 polypeptide, a polynucleotide encoding p300, or a compound that activates or inhibits expression of p300 or of a p300 target gene. Similarly, the methods of the invention may further comprise contacting a cell or cells with a pancreas duodenum homeobox-1 (PDX-1) polypeptide, a polynucleotide encoding PDX-1, or a compound that activates or inhibits expression of PDX-1 or of a PDX-1 target gene. Likewise, in various embodiments of each method of the invention involving an animal, the method may further comprise administering to the animal a p300 polypeptide, a polynucleotide encoding p300, or a compound that activates or inhibits expression of p300 or of a p300 target gene. Similarly, the methods of the invention involving animals may further comprise administering to the animal a PDX-1 polypeptide, a polynucleotide encoding PDX-1, or a compound that activates or inhibits expression of PDX-1 or of a PDX-1 target gene.

The invention is also directed to methods for modulating the activity of proteins that interact with Bridge-1. Thus, in another aspect, the invention features a method for modulating PDX-1 activity in a cell or cells comprising contacting the cell or cells with a Bridge-1 polypeptide, a polynucleotide encoding Bridge-1, or a compound that activates or inhibits expression of Bridge-1 or of a Bridge-1 target gene. In one embodiment, the PDX-1 activity is increased. In another embodiment, the PDX-1 activity is decreased. In one embodiment expression of a PDX-1 target gene is increased, or, alternatively expression of a PDX-1 target gene is decreased. In various embodiments, the compound that activates or inhibits expression of Bridge-1 or of a Bridge-1 target gene is a peptide, small molecule, or an anti-Bridge-1 antibody. For example, the compound can be Activin A, Trichostatin A, or Progesterone.

In another aspect, the invention features a method for modulating p300 activity in a cell or cells comprising contacting the cell or cells with a Bridge-1 polypeptide, a polynucleotide encoding Bridge-1, or a compound that activates or inhibits expression of Bridge-1 or of a Bridge-1 target gene. In one embodiment, the p300 activity is increased, or, alternatively the p300 activity is decreased. In one embodiment, expression of a p300 target gene is increased, or, alternatively, expression of a p300 target gene is decreased. In various embodiments, the compound that activates or inhibits expression of Bridge-1 or of a Bridge-1 target gene is a peptide, small molecule, or an anti-Bridge-1 antibody. For example, the compound can be Activin A, Trichostatin A, or Progesterone.

In various embodiments of the foregoing methods of the invention, the method may comprise contacting the cell or cells with a Bridge-1 antisense cDNA and/or an anti-Bridge-1 small interfering RNA (siRNA). Such antisense cDNAs and siRNAs can be made and used in accordance with conventional techniques to decrease Bridge-1 activity in a cell.

BRIEF DESCRIPTION OF THE DRAWINGS/FIGURES

FIG. 1 (a-d). Transgenic mouse model for the pancreatic overexpression of Bridge-1. (a) Schematic model of the transgene consisting of a 4.6 kb segment of the mouse pdx-1 promoter, a 900 bp segment of rat Bridge-1 cDNA coding sequence, and a 550 bp segment of rabbit β-globin poly A sequence. (b) Expression of the Bridge-1 transgene in genomic DNA. An autoradiogram from a Southern blot of genomic DNA derived from 5 distinct lines of Bridge-1 transgenic mice (TG) probed with a radiolabeled probe spanning the indicated region (*) of the transgene is shown. (c) Pancreatic Bridge-1 mRNA expression in two distinct lines (TG2 and TG5) of Bridge-1 transgenic mice. cDNA was synthesized from total pancreatic RNA isolated from transgenic (+) or control (−) mice. A 402 bp segment of amplified Bridge-1 cDNA was identified by PCR and subjected to agarose gel electrophoresis. An image of the ethidium bromide-stained gel is shown with the 500 bp marker migration position indicated. (d) Images are shown of paraffin sections of pancreas samples from male Bridge-1 transgenic (TG) or strain-matched control (WT) mice immunostained with anti-Bridge-1 antiserum (in brown) and counterstained with hematoxylin. Pancreatic islets are indicated with arrows.

FIG. 2 (a-f). Pancreatic islet, ductal, and acinar architecture are disrupted in Bridge-1 transgenic mice. (a-f) Hematoxylin- and eosin-stained paraffin sections of male Bridge-1 transgenic (a-c) or control (d-f) mouse pancreas. Pancreatic endocrine tissue (ISLET) in Bridge-1 transgenic mice (arrows, a) shows a loss of defined endocrine/exocrine boundaries and increased cellular and nuclear heterogeneity as compared to control islets (arrow, d). Enlarged and dilated pancreatic ducts (DUCT) are noted in transgenic (arrow, b) as compared to control pancreas (e). Patchy regions of acinar cell disorganization (ACINAR) also are seen in transgenic pancreas (c) as compared to control exocrine tissue (f).

Figure 3:
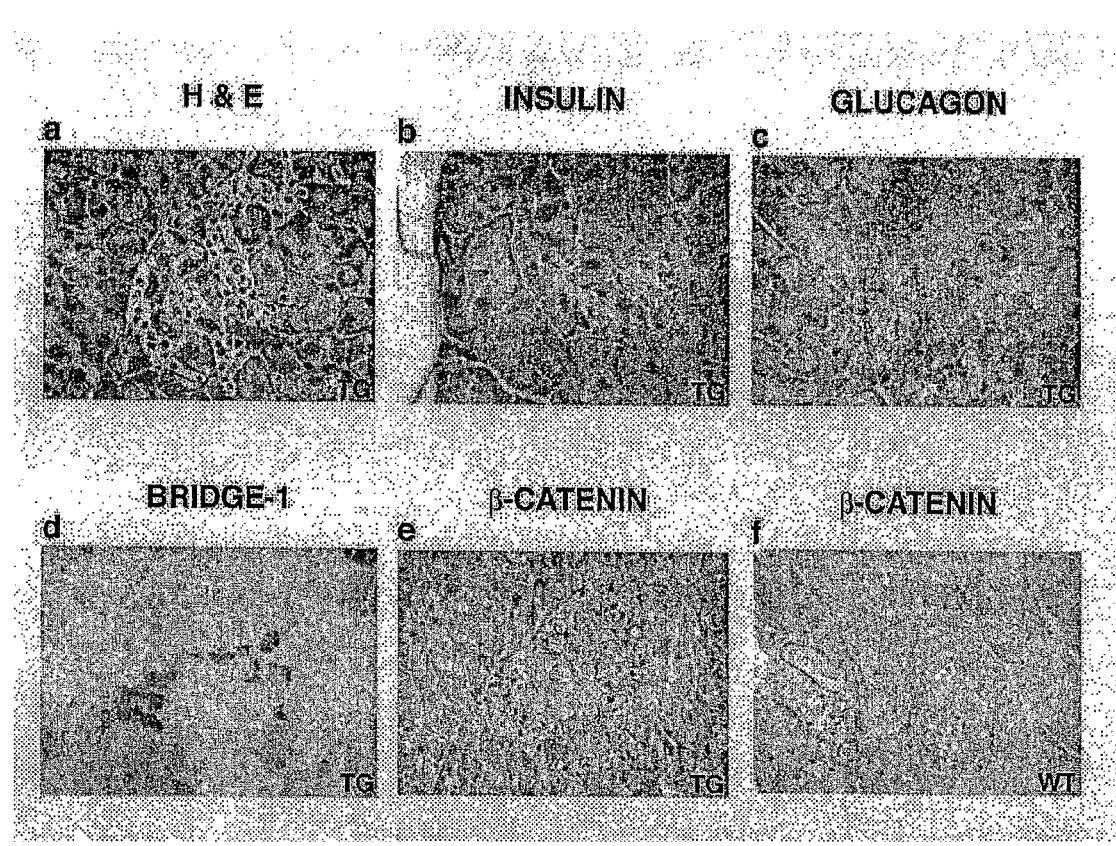

FIG. 3 (a-f). Pancreatic endocrine cells are disorganized with loss of endocrine and exocrine compartment boundaries in Bridge-1 transgenic mice. (a-f) Paraffin sections of Bridge-1 transgenic mouse pancreas stained with hematoxylin and eosin (a, H & E) or immunostained for insulin (b), glucagon (c), and Bridge-1 (d) (in brown) and counterstained with hematoxylin are shown as indicated. The immunostaining pattern for $\beta$-catenin as indicated (in brown) is markedly different for Bridge-1 transgenic (e) as compared to control (f) mice.

Figure 4:
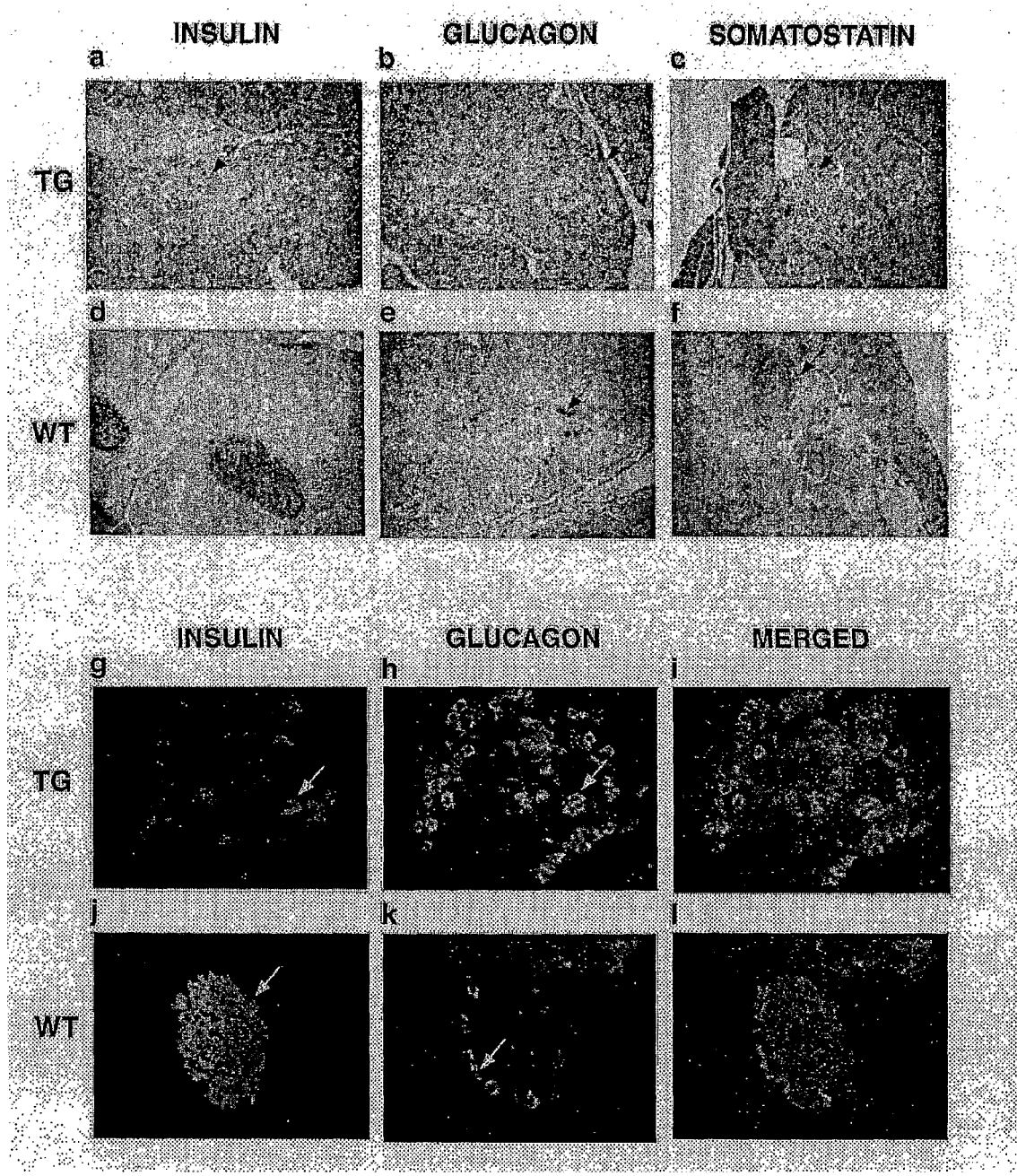

FIG. 4 (a-l). The spatial relationship of insulin- and glucagon-expressing cells is disrupted in Bridge-1 transgenic mice. (a-f) Pancreatic sections from male transgenic (TG, a-c) and control (WT, d-f) mice were stained with antiserum directed against insulin, glucagon or somatostatin as indicated (brown) and counterstained with hematoxylin. Few insulin-expressing cells are seen within a region of acinar cell enlargement and disorganization in the transgenic pancreas (arrow, a) as compared to control islets (d). Glucagon expression is seen in strands and clusters that surround acinar cells in the transgenic pancreas (arrow, b) as compared to the normal pattern of peripheral glucagon expression surrounding a central core of insulin-expressing cells within the islet (arrow, e). Somatostatin-expressing cells are observed in the endocrine compartment of both transgenic (arrow, c) and control (arrow, f) pancreas. (g-l) Indirect immunofluorescence of pancreas sections from transgenic (TG, g-i) and control (WT, j-l) mice stained for insulin in red (g,j) and glucagon in green (h,k) are shown with the merged images as indicated (i,l). Pancreatic islet architecture is abnormal in the transgenic mice with diminished numbers of insulin-expressing-cells (arrow, g) and a disorganized arrangement of glucagon-expressing cells (arrow, h).

Figure 5:
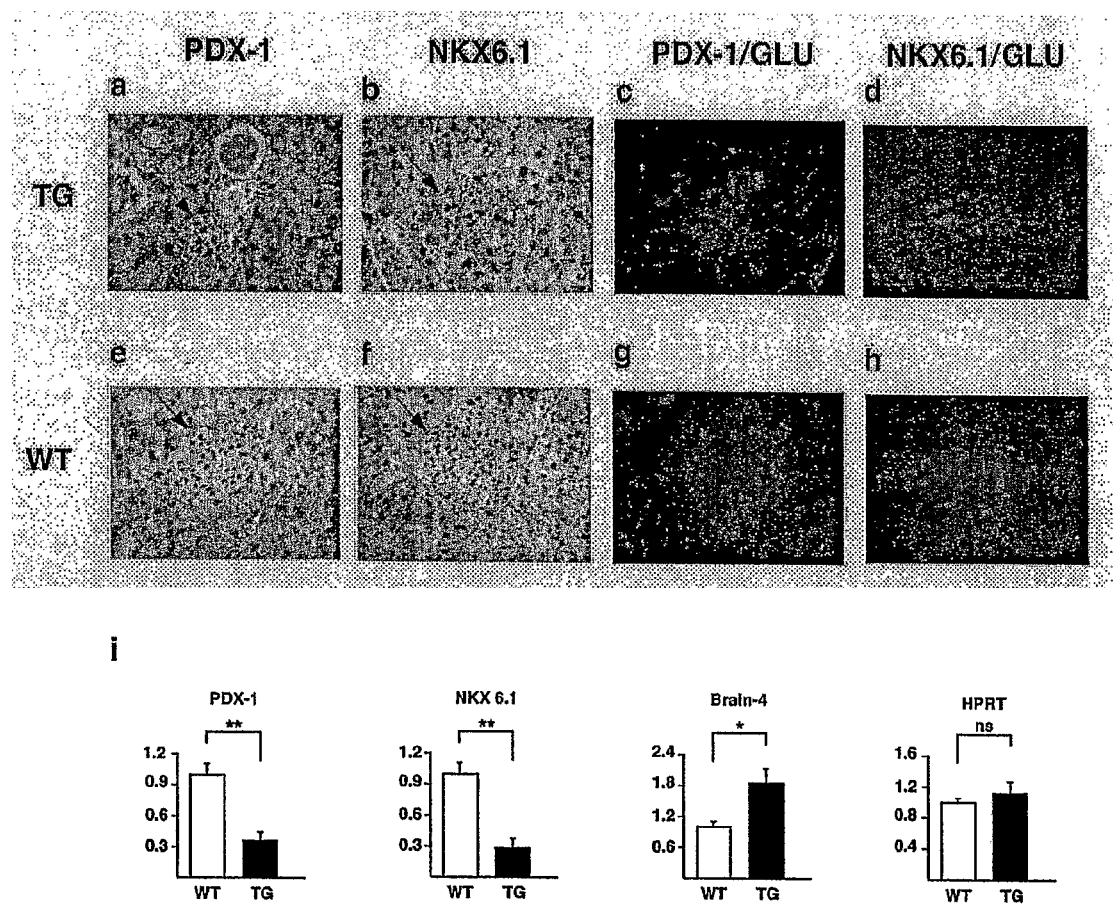

FIG. 5 (a-i). Expression levels of pancreatic $\beta$-cell specific transcription factors are reduced in the pancreatic endocrine cells of Bridge-1 transgenic mice. (a-h) Protein expression patterns of PDX-1 and Nkx 6.1 are disrupted in Bridge-1 transgenic mice. Representative images from pancreatic sections from male transgenic (TG, a-d) and control (WT, e-h) mice stained with antiserum directed against PDX-1 (a, e) or Nkx 6.1 (b, f) (in brown) and counterstained with hematoxylin are shown (a, b, e, f). Within the disorganized endocrine cell clusters of Bridge-1 transgenic mice (arrows, a, b) differences in nuclear sizes are seen. PDX-1 (e) and Nkx 6.1 (f) are expressed in the cytoplasm and nuclei of pancreatic $\beta$ cells comprising the central core of the wild type pancreatic islets. (c, d, g, h) Indirect immunofluorescence images of pancreatic sections costained for PDX-1 in red and glucagon in green (c, g) or for Nkx 6.1 in red and glucagon in green (d, h) are shown. (i) Pancreatic mRNA expression levels of PDX-1 and Nkx 6.1 are reduced in Bridge-1 transgenic mice. We prepared total pancreatic RNA from male Bridge-1 transgenic (TG) and strain- and age-matched control (WT) mice and performed realtime rt-PCR for each sample in triplicate with primers and probes to detect PDX-1, Nkx 6.1, Brain-4, and hypoxanthine phosphoribosyltransferase (HPRT), as indicated. Results shown are the means+/−SEM of the relative expression levels normalized to cyclophilin expression with the mean expression level for the control mice (WT) set at 1 (n=3-5 mice per genotype; *P<0.05; **P<0.01; ns, no significant difference by Student's T test).

Figure 6:
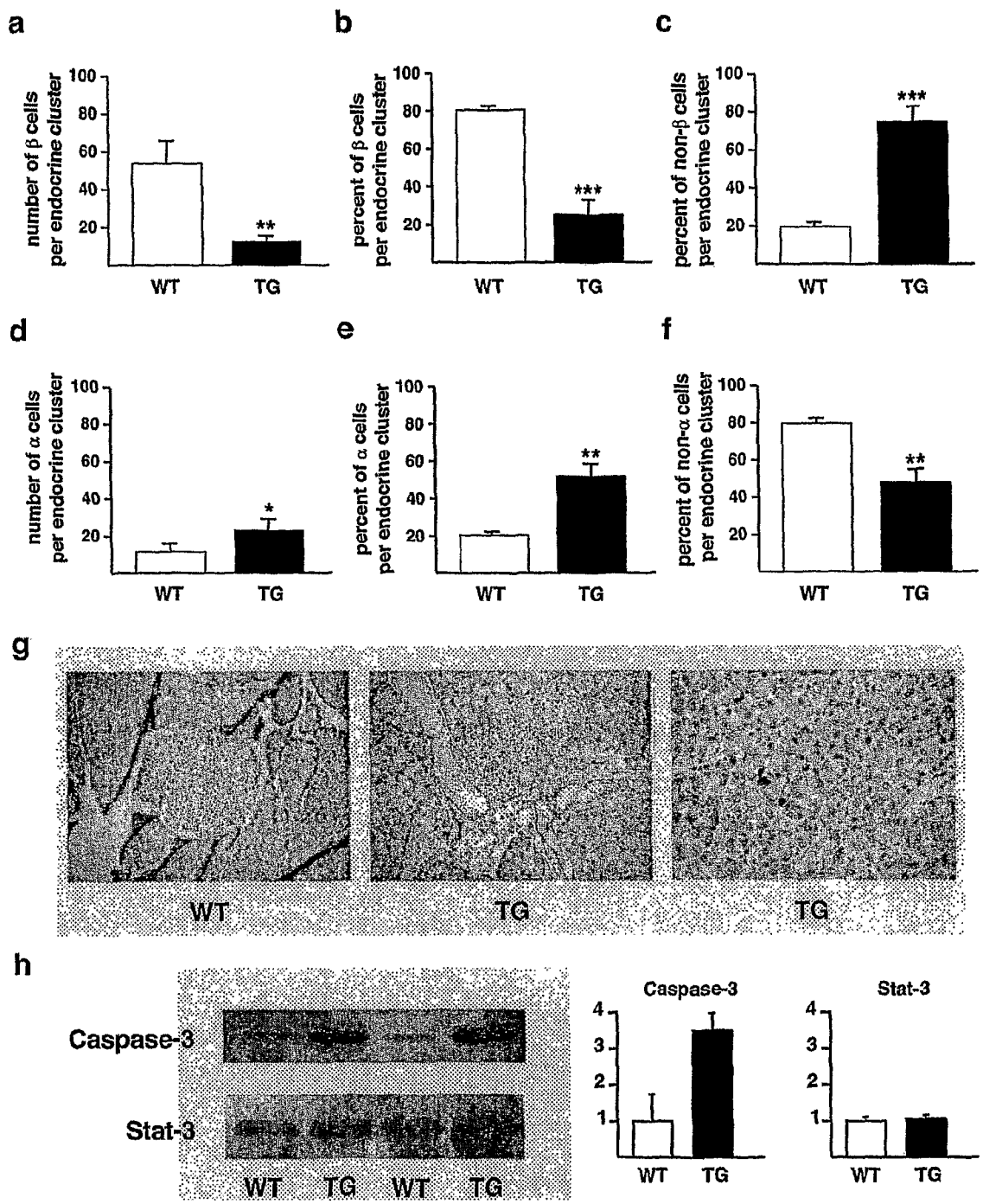

FIG. 6 (a-h). Bridge-1 transgenic mice have reduced pancreatic $\beta$-cell mass and increased pancreatic apoptosis. (a-c) Paraffin sections of pancreas derived from male Bridge-1 transgenic (TG) or control (WT) mice were immunostained for insulin and counterstained with hematoxylin. For each endocrine cell cluster or islet, insulin-expressing ($\beta$ cells) and non-expressing (non-$\beta$ cells) cells were counted. Data presented are the mean+/−SEM (n=3 mice per genotype; 2400-4294 endocrine cells per genotype; P<0.01; *P<0.001). (d-f) Paraffin sections of pancreas derived from male Bridge-1 transgenic (TG) or control (WT) mice were immunostained for glucagon and counterstained with hematoxylin. For each endocrine cell cluster or islet, glucagon-expressing (a cells) and non-expressing (non-$\alpha$ cells) cells were counted. Data presented are the mean+/−SEM (n=3 mice per genotype; 5076-8028 endocrine cells per genotype; *P=0.066; **P<0.01). (g) Peroxidase-based TUNEL assays were performed on paraffin sections of pancreas derived from male Bridge-1 transgenic (TG) or control (WT) mice and counterstained with hematoxylin. Representative images of TUNEL-positive cells (in brown) are shown. (h) We prepared total pancreatic protein extracts from two male Bridge-1 transgenic (TG) and two control (WT) mice and conducted Western blots first with anti-cleaved Caspase-3 antiserum and then with anti-Stat-3 antiserum as a loading control. Representative images of Western blots for Stat-3 and the 17 kD activated, cleaved form of Caspase-3 are shown (at left). Densitometric scanning of the Western blots was used to quantify expression of the 17 kD form of Caspase-3 and of Stat-3. Data shown (at right) are the average+/−range of relative expression levels normalized to the average of WT controls (n=2 mice per genotype).

Figure 7:
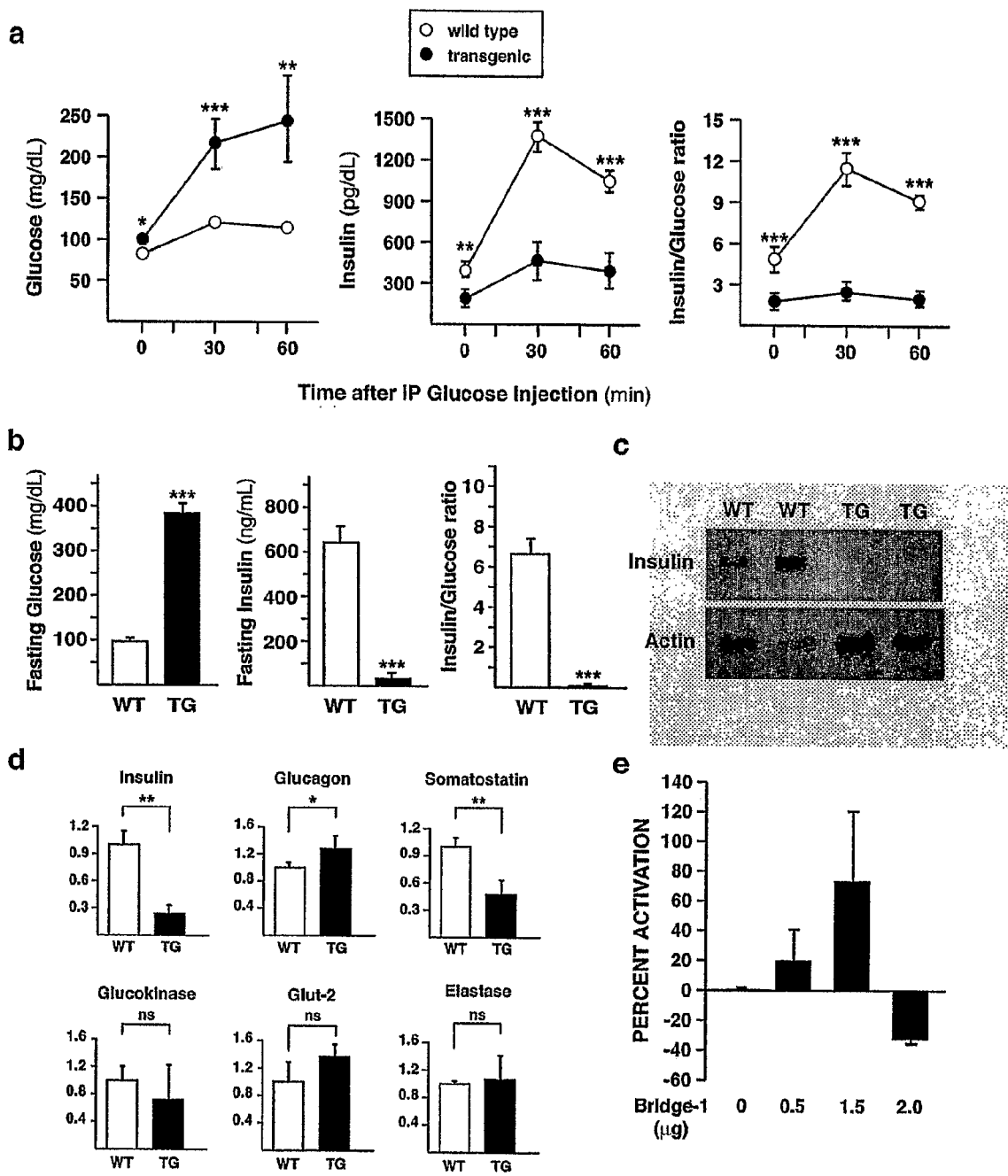

FIG. 7 (a-e). Bridge-1 transgenic mice have insulin deficiency and diabetes. (a) Intraperitoneal glucose tolerance testing of female transgenic mice (closed circles) demonstrates hyperglycemia, reduced glucose-stimulated insulin production and markedly diminished insulin/glucose ratios (n=6 mice per genotype; *P=0.056, P<0.01; *P<0.001) as compared to age- and strain-matched control mice (open circles). (b) Fasting glucose and insulin levels and insulin/glucose ratios are shown for male transgenic (TG) and age- and strain-matched control (WT) mice (n=5-7 mice per genotype; ***P<0.001). (c) Bridge-1 transgenic mice with severe diabetes (TG) have marked deficits in pancreatic insulin mRNA expression as compared to control (WT) mice. Autoradiograms are shown of a Northern blot of total pancreatic RNA samples from two transgenic (TG) and two control (WT) male mice probed for insulin or actin mRNA as indicated. (d) We prepared total pancreatic RNA from male Bridge-1 transgenic (TG) and strain- and age-matched control (WT) mice and performed real-time rt-PCR for each sample in triplicate with primers and probes to detect insulin, glucagon, glucokinase, glucose transporter-2 (Glut-2), elastase, and somatostatin, as indicated. Results shown are the means+/−SEM of the relative expression levels normalized to cyclophilin expression with the mean expression level for the control mice (WT) set at 1 (n=3-5 mice per genotype; *P=0.058; **P<0.01; ns, no significant difference by Student's T test). (e) Dose-dependent activation of insulin promoter enhancer elements by Bridge-1 is biphasic. HeLa cells were transiently transfected in triplicate with a multimerized FarFlat enhancer-reporter plasmid and the empty expression vector pcDNA3 or pcDNA3-Bridge-1. For each condition the total amount of pcDNA3 plasmids was constant. Results shown are the mean+/−SEM normalized to the basal activation of the reporter in the presence of pcDNA3 alone.

FIG. 8 Pancreatic islets are enlarged in mutant Bridge-1 (1-184) transgenic mice compared to wild-type mice. Mutant Bridge-1 (1-184) transgenic mice were generated from a transgene encoding mutant rat Bridge-1 (1-184) cDNA downstream of a previously characterized –4.6 kb segment of the mouse PDX-1 promoter and upstream of rabbit β globin poly A tail sequences. The Bridge-1 (1-184) mutant was generated by the introduction of an in-frame premature stop codon that resulted in a truncated expression product comprising amino acids 1-184. Pancreatic sections from mutant transgene and wild-type mice were stained with antiserum directed against insulin and counterstained with hematoxylin. Enlarged pancreatic islets in Bridge-1 mutant (1-184) transgenic mouse pancreas are shown.

Figure 9:
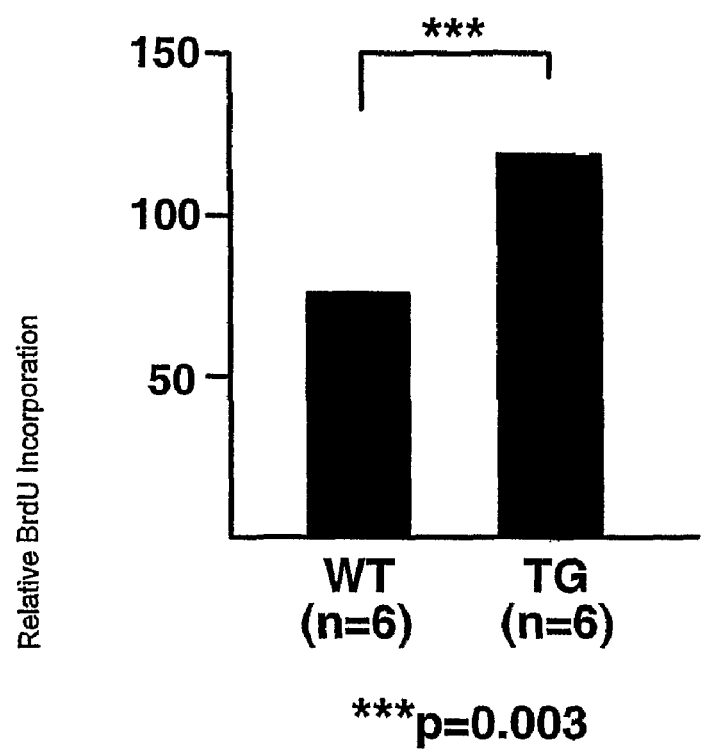

FIG. 9. Relative BrdU incorporation in pancreatic islet cells from mutant Bridge-1 (1-184) transgenic mice compared to wild-type. Mutant Bridge-1 transgenic and wild-type mice were injected with BrdU prior to pancreatic harvesting. Replicating islet cells were detected and counted in pancreatic sections with immunodetection of BrdU incorporation. Pancreatic islet cells from Bridge-1 mutant (1-184) transgenic mice have increased replication rates.

Figure 10:
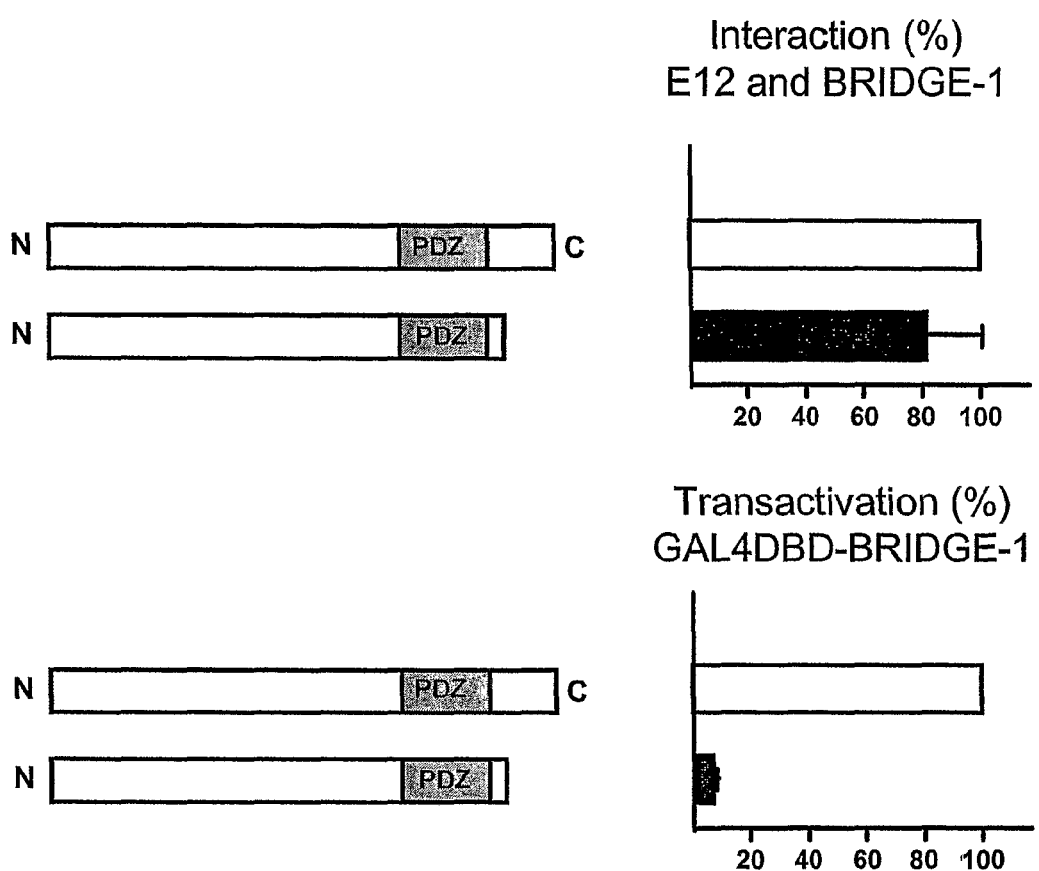

FIG. 10. The Bridge-1(1-184) mutant interacts with E12 but lacks transactivation activity. In mammalian two-hybrid studies in HeLa cells, the Bridge-1(1-184) mutant interacts well with E12 (from Thomas et al. 1999) (upper panel). However, the Gal4 DNA-binding domain-Bridge-1(1-184) fusion construct does not activate the Gal4CAT reporter in BHK cells (lower panel). Activities of Bridge-1(1-184) are compared with those of full length Bridge-1(1-222) (100%) in both experiments.

Figure 11:
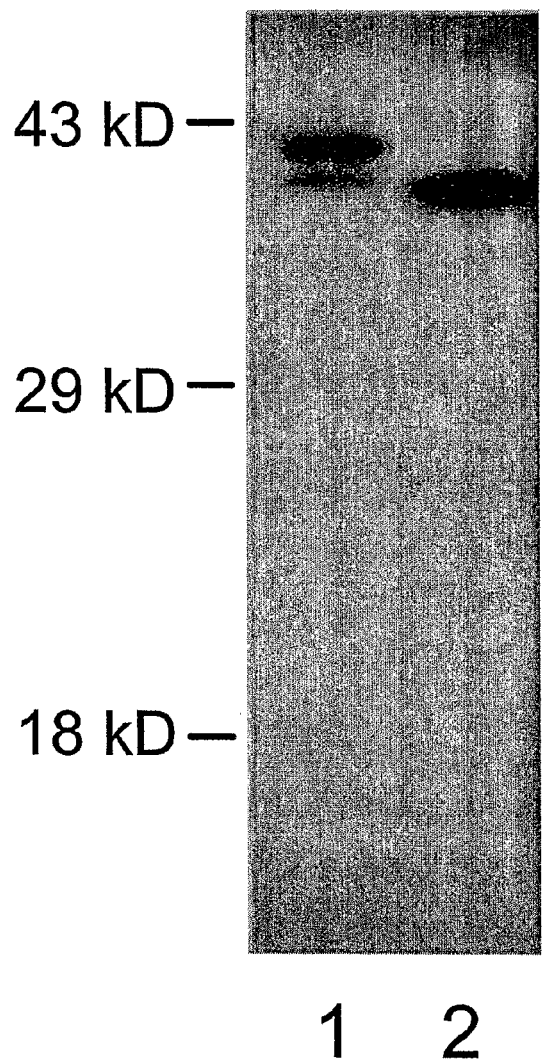

FIG. 11. The Bridge-1(1-184) mutant protein is expressed in BHK cells. Western blot of Gal4 DNA-binding domain-Bridge-1(1-222) (lane 1) and Gal4 DNA-binding domain-Bridge-1(1-184) (lane 2) fusion proteins from representative extracts of transfected BHK cells. Protein extracts were separated by SDS-PAGE, electroblotted and detected with anti-Gal4-DNA-.

FIG. 12. Schematic models of the pIDX-1-Bridge-1(1-222) and pIDX-1-Bridge-1(1-184) transgenes. PDX-1 is designated IDX-1 in this figure. The asterisk designates the in-frame premature stop codon that truncates the Bridge-1(1-184) mutant protein at amino acid 184.

Figure 13:
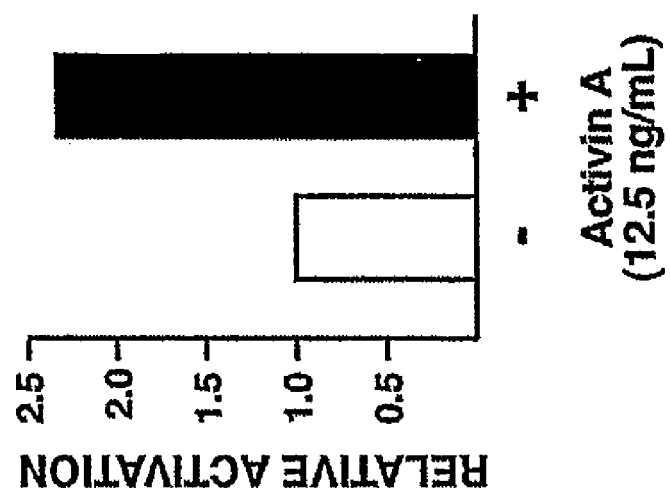
Figure 14:
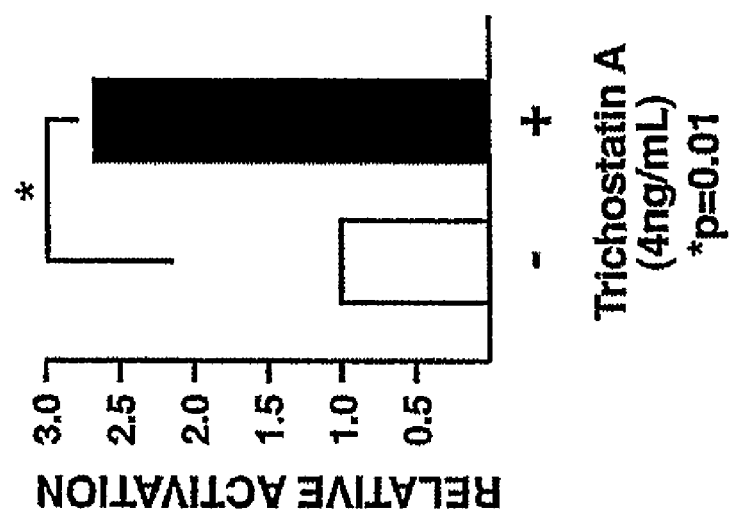
Figure 15:
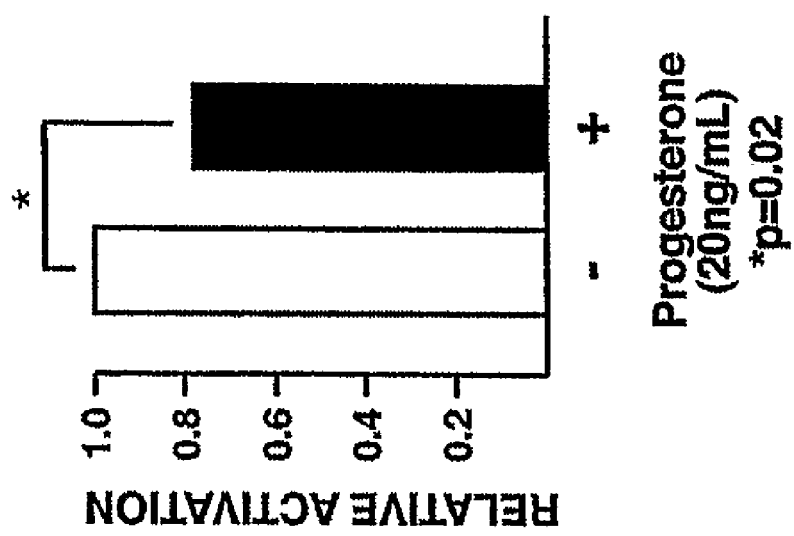

FIGS. 13-15. Figures show activating or inhibitory effect of Activin A, Trichostatin A, or Progesterone, respectively, in Bridge-1 transactivation assay.

FIG. 16. Nucleotide and amino acid sequences of rat Bridge-1 (SEQ ID Nos: 1 and 2).

FIG. 17 (*a-d*). The coactivator Bridge-1 interacts with multiple domains of p300. (a) Trichostatin A increases transcriptional activation by Bridge-1. BHK cells were transfected in duplicate with 1.5 µg Gal4-Bridge-1 or empty Gal4 expression vector, 3.25 µg pBluescript, and 250 ng of a Gal4-luciferase reporter and treated with vehicle (0), 2, or 4 ng/mL trichostatin A for 24 hours. Results shown are the mean+/– SEM relative luciferase activity of Gal4-Bridge-1 normalized to the empty Gal4 expression vector (n=3-5 transfections). (b) p300 increases the transcriptional activation by Bridge-1. BHK cells were transfected in duplicate with 0-3 µg of the p300 expression vector pCMV-p300 and 0.5 µg Gal4-Bridge-1 or empty Gal4 expression vector and 1 µg of a Gal4-CAT reporter. pBluescript was used to normalize the total DNA content for all conditions. Data shown are the mean of two transfections. (c) Bridge-1 directly interacts with p300. GST-Bridge-1 or GST control proteins were incubated with in vitro translated, radiolabeled [$^{35}$S]-p300 in GST protein interaction assays. A representative autoradiogram is shown of an SDS polyacrylamide gel from a GST pull-down protein interaction assay with the migration position of [$^{35}$S]-p300 designated (arrow). (d) Bridge-1 interacts with multiple domains within p300. A schematic diagram depicts protein interaction domains within p300 (adapted from (Chakravarti, E. A., et al., *Nature* 383:99-103 (1996)) (upper panel). In vitro translated, radiolabeled [$^{35}$S]-Bridge-1 (+) or empty vector control in vitro transcription and translation reactions (–) were incubated with GST-p300 (1-595), GST-p300 (744-1571), GST-p300 (1572-2370) or GST control (GST) proteins in GST protein interaction assays. Representative autoradiograms of SDS-polyacrylamide gels from a GST pull-down protein interaction assay and of 10% input of the [$^{35}$S]-Bridge-1 are shown (lower panel).

Figure 18:
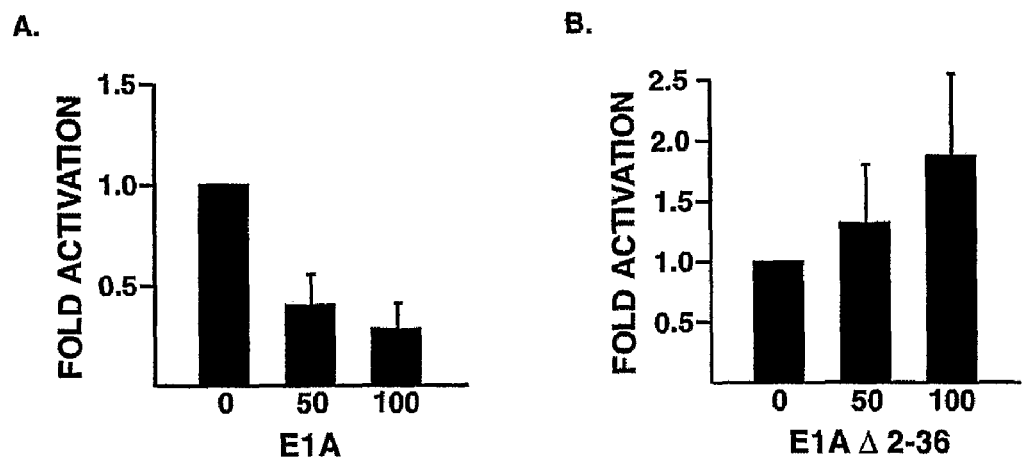

FIG. 18 (*a-b*). Sequestration of p300 by the adenoviral protein E1A interferes with transcriptional activation by Bridge-1. (a) Transcriptional activation by Bridge-1 is suppressed by E1A. BHK cells were transfected in duplicate with 1 µg Gal4-Bridge-1 and 0, 50, or 100 ng E1A and 1 µg Gal4-CAT reporter. pBluescript was added to normalize the total amount of DNA for all conditions. Results shown are the mean relative activation levels derived from two transfections, normalized to the activity of Gal-Bridge-1 set at 1.0. (b) Mutant E1A does not interfere with transcriptional activation by Bridge-1. BHK cells were transfected in duplicate with 1 µg Gal4-Bridge-1 and 0, 50, or 100 ng mutant E1A(Δ2-36) and 1 µg Gal4-CAT reporter. Results shown are the mean relative activation levels derived from two transfections, normalized to the activity of Gal-Bridge-1 set at 1.0.

FIG. 19 (*a-c*). The carboxy-terminal domains of Bridge-1 are required for transcriptional activation. (a) Deletion of carboxy-terminal domains of Bridge-1 reduce transcriptional activation in yeast. Quantitative beta-galactosidase assays were conducted on yeast transformed with LexA-Bridge-1, LexA-Bridge-1(1-72), or LexA-Bridge-1(1-132) expression vectors in conjunction with a LexA-operator-beta-galactosidase reporter. Results shown are the mean of two transformations, normalized to the activity of LexA-Bridge-1 set at 100 percent. (b) Deletion of carboxy-terminal domains of Bridge-1 reduce transcriptional activation in mammalian cells. BHK cells were transfected in duplicate with 1.5 µg Gal4-Bridge-1, Gal4-Bridge-1 (1-72), or Gal4-Bridge-1 (1-133), 3.25 µg pBluescript, and 250 ng of a Gal4-luciferase reporter. Results shown are the mean of 5 transfections, normalized to the activity of Gal4-Bridge-1 set at 100 percent. (c) Relative protein expression levels of Gal4-Bridge-1 deletion mutants on a Western blot of extracts from BHK cells transfected with Gal4-Bridge-1, Gal4-Bridge-1 (1-72), or Gal4-Bridge-1 (1-133), as indicated (+), conducted with anti-Gal4 antiserum.

FIG. 20 (*a-e*) Mutagenesis of the PDZ domain of Bridge-1 disrupts transcriptional activation. (a) Point mutations within conserved amino acids of the Bridge-1 PDZ domain disrupt transcriptional activation. BHK cells were transfected in duplicate with 4 µg Gal4-Bridge-1 (WT), Gal4-Bridge-1 (V159P), Gal4-Bridge-1 (V164P), Gal4-Bridge-1 (V175P), Gal4-Bridge-1 (D156P), Gal4-Bridge-1 (G151P), or empty Gal4 expression vector (Gal4), as indicated, with 1 µg of a Gal4-CAT reporter. A fluorescence image of a thin layer chromatogram from a representative CAT assay is shown with the fluorescent acetylated products (*) and substrate (S) indicated. (b) Relative Gal4-Bridge-1 mutant protein expression levels are shown on a Western blot of extracts from BHK cells transfected with Gal4-Bridge-1 (WT), Gal4-Bridge-1 (V159P), Gal4-Bridge-1 (V164P), Gal4-Bridge-1 (V175P), Gal4-Bridge-1 (D156P), or Gal4-Bridge-1 (G151P), as indicated, conducted with anti-Gal4 antiserum. (c) The Bridge-1

(D156P) mutant has diminished transcriptional activation. BHK cells were transfected in duplicate with 4 μg Gal4-Bridge-1 or Gal4-Bridge-1 (D156P), as indicated with 1 μg Gal4-CAT reporter. Results shown are the mean+/−SEM of three transfections, normalized to the activity of Gal4-Bridge-1 set at 100 percent. (d) Deletion of the PDZ domain decreases Bridge-1 interactions with p300. GST-Bridge-1, GST-Bridge-1 (1-72), GST-Bridge-1 (1-133), or GST control (GST) proteins were incubated with in vitro translated, radiolabeled [$^{35}$S]-p300 in GST pull-down protein interaction assays. A representative autoradiogram is shown of an SDS-polyacrylamide gel from a GST pull-down protein interaction assay with the migration position of [$^{35}$S]-p300 (arrow) indicated. (e) Mutagenesis of the PDZ domain decreases Bridge-1 interactions with p300. GST-Bridge-1, GST-Bridge-1 (D156P), or GST control (GST) proteins were incubated with in vitro translated, radiolabeled [$^{35}$S]-p300 in GST protein interaction assays in duplicate or triplicate samples. A representative autoradiogram is shown of an SDS-polyacrylamide gel from a GST pull-down protein interaction assay with the migration position of [$^{35}$S]-p300 (arrow) indicated.

Figure 21:
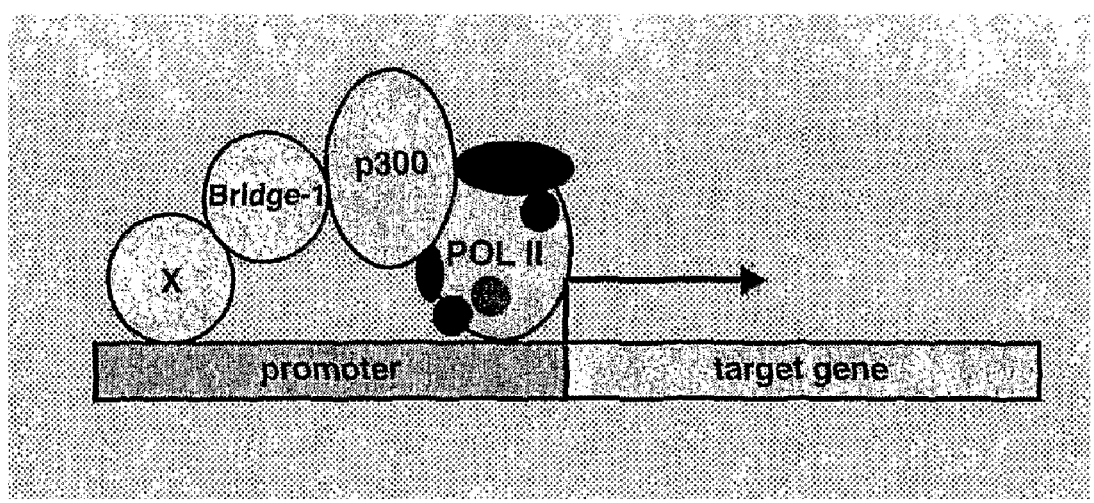

FIG. 21. Proposed model of Bridge-1 interactions with p300 in the activation of target gene transcription. In this schematic diagram p300 interacts with Bridge-1 in multiprotein complexes coupled to the basal transcription machinery (Pol II). Bridge-1 may recruit other transcriptional regulators (designated by X) to p300-containing protein complexes to activate target gene transcription.

Figure 22:
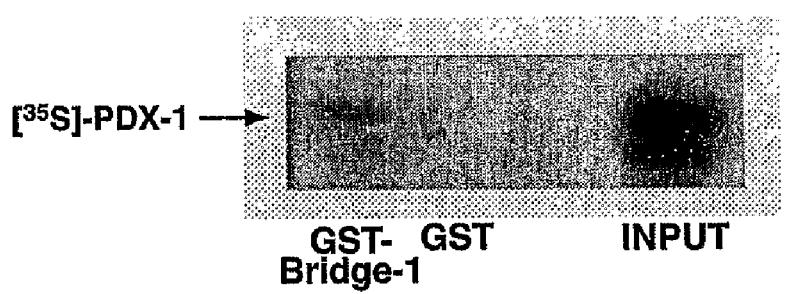

FIG. 22. PDX-1 interacts with Bridge-1 in GST pull-down assays. Radiolabeled in vitro translated rat PDX-1 was incubated with glutathione S-transferase (GST) control or glutathione S-transferase fusion proteins encoding rat Bridge-1 (GST-Bridge-1) in GST pull-down assays followed by separation on SDS-polyacrylamide gels and autoradiography. A representative autoradiogram is shown. The migration position of the radiolabeled PDX-1 protein is shown (arrow) and input PDX-1 protein is indicated (INPUT).

FIG. 23 (a-c). Bridge-1 interacts with the amino-terminal transactivation domain of PDX-1. (a) Schematic model of PDX-1 proteins. The full length PDX-1 protein (WT) and PDX-1 protein fragments encoding amino acids 1-38, 1-143, 1-206, and 143-283 are designated as indicated. The amino-terminal transactivation domain and the central DNA-binding homeodomain are designated. (b) Amino-terminal fragments of PDX-1 interact with GST-Bridge-1 in GST pull-down assays. Radiolabeled in vitro translated rat PDX-1 proteins encoding amino acids 1-143 (1), 143-283 (2), 1-206 (3), and full-length PDX-1 (WT, 4) or control in vitro translation reactions conducted with empty expression vector (Vector, 5) were incubated with GST-Bridge-1 or GST control proteins as indicated (+) in GST pull-down assays, separated on SDS-polyacrylamide gels, and assessed by autoradiography. Representative autoradiograms of the GST pull-down assay with arrows indicating the migration positions of PDX-1 mutant proteins (left panel) and relative amounts of input proteins (right panel, INPUT) are shown. (c) Radiolabeled Bridge-1 interacts with amino-terminal fragments of GST-PDX-1. Radiolabeled in vitro translated Bridge-1 (+) or control in vitro translation reactions conducted with empty expression vector (−) were incubated with glutathione S-transferase control (GST) or glutathione S-transferase fusion proteins encoding rat PDX-1 proteins with amino acids 1-38, 1-206, or full-length PDX-1 (WT), as indicated. GST pull-down assays were conducted followed by separation on SDS-polyacrylamide gels and autoradiography. A representative autoradiogram is shown. The migration position of the radiolabeled Bridge-1 protein is shown (arrow) and input Bridge-1 protein is indicated (INPUT).

Figure 24:
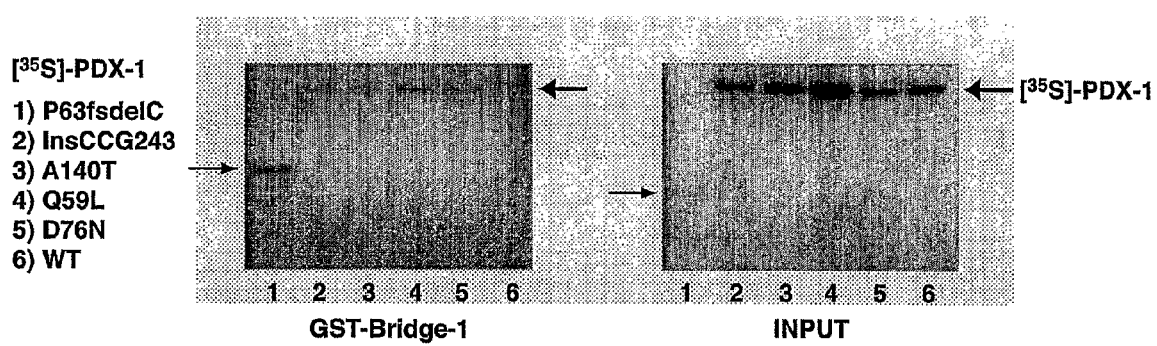

FIG. 24. Bridge-1 interacts with wild-type and mutant human PDX-1/IPF-1 proteins. Radiolabeled in vitro translated human PDX-1/IPF-1 proteins encoding the wild-type (WT, 6), or mutant sequences P63fsdelC (1), InsCCG243 (2), A140T (3), Q59L (4), or D76N (5) were incubated with GST-Bridge-1 in GST pull-down assays, separated on SDS-polyacrylamide gels, and assessed by autoradiography. Representative autoradiograms of the GST pull-down assay (left panel) and relative amounts of input proteins (right panel, INPUT) are shown. Arrows indicate the migration positions of wild-type (thick, at right) and of P63fsdelC mutant (thin, at left) radiolabeled PDX-1/IPF-1 proteins.

FIG. 25 (a-c). Bridge-1 increases the transcriptional activation of PDX-1. (a) Combination of Gal4-Bridge-1 and Gal4-PDX-1 proteins results in synergistic transcriptional activation. BHK cells were transiently transfected with 500 ng Gal4-CAT reporter and, as indicated (+), 25 ng Gal4-PDX-1, 100 ng Gal4-Bridge-1, or Gal4 empty expression vector for a total of 125 ng of expression vector per sample. Results shown are the mean+/−SEM (n=3 transfections, each conducted in duplicate; *p=0.06 for the Gal4-PDX-1 and Gal4-Bridge-1 combination as compared to Gal4-PDX-1 alone). (b) Bridge-1 increases the activation of rat somatostatin promoter enhancer sequences by PDX-1. BHK cells were transiently transfected with 500 ng (SMS-TAAT1)$_5$-65SMS-CAT reporter, and 150 ng pCMV-PDX-1 (+) or empty pCMV expression vector (−) with 0, 200, or 500 ng pcDNA3-Bridge-1, as indicated. Empty pcDNA3 vector was added as needed to normalize total amounts of DNA in all transfections. A fluorescent image of the acetylated product from a thin layer chromatogram of a CAT assay conducted in duplicate is shown. (c) Bridge-1 increases the synergistic activation of the rat insulin I promoter enhancer FarFlat by PDX-1, E12, and E47. HeLa cells were transiently transfected with 500 ng FarFlat-CAT reporter and 125 ng pCMV-PDX-1, 50 ng pcDNA3-E12, and 50 ng pcDNA3-E47 with 200 ng empty pcDNA3 expression vector (−) or pcDNA3-Bridge-1 (+). Results shown are the mean+/−SEM (n=9 transfections, each conducted in duplicate; p=0.00003).

Figure 26:
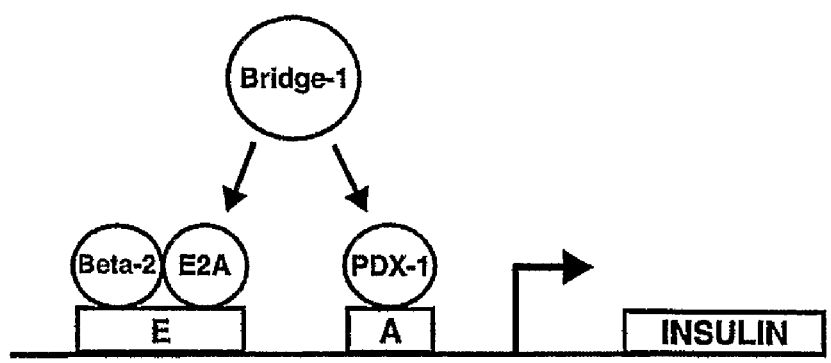

FIG. 26. Working model of Bridge-1 coactivator function on glucose-response elements of the insulin promoter. Bridge-1 can activate the insulin promoter indirectly via protein-protein interactions with PDX-1 and/or by interactions with E2A proteins such as E12 and E47 (Thomas et al., 1999).

FIG. 27 (a-c). Nucleotide (FIG. 27(a)) and amino acid (FIG. 27(b)) sequences of a human PSMD9 coding sequence (accession no. NM_002813) (SEQ ID Nos: 154 and 155). Genomic sequence of human PSMD9 gene, with the location of various single nucleotide polymorphisms indicated (FIG. 27(c)) (SEQ ID NO:164).

Figure 28A:
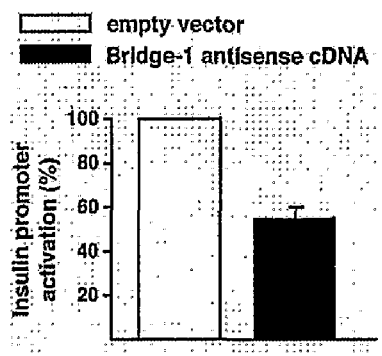
Figure 28B:
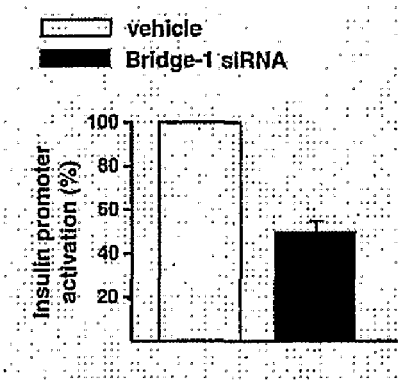
Figure 28C:
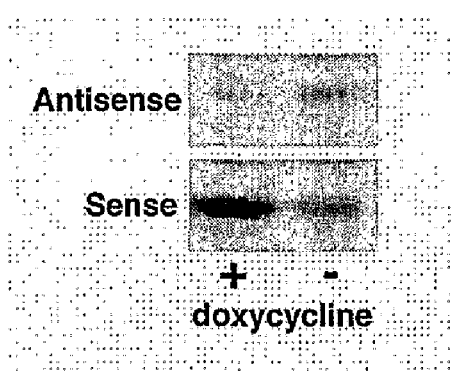

FIG. 28. (a-c) Endogenous Bridge-1 expression is required for insulin promoter activity. (a). In transient transfections of INS-1 cells an antisense Bridge-1 cDNA construct decreased the activation of a rat insulin I promoter (−410-+47)-luciferase reporter. (b). Rat insulin I promoter-reporter activation was reduced to a similar extent by administration of an anti-Bridge-1 small interfering duplex RNA to INS-1 cells. (c). Bridge-1 protein expression levels can be inducibly increased or suppressed in stable INS-1 cells. Double stable rtTA/Tet-Bridge-1 (Sense) or rtTA/Tet-Antisense-Bridge-1 (Antisense) INS-1 cells were treated with 1 μg/mL doxycycline (+) or vehicle (−) prior to isolation of whole cell protein extracts and Western blots with anti-Bridge-1 antiserum.

FIG. 29. (a-c) (a). Neurogenin-3 activates the expression of NeuroD1/Beta-2 in embryonic progenitor cells in the early stages of commitment to the insulin- or glucagon-producing lineages. (b). Neurogenin-3 and NeuroD1/Beta-2 pancreatic mRNA expression levels are upregulated in adult Bridge-1 transgenic mice with diabetes. (c). Neurogenin-3 is expresses in pancreas of adult Bridge-1 transgenic mice but not in the pancreas of control mice.

DETAILED DESCRIPTION OF THE INVENTION

Multiple forms of heritable diseases are associated with mutations in transcription factors that regulate insulin gene transcription and the development and maintenance of pancreatic β-cell mass. The coactivator Bridge-1 increases the transcriptional activation of glucose-responsive enhancers in the insulin gene via PDZ-domain mediated interactions with E2A transcription factors.

The present inventors have discovered that disruption of Bridge-1 signaling by the pancreatic overexpression of Bridge-1 in transgenic mice represses insulin gene expression to result in insulin deficiency and severe early-onset diabetes. Dysregulation of Bridge-1 signaling increases pancreatic apoptosis with a reduction in the number of insulin-producing pancreatic cells and an expansion of the complement of glucagon-expressing pancreatic a cells. Increased expression of Bridge-1 alters pancreatic islet, acinar, and ductal architecture and disrupts the boundaries between endocrine and exocrine cellular compartments, suggesting that signals transduced through this coactivator influence pancreatic islet morphogenesis and endocrine cell migration. The results indicate that the coactivator Bridge-1 regulates both glucose homeostasis and pancreatic β-cell survival and that coactivator dysfunction in pancreatic β cells limits insulin production and contributes to the pathogenesis of diabetes.

Nucleic Acid Molecules

Nucleic acid molecules useful in the methods of the present invention are disclosed, for example, in pending U.S. application Ser. No. 09/959,123, the entire contents of which are hereby incorporated by reference. Thus, a Bridge-1 "polynucleotide" refers to a molecule having a nucleic acid sequence contained in the full-length Bridge-1 sequence. As used herein, the term "Bridge-1" is intended to encompass rat Bridge-1, its mouse homolog, as well as the human homolog (also known as PSMD9), (See, e.g., Watanabe, T. K et al., Genomics 50 (2), 241-250 (1998). For example, the Bridge-1 polynucleotide can contain the nucleotide sequence of the full-length Bridge-1 cDNA sequence described in 09/959, 123, including the 5' and 3' untranslated sequences, the coding region, with or without any signal sequence, the protein coding region, as well as fragments, epitopes, domains, and variants of the nucleic acid sequence. Moreover, as used herein, a Bridge-1 "polypeptide" refers to a molecule having the translated amino acid sequence generated from the polynucleotide as broadly defined.

In one embodiment of the present invention, isolated polynucleotides are provided which encode the Bridge-1 protein. Using information provided herein, a nucleic acid molecule of the present invention encoding a Bridge-1 polypeptide may be obtained using standard cloning and screening procedures. As described in U.S. application Ser. No. 09/959,123, the nucleic acid molecule encoding rat Bridge-1 was obtained from a cDNA expression library from rat pancreatic islet cells. The rat Bridge-1 cDNA encodes a protein of about 222 amino acids, which includes a PDZ-like domain. Bridge-1 is widely expressed, since the corresponding transcript was found in several human tissues, including pancreas, testes, kidney, and liver.

Isolated nucleic acids useful in the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the antisense strand.

By "isolated" nucleic acid molecule(s) is intended a nucleic acid molecule, DNA or RNA, which has been removed from its native environment (e.g., the natural environment if it is naturally occurring), and thus is altered "by the hand of man" from its natural state. For example, recombinant DNA molecules contained in a vector are considered isolated for purposes of the present invention. Additional illustrative examples of isolated DNA molecules include recombinant DNA molecules maintained in heterologous host cells and purified (partially or substantially) DNA molecules in solution. Isolated RNA molecules include in vitro RNA transcripts of the DNA molecules of the present invention as well as partially or substantially purified mRNA molecules. "Purified" as it refers to preparations made from biological cells or hosts should be understood to mean any cell extract containing the indicated DNA or protein including a crude extract of the DNA or protein of interest. For example, in the case of a protein, a purified preparation can be obtained by following an individual technique or a series of preparative or biochemical techniques and the DNA or protein of interest can be present at various degrees of purity in these preparations. The procedures may include for example, but are not limited to, ammonium sulfate fractionation, gel filtration, ion exchange chromatography, affinity chromatography, density gradient centrifugation and electrophoresis. "Substantially pure" should be understood to mean a "highly" purified preparation that contains at least 95% of the DNA or protein of interest. Isolated nucleic acid molecules according to the present invention further include nucleic acid molecules produced synthetically.

Isolated polynucleotides useful of the present invention include DNA molecules comprising the rat or human Bridge-1 and DNA molecules which comprise a sequence substantially different than these molecules but which, due to the degeneracy of the genetic code, still encode the Bridge-1 protein. Of course, the genetic code is well known in the art. Thus, it would be routine for one skilled in the art to generate the degenerate variants described above.

In another aspect, the methods of the present invention utilize isolated nucleic acid molecules encoding the Bridge-1 polypeptide having an amino acid sequence as encoded by the cDNA clone in the plasmid pcDNA3-Bridge-1 deposited with the American Type Culture Collection (ATCC, 10801 University Blvd., Manassas, Va. 20110-2209) and assigned accession number 203947. The methods of the invention also may utilize an isolated polynucleotide having the nucleotide sequence of the Bridge-1 coding region or the nucleotide sequence of the Bridge-1 cDNA contained in the above-described clone, or a nucleic acid molecule having a sequence complementary to one of the above sequences. Such isolated nucleic acid molecules, preferably DNA molecules, are useful as probes for gene mapping by in situ hybridization with chromosomes and for detecting expression of the Bridge-1 gene, or genes homologous to the Bridge-1 gene, in human tissue, for instance, by Northern blot analysis.

In another aspect, the methods of the invention utilize an isolated nucleic acid molecule that hybridizes under stringent conditions to the above-described nucleic acid molecules. As used herein "stringent conditions" is intended to mean, as a non-limiting example, overnight incubation at 42EC in a solution comprising 50% formamide, 5×SSC (150 mM NaCl, 15 mM trisodium citrate), 50 mM sodium phosphate (pH7.6), 5× Denhardt's solution, 10% dextran sulfate, and 20 µg/ml denatured, sheared salmon sperm DNA, followed by washing the filters in 0.1×SSC at about 65EC. Preferably, such "an isolated nucleic acid molecule that hybridizes under stringent conditions" will be at least 15 bp, preferably at least 20 bp, more preferably at least 30 bp, more preferably at least 40 bp, and most preferably, at least 50 bp in length.

As used herein, "fragments" of an isolated DNA molecule having the nucleotide sequence of the deposited cDNA clone described above or the nucleotide sequence as shown in FIG. 16 or the nucleotide sequence of the ORF, i.e. the coding region, as shown in FIG. 16, is intended to mean DNA fragments at least 15 bp, more preferably at least 20 bp, more preferably at least 30 bp, more preferably at least 40 bp, more preferably at least 50 bp, more preferably at least 60 bp, more preferably at least 70 bp, more preferably at least 80 bp, more preferably at least 90 bp, more preferably at least 100 bp length, and most preferably at least 200 bp, in length. Such fragments are useful, inter alia, as diagnostic probes and primers. Larger DNA fragments, up to, for example, 500 bp in length, are also useful as probes according to the present invention. A fragment of at least 20 bp in length, for example, is intended to mean fragments which include 20 or more contiguous bases from the nucleotide sequence of the deposited cDNA or the nucleotide sequence of the ORF, i.e. coding region, as shown in FIG. 1. As indicated, such fragments are useful diagnostically inter alia as a probe according to conventional DNA hybridization techniques or as primers for amplification of a target sequence by the polymerase chain reaction (PCR).

In a preferred embodiment, polynucleotide fragments of the invention comprise at least 15 contiguous nucleotides of the Bridge-1 coding sequence shown in FIG. 1, but do not comprise all or a portion of any Bridge-1 intron. In another embodiment, the nucleic acid comprising Bridge-1 coding sequence does not contain coding sequences of a genomic flanking gene (i.e., 5N or 3N to the Bridge-1 gene in the genome.)

Many polynucleotide sequences, such as EST sequences, are publicly available and accessible through sequence databases. The EST sequences referred to below were identified in a BLAST search of the EST database. These sequences are believed to be partial sequences of the cDNA insert identified in the recited GenBank accession numbers.

For example, the following sequences are related to the coding region of Bridge-1, GenBank Accession Nos: AW140997 (SEQ ID NO:29); AI410372 (SEQ ID NO:30); AI710949 (SEQ ID NO:31); AI410370 (SEQ ID NO: 32); AI175576 (SEQ ID NO:33); A1410377 (SEQ ID NO:34); AI176737 (SEQ ID NO:35); AI059501 (SEQ ID NO:36); AI577670 (SEQ ID NO:37); AI030624 (SEQ ID NO:38); W97405 (SEQ ID NO:39); W59260 (SEQ ID NO:40); AA990371 (SEQ ID NO:41); AV085226 (SEQ ID NO:42); AA458312 (SEQ ID NO:43); AA244824 (SEQ ID NO:44); W41287 (SEQ ID NO:45); AA764187 (SEQ ID NO:46); AA530067 (SEQ ID NO:47); AA760338 (SEQ ID NO:48); AV239440 (SEQ ID NO:49); AA230657 (SEQ ID NO:50); AA832760 (SEQ ID NO:51); AV018936 (SEQ ID NO:52); AA033111 (SEQ ID NO:53); W41542 (SEQ ID NO:54); AI426803 (SEQ ID NO:55); AV117212 (SEQ ID NO:56); A1853315 (SEQ ID NO:57); W61442 (SEQ ID NO:58); AV043811 (SEQ ID NO:59); A1194159 (SEQ ID NO:60); AA958415 (SEQ ID NO:61); W77431 (SEQ ID NO:62); AA940225 (SEQ ID NO:63); AW495918 (SEQ ID NO:64); AV019366 (SEQ ID NO:65); AW124782 (SEQ ID NO:66); AW496344 (SEQ ID NO:67); W83144 (SEQ ID NO:68); AA110868 (SEQ ID NO:69); AV204705 (SEQ ID NO:70); AV117489 (SEQ ID NO:71); AV204580 (SEQ ID NO:72); AV149555 (SEQ ID NO:73); AV217918 (SEQ ID NO:74); AV144222 (SEQ ID NO:75); AV363935 (SEQ ID NO:76); AV367917 (SEQ ID NO:77); AV131095 (SEQ ID NO:78); AA038844 (SEQ ID NO:79); AV000269 (SEQ ID NO:80); AV215700 (SEQ ID NO:81); AA574257 (SEQ ID NO:82); A1580764 (SEQ ID NO:83); AI421341 (SEQ ID NO:84); A1624271 (SEQ ID NO:85); AI673018 (SEQ ID NO:86); A1826486 (SEQ ID NO:87); AW025889 (SEQ ID NO:88); A1690995 (SEQ ID NO:89); AI934145 (SEQ ID NO:90); AI 805491 (SEQ ID NO:91); AI318424 (SEQ ID NO:92); AI694835 (SEQ ID NO:93); AI915915 (SEQ ID NO:94); AI347155 (SEQ ID NO:95); H79248 (SEQ ID NO:96); H79154 (SEQ ID NO:97); AA883244 (SEQ ID NO:98); AI925943 (SEQ ID NO:99); AI027566 (SEQ ID NO:100); AI422908 (SEQ ID NO:101); H12345 (SEQ ID NO:102); H12296 (SEQ ID NO:103); AA147029 (SEQ ID NO:104); AA147030 (SEQ ID NO:105); R21923 (SEQ ID NO:106); R22572 (SEQ ID NO:107); AI264294 (SEQ ID NO:108); AI439891 (SEQ ID NO:109); W88749 (SEQ ID NO:110); AI698667 (SEQ ID NO:111); AI439894 (SEQ ID NO:112); AI421551 (SEQ ID NO:113); H63468 (SEQ ID NO:114); AI082760 (SEQ ID NO:115); W73843 (SEQ ID NO:116); W73699 (SEQ ID NO:117); AA535984 (SEQ ID NO:118); AW000865 (SEQ ID NO:119); R25346 (SEQ ID NO:120); R26538 (SEQ ID NO:121); AA936901 (SEQ ID NO:122); A1350558 (SEQ ID NO:123); AW296973 (SEQ ID NO:124); A1003420 (SEQ ID NO:125); AI880806 (SEQ ID NO:126); R60563 (SEQ ID NO:127); AA356988 (SEQ ID NO:128); AL037250 (SEQ ID NO:129); AW389915 (SEQ ID NO:130); AI439880 (SEQ ID NO:131); N30591 (SEQ ID NO:132); AW242490 (SEQ ID NO:133); AI950686 (SEQ ID NO:134); AW389884 (SEQ ID NO:135); AA374147 (SEQ ID NO:136); AW368137 (SEQ ID NO:137); AW389910 (SEQ ID NO:138); AA640616 (SEQ ID NO:139); AW079701 (SEQ ID NO:140); AI202368 (SEQ ID NO:141); N51558 (SEQ ID NO:142); AA401853 (SEQ ID NO:143); AW410681 (SEQ ID NO:144); N40375 (SEQ ID NO:145); AW385667 (SEQ ID NO:146); N27557 (SEQ ID NO:147); AW368222 (SEQ ID NO:148); AW368132 (SEQ ID NO:149); R60619 (SEQ ID NO:150); D20400 (SEQ ID NO:151); AW517221 (SEQ ID NO:152); AA403126 (SEQ ID NO:153).

Thus, in one embodiment the present invention is directed to polynucleotides comprising the polynucleotide fragments and full-length polynucleotide (e.g. the coding region) described herein exclusive of one or more of the above recited ESTs.

Since the plasmid containing the cDNA clone has been deposited and the nucleotide sequence shown in FIG. 1 is provided, generating such DNA fragments would be routine to the skilled worker in the relevant art. Restriction endonuclease cleavage or shearing by sonication, for example, may easily be used to generate fragments of various sizes. Alternatively, the DNA fragments of the present invention can be generated synthetically according to the methods and techniques known and available to those skilled in the art.

The present invention further relates to variants of the nucleic acid molecules of the present invention, which encode for fragments, analogs or derivatives of the Bridge-1 protein, e.g., polypeptides having biological activity substantially similar to the Bridge-1 protein. Variants may occur naturally, such as isoforms and allelic variants. Non-naturally occurring variants may be produced using any of the mutagenesis techniques known and available to those skilled in the art.

Such variants include those produced by nucleotide substitutions, deletions or additions. The substitutions, deletions or additions may involve one or more nucleotides. The variants may be altered in coding or non-coding regions or both. Alterations in the coding regions may produce conservative or non-conservative amino acid substitutions, deletions or additions. Especially preferred among these are silent substitutions, additions and deletions, which do not alter the properties and activities of the Bridge-1 protein or fragment thereof. Also especially preferred in this regard are substitution of nucleotides that encode a conservative amino acid substitution. In a preferred embodiment, such variants contain no more than five total substitutions, deletions, and/or additions.

Further embodiments of the invention include isolated nucleic acid molecules comprising a polynucleotide having a nucleotide sequence at least 80% identical, more preferably at least 85% identical, more preferably at least 90% identical, and most preferably at least 95%, 96%, 97%, 98%, or 99% identical to: (a) the nucleotide sequence of the cDNA clone in the plasmid pcDNA3-Bridge-1 deposited with the American Type Tissue Culture ("ATCC") and assigned accession number 203947; (b) the nucleotide sequence shown in FIG. 16; (c) the nucleotide sequence of the cDNA clone in the plasmid pcDNA3-Bridge-1 deposited with the American Type Tissue Culture ("ATCC") and assigned accession number 203947, which encodes the full-length Bridge-1 protein; (d) the nucleotide sequence of the ORF, i.e. coding region, shown in FIG. 16, which encodes the full-length Bridge-1 protein; (e) a nucleotide sequence complimentary to any of (a)-(d).

Whether any two nucleic acid molecules have nucleotide sequences that are at least 80%, 85%, 90%, 95%, 96%, 97%, 98%, or 99% "identical" can be determined conventionally using known computer algorithms. A preferred method for determining the best overall match between a query sequence (a sequence of the present invention) and a subject sequence, also referred to as a global sequence alignment, can be determined using the FASTDB computer program based on the algorithm of Brutlag et al., *Comp. App. Biosci.* 6:237-245 (1990). In a sequence alignment the query and subject substances are both DNA sequences. An RNA sequence can be compared by converting U's to T's. The result of the global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter. The present application is directed to such nucleic acid molecules having a nucleotide sequence at least 90%, 95%, 96%, 97%, 98%, 99%, identical to the nucleotide sequence of the above-recited nucleic acid molecules irrespective of whether they encode a polypeptide having Bridge-1 activity. This is because, even where a particular nucleic acid molecule encodes a polypeptide that does not have Bridge-1 activity, one of skill in the art would still know how to use the nucleic acid molecule as a probe. In at least one embodiment, the percent identity is measured by comparing the obtained DNA sequence to that of nucleotides 495-1162 (i.e., the ORF or coding region) of the nucleotide sequence in FIG. 16. Uses of the nucleic acid molecules of the present invention that do not encode a polypeptide having Bridge-1 activity include, inter alia, (1) isolating the Bridge-1 gene or allelic variants thereof in a cDNA library; (2) in situ hybridization (FISH) to metaphase chromosomal spreads to provide precise chromosomal location of the Bridge-1 gene as described in Verma et al., *Human Chromosomes: a Manual of Basic Techniques*, Pergamon Press, New York (1988); and Northern Blot analysis for detecting Bridge-1 mRNA expression in specific tissues, such as placenta tissue.

As used herein, "Bridge-1 activity" is intended to mean one or more of the following: protein-protein binding activity, transcription coactivation activity, or transcription activation activity. By "transcription activation activity" is meant increased or decreased regulation of gene expression consisting of an increase or decrease in the level of transcription and/or translation resulting from interaction with core cellular transcriptional or translational machinery. By "transcription coactivation activity" is meant increased or decreased regulation of gene expression consisting of an increase or decrease in the level of transcription and/or translation resulting from interaction with other proteins with transcription activation activity. The term "Bridge-1 activity" also encompasses increases and decreases in expression of Bridge-1 itself or in expression of a Bridge-1 target gene.

As used herein, "Bridge-1 target gene" is intended to mean a gene, the expression and/or function of which is modulated by Bridge-1 activity as defined herein.

As used herein, "Bridge-1 mediated disorder" is intended to mean a disease or disorder that is caused at least in part by abnormal levels of Bridge-1 activity.

Preferred, however, are nucleic acid molecules having a nucleotide sequence at least 80%, and preferably at least 85%, 90%, 95%, 96%, 97%, 98%, or 99% identical to the nucleotide sequence of the above-described nucleic acid molecules which do, in fact, encode a polypeptide having Bridge-1 activity. As used herein, "a polypeptide having a Bridge-1 activity" is intended to mean polypeptides exhibiting similar, but not necessarily identical, activity as to the Bridge-1 activity as measured in a particular biological assay. For example, the Bridge-1 protein of the present invention interacts directly with known transcription factors such as PDX-1, E12, E47 and P300. Moreover, when recombinantly expressed in mammalian cells, the Bridge-1 protein of the present invention enhances transcription genes modulated by these transcription factors. Thus, "a polypeptide having a Bridge-1 protein activity" includes polypeptides that interact with, or otherwise enhance or inhibit, PDX-1, E12, E47, P300 and other transcription factors or otherwise enhance PDX-1, P300 or E2A protein dependent transcriptional activation or PDX-1, P300 or E2A independent transcription activation.

Due to the degeneracy of the genetic code, one of ordinary skill in the art will immediately recognize that a large number of the nucleic acid molecules having a nucleotide sequence at least 90%, preferably at least 95%, 96%, 97%, 98%, 99% identical to the nucleotide sequence of the above-described nucleic acid molecules will encode "a polypeptide having Bridge-1 activity." In fact, since degenerate variants all encode the same polypeptide, this will be clear to the skilled artisan. It will be further recognized by those skilled in the art that, for such nucleic acid molecules that are not degenerate variants, a reasonable number will also encode a polypeptide having Bridge-1 activity. This is because the skilled artisan is fully aware of possible amino acid substitutions that are either less likely or not likely to significantly affect protein function (e.g., replacing one aliphatic amino acid with a second aliphatic amino acid).

Guidance concerning how to make phenotypically silent amino acid substitutions is provided, for example, in J. U. Bowie et al., "Deciphering the Message in Protein Sequences: Tolerance to Amino Acid Substitutions," *Science* 247:1306-1310 (1990), the entire contents of which is hereby incorporated by reference herein, wherein the authors indicate that there are two main approaches for studying the tolerance of an amino acid sequence to change. The first method relies on the process of evolution, in which mutations are either accepted or rejected by natural selection. The second approach uses genetic engineering to introduce amino acid changes at specific positions of a cloned gene and selections or screens to identify sequences that maintain functionality. As the authors state, these studies have revealed that proteins are surprisingly tolerant of amino acid substitutions. The authors further indicate which amino acid changes are likely to be permissive at a certain position of the protein. For example, most buried amino acid residues require nonpolar side chains, whereas few features of surface side chains are generally conserved. Other such phenotypically silent substitutions are described in Bowie et al., supra, and the references cited therein.

Vectors and Host Cells

Vectors and host cells useful in practicing the methods of the present invention are described in U.S. application Ser. No. 09/959,123, the entire contents of which are hereby incorporated by reference. Thus, the methods of the present invention may utilize vectors which include the isolated DNA molecules of the present invention, host cells which are genetically engineered with the recombinant vectors, and the production of Bridge-1 or Bridge-1 fragments. As used herein, "Bridge-1 fragment" means a shortened sequence of an amino acid sequence that retains some or all of the Bridge-1 activity of the full-length sequence, such as a fragment comprising the Bridge-1 PDZ-like domain (amino acids 138-178 of the amino acid sequence shown in FIG. 16, the Bridge-1 carboxyl terminus domain (amino acids 186-222 of the amino acid sequence shown in FIG. 16), or the Bridge-1 PDZ-like domain and the Bridge-1 carboxyl terminus domain (amino acids 138-222 of the amino acid sequence shown in FIG. 16). The term "Bridge-1 fragment" is also intended to refer to splice-variants and proteolytic fragments of the full-length Bridge-1 amino acid sequence shown in FIG. 1, including the "small form" Bridge-1 which migrates at approximately 18 kD in SDS-PAGE Western Blots, is detected with rabbit polyclonal Bridge-1 antisera, and is differentially expressed in cell lines derived from different tissues with preferential expression in pancreatic beta cells. Recombinant constructs may be introduced into host cells using well known techniques such as infection, transduction, transfection, transvection, electroporation and transformation. The vector may be, for example, a phage, plasmid, viral or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

Preferred are vectors comprising cis-acting control regions to the polynucleotide of interest. Appropriate trans-acting factors may be supplied by the host, supplied by a complementing vector or supplied by the vector itself upon introduction into the host.

In certain preferred embodiments in this regard, the vectors provide for specific expression, which may be inducible and/or cell type-specific. Particularly preferred among such vectors are those inducible by environmental factors that are easy to manipulate, such as temperature and nutrient additives.

Expression vectors useful in the present invention include chromosomal-, episomal- and virus-derived vectors, e.g., vectors derived from bacterial plasmids, bacteriophage, yeast episomes, yeast chromosomal elements, viruses such as baculoviruses, papova viruses, vaccinia viruses, adenoviruses, fowl pox viruses, pseudorabies viruses and retroviruses, and vectors derived from combinations thereof, such as cosmids and phagemids.

The DNA insert should be operatively linked to an appropriate promoter, such as the phage lambda PL promoter, the *E. coli* lac, trp and tac promoters, the SV40 early and late promoters, CMV promoters, promoters of retroviral LTRs, and inducible promoters such as tetracycline and IPTG inducible promoters as well as promoters inducible with heavy metals to name a few. Other suitable promoters will be known to the skilled artisan. The expression constructs will further contain sites for transcription initiation, termination and, in the transcribed region, a ribosome binding site for translation. The coding portion of the mature transcripts expressed by the constructs will preferably include a translation initiating AUG at the beginning and a termination codon (UAA, UGA or UAG) appropriately positioned at the end of the polypeptide to be translated. As indicated, the expression vectors will preferably include at least one selectable marker. Such markers include dihydrofolate reductase or neomycin resistance for eukaryotic cell culture and tetracycline or ampicillin resistance genes for culturing in *E. coli* and other bacteria. Representative examples of appropriate hosts include, but are not limited to, bacterial cells, such as *E. coli, Streptomyces* and *Salmonella typhimurium* cells; fungal cells, such as yeast cells; insect cells such as *Drosophila* S2 and *Spodoptera* Sf9 cells; animal cells such as CHO, Cos and Bowes melanoma cells; and plant cells. Appropriate culture mediums and conditions for the above-described host cells are known in the art.

Illustrative examples of vectors preferred for use in bacteria include, but are not limited to, pA2, pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Preferred eukaryotic vectors include, but are not limited to, pcDNA-3 (Invitrogen), pM, pVP16 (Clonetech), pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Among known bacterial promoters suitable for use in the present invention include the *E. coli* lacI and lacZ promoters, the T3 and T7 promoters, the gpt promoter, the lambda PR and PL promoters and the trp promoter. Suitable eukaryotic promoters include the CMV immediate early promoter, the HSV thymidine kinase promoter, the early and late SV40 promoters, the promoters of retroviral LTRs, such as those of the Rous sarcoma virus ("RSV"), and metallothionein promoters, such as the mouse metallothionein-I promoter. Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., BASIC METHODS IN MOLECULAR BIOLOGY (1986) and Ausubel, F. M. et al., CURRENT PROTOCOLS IN MOLECULAR BIOLOGY, (John Wiley and Sons, Inc.) 1994-1997.

Transcription of the DNA encoding the polypeptides of the present invention by higher eukaryotes may be increased by inserting an enhancer sequence into the vector. Enhancers are cis-acting elements of DNA, generally about 10 to 300 bp in size, that act to increase transcriptional activity of a promoter in a given host cell-type. Illustrative examples of enhancers include, but are not limited to, the SV40 enhancer, which is located on the late side of the replication origin at bp 100 to 270, the cytomegalovirus early promoter enhancer, the polyoma enhancer on the late side of the replication origin, and adenovirus enhancers.

For secretion of the translated protein into the lumen of the endoplasmic reticulum, into the periplasmic space or into the extracellular environment, appropriate secretion signals may be incorporated into the expressed polypeptide. The signals may be endogenous to the polypeptide or they may be heterologous signals.

The polypeptide may be expressed in a modified form, such as a fusion protein, and may include not only secretion signals, but also additional heterologous functional regions. Thus, for instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification.

The Bridge-1 protein or fraction thereof can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

Polypeptides of the present invention include, but are not limited to, naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be post translationally modified (e.g., glycosylated, phosphorylated, farnesylated, etc.). In addition, polypeptides of the invention may also include an initial modified methionine residue, in some cases as a result of host-mediated processes.

Bridge-1 Polypeptides and Fragments

Bridge-1 polypeptides and fragments thereof useful in practicing the methods of the present invention are described in U.S. application Ser. No. 09/959,123, the entire contents of which is incorporated herein by reference. Thus, the methods of the present invention may utilize an isolated mammalian Bridge-1 polypeptide having the amino acid sequence encoded by the deposited cDNA, or the amino acid sequence as shown in FIG. 16, or a fragment thereof. Preferred Bridge-1 fragments will have Bridge-1 activity. Preferred Bridge-1 fragments should at least include amino acid residues 138 to 178 as shown in FIG. 116 and/or amino acid residues 186-222 as shown in FIG. 16, or amino acid substitutions, additions or deletions thereof that are not significantly detrimental to Bridge-1 activity.

Bridge-1 polypeptide fragments may be "free-standing" or comprised within a larger polypeptide of which the fragment forms a part or region, most preferably as a single continuous region. Polypeptide fragments may comprise 9, 15, 20, 30, 40, 50, 60, 70, 80, 90, or 100 or more amino acids in length.

As used herein, an "isolated" polypeptide or protein is intended to mean a polypeptide or protein removed from its native environment, such as recombinantly produced polypeptides and proteins expressed in host cells and native or recombinant polypeptides which have been substantially purified by any suitable technique (e.g., the single-step purification method disclosed in Smith and Johnson, Gene 67:31-40 (1988), which is incorporated by reference herein). Isolated polypeptides or proteins according to the present invention further include such compounds produced synthetically.

The full-length rat Bridge-1 protein is about 222 amino acid residue protein with a deduced molecular weight of about 24.8 kD and a pI of 6.70. It will be recognized by those skilled in the art that some of the amino acid sequence of the Bridge-1 protein can be varied without significant effect on the structure or function of the protein. If such differences in sequence are contemplated, it should be remembered that there will be critical areas on the protein which determine activity, such as the PDZ-like domain and the carboxyl terminus domain described above which have been determined by the inventors as being critical to Bridge-1 activity. In general, it is often possible to replace residues which form the tertiary structure, provided that residues performing a similar function are used. In other instances, the type of residue may be completely unimportant if the alteration occurs at a non-critical region of the protein.

Thus, the present invention further includes variations of the Bridge-1 polypeptide which show substantial Bridge-1 polypeptide activity or which include regions of Bridge-1 protein. Such mutants include deletions, insertions, inversions, repeats, and type substitutions (for example, substituting one hydrophilic residue for another, but not strongly hydrophilic for strongly hydrophobic as a rule). Small changes or such "neutral" amino acid substitutions will generally have little effect on activity.

Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe and Tyr.

As indicated in detail above, further guidance concerning which amino acid changes are likely to be phenotypically silent (i.e., not likely to have a significant deleterious effect on a function) can be found in Bowie et al., "Deciphering the Message in Protein Sequences: Tolerance to Amino Acid Substitutions," *Science* 247:1306-1310 (1990), the entire contents of which is hereby expressly incorporated herein by reference.

The polypeptides useful in the methods of the present invention include polypeptides having an amino acid sequence as encoded by the deposited cDNA, an amino acid sequence as shown in FIG. 16, as well as an amino acid sequence at least 80% identical, more preferably at least 85% identical, more preferably at least 90% identical, and most preferably at least 95%, 96%, 97%, 98%, or 99% identical, to the amino acid sequence encoded by the deposited cDNA, to the amino acid sequence as shown in FIG. 16, or to the amino acid sequence of a polypeptide fragment described above. Whether two polypeptides have an amino acid sequence that is at least 80%, 90% or 95% identical can be determined using a computer algorithm as described above.

As described in detail below, the nucleic acid molecules and polypeptides of the present invention are useful in screening assays for identifying proteins and protein fragments that bind to Bridge-1 or a Bridge-1 fragment, including proteins, protein fragments, biological and chemical compounds and other small molecules that enhance or inhibit Bridge-1 activity. Accordingly, the nucleic acid molecules and polypeptides of the present invention are useful in assays for identifying drugs capable of enhancing or inhibiting Bridge-1 activity.

Pharmaceutical Compositions

The Bridge-1 polynucleotides, Bridge-1 polypeptides, Bridge-1 modulators, and anti-Bridge-1 antibodies (also referred to herein as "active compounds") useful in the methods of the present invention can be incorporated into pharmaceutical compositions suitable for administration to a subject, e.g., a human. Such compositions typically comprise the nucleic acid molecule, protein, modulator, or antibody and a pharmaceutically acceptable carrier. As used herein the language "pharmaceutically acceptable carrier" is intended to include any and all solvents, dispersion media, coatings, antibacterial and antifungal agents. isotonic and absorption delaying agents, and the like, compatible with pharmaceutical administration. The use of such media and agents for pharmaceutically active substances is well known in the art. Except insofar as any conventional media or agent is incompatible with the active compound, such media can be used in the compositions of the invention. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a BRIDGE-1 protein or anti-BRIDGE-1 antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyarhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) Proc. Natl. Acad. Sci. USA 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

Viral vectors include, for example, recombinant retroviruses, adenovirus, adeno-associated virus, and herpes simplex virus-1. Retrovirus vectors and adeno-associated virus vectors are generally understood to be the recombinant gene delivery system of choice for the transfer of exogenous genes in vivo, particularly into humans. In particular, adenovirus is particularly preferred in the instant invention because it preferentially targets the liver (e.g. the major site of gluconeogenesis) when administered systemically (greater than 90+%; (Antinozzi et al. (1999) Annu. Rev. Nutr. 19:511-544) for reasons that may have to do with the expression of viral receptors or the lack of vascular barriers in the liver. Alternatively they can be used for introducing exogenous genes ex vivo into liver cells in culture. These vectors provide efficient delivery of genes into liver cells, and the transferred nucleic acids are stably integrated into the chromosomal DNA of the host cell.

A major prerequisite for the use of viruses is to ensure the safety of their use, particularly with regard to the possibility of the spread of wild-type virus in the cell population. The development of specialized cell lines (termed "packaging cells") which produce only replication-defective retrovinises has increased the utility of retroviruses for gene therapy, and defective retroviruses are well characterized for use in gene transfer for gene therapy purposes (for a review see Miller, A. D. (1990) Blood 76:271). Thus, recombinant retrovirus can be constructed in which part of the retroviral coding sequence (gag, pol, env) is replaced by a gene of interest rendering the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in Current Protocols in Molecular Biology, Ausubel, F. M. et al. (eds.) Greene Publishing Associates, (1989), Sections 9.10-9.14 and other standard laboratory manuals. Examples of suitable retroviruses include pLJ, pZIP, pWE and pEM which are well known to those skilled in the art. Examples of suitable packaging virus lines for preparing both ecotropic and amphotropic retroviral systems include .psi.Crip, .psi.Cre, .psi.2 and .psi.Am.

Furthermore, it has been shown that it is possible to limit the infection spectrum of retroviruses and consequently of retroviral-based vectors, by modifying the viral packaging proteins on the surface of the viral particle (see, for example PCT publications WO93/25234 and WO94/06920). For instance, strategies for the modification of the infection spectrum of retroviral vectors include: coupling antibodies specific for cell surface antigens to the viral env protein (Roux et al. (1989) Proc. Natl. Acad. Sci. USA 86:9079-9083; Julan et al. (1992) J. Gen. Virol. 73:3251-3255; and Goud et al. (1983) Virology 163:251-254); or coupling cell surface receptor ligands to the viral env proteins (Neda et al. (1991) J. Biol. Chem. 266:14143-14146). Coupling can be in the form of the chemical cross-1 inking with a protein or other variety (e g. lactose to convert the env protein to an asialoglycoproicin), as well as by generating fusion proteins (e.g. single-chain antibody/env fusion proteins). Thus, in a specific embodiment of the invention, viral particles containing a nucleic acid molecule containing a gene of interest operably linked to appropriate regulatory elements, are modified for example according to the methods described above, such that they can specifically target subsets of liver cells. For example, the viral particle can be coated with antibodies to surface molecule that are specific to certain types of liver cells. This method is particularly useful when only specific subsets of liver cells are desired to be transfected.

Another viral gene delivery system useful in the present invention utilizes adenovirus-derived vectors. The genome of an adenovirus can be manipulated such that it encodes and expresses a gene product of interest but is inactivated in terms of its ability to replicate in a normal lytic viral life cycle. See for example Berkner et al. (1988) Biotechniques 6:616; Rosenfeld et al. (1991) Science 252:431-434; and Rosenfeld et al. (1992) Cell 68:143-155. Suitable adenoviral vectors derived from the adenovirus strain Ad type 5 d1324 or other strains of adenovirus (e.g., Ad2, Ad3, Ad7 etc.) are well known to those skilled in the art. Recombinant adenoviruses can be advantageous in certain circumstances in that they are not capable of infecting nondividing cells. Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berlcner et al. cited supra; Haj-Ahmand and Graham (1986) J. Virol. 57:267). Most replication-defective adenoviral vectors currently in use and therefore favored by the present invention are deleted for all or parts of the viral E1 and E3 genes but retain as much as 80% of the adenoviral genetic material (see, e.g., Jones et al.

(1979) Cell 16:683; Berkner et al., supra; and Graham et al. in Methods in Molecular Biology, E. J. Murray, Ed. (Humana, Clifton, N.J., 1991) vol. 7. pp. 109-127). Expression of the gene of interest comprised in the nucleic acid molecule can be under control of, for example, the E1A promoter, the major late promoter (MLP) and associated leader sequences, the E3 promoter, or exogenously added promoter sequences.

Yet another viral vector system useful for delivery of a nucleic acid molecule comprising a gene of interest is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al. Curr. Topics Microbiol. Immunol. (1992) 158:97-129). Adeno-associated viruses exhibit a high frequency of stable integration (see for example Flotte et al. (1992) Am. J. Respir. Cell. Mol. Biol. 7:349-356; Samulski et al. (1989) J. Virol. 63:3822-3828; and McLaughlin et al. (1989) J. Virol 62:1963-1973). Vectors containing as few as 300 base pairs of AAV can be packaged and can integrate. Space for exogenous DNA is limited to about 4.5 kb. An AAV vector such as that described in Tratschin et al. (1985) Mol. Cell. Biol. 5:3251-3260 can be used to introduce DNA into T cells. A variety of nucleic acids have been introduced into different cell types using AAV vectors (see for example Hermonat et al. (1984) Proc. Natl. Acad. Sci. USA 81:6466-6470; Tratschin et al. (1985) Mol. Cell. Biol. 4:2072-2081; Wondisford et al. (1988) Mol. Endocrinol. 2:32-39; Tratschin et al. (1984) J. Virol. 51:611-619; and Flotte et al. (1993) J. Biol. Chem. 268:3781-3790). Other viral vector systems that may have application in gene therapy have been derived from herpes virus, vaccinia virus, and several RNA viruses.

Other methods relating to the use of viral vectors in gene therapy can be found in, e.g., Kay, M. A. (1997) Chest 111(6 Supp.):138S-142S; Ferry, N. and Heard, J. M. (1998) Hum. Gene Ther. 9:1975-81; Shiratory, Y. et al. (1999) Liver 19:265-74; Oka, K. et al. (2000) Curr. Opin. Lipidol. 11:179-86; Thule, P. M. and Liu, J. M. (2000) Gene Ther. 7:1744-52; Yang, N. S. (1992) Crit. Rev. Biotechnol. 12:335-56; Alt, M. (1995) J. Hepatol. 23:746-58; Brody, S. L. and Crystal, R. G. (1994) Ann. N.Y. Acad. Sci. 716:90-101; Strayer, D. S. (1999) Expert Opin. Invetig. Drugs 8:2159-2172; Smith-Arica, J. R. and Bartlett, J. S. (2001) Curr. Cardiol. Rep. 3:43-49; and Lee, H. C. et al. (2000) Nature 408:483-8.

The pharmaceutical compositions can be included in a container, pack, or dispenser together with instructions for administration.

Screening Assays

The invention provides a method (also referred to herein as a "screening assay") for identifying modulators, i.e., candidate or test compounds or agents (e.g., peptides, peptidomimetics, small molecules or other drugs) which bind to Bridge-1 polypeptides, have a stimulatory or inhibitory effect on, for example, Bridge-1 expression or Bridge-1 activity, or have a stimulatory or inhibitory effect on, for example, the expression or activity of a Bridge-1 target gene.

In one embodiment, the invention provides assays for screening candidate or test compounds which are target molecules of a Bridge-1 protein or polypeptide or biologically active portion thereof. In another embodiment, the invention provides assays for screening candidate or test compounds which bind to or modulate the activity of a Bridge-1 protein or polypeptide or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) Anticancer Drug Des. 12:45).

Examples of methods for the synthesis of molecular libraries can be found in the art, for example, in: DeWitt et al. (1993) Proc. Natl. Acad. Sci. USA 90:6909; Erb et al. (1994) Proc. Natl. Acad. Sci. USA 91:11422; Zuckermann et al. (1994). J. Med. Chem. 37:2678; Cho et al. (1993) Science 261:1303; Carrell et al. (1994) Angew. Chem. Int. Ed. Engl. 33:2059; Carell et al. (1994) Angew. Chem. Int Ed. Engl. 33:2061; and Gallop et al. (1994) J. Med. Chem. 37:1233.

Libraries of compounds may be presented in solution (e.g., Houghten (1992) Biotechniques 13:412-421), or on beads (Lam (1991) Nature 354:82-84), chips (Fodor (1993) Nature 364:555-556), bacteria (Ladner U.S. Pat. No. 5,223,409), spores (Ladner U.S. Pat. No. '409), plasmids (Cull et al. (1992) Proc. Natl. Acad. Sci. USA 89:1865-1869) or on phage (Scott and Smith (1990) Science 249:386-390); (Devlin (1990) Science 249:404-406); (Cwirla et al. (1990) Proc. Natl. Acad. Sci. USA 87:6378-6382); (Felici (1991) J. Mol. Biol. 222:301-310); (Ladner supra.).

In one embodiment, an assay is a cell-based assay in which a cell which expresses a Bridge-1 protein or biologically active portion thereof is contacted with a test compound and the ability of the test compound to modulate Bridge-1 activity is determined. The cell, for example, can be of mammalian origin.

The ability of the test compound to modulate Bridge-1 binding to a target molecule can also be determined. Determining the ability of the test compound to modulate Bridge-1 binding to a target molecule can be accomplished, for example, by coupling the Bridge-1 target molecule with a radioisotope or enzymatic label such that binding of the Bridge-1 target molecule to Bridge-1 can be determined by detecting the labeled Bridge-1 target molecule in a complex. Alternatively, Bridge-1 could be coupled with a radioisotope or enzymatic label to monitor the ability of a test compound to modulate Bridge-1 binding to a Bridge-1 target molecule in a complex. Determining the ability of the test compound to bind Bridge-1 can be accomplished, for example, by coupling the compound with a radioisotope or enzymatic label such that binding of the compound to Bridge-1 can be determined by detecting the labeled Bridge-1 compound in a complex. For example, compounds (e.g., Bridge-1 target molecules) can be labeled either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

In another embodiment, an assay is a cell-based assay comprising contacting a cell expressing Bridge-1 with a test compound and determining the ability of the test compound to modulate (e.g. stimulate or inhibit) the expression of Bridge-1 or a Bridge-1 target gene. Determining the ability of the test compound to modulate the activity of a Bridge-1 target gene can be accomplished, for example, by determining the ability of a Bridge-1 protein to bind to or interact with the Bridge-1 target molecule, or by determining the ability of a Bridge-1 protein to induce expression of the Bridge-1 target gene.

Determining the ability of the Bridge-1 protein, or a biologically active fragment thereof, to bind to or interact with a Bridge-1 target molecule, for example PDX-1 or E12, can be accomplished by one of the methods described above for determining direct binding. In a preferred embodiment, determining the ability of the Bridge-1 protein to bind to or interact with a Bridge-1 target molecule can be accomplished by determining the activity of the target molecule. For example, the activity of the target molecule can be determined by detecting induction of a cellular response, detecting catalytic/enzymatic activity of the target molecule upon an appropriate substrate, detecting the induction of a reporter gene (comprising a target-responsive regulatory element operatively linked to a nucleic acid encoding a detectable marker, e.g., luciferase), or detecting a target-regulated cellular response (i.e., glucose output).

In yet another embodiment, an assay of the present invention is a cell-free assay in which a Bridge-1 protein or biologically active portion thereof is contacted with a test compound and the ability of the test compound to bind to the Bridge-1 protein or biologically active portion thereof is determined. Binding of the test compound to the Bridge-1 protein can be determined either directly or indirectly as described above. In a preferred embodiment, the assay includes contacting the Bridge-1 protein or biologically active portion thereof with a known compound which binds Bridge-1 to form an assay mixture, contacting the assay mixture with a test compound, and determining the ability of the test compound to interact with a Bridge-1 protein, wherein determining the ability of the test compound to interact with a Bridge-1 protein comprises determining the ability of the test compound to preferentially bind to Bridge-1 or biologically active portion thereof as compared to the known compound.

In another embodiment, the assay is a cell-free assay in which a Bridge-1 protein or biologically active portion thereof is contacted with a test compound and the ability of the test compound to modulate (eg., stimulate or inhibit) the activity of the Bridge-1 protein or biologically active portion thereof is determined. Determining the ability of the test compound to modulate the activity of a Bridge-1 protein can be accomplished. for example, by determining the ability of the Bridge-1 protein to bind to a Bridge-1 target molecule by one of the methods described above for determining direct binding.

In an alternative embodiment, determining the ability of the test compound to modulate the activity of a Bridge-1 protein can be accomplished by determining the ability of the Bridge-1 protein to further modulate the activity of a downstream effector of a Bridge-1 target molecule. For example, the activity of the effector molecule on an appropriate target can be determined or the binding of the effector to an appropriate target can be determined as previously described.

In yet another embodiment, the cell-free assay involves contacting a Bridge-1 protein or biologically active portion thereof with a known compound which binds the Bridge-1 protein to form an assay mixture, contacting the assay mixture with a test compound, and determining the ability of the test compound to interact with the Bridge-1 protein, wherein determining the ability of the test compound to interact with the Bridge-1 protein comprises determining the ability of the Bridge-1 protein to preferentially bind to or modulate the activity of a Bridge-1 target molecule.

In more than one embodiment of the above assay methods of the present invention, it may be desirable to immobilize either Bridge-1 or its target molecule to facilitate separation of complexed from uncomplexed forms of one or both of the proteins, as well as to accommodate automation of the assay. Binding of a test compound to a Bridge-1 protein, or interaction of a Bridge-1 protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase/BRIDGE-1 fusion proteins or glutathione-S-transferase/target fusion proteins can be adsorbed onto glutathione sepharose beads (Sigma Chemical, St. Louis, Mo.) or glutathione derivatized micrometer plates, which are then combined with the test compound or the test compound and either the non-adsorbed target protein or Bridge-1 protein, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of Bridge-1 binding or activity determined using standard techniques.

Other techniques for immobilizing proteins on matrices can also be used in the screening assays of the invention. For example, either a Bridge-1 protein or a Bridge-1 target molecule can be immobilized utilizing conjugation of biotin and streptavidin. Biotinylated Bridge-1 protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). Alternatively, antibodies reactive with Bridge-1 protein or target molecules but which do not interfere with binding of the Bridge-1 protein to its target molecule can be derivatized to the wells of the plate, and unbound target or Bridge-1 protein trapped in the wells by antibody conjugation. Methods for detecting such complexes, in addition to those described above for the GST-immobilized complexes, include immunodetection of complexes using antibodies reactive with the Bridge-1 protein or target molecule, as well as enzyme-linked assays which rely on detecting an enzymatic activity associated with the Bridge-1 protein or target molecule.

In another embodiment, modulators of Bridge-1 expression are identified in a method wherein a cell is contacted with a candidate compound and the expression of Bridge-1 mRNA or protein in the cell is determined. The level of expression of Bridge-1 mRNA or protein in the presence of the candidate compound is compared to the level of expression of Bridge-1 mRNA or protein in the absence of the candidate compound. The candidate compound can then be identified as a modulator of Bridge-1 expression based on this comparison. For example, when expression of Bridge-1 mRNA or protein is greater (statistically significantly greater) in the presence of the candidate compound than in its absence, the candidate compound is identified as a stimulator of Bridge-1 mRNA or protein expression. Alternatively, when expression of Bridge-1 mRNA or protein is less (statistically significantly less) in the presence of the candidate compound than in its absence, the candidate compound is identified as an inhibitor of Bridge-1 mRNA or protein expression. The level of Bridge-1 mRNA or protein expression in the cells can be determined by methods described herein for detecting Bridge-1 mRNA or protein.

In yet another aspect of the invention, the Bridge-1 proteins can be used as "bait proteins" in a two-hybrid assay or three-hybrid assay (see, e.g., U.S. Pat. No. 5,283,317; Zervos et al, (1993) Cell 72:223-232; Madura et al. (1993) J. Biol. Chem. 268:12046-12054; Bartel et al. (1993) Biotechniques 14:920-924; Iwabuchi et al. (1993) Oncogene 8:1693-1696; and Brent WO94/10300) to identify other proteins which bind to or interact with Bridge-1 and are involved in Bridge-1 activity. Such Bridge-1-binding proteins are also likely to be involved in the propagation of signals by the Bridge-1 proteins or Bridge-1 targets as, for example, downstream elements of a Bridge-1-mediated signaling pathway. Alternatively, such Bridge-1-binding proteins may be Bridge-1 inhibitors.

In another aspect, the invention pertains to a combination of two or more of the assays described herein. For example, a modulating agent can be identified using a cell-based or a cell-free assay, and the ability of the agent to modulate the activity of a Bridge-1 protein can be confirmed in vivo, e.g, in an animal such as an animal model for diabetes. Such an animal can be produced, for example, by treating a mouse or a rat with streptozotocin, as described in the examples section.

This invention further pertains to novel modulators identified by the above-described screening assays. Accordingly, it is within the scope of this invention to further use an agent identified as described herein in an appropriate animal model. For example, an agent identified as described herein (e.g., a Bridge-1 modulating agent, an antisense Bridge-1 nucleic acid molecule, a Bridge-1-specific antibody, or a Bridge-1 binding partner) can be used in an animal model to determine the efficacy, toxicity or side effects of treatment with such an agent. Alternatively, an modulator identified as described herein can be used in an animal model to determine the mechanism of action of such an agent. Furthermore, this invention pertains to uses of novel agents identified by the above-described screening assays for treatments as described herein.

In yet another embodiment, the invention provides a method for identifying a compound (e.g., a screening assay) capable of use in the treatment of a disorder characterized by (or associated with) aberrant or abnormal Bridge-1 nucleic acid expression or Bridge-1 polypeptide activity. This method typically includes the step of assaying the ability of the compound or agent to modulate the expression of the Bridge-1 nucleic acid or the activity of the Bridge-1 protein thereby identifying a compound for treating a disorder characterized by aberrant or abnormal Bridge-1 nucleic acid expression or Bridge-1 polypeptide activity. Disorders characterized by aberrant or abnormal Bridge-1 nucleic acid expression or Bridge-1 protein activity are described herein. Methods for assaying the ability of the compound or agent to modulate the expression of the Bridge-1 nucleic acid or activity of the Bridge-1 protein are typically cell-based assays. For example, cells which are sensitive to ligands which transduce signals via a pathway involving Bridge-1 can be induced to overexpress a Bridge-1 protein in the presence and absence of a candidate compound. Candidate compounds which produce a statistically significant change in Bridge-1-dependent responses (either stimulation or inhibition) can be identified. In one embodiment, expression of the Bridge-1 nucleic acid or activity of a Bridge-1 protein is modulated in cells and the effects of candidate compounds on the readout of interest (such as rate of cell proliferation or differentiation) are measured. For example, the expression of genes which are up- or down-regulated in response to a Bridge-1 protein-dependent signal cascade can be assayed. In preferred embodiments, the regulatory regions of such genes, e.g., the 5' flanking promoter and enhancer regions, are operably linked to a detectable marker (such as luciferase) which encodes a gene product that can be readily detected. Phosphorylation of Bridge-1 or Bridge-1 target molecules can also be measured, for example, by immunoblotting.

Alternatively, modulators of Bridge-1 nucleic acid expression (e.g., compounds which can be used to treat a disorder characterized by aberrant or abnormal Bridge-1 nucleic acid expression or Bridge-1 protein activity) can be identified in a method wherein a cell is contacted with a candidate compound and the expression of Bridge-1 mRNA or protein in the cell is determined. The level of expression of Bridge-1 mRNA or protein in the presence of the candidate compound is compared to the level of expression of Bridge-1 mRNA or protein in the absence of the candidate compound. The candidate compound can then be identified as a modulator of Bridge-1 nucleic acid expression based on this comparison and be used to treat a disorder characterized by aberrant Bridge-1 nucleic acid expression. For example, when expression of Bridge-1 mRNA or polypeptide is greater (statistically significantly greater) in the presence of the candidate compound than in its absence, the candidate compound is identified as a stimulator of Bridge-1 nucleic acid expression. Alternatively, when Bridge-1 nucleic acid expression is less (statistically significantly less) in the presence of the candidate compound than in its absence, the candidate compound is identified as an inhibitor of Bridge-1 nucleic acid expression. The level of Bridge-1 nucleic acid expression in the cells can be determined by methods described herein for detecting Bridge-1 mRNA or protein.

Modulators of Bridge-1 protein activity and/or Bridge-1 nucleic acid expression identified according to these drug screening assays can be used to treat, for example, glucose homeostasis disorders such as diabetes (e.g., type 1 diabetes, type 2 diabetes, and maturity onset diabetes of the young (MODY)) and hepatic enzyme abnormalities that lead to hypoglycemia. Modulators of Bridge-1 protein activity and/or Bridge-1 nucleic acid expression may also be used to treat disorders related to other functions of Bridge-1 unrelated to insulin production, such as weight disorders, e.g. obesity, or cancer. These methods of treatment include the steps of administering the modulators of Bridge-1 protein activity and/or nucleic acid expression, e.g., in a pharmaceutical composition as described herein, to a subject in need of such treatment, e.g., a subject with a disorder described herein.

Therapeutic Methods

In another aspect, the present invention is directed to a method for modulating apoptosis in a cell or cells comprising modulating Bridge-1 activity in the cell or cells. Bridge-1 activity may either be increased or decreased. In one embodiment, the modulator increases or, alternatively, decreases expression of Bridge-1 in the cell. In a preferred embodiment, apoptosis is increased and the cells are tumor cells. Modulation of apoptosis may also be the result of modulation of a Bridge-1 target gene. Particularly preferred are methods for modulating apoptosis in a cell or cells comprising treating the cells with a Bridge-1 polypeptide, a polynucleotide encoding Bridge-1, or a compound that activates or inhibits expression of a Bridge-1 gene. Suitable polynucleotides include naked DNA or vectors encoding Bridge-1. Preferably, the apoptosis is modulated in pancreatic β cells.

The invention is further directed to method for modulating islet cell apoptosis in a mammal, such as a human, comprising administering to the mammal a Bridge-1 polypeptide, a polynucleotide encoding Bridge-1, or a compound that activates or inhibits expression of a Bridge-1 gene.

In another aspect, the invention is directed to a method for modulating cellular replication in a cell or cells comprising modulating Bridge-1 activity in the cell or cells. Bridge-1 activity may be increased or, alternatively, decreased as a result of the modulation. Likewise, replication may either be increased or decreased. In one embodiment, the Bridge-1 activity is expression of Bridge-1. In another embodiment, the Bridge-1 activity is expression of a Bridge-1 target gene. In a preferred embodiment, the invention is directed to a method for modulating replication in a cell or cells comprising treating the cells with a Bridge-1 polypeptide, a polynucleotide encoding Bridge-1, or a compound that activates or inhibits expression of a Bridge-1 gene. Preferably, the polynucleotides are DNA or vectors encoding Bridge-1. In preferred embodiments, the cells are pancreatic βcells. The invention is also directed to a method for modulating replication of pancreatic β cells in a mammal, such as a human, comprising administering to the mammal a Bridge-1 polypeptide, a polynucleotide encoding Bridge-1, or a compound that activates or inhibits expression of a Bridge-1 gene.

In another aspect, the present invention is directed to a method for modulating the mass of a cell or cells comprising modulating Bridge-1 activity in the cell or cells. In such methods, Bridge-1 activity may be increased or, alternatively, decreased. Likewise, cell mass may be either increased or decreased. In one embodiment, the Bridge-1 activity is expression of Bridge-1. In another embodiment, the Bridge-1 activity is expression of a Bridge-1 target gene. In a preferred embodiment, the invention is directed to a method for modulating the mass of a cell or cells comprising treating the cells with a Bridge-1 polypeptide, a polynucleotide encoding Bridge-1, or a compound that activates or inhibits expression of a Bridge-1 gene. In these methods, the polynucleotide may be DNA, such as a vector, encoding Bridge-1. Preferably, the cells are are pancreatic β cells. In a particularly preferred embodiment, the invention is directed to a method for modulating pancreatic β cell mass in a mammal comprising administering to the mammal a Bridge-1 polypeptide, a polynucleotide encoding Bridge-1, or a compound that activates or inhibits expression of a Bridge-1 gene.

In another aspect, the present invention is directed to a method for modulating insulin production in a cell or cells comprising modulating Bridge-1 activity in the cell or cells. In such methods, Bridge-1 activity may either be increased or decreased. Likewise, insulin production may be increased or decreased as a result of the modulation. In one embodiment, the Bridge-1 activity is expression of Bridge-1. In another embodiment, the Bridge-1 activity is expression of a Bridge-1 target gene. A preferred embodiment of the invention is directed to a method for modulating insulin production in a cell or cell comprising treating the cells with a Bridge-1 polypeptide, a polynucleotide encoding Bridge-1, or a compound that activates or inhibits expression of a Bridge-1 gene. Such polynucleotide can be DNA, such as a vector, encoding Bridge-1. Preferably, the cells are pancreatic β cells. In a particularly preferred embodiment, the present invention is directed to a method for modulating insulin production in a mammal, such as a human, comprising administering to the mammal a Bridge-1 polypeptide, a polynucleotide encoding Bridge-1, or a compound that activates or inhibits expression of a Bridge-1 gene.

In another aspect, the invention is directed to a method for modulating blood glucose levels in a mammal, such as a human, comprising administering to the mammal a Bridge-1 polypeptide, a polynucleotide encoding Bridge-1, or a compound that activates or inhibits expression of a Bridge-1 gene.

In yet another aspect, the invention is directed to a method for treating a Bridge-1 mediated disorder in a mammal, such as a human, comprising administering to the mammal a Bridge-1 polypeptide, a polynucleotide encoding Bridge-1, or a compound that activates or inhibits expression of a Bridge-1 gene in the mammal. In a preferred embodiment, the mammal is a human. In another embodiment, the disorder is caused by a mutation in the endogenous Bridge-1 gene. In a preferred embodiment, the disorder is diabetes, such as Type II diabetes mellitus.

EXAMPLE 1

Materials and Methods for Examples 2-10

Generation of transgenic mice. The 6 kb Bridge-1 transgene was constructed by cloning the full length rat Bridge-1 cDNA coding sequence (Thomas, M. K., et al., *Mol Cell Biol* 19:8492-8404 (1999)) (nucleotides 492-1392) downstream of a previously characterized −4.6 kb segment of the mouse pdx-1 promoter (Stoffers, D. A., et al., *Endocrinology* 140: 5374-5381 (1999); Gannon, M., et al., *Dev Biol* 238:185-201 (2001)) and upstream of rabbit β-globin poly A tail sequences. Bridge-1 overexpression mice were generated in the FVB strain at the Beth Israel Hospital Transgenic Facility using standard procedures (Hogan, B., et al., "*Manipulating the mouse embryo: a laboratory manual*," Cold Spring Harbor Laboratory Press, Plainview, N.Y., United States, pp. 487 (1994)). Transgenic mice were compared with age-, gender-, and strain-matched control mice for all analyses. Animal studies were approved by and conducted according to the policies of the Massachusetts General Hospital Institutional Animal Care and Use Committee.

Southern blots. Transgenic mice were identified by the amplification of a 400 bp fragment of transgenic genomic DNA that extends from nucleotide −92 in the mouse pdx-1 promoter to nucleotide 744 within rat Bridge-1 cDNA. Transgene incorporation was confirmed by Southern blots of genomic DNA according to published methods (Ausubel, F. M., et al., "*Current protocols in molecular biology*," John Wiley and Sons, New York, N.Y., United States (1994)) with a radiolabeled 223 bp fragment of the transgene that spans the junction of the pdx-1 promoter and rat Bridge-1 cDNA.

Western blots. Total pancreatic and liver protein extracts were prepared and Western blots were conducted using enhanced chemiluminescence as described (Andreassen, O. A., et al, *Neurobiol Dis* 11:410-424 (2002)). Protein concentrations were determined by a Micro BCA assay (Pierce, Rockford, Ill.) for sample normalization. Antisera used included rabbit polyclonal anti-Bridge-1, rabbit polyclonal anti-Stat-3 (K-15) (Santa Cruz Biotechnology, Santa Cruz, Calif.) and human anti-cleaved caspase-3 that reacts with both the inactive 32 kD and the active cleaved 17 kD forms of caspase-3 (Biocarta, San Diego, Calif.). Densitometric scanning of Western blots was conducted with an Image Station 440CF and Image Analysis software (Eastman Kodak, Rochester, N.Y.).

RNA expression analyses. Total pancreatic RNA isolation, rt-PCR, and Northern blots for insulin and actin were conducted with previously reported methods (Andreassen, O. A., et al., *Neurobiol Dis* 11:410-424 (2002); Thomas, M. K., et al., *Diabetes* 49:2039-2047 (2000)). Quantitative real-time PCR was conducted for each sample in triplicate on an ABI Prism 7900HT sequence detection system using the manufacturer's reagents and methods (Applied Biosystems, Foster City, Calif.). We designed primer and MGB probe sets for Brain-4, Bridge-1, cyclophilin, elastase, glucagon, glucokinase, glucose transporter-2, hypoxanthine phosphoribosyltransferase, insulin Nkx6.1, PDX-I, and somatostatin. Sequences of primers and probes are available upon request.

Histologic analyses. Mouse pancreas samples were fixed in 10% saline-buffered formalin, embedded in paraffin and sectioned at 4-micron intervals. Immunostaining was conducted according to standard methods (Thomas, M. K., et al., *Mol Cell Biol* 19:8492-8404 (1999); Harlow, E., and Lane, D., "*Using antibodies: a laboratory manual*," Cold Spring Harbor Laboratory Press. Plainview, N.Y., United States. 495 pp. (1999)). Sections were incubated for one hour with primary antiserum including rabbit polyclonal β-catenin (Chemicon International, Temecula, Calif.), rabbit polyclonal anti-Bridge-1, mouse monoclonal anti-glucagon (K79bB 10, Sigma, St. Louis, Mo.), guinea pig anti-human insulin (IgG fraction, Linco Research, St. Charles, Mo.), rabbit polyclonal anti-GST-Nkx 6.1 (gift from P. Serup and R. Heller), rabbit polyclonal anti-PDX-1 (gift from J. Habener), or rabbit polyclonal anti-human somatostatin (A0566, Dako Corporation, Carpinteria, California) as indicated. Biotinylated species-specific secondary antiserum and avidin-biotinylated horseradish peroxidase complexes (Vector Laboratories, Burlingame, Calif.) were used for peroxidase-based staining. Hematoxylin and/or eosin counterstaining was conducted as indicated. Alternatively Cy-3 or FITC-conjugated species-specific anti-IgG secondary antiserum (Jackson Immunoresearch Laboratories, West Grove, Pa.) was employed for indirect immunofluorescence studies as described (Thomas, M. K., et al., *Mol Cell Biol* 19:8492-8404 (1999)). TUNEL assays were conducted with peroxidase-based In Situ Cell Death Detection kits (Roche Diagnostics Corporation, Indianapolis, Ind.) according to the manufacturer's instructions with modifications including the addition of a 20-minute incubation in a blocking solution consisting of 3% bovine serum albumin in phosphate-buffered saline prior to peroxidase treatment and of signal conversion in a 0.5 X converter-POD solution diluted in phosphate-buffered saline. Digital images were acquired with a SPOT-RT Slider color camera (Diagnostic Instruments, Sterling Heights, Mich.) and a Nikon epifluorescence microscope interfaced with a Macintosh G4 computer and processed with Adobe Photoshop software (Adobe Systems Incorporated, San Jose, Calif.).

Metabolic studies. Metabolic studies were conducted with transgenic and age-, gender-, and strain-matched control mice. Glucose levels were determined with a YSI 2300 STAT glucose analyzer (Yellow Springs Instrument Co., Yellow Springs, Ohio). Serum insulin levels were measured in duplicate by a rat insulin ELISA kit with mouse insulin standards (Crystal Chem, Chicago, Ill.). Glucose tolerance tests were conducted with intraperitoneal injection of 1.5 g glucose per kg body weight following an 8-hour fast as previously reported (Thomas, M. K., et al., *J Clin Invest* 108:319-329 (2001)). Serum triglycerides were measured with an Infinity Triglyceride assay according to the manufacturer's instructions (Sigma). Urine ketone and glucose levels were detected by Chemstrip uGK (Roche, Basel, Switzerland).

Cell culture and transfection studies. HeLa cells were cultured in Dulbecco's Modified Eagle Medium supplemented with 10% fetal bovine serum, 100 U of penicillin G, and 100 μg of streptomycin sulfate per mL. Transfections and chloramphenicol acetyltransferase (CAT) reporter assays were conducted as described (Thomas, M. K., et al., *Mol Cell Biol* 19:8492-8404 (1999)). The pcDNA3-Bridge-1 expression vector encoding full-length rat Bridge-1 cDNA was constructed as reported (Thomas, M. K., et al., *Mol Cell Biol* 19:8492-8404 (1999)), and the multimerized FarFlat enhancer-CAT reporter plasmid (5FF1 CAT) was a gift from L. G. Moss.

EXAMPLE 2

Generation of Bridge-1 Transgenic Mice

To disrupt the assembly and composition of supramolecular protein complexes regulated by Bridge-1 signaling in the endocrine pancreas, we developed a transgenic mouse model of pancreatic Bridge-1 overexpression. We used a −4.6 kb segment of the mouse pdx-1 promoter that is known to confer expression in the developing pancreas and adult pancreatic β cells (Stoffers, D. A., et al., *Endocrinology* 140:5374-5381 (1999); Gannon, M., et al., *Dev Biol* 238:185-201 (2001)) to express rat Bridge-1 cDNA in transgenic mice (FIG. 1a). We identified multiple independent founder lines by Southern blots of genomic DNA (FIG. 1b). We observed pancreatic Bridge-1 mRNA overexpression by rt-PCR of total pancreatic RNA derived from transgenic as compared to control mice (FIG. 1c). The pancreatic overexpression of the Bridge-1 protein in transgenic mice was confirmed by Western blots of total pancreatic extracts with anti-Bridge-1 antiserum in the setting of unchanged expression patterns for control proteins such as Stat-3 (data not shown). No differences in Bridge-1 protein expression levels in liver extracts from transgenic or control mice were seen on Western blots. Bridge-1 protein expression in the transgenic mice was heterogeneous with overexpression observed by immunostaining in the endocrine, exocrine, and ductal compartments of the pancreas (FIG. 1d). This protein expression pattern was consistent with that expected from the in vivo regulatory properties of the pdx-1 promoter. In mouse models in which the −4.6 kb pdx-1 promoter directed a β-galactosidase reporter, the expression of β-galactosidase was seen primarily in pancreatic islets and, at lower levels, in the pancreatic ducts and exocrine pancreas (Stoffers, D. A., et al., Endocrinology 140:5374-5381 (1999); Gannon, M., et al., *Dev Biol* 238:185-201 (2001)).

EXAMPLE 3

Overexpression of Bridge-1 Disrupts Pancreatic Architecture

We observed a spectrum of phenotypes of altered pancreatic architecture on hematoxylin- and eosin-stained sections derived from the Bridge-1 transgenic mice. A phenotype of pancreatic duct enlargement occurred with variable penetrance in male transgenic (FIG. 2b) in comparison to age- and strain-matched control mice (FIG. 2e). We did not observe any evidence of ductal metaplasia or loss of epithelial cell polarity in association with the enlarged ducts. We also observed scattered areas of disorganization of exocrine cells with marked variability in the size of cells and nuclei in the acinar compartment of the Bridge-1 transgenic mice (FIG. 2c) as compared to the more orderly arrangement of the exocrine pancreas in control mice (FIG. 2f).

We noted the most striking morphologic changes in the arrangement and distribution of pancreatic endocrine cells. In male Bridge-1 transgenic mice the pancreatic islet morphology ranged from nearly normal to streak-like nests of cells. In contrast to wild-type pancreatic islets in which endocrine cells were assembled in well-organized spherical structures (FIG. 2d), in the pancreas of transgenic mice strands of endocrine cells were interwoven among exocrine cells in disordered patterns (FIGS. 2a, 3a) with loss of the normal tissue boundaries between the endocrine and exocrine compartments. These wandering strands of cells were identified as endocrine cell clusters by their expression of the hormones insulin (FIG. 3b) or glucagon (FIG. 3c) and correlated with observed patterns of Bridge-1 overexpression (FIG. 3d). The endocrine cells of the transgenic mice had marked heterogeneity of nuclear size and shape. The loss of both intracellular and extracellular organization was illustrated by marked changes in expression patterns for β-catenin in endocrine cell clusters derived from Bridge-1 transgenic (FIG. 3e) relative to control mice (FIG. 3f).

EXAMPLE 4

Endocrine Cell Distribution is Altered in Bridge-1 Transgenic Mice

When we examined pancreatic endocrine hormone expression patterns of severely affected male Bridge-1 transgenic mice, we observed a reduction in the extent and intensity of insulin expression in transgenic (TG, FIG. 4a) as compared to wild-type control (WT, FIG. 4d) mice. In contrast we found a relative increase in glucagon expression within transgenic (FIG. 4b) as compared to control (FIG. 4e) endocrine cell clusters. Only a small fraction of endocrine cells expressed somatostatin in transgenic (FIG. 4c) or control (FIG. 4f) mice.

The spatial organization of the glucagon-expressing cells relative to the insulin-expressing cells also was disrupted in the pancreatic endocrine cell clusters of the Bridge-1 transgenic mice. In pancreatic islets of control mice we observed the typical endocrine cell arrangement of glucagon-expressing β cells in an outer rim (FIG. 4k) surrounding a central core of insulin-expressing β cells (FIGS. 4j and l). However in transgenic endocrine cell clusters, a disorganized pattern of insulin-expressing β cells (FIG. 4g) with a relative increased complement of glucagon-expressing α cells (FIG. 4h) was seen in the context of poorly-defined endocrine and exocrine compartment boundaries. No coexpression of insulin and glucagon was observed (FIG. 4i) to suggest a population of multipotential endocrine cells.

Next we examined the expression patterns of the transcription factors PDX-1 and Nkx 6.1 as markers of pancreatic β cells (Sander, M., et al., *Development* 127:5533-5540 (2000); Thomas, M. K., and Habener, J R., "IDX-1: Pancreatic Agenesis And Type 2 Diabetes," In *Molecular Basis Of Inborn Errors Of Development*, P. Erikson, et al., editors. Oxford Univ. Press. Oxford, United Kingdom. 552-556 (2004)). In contrast to the well-organized protein expression patterns in β cells within the central core of control islets (FIGS. 5e and f), the expression levels of both transcription factors were reduced in disorganized patterns within endocrine cell clusters from male Bridge-1 transgenic mice (FIGS. 5a-d). These β-cell marker protein expression patterns resembled that of insulin, consistent with a reduction in the functioning mass of pancreatic β cells. We did not observe coexpression of glucagon with PDX-1 (FIG. 5c) or Nkx 6.1 (FIG. 5d) that would support a model of β-cell transdifferentiation to an intermediate α-cell phenotype. The nuclear expression patterns of both PDX-1 and Nkx 6.1 illustrated the heterogeneous range of nuclear sizes observed in the transgenic β cells.

To complement the protein expression patterns of the β-cell-specific transcription factors, we isolated total pancreatic RNA from male Bridge-1 transgenic and age- and strain-matched control mice for quantitative real-time rt-PCR analysis of differences in gene expression. In concordance with the observed protein expression patterns, we observed substantial and significant reductions in PDX-1 (64% reduction) and Nkx 6.1 (72% reduction) pancreatic mRNA expression levels in the transgenic relative to control mice (FIG. 5i). In the same series of experiments we found an 85% increase in the pancreatic mRNA expression levels of the α-cell-specific transcription factor Brain-4 (Hussain, M. A., et al., *Mol Cell Biol* 17:7186-7194 (1997)) in the transgenic relative to control mice. We did not observe any significant differences in pancreatic mRNA expression of the ubiquitously expressed hypoxanthine phosphoribosyltransferasegene between transgenic and control mice.

Figure 29A:
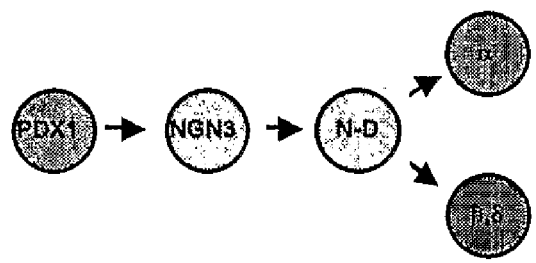
Figure 29B:
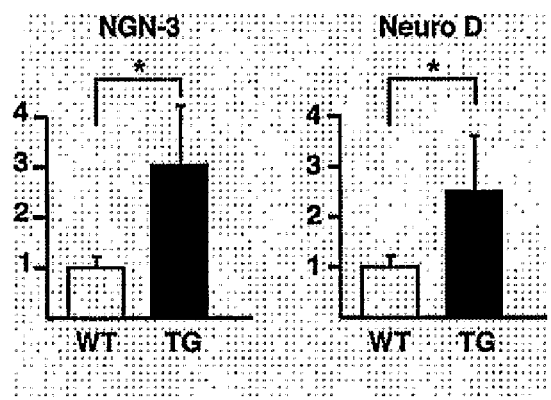
Figure 29C:
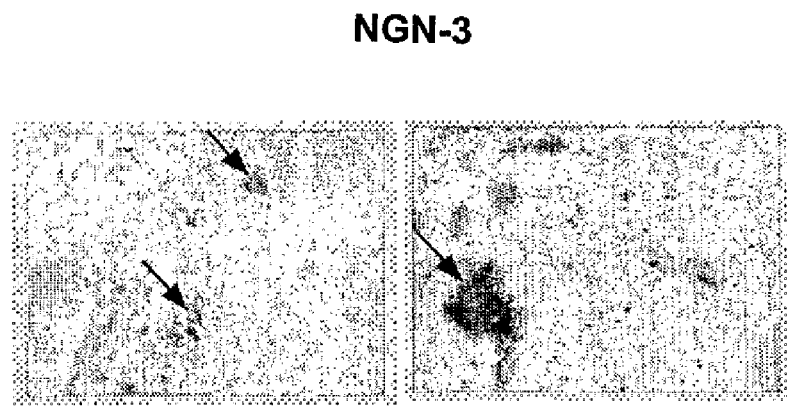

In analyzing Bridge-1 transgenic mice with diabetes and strain-, age-, and gender-matched control mice for the mRNA expression patterns of transcription factors known to be of importance in endocrine cell development, we identified some surprising differences. Notably, both neurogenin-3 and NeuroD1/Beta-2 pancreatic mRNA expression levels were upregulated 2- to 3-fold in adult Bridge-1 transgenic mice with diabetes (FIG. 29B). This finding was surprising, as neurogenin-3 expression is known to be upregulated in endocrine progenitor cells early in embryonic pancreas development and downregulated later with the progression of endocrine cell differentiation. These results were in marked contrast to the 64% to 72% reductions in the pancreatic mRNA expression levels of PDX-1 and Nkx 6.1 observed in the same mice. Although we did not observe convincing evidence of neurogenin-3 protein in the adult control pancreas sections, we found occasional scattered neurogenin-3-expressing cells in pancreas sections derived from adult Bridge-1 transgenic mice with diabetes (FIG. 29C). Neurogenin-3 protein expression was found in isolated cells near ducts but not within endocrine cell clusters. As part of the program of embryonic endocrine cell differentiation, neurogenin-3 activates the expression of NeuroD1/Beta-2 in embryonic progenitor cells in the early stages of commitment to the insulin- or glucagon-producing lineages (FIG. 29A). The combination of the upregulation of both neurogenin-3 and NeuroD1/Beta-2 expression in the adult pancreas of Bridge-1 mice with diabetes suggests that a transcriptional program for new endocrine cell development has been activated in the adult pancreas in this mouse model. This evidence of the reactivation of an embryonic pancreatic endocrine cell differentiation program in the adult pancreas is of particular importance when considered in the context of recent studies emphasizing the predominant importance of pancreatic β-cell replication in replenishing insulin-producing cells of the adult mouse endocrine pancreas (Dor et al., *Nature* 429:41-46 (2004)).

EXAMPLE 5

Pancreatic β-cell Mass is Reduced and α-cell Mass is Increased in Bridge-1 Transgenic Mice To determine whether the observed altered patterns of insulin and glucagon expression were indicative of differences in cell numbers, we estimated the relative numbers of pancreatic α and β cells in control and transgenic mouse pancreas by counting stained and unstained endocrine cells in paraffin-embedded pancreatic sections stained for insulin (FIGS. 6a-c) or for glucagon (FIGS. 6d-f). Pancreatic sections derived from male Bridge-1 transgenic mice (TG) had an average of 12 insulin-expressing cells per endocrine cell cluster as compared to an average of 54 insulin-expressing cells in those derived from male control (WT) mice (FIG. 6a). On average only 25% of the cells in an endocrine cell cluster expressed insulin in transgenic mice while 80% expressed insulin in control islets (FIG. 6b). These data suggest that β-cell mass in severely affected Bridge-1 transgenic mice is reduced by approximately 70%. The reduction in the estimated number of pancreatic β cells was notably similar in magnitude to the decrements in pancreatic mRNA expression levels observed for the β-cell-specific transcription factors PDX-1 and Nkx 6.1.

Both increased numbers and relative proportions of pancreatic α cells were seen in endocrine cell clusters in Bridge-1 transgenic mice (FIGS. 6d-f). On average 12 glucagon-expressing cells per islet were found in control (WT) mouse pancreas sections while 23 glucagon-expressing cells per endocrine cell cluster were seen in transgenic (TG) mouse pancreas sections (FIG. 6d). Similarly the average proportion of glucagon-expressing cells per islet or endocrine cell cluster was higher at 52% for transgenic mice than the 20% observed for control mice (FIG. 6e). These counts estimate at least a 2-fold increase in α-cell number in Bridge-1 transgenic as compared to control mice, similar to the increase predicted by the pancreatic mRNA expression levels of the α-cell-specific transcription factor Brain-4.

EXAMPLE 6

Pancreatic Apoptosis is Increased in Bridge-1 Transgenic Mice

To identify potential mechanisms by which pancreatic β-cell mass is reduced in Bridge-1 transgenic mice, we performed TUNEL assays to determine the extent of apoptosis in pancreatic sections derived from transgenic and age-, strain-, and gender-matched control mice. In control (WT) mice, we rarely observed TUNEL-positive cells (in brown) within pancreatic islets (FIG. 6g, left panel). However, in Bridge-1 transgenic (TG) mice TUNEL-positive cells were frequently found within endocrine cell clusters (FIG. 6g, middle panel) and in wandering strands of cells interspersed between acinar cells of the exocrine pancreas (FIG. 6g, right panel). The TUNEL-positive cells often had morphologic features of nuclear fragmentation or condensation. To confirm this finding we measured the relative protein levels of the activated, cleaved form of the protease caspase-3 that is central to the apoptotic protease cascade. By Western blot analysis of total pancreatic protein extracts we observed an increase of greater than 3-fold in the levels of the 17 kD cleaved form of caspase-3 in contrast to unchanged levels of pancreatic Stat-3 protein expression in Bridge-1 transgenic as compared to control mice (FIG. 6h). These data indicate that increased pancreatic apoptosis occurs in Bridge-1 transgenic mice.

EXAMPLE 7

Overexpression of Bridge-1 Results in Insulin Deficiency and Hyperglycemia

The metabolic phenotypes in Bridge-1 transgenic mice ranged from mild hyperglycemia to severe diabetes. Female Bridge-1 transgenic mice had modest fasting hyperglycemia and insulin deficiency demonstrated by intraperitoneal glucose tolerance testing (FIG. 7a). Fasting insulin levels were reduced and serum insulin levels rose minimally in response to a glucose challenge in the female transgenic mice.

In male transgenic mice with marked abnormalities in pancreatic histology we observed the most severe diabetes. We detected glycosuria by urine dipstick analysis of male transgenic mice as early as three weeks of age at the time of weaning. Male transgenic mice with diabetes had fasting blood glucose levels as high as 438 mg/dL and random fed plasma glucose levels as high as 855 mg/dL associated with nearly undetectable fasting serum insulin levels (FIG. 7b). Elevated random-fed triglyceride levels accompanied the hyperglycemia with an average triglyceride level of 620 mg/dL (n=6) in Bridge-1 transgenic mice with severe diabetes as compared to 158 mg/dL (n=4) in nontransgenic control mice. The severity of the observed metabolic phenotypes partially correlated with transgene copy number by Southern blot or realtime quantitative PCR analyses.

Insulin deficiency in hyperglycemic Bridge-1 transgenic mice was associated with markedly reduced levels of pancreatic preproinsulin mRNA that was scarcely detectable by Northern blot analyses (FIG. 7c). Insulin mRNA levels could be detected by real-time quantitative rt-PCR of total pancreatic RNA in another series of Bridge-1 transgenic and control mice. In this cohort insulin mRNA levels were reduced by 76% in Bridge-1 transgenic (TG) relative to control (WT) mice (FIG. 7d). The most severe insulin deficiency that we observed in a Bridge-1 transgenic mouse was accompanied by ketonuria as detected by urine dipstick testing, a clinical finding most commonly associated with Type 1 diabetes and an absolute insulin deficit.

Pancreatic glucagon mRNA levels were increased by 28% and somatostatin mRNA levels were decreased by 53% in Bridge-1 transgenic mice, but elastase mRNA levels were not significantly different in the same experimental series (FIG. 7d). The relative increase of glucagon mRNA expression in the transgenic mouse pancreas was modest in comparison to the observed increases in α-cell complement or Brain-4 mRNA expression. Pancreatic mRNA expression levels of the β-cell-specific glucose sensors glucokinase and glucose transporter-2 (Glut-2) were not significantly different between Bridge-1 transgenic and control mice. These findings were somewhat surprising in the setting of the substantial reductions in β-cell mass in the transgenic mice and may reflect adaptive changes in the surviving transgenic p cells to augment glucose-sensing.

EXAMPLE 8

Bridge-1 Regulation of the Insulin Promoter is Biphasic

We previously proposed that the endogenous coactivator Bridge-1 functions to augment insulin promoter activity (Thomas, M. K., et al., *Mol Cell Biol* 19:8492-8404 (1999)), but in this experimental model we found a reduction in insulin mRNA levels in the setting of increased pancreatic Bridge-1 expression. The overexpression of other insulin gene activators, including PDX-1 and E47, results in the suppression of the transcriptional activation of the insulin promoter (Ohneda, K., et al., *Mol Cell Biol* 20:900-911 (2000); German. M. S., and Wang, J., *Mol Cell Biol* 14:4067-4075 (1994); Marshak, S., et al., *Proc Natl Acad Sci USA* 93:15057-15062 (1996); Seijffers, R., et al., *Endocrinology* 140:3311-3317 (1999)). Therefore, we wondered whether varying the levels of Bridge-1 expression also might result in a dose-dependent, biphasic pattern of insulin promoter activation, first by promoting and then disrupting the assembly of supramolecular transcriptional regulatory complexes. In transient transfections in HeLa cells, we observed that increasing the amounts of exogenous Bridge-1 expression resulted in a shift from activation of a rat insulin I enhancer-reporter construct to repression in a pattern reminiscent of those observed for other transcriptional activators of insulin gene expression (Ohneda, K., et al., *Mol Cell Biol* 20:900-911 (2000); German. M. S., and Wang, J., *Mol Cell Biol* 14:4067-4075 (1994); Marshak, S., et al., *Proc Natl Acad Sci USA* 93:15057-15062 (1996); Seijffers, R., et al., *Endocrinology* 140:3311-3317 (1999)) (FIG. 7e). These data support a model of Bridge-1 function in which increases of Bridge-1 expression within a distinct range augment the transcriptional activation of the insulin gene. Beyond this range larger increases in Bridge-1 may disrupt or modify transcriptional activation complexes to limit insulin production.

EXAMPLE 9

Expression of Bridge-1 Mutant (1-184) Increases Pancreatic β Cell Mass and Replication In a series of targeted mutagenesis studies, we previously identified a mutation in Bridge-1 that substantially reduces its transcriptional activation potential in vitro. Specifically, a point mutation was introduced into the Bridge-1 coding region to produce a premature in-frame stop codon that resulted in a truncated expression product comprising only amino acids 1-184. In mammalian two-hybrid studies in HeLa cells, the Bridge-1 (1-184) mutant was found to interact well with E12; however, a Gal4 DNA-binding domain-Bridge-1 (1-184) fusion construct did not activate the Gal4CAT reporter in BHK cells (FIG. 10). Western blot showing expression of Gal4 DNA-binding domain-Bridge-1 (1-222) and Gal4 DNA-binding domain-Bridge-1(1-184) fusion proteins from representative extracts of transfected BHK cells is shown in FIG. 11. Schematic models of the pIDX-1-Bridge-1(1-222) and pIDX-1-Bridge-1 (1-184) transgenes is shown in FIG. 12. PDX-1 is designated IDX-1 in this figure.

Here, we developed a transgenic mouse model in which the pancreas-specific pdx-1 (MODY4) promoter regulates expression of the mutant Bridge-1 (1-184) protein. The mutant Bridge-1(1-184) transgenic mice had marked changes in the endocrine compartment of the pancreas with altered pancreatic islet architecture. Although we observed no differences in islet numbers, pancreatic islets from mutant Bridge-1(1-184) transgenic mice (Tg) contained approximately 80% more cells than those from nontransgenic littermate control (WT) mice (n=6 Tg, 6 WT; p=0.02). We found a 75% increase in the average number of insulin-expressing pancreatic beta cells per islet within the mutant Bridge-1(1-184) transgenic as compared to control mice (n=6 Tg, 6 WT; p=0.006). No substantial differences were observed in the average numbers of somatostatin- and glucagon-expressing cells per islet from mutant Bridge-1(1-184) transgenic versus control mice. In the mutant Bridge-1(1-184) transgenic mice with the most striking phenotypes, enlarged pancreatic islets were distributed in close proximity to one another along the longitudinal axis of the pancreas. (FIG. 8). Pancreatic islet cells from mutant Bridge-1(1-184) transgenic mice also exhibited increased replication rates (FIG. 9).

Among the mutant Bridge-1(1-184) transgenic mice analyzed, there was a tendency for the most prominent pancreatic islet phenotypes to be associated with lower fasting blood glucose levels. In conclusion we have identified an important function for signaling by the coactivator Bridge-1 in the regulation of pancreatic beta-cell mass. Signals transduced through this coactivator are likely to modulate pancreatic beta-cell neogenesis, replication, and/or apoptosis. Understanding Bridge-1 signaling in pancreatic beta cells should facilitate efforts to restore pancreatic beta-cell mass and insulin production in the treatment of diabetes.

EXAMPLE 10

Inhibitors and Activators of Bridge-1 Transactivation Function

Various compounds were assayed for their ability to activate or inhibit Bridge-1 transactivation function. In these experiments, the transactivation assay previously described (Thomas, M. K. et al., *Mol. Cell. Biol.* 19(12):8492-8504 (1999)) incorporated herein by reference) was used with the modification that the plasmid reporter was a Gal4 luciferase reporter with luciferase activity measured rather than the Gal4CAT reporter used in 1999. BHK cells were plated at 30-40 percent confluency and transiently transfected with 5 or 10 microliters of Lipofectamine (Life Technologies/Invitrogen) and 5 micrograms total DNA consisting of 250 ng Gal4-luciferase reporter plasmid, 1.5 micrograms pM(Gal4 DBD) or pM-Bridge-1 (Gal4 DBD-Bridge-1) and 3.25 micrograms of bluescript plasmid incubated for 6 hours in the transfection cocktail. After 6 hours, the transfection cocktail was replaced with fresh culture medium (DMEM, 10% fetal bovine serum, 1% antibiotic/antimycotic (Life Technologies). Agonists or inhibitors were added (+) or the corresponding vehicle solution (−) and cells were incubated at 37° C. in a $CO_2$ incubator for 24 hours prior to harvest. Luciferase assays were conducted as previously referenced (Thomas, M. K. et al., *Mol. Cell. Biol.* 19(12):8492-8504 (1999)). Agonists and their final concentration in the assay are shown in FIGS. 13-15. Experiments shown were conducted three times (n=3, each at least in duplicate) for Activin A (2.34 fold activation) and Trichostatin A (2.7 fold activation) and five times (n=5, each at least in duplicate) for Progesterone (a 22 percent inhibition).

Discussion

In the Bridge-1 overexpression transgenic mouse model the pancreatic overexpression of the coactivator Bridge-1 results in insulin deficiency and diabetes. Our initial description of Bridge-1 as a coactivator of insulin gene expression in vitro emphasized the capacity of Bridge-1 to augment the transcriptional activation of glucose-responsive enhancers within the rat insulin I promoter via PDZ-domain mediated protein-protein interactions with the basic helix-loop-helix transcription factors E12 and E47 (Thomas, M. K., et al., *Mol Cell Biol* 19:8492-8404 (1999)). We overexpressed Bridge-1 to disrupt supramolecular protein complexes in PDZ-based scaffolds that regulate Bridge-1 target genes in the pancreas. We provide herein evidence for additional functions for Bridge-1 signaling in the regulation of glucose homeostasis and of pancreatic β-cell survival based on these in vivo studies.

The marked reduction in the number of insulin-expressing cells observed in the transgenic mice was unexpected. Bridge-1 transgenic mice had only one-third of the normal number of insulin-producing pancreatic β cells as assessed by the expression levels of insulin or of pancreatic β-cell-specific transcription factors Nkx 6.1 and PDX-1. This reduction in pancreatic β-cell mass is accompanied by an increase in pancreatic apoptosis, particularly within the endocrine cell compartment. A similar phenotype of increased pancreatic β-cell apoptosis and decreased β-cell mass is found in humans with Type 2 diabetes (Butler, A. E., et al., *Diabetes* 52:102-110 (2003)).

Multiple potential mechanisms exist for the induction of apoptosis by Bridge-1 overexpression. Bridge-1 may directly regulate the expression of anti- or pro-apoptotic genes to promote programmed cell death. In addition, insulin deficiency resulting from the repression of insulin gene expression may accelerate β-cell apoptosis. Decreased intrapancreatic insulin signaling is known to negatively impact pancreatic β-cell mass. The targeted disruption of the insulin signaling protein IRS-2 or the β-cell specific deletion of the insulin receptor reduce the mass of insulin-producing cells in genetically-modified mouse models (Withers, D. J., et al., *Nature* 391:900-904 (1998); Kubota, N., et al., *Diabetes* 49:1880-1889 (2000); Otani., K., et al., *Am J Physiol Endocrinol Metab* 286:E41-49 (2004)). Insulin regulates pancreatic β-cell mass through protein kinase B (AKT) (Tuttle, R. L., et al., *Nat Med* 7:1133-1137 (2001); Bemal-Mizirachi, E., et al., *J Clin Invest* 108:1631-1638 (2001)) and by regulating PDX-1 expression levels in a Foxol-dependent manner (Kushner, J. A., et al., *J Clin Invest* 109:1193-1201 (2002); Kitamura, T., et al., *Clin Invest* 110:1839-1847 (2002)). Furthermore, sustained hyperglycemia may be an independent stimulus of pancreatic β-cell apoptosis in vivo (Donath, M.Y., and Halban, P. A., *Diabetologia* (February 2004) [Epub ahead of print]).

Metabolic dysfunction was apparent as early as three weeks of age in this model and ranged from mild to severe hyperglycemia. In many mouse models of Type 2 diabetes hyperglycemia is more prominent in males than females (Thomas, M. K., et al., *J Clin Invest* 108:319-329 (2001); Bruning, J. C., et al, *Cell* 88:561-572 (1997)) as we noted in Bridge-1 transgenic mice. It is possible that gender-specific differences in steroid hormone levels attenuated the insulin deficiency in the female transgenic mice. Although the female transgenic mice demonstrated a mild hyperglycemic phenotype, they were unable to appropriately augment insulin production in response to a glucose challenge. We observed severe diabetes that was accompanied by extremely low serum insulin levels and insulin-to-glucose ratios in the male transgenic mice. In this respect the phenotype in Bridge-1 transgenic mice resembles those of defective insulin production in humans with MODY and of minimal residual β-cell function in humans with early Type 1 diabetes.

We consider the hyperglycemia and hyperlipidemia in Bridge-1 transgenic mice to be the result of insulin deficiency. However, in the setting of an increased proportion of glucagon-expressing α cells relative to β cells, it is possible that abnormal regulation of glucagon production exacerbates hyperglycemia. The smaller increases that we found in pancreatic glucagon mRNA expression levels relative to the greater increases in the number of α cells estimated both by cell counting and by the mRNA expression levels of the α-cell-specific transcription factor Brain-4 suggest that the α cells in the transgenic mice were able to downregulate glucagon gene expression in the context of elevated glucose levels. An increased proportion of α cells relative to β cells is found in pancreatic islets from many other mouse models of β-cell dysfunction and diabetes as well as in islets from humans with type 2 diabetes (Yoon, K. H., et al., *J Clin Endocrinol Metab* 88:2300-2308 (2003)). This shift in islet composition to a relative excess of glucagon-expressing cells is of unclear pathophysiologic significance. The reduction of somatostatin mRNA expression in Bridge-1 transgenic mice likely is a result of increased Bridge-1 expression from the transgene because the pdx-1 promoter is known to be active in selected somatostatin-expressing δ cells (Thomas, M. K., and Habener, J. F., "IDX-1: Pancreatic Agenesis And Type 2 Diabetes," In *Molecular Basis Of Inborn Errors Of Development*, P. Erikson, et al., editors, Oxford Univ. Press, Oxford, United Kingdom, 552-556 (2004)).

We were surprised to find no significant reductions in the pancreatic expression levels of glucokinase or Glut-2 in the setting of marked reductions in the numbers of pancreatic β cells. These two proteins constitute rate-limiting steps in glucose sensing with pancreatic expression restricted primarily to the β cell. Our data suggest that the remaining pancreatic β cells in Bridge-1 transgenic mice with diabetes upregulated the expression of these glucose sensors either directly in response to increased levels of Bridge-1 expression or as an adaptive response to the reduction in β-cell mass. It is interesting to note that both glucokinase and Glut-2 expression levels are decreased in pancreatic islets in response to the adenoviral overexpression of the coactivator PGC-1 (Yoon, J. C., et al., *Dev Cell* 5:73-83 (2003)). In mice in which PDX-1 expression is deleted in adult pancreatic β cells, Glut-2 expression levels decline in parallel with reductions in PDX-1 expression levels (Ahlgren, U., et al., *Genes Dev* 12:1763-1768 (1998)). The observed robust levels of expression of the Bridge-1 transgene indicate that the pdx-1 promoter is active in Bridge-1 transgenic mice despite reductions in PDX-1 protein and mRNA expression, diminished β-cell mass, and systemic hyperglycemia and hypoinsulinemia.

The overexpression of Bridge-1 disrupts several aspects of pancreatic architecture. The loss of spatial organization of the pancreatic endocrine cells in Bridge-1 transgenic mice is a striking phenotype. The usual distinct boundaries between endocrine and exocrine cells are not respected in this model with the appearance of wandering endocrine cells intermingled among acinar tissue. The endocrine cells in Bridge-1 transgenic mice have the apparent capacity to move beyond or to extend normal tissue compartments with a histologic appearance that resembles metastatic tumor cells more than pancreatic islets. The rearrangement of cells in this model can be viewed either as a gain of endocrine cell motility or the loss of the capacity for endocrine cells to aggregate and organize islet structures. The spatial relationships of glucagon-expressing α cells and insulin-expressing β cells also are altered. The disorganization of both the endocrine and exocrine compartments of the pancreas implies that signals transduced through Bridge-1 regulate intercellular communication. The signals that maintain the normal boundaries between pancreatic islets and adjacent exocrine tissue are unknown but are likely to be of clinical significance. A failure to maintain distinct endocrine and exocrine cellular compartments is seen in a small number of pancreatic diseases in humans, including nesidioblastosis and selected pancreatic cancers. Although we observed a phenotype of ductal enlargement, we did not identify metaplastic features in the transgenic ductal epithelium.

Considerable heterogeneity in pancreatic nuclear and cellular sizes also was apparent in Bridge-1 transgenic mice. This variability may reflect local differences in insulin signaling that are capable of altering cell size in *Drosophila* and in mice (Tuttle, R. L., et al., Nat Med 7:1133-1137 (2001); Edgar, B. A., *Nat Cell Biol* 1:E191-E193 (1999)). In this context it is interesting to note that the targeted disruption of the mouse coactivator gene tif2 reduces the size of adipocytes (Picard, F., et al., *Cell* 111:931-941 (2002)). Future studies will be needed to identify the components of the intracellular pathways that regulate signals through Bridge-1.

The pdx-1 promoter is active both in embryonic pancreas development and in the adult pancreas, so it is possible that some of the observed changes in pancreatic architecture in Bridge-1 transgenic mice were a result of the embryonic overexpression of Bridge-1. The endogenous Bridge-1 protein is expressed in the early developing pancreas (M. Thomas, unpublished results) and may regulate the function of a subgroup of transcriptional regulators of pancreas development. However, by gross inspection the pancreata in Bridge-1 transgenic mice were of normal size, location, and appearance. Because all three cellular compartments of the pancreas, i.e., ductal, exocrine, and endocrine, were formed in the Bridge-1 transgenic mice it is unlikely that the overexpression of Bridge-1 substantively interfered with the early stages of embryonic pancreas development. Because we observed hyperglycemia as early as three weeks of age in Bridge-1 transgenic mice, it is possible that the pancreatic overexpression of Bridge-1 influenced late prenatal or early postnatal pancreas development when substantial remodeling of pancreatic β-cell mass occurs.

The structural changes in the pancreas in response to the overexpression of Bridge-1 predict a broad range of targets for Bridge-1 signaling. The characterization of the human Bridge-1 homologue, PSMD9, as a proteasomal modulator expands the potential scope of Bridge-1 functions. PSMD9 was isolated in a complex with the proteasomal subunit TBP-1/Rpt5 (Watanabe, T. K., et al., *Genomics* 50:241-250 (1998); DeMartino, G. N., et al., *Biol Chem* 271:3112-3118 (1996)) that is implicated in transcriptional regulation in yeast and mammals (Ohana, B., et al., *Proc Natl Acad Sci USA* 90:138-142 (1993); Goizales. F., et al., *Science* 296:548-550 (2002)). The processes of transcriptional activation and protein degradation often are closely coupled (Salghetti. S. E., et al., *Science* 293:1651-1653 (2001); Ottosen. S., et al., *Science* 296:479-481 (2002); Conaway, R. C., et al., *Science* 296: 1254-1258 (2002); Grossman, S. R., et al., *Science* 300:342-344 (2003)). A dual capacity of Bridge-1 to regulate gene expression and to modulate proteasomal function would be similar to dual functions ascribed to a small group of proteasomal subunits, coactivators, and ubiquitin ligases.

The precise stoichiometric assembly of transcription factors and coactivators is essential for appropriately regulated gene expression. We identified Bridge-1 as a coactivator of insulin gene transcription, but Bridge-1 overexpression decreased insulin gene expression in Bridge-1 transgenic mice. The deficit in insulin gene expression correlated both with the reduced pancreatic β-cell mass and with diminished levels of insulin protein expression in the surviving β cells. The pancreatic overexpression of the PDZ-scaffold protein Bridge-1 may disrupt and misdirect the protein-protein interactions within the transcriptional regulatory complexes of Bridge-1 target genes in vivo, effectively interrupting normal Bridge-1 signaling and suppressing insulin gene expression. Increased levels of Bridge-1 also may promote the formation of nonproductive complexes of transcription factors or alternatively recruit corepressors. This mechanism for insulin gene regulation is consistent with reports that the overexpression of the insulin gene activators PDX-1 or E47 results in the repression of insulin promoter activity (Ohleda, K., et al., *Mol Cell Biol* 20:900-911 (2000); German. M. S., and Wang, J., *Mol Cell Biol* 14:4067-4075 (1994); Marshak, S., et al., *Proc Natl Acad Sci USA* 93:15057-15062 (1996); Seijffers, R., et al., *Endocrinology* 140:3311-3317 (1999)). Increasing concentrations of E47 first promote and then interfere with the synergistic activation of glucose-responsive enhancers of the insulin promoter in conjunction with PDX-1 (Ohneda, K., et al., *Mol Cell Biol* 20:900-911 (2000)). Dose-dependent expression of PDX-1 is essential to maintain normal glucose homeostasis, and relatively small changes in PDX-1 expression levels result in metabolic dysfunction (Thomas, M. K., et al., *J Clin Invest* 108:319-329 (2001)). Our data indicate that changes in the levels of Bridge-1 expression have a similar capacity to augment or impair insulin gene expression. Inactivation of endogenous Bridge-1 in insulin-producing cells reduces the transcriptional activation of the insulin promoter (Thomas, M. K., et al., *Mol Cell Biol* 19:8492-8504 (1999)), and increasing Bridge-1 expression levels result in a dose-dependent, biphasic activation of insulin gene enhancers. Thus we propose that the coactivator Bridge-1 can serve as a rheostat to receive intracellular signals and translate them into graded levels of insulin gene expression. Bridge-1 may have a similar modulatory function to regulate pancreatic β-cell mass via additional target genes Coactivator dysfunction is implicated in the pathogenesis of many diseases, including malignancies, neurodegenerative disorders, and mental retardation (Giles, R. M., et al., *Trends in Genetics* 14:178-182 (1998)). Accumulating evidence indicates that coactivators regulate insulin action and nutrient metabolism in extrapancreatic tissues. CBP alters insulin sensitivity (Yamauchi, T., et al., *Nat Genet.* 30:221-226 (2002)), and SRC1 and TIF2 adjust rates of energy expenditure (Picard, F., et al., *Cell* 111:931-941 (2002)). PGC-1α regulates glucose uptake and gluconeogenesis (Puigserver, P., and Spiegelman, B. M., *Endo Rev* 24:78-90 (2003)) and its overexpression inhibits glucose-stimulated insulin secretion (Yoon, J. C., et al., *Dev Cell* 5:73-83 (2003)). Genetic variations in the pgc-1 gene may increase susceptibility to insulin resistance and diabetes in humans (Hara, K., et al., *Diabetologia* 45:740-743 (2002)). Furthermore, mutations in the MODY genes hnf-4α, neuroD1, and ipf-1 (pdx-1) that are associated with heritable forms of diabetes in humans also alter their interactions with the coactivators CBP or p300 (Stanojevic, V., et al., *Endocrinology p.* 300 (March 2004) [Epub ahead of print]; Malecki, M. T., et al., *Nat Genet.* 23:323-328 (1999); Eeckhoute, J., et al., *Mol Endocrinol* 15:1200-1210 (2001)).

Coactivator dysfunction in pancreatic p cells may limit insulin production and contribute to the pathogenesis of diabetes in humans. The locus of the human Bridge-1 gene, chr 12q24.31-32 (Watanabe, T. K., et al., *Genomics* 50:241-250 (1998)), lies within a region identified by multiple genome-wide scans for candidate type 2 or MODY diabetes genes that is distinct from the adjacent MODY3 locus (Mahtani, M. M., et al., *Nat Genet.* 14:90-94 (1996); Shaw. J. T., et al., *Diabetes* 47:173-1796 (1998); Ehm, M. G., et al., *Am J Hum Genet.* 66:1871-1881 (2000); Lindgren, C. M., et al, *Am J Hum Genet.* 70:509-516 (2002); Frayling, T. M., et al., *Diabetes* 52:872-881 (2003); Wiltshire, S., et al., *Diabetes* 53:855-860 (2004)). Mutations or polymorphisms in the Bridge-1 gene may contribute to metabolic dysfunction by decreasing insulin production and reducing pancreatic β-cell mass. Thus, we conclude that Bridge-1 represents a diabetes gene.

The therapeutic effectiveness of selective estrogen receptor modulators demonstrates the feasibility of targeting distinct tissue-specific and promoter-specific recruitment of coactivators in the treatment of disease (Shang, Y., and Brown, M., *Science* 295:2465-2468 (2002)). We expect that the regulation of pancreatic β-cell function by coactivators like Bridge-1 will provide new therapeutic opportunities to restore insulin production in individuals with diabetes.

EXAMPLE 11

Materials and Methods for Examples 12-17

Examples 12-17 demonstrate that the PDZ domain of Bridge-1 is required for transcriptional activation, and p300 is identified as a Bridge-1 interaction partner that augments transcriptional activation by Bridge-1 in a PDZ-domain dependent manner.

Cell culture and transfections. BHK-21 (C-13) cells were obtained from American Type Culture Collection (Manassas, Va.) and cultured in Dulbecco's modified Eagle medium supplemented with 10% fetal bovine serum, 100 U/mL Penicillin G, and 100 ug/mL streptomycin sulfate (Invitrogen Life Technologies, Carlsbad, Calif.). Transfections were conducted with Lipofectamine or Lipofectamine 2000 (Invitrogen Life Technologies) according to published methods (Thomas, M. K., et al., *Molec. Cell. Biol.* 19:8492-8504 (1999). Yeast transcriptional activation assays were conducted as previously reported (Thomas, M. K., et al., supra; Golemis, E. A., et al., *Current Protocols in Molecular Biology*, Ausubel, F. M., et al., eds., John Wiley and Sons, pp. 13.14.1-13.14.17 (1994)) with quantitative LexA-operator responsive beta-galactosidase reporter assays as outlined by the manufacturer (BD Biosciences Clontech, Palo Alto, Calif.).

Plasmids and mutagenesis. The Gal4 DNA-binding domain Bridge-1 fusion protein expression vectors Gal4-Bridge-1, Gal4-Bridge-1(1-72) and Gal4-Bridge-1(1-133) were generated in the pM vector (BD Biosciences Clontech, Palo Alto, Calif.) as described (Thomas, M. K., et al., supra). Additional mutant Gal4 Bridge-1 fusion protein expression vectors were generated by site-directed mutagenesis of the pM-Bridge-1 plasmid. Site-directed mutagenesis was performed with the QuikChange site-directed mutagenesis kit (Stratagene, La Jolla, Calif.) according to the manufacturer's instructions by using the following oligonucleotides and their respective reverse complements: Gal4-Bridge-1 (V159P): 5'-TGGATGATGAAATTCCG GAGTTCGGCTCTGT-3' (SEQ ID NO: 156); Gal4-Bridge-1(V164P): 5'-TGGAGTTCGGCTCTCCGAACACCCAAAACTT-3' (SEQ ID NO: 157); Gal4-Bridge-1 (V175P): 5'-AGTCTCTGCAGAACCCGGGCACTGTGG TGCA-3' (SEQ ID NO: 158); Gal4-Bridge-1(D156P): 5'-CCTGCAAGTGGATCCTGAAATTGTGGAGTT-3' (SEQ ID NO: 159); and Gal4-Bridge-1 (G151P): 5'-AGCCAGTATTGCGCCCCTGCAAGTGGA TGAT-3' (SEQ ID NO: 160). Mutant constructs were verified by automated sequencing. The glutathione-S-transferase (GST)-Bridge-1 vector was cloned by excising rat Bridge-1 cDNA from the pM-Bridge-1 vector with BamH I and EcoR I digestion and subcloning into the multiple cloning site of the pGEX-5X-1 GST fusion protein expression vector (Amersham Biosciences, Piscataway, N.J.). Mutant GST-Bridge-1 expression vectors were generated by site-directed mutagenesis of the pGEX-5X-1-Bridge-1 vector by using the following oligonucleotides and their respective reverse complements: GST-Bridge-1 (1-72): 5'-GGATTTGTATCAGGTCTGAACAGCAAGGCAC-3' (SEQ ID NO; 161); GST-Bridge-1(1-133): 5'-CAGTCCCGCCCTACCC TAGGCCTTTGCCA GAG-3' (SEQ ID NO; 162); and GST-Bridge-1(D156P): 5'-CCTGCAAGTGGATCCTGAAATTGTGGAGTT-3' (SEQ ID NO; 163). Mutant constructs were verified by automated sequencing. Yeast expression vectors for LexA-Bridge-1, LexA-Bridge-1(1-72), and LexA-Bridge-1(1-132) fusion protein constructs were previously described (Thomas, M. K., et al., supra). The pCMVβ-p300 plasmid was obtained from Upstate Biotechnology (Lake Placid, N.Y.). The Gal4-chloramphenicol acetyltransferase (CAT, pG5-CAT) reporter plasmid was purchased from BD Biosciences Clontech and the Gal4-luciferase reporter plasmid (pFR-luc) was obtained from Stratagene. The pCMV-E1A wild-type and mutant E1A(Δ2-36) plasmids were gifts from R. Stein (Vanderbilt University School of Medicine, Nashville, Tenn.), and the GST-p300 expression plasmids were obtained from H. Lu (Oregon Health and Science University, Portland, Oreg.) and D. Livingston (Dana-Farber Cancer Institute, Boston, Mass.).

GST pull-down protein interaction assays. GST pull-down protein interaction assays were conducted as previously described (Stanojevic, V., et al., supra). Recombinant GST fusion protein input was determined and normalized by sodium dodecyl sulfate-polyacrylamide gel electrophoresis (SDS-PAGE) of fusion proteins that were synthesized in bacteria. Radiolabeled in vitro translated proteins were generated in rabbit reticulocyte lysate kits purchased from Promega (Madison, Wis.) with [$^{35}$S]-methionine according to the manufacturer's protocol. Protein interaction assays were conducted with glutathione Sepharose 4B beads (Amersham Biosciences, Piscataway, N.J.) as described (Stanojevic, V., et al., supra).

Western blots. Western blots were conducted by SDS-PAGE fractionation of whole cell extracts prepared from transfected cells in 1× Reporter Lysis Buffer (Promega, Madison, Wis.) and electroblotting onto Inmobilon-P membranes (Millipore, Bedford, Mass.) (Thomas, M. K., et al., supra). Blots were incubated with primary rabbit polyclonal anti-Gal4 DBD:antiserum (1:1000 dilution) (sc-577 from Santa Cruz Biotechnology, Inc., Santa Cruz, Calif.) and secondary horseradish peroxidase-conjugated goat anti-rabbit antiserum (Bio-Rad Laboratories, Richmond, Calif.). Proteins were visualized by chemiluminescence with ECL Western blotting detection reagents (Amersham Life Sciences, Arlington Heights, Ill.).

EXAMPLE 12

Histone Deacetylase Inhibition Increases Transcriptional Activation by Bridge-1

We previously identified an assay for studies of transcriptional activation by the coactivator Bridge-1 in mammalian cells. In this transfection assay, a Gal4 DNA binding domain-Bridge-1 fusion protein (Gal4-Bridge-1) activated a Gal4-reporter construct by as much as 30-fold as compared to the control Gal4 DNA-binding domain construct (Gal4) alone (Thomas, M. K., et al., supra). Using this transcriptional activation assay, we found that incubation with the histone deacetylase inhibitor trichostatin A increased the transcriptional activation by Bridge-1 in a dose-dependent manner (FIG. 17A), suggesting that the regulation of transcriptional activation by Bridge-1 is governed by the activity of histone-modifying enzymes within transcriptional regulatory complexes.

EXAMPLE 13

Bridge-1 Interacts with the Histone Acetyltransferase p300

Figure 17A:
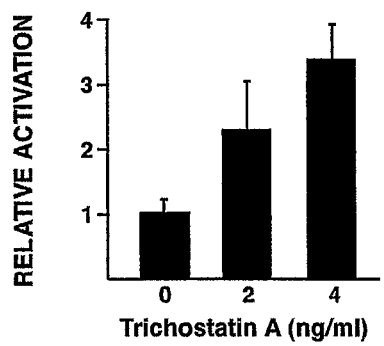
Figure 17B:
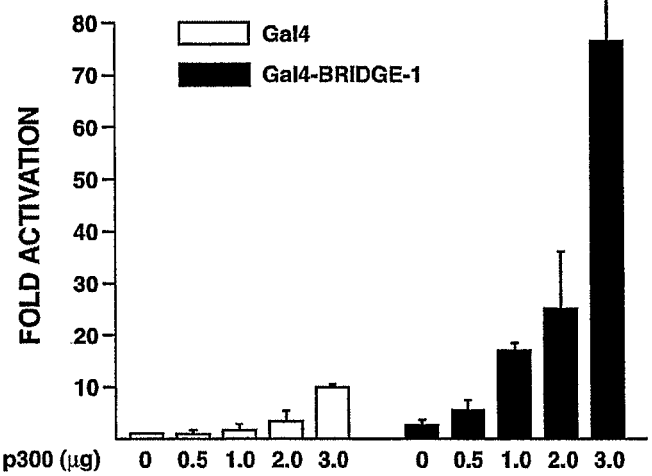

Because the histone acetyltransferase and nuclear receptor coactivator p300 is one of the principal coactivators implicated in the regulation of gene transcription in the endocrine pancreas, we conducted a series of studies to determine whether interactions between Bridge-1 and p300 could contribute to the regulation of transcriptional activation by Bridge-1. First, we demonstrated that transcriptional activation of the Gal4-reporter construct by Gal4-Bridge-1 was augmented by the addition of exogenous p300 in vivo. In a dose-dependent manner, the addition of p300 to Gal4-Bridge-1 increased activation of the reporter by over 70-fold, an effect in marked excess of that observed for p300-mediated activation of the basal activity of the control Gal4 expression vector (FIG. 17B). These data suggest that p300 cooperates with Bridge-1 to augment transcriptional activation.

Figure 17C:
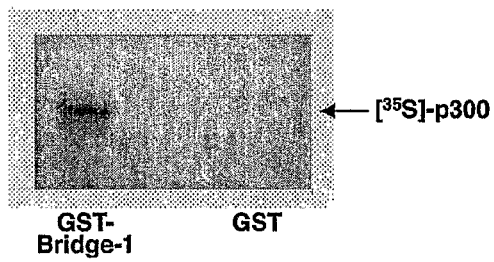
Figure 17D:
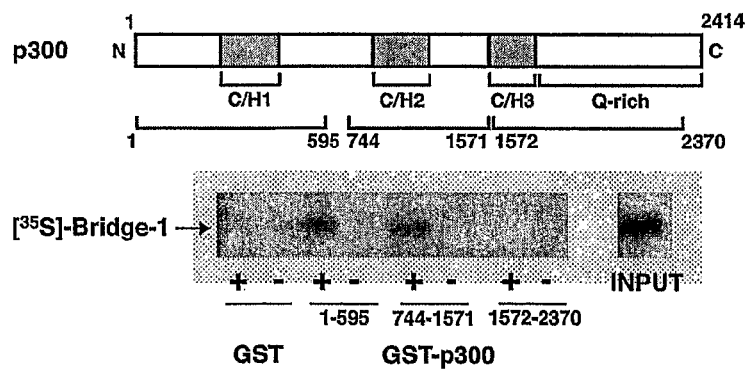

To determine whether Bridge-1 could directly interact with p300, we conducted a series of GST pull-down protein interaction assays. In these assays we observed Bridge-1 interactions with p300 by combining GST-Bridge-1 fusion proteins with [$^{35}$S]-radiolabeled in vitro translated full-length p300. Radiolabeled p300 strongly interacted with GST-Bridge-1 but not with the GST control protein (FIG. 17C). The coactivator p300 is a large modular protein with multiple interaction domains, including cysteine-histidine rich regions known as C/H domains (Chakravarti, D., et al., supra) (FIG. 17D, upper panel). To identify the regions within p300 that interacted with Bridge-1, we combined [$^{35}$S]-radiolabeled in vitro translated Bridge-1 with GST-p300 fusion proteins that spanned the three C/H protein interaction domains within p300. We identified strong interactions between Bridge-1 and GST-p300 fusion protein segments encompassing p300 amino acids 1-595 and 744-1571 but not with the GST-p300 fusion protein encompassing amino acids 1572-2370 (FIG. 17D, lower panel). These results indicated that Bridge-1 can interact with multiple regions within p300, including those encompassing the C/H1 and C/H2 protein interaction domains. The histone acetyltransferase domain of p300 is included within amino acids 744-1571 (Chan, H. M., et al., supra). We noted that Bridge-1 did not directly interact with the carboxy-terminal segment of p300 that is implicated in interactions with the insulin gene regulators PDX-1 and NeuroD1 (Qiu, Y., et al., *Molec. Cell. Biol.* 18:2957-2964 (1998); Qiu, Y., et al., *Molec. Cell. Biol.* 22:412-420 (2002); Stanojevic, V., et al., *Endocrinol.* 145:2918-2928 (2004)).

EXAMPLE 14

Sequestration of p300 by E1A Impairs Transcriptional Activation by Bridge-1

To determine whether endogenous p300 might regulate the extent of transcriptional activation by Bridge-1, we overexpressed the exogenous adenoviral protein E1A to sequester p300 (Qiu, Y., et al., *Molec. Cell. Biol.* 18:2957-2964 (1998); Stein, R. W., et al., *J. Virol.* 64:4421-4427 (1990)). The expression of increasing amounts of E1A decreased the transcriptional activation of a Gal4-CAT reporter construct by Gal4-Bridge-1 (FIG. 18A) while preserving the expression of the transfected Gal4-Bridge-1 fusion proteins on Western blots (data not shown). Although exogenous E1A reduced transcriptional activation by Bridge-1, a mutant E1A protein (E1AΔ2-36) that is unable to bind and sequester p300 (Stein, R. W., et al., *J. Virol.* 64:4421-4427 (1990)) did not interfere with transcriptional activation (FIG. 18B). Collectively these data suggest that transcriptional activation by Bridge-1 depends, in part, on the availability of p300.

EXAMPLE 15

PDZ and Carboxy-Terminal Domains within Bridge-1 are Required for Transcriptional Activation To identify domains within Bridge-1 that are required for transcriptional activation, we generated Bridge-1 deletion mutants and assessed their function in both yeast and mammalian cells. Bridge-1 segments containing amino acids 1-72 or 1-132 that lack carboxy-terminal portions of the protein that encompass the PDZ domain had markedly impaired transcriptional activation in yeast cells, ranging between 4 and 11 percent of the wild-type Bridge-1 activity (FIG. 19A). Similarly in mammalian cells, the levels of activation of the Gal4-reporter construct by Gal4-Bridge-1 mutant proteins encoding amino acids 1-72 or 1-133 were nearly undetectable (FIG. 19B), despite comparable protein expression of transfected wild-type and mutant Bridge-1 fusion proteins as determined by Western blots (FIG. 19C). Therefore the carboxy-terminal segment of Bridge-1 that includes the PDZ domain is required for transcriptional activation.

Figure 20A:
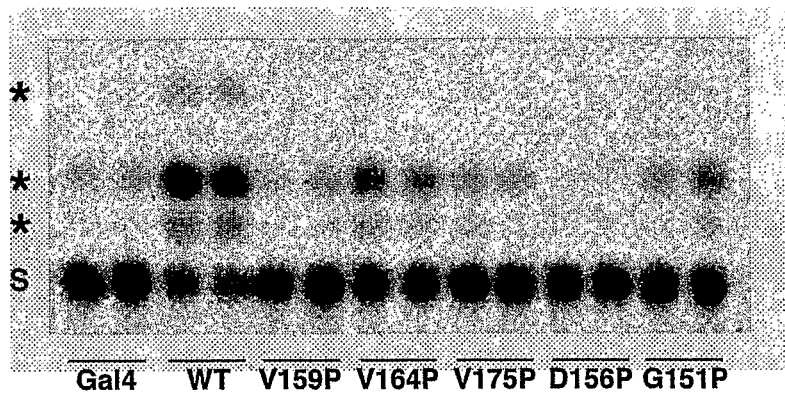
Figure 20B:
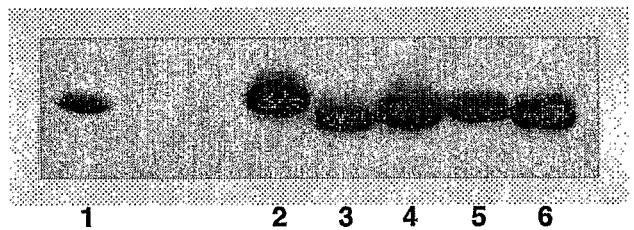
Figure 20C:
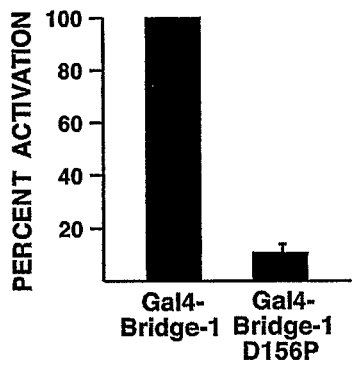

To determine the importance of the PDZ domain within Bridge-1 for transcriptional activation, we introduced proline substitution point mutations within several conserved amino acids of the PDZ domain of Bridge-1. As compared to the wild-type Gal4-Bridge-1 fusion protein, the mutant Gal4-Bridge-1 fusion proteins V159P, V164P, V175P, D156P, and G151P all demonstrated severe impairment in the activation of the Gal4-reporter construct (FIG. 20A), despite evidence of sufficient protein expression levels (FIG. 20B). We noted the most severe impairment in transcriptional activation in the Gal4-Bridge-1 fusion protein D156P. The level of transcriptional activation of the Gal4-reporter construct by Gal4-Bridge-1 (D156P) was only about 10 percent of that observed with expression of the wild-type Gal4-Bridge-1 fusion protein (FIG. 20C).

EXAMPLE 17

Deletion or Mutagenesis of the Bridge-1 PDZ Domain Disrupts Interactions with p300

Figure 20D:
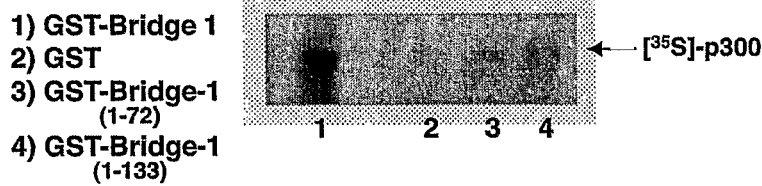
Figure 20E:
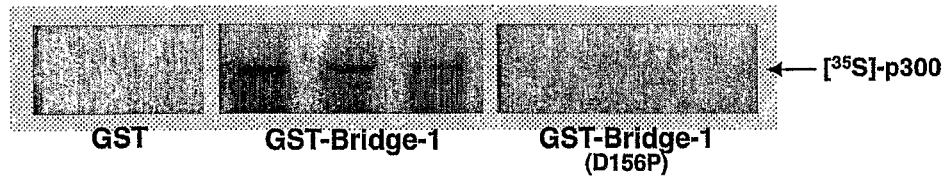

Because our transfection data suggested that transcriptional activation by Bridge-1 partially depends on the availability of p300, we wondered whether mutations that reduce transcriptional activation by Bridge-1 might also disrupt the interactions of Bridge-1 with p300. In GST pull-down protein interaction assays, the deletion of carboxy-terminal segments of Bridge-1 that include the PDZ domain to generate GST-Bridge-1 fusion proteins encoding Bridge-1 amino acids 1-72 and 1-133 interfered with interactions with [$^{35}$S]-radiolabeled in vitro translated p300 (FIG. 20D). Similarly, the mutant GST-Bridge-1 fusion protein D156P did not interact with radiolabeled wild-type p300 in contrast to the wild-type GST-Bridge-1 fusion protein (FIG. 20E). Thus mutations of Bridge-1 that disrupted transcriptional activation also interfered with interactions with p300.

Discussion

As discussed above, we have identified the PDZ-domain coactivator of insulin gene expression Bridge-1 as an interaction partner for the nuclear receptor coactivator p300. The coactivator Bridge-1 is believed to regulate target gene transcription by participating in multiple protein interactions to enhance transcriptional activation. Although our previous studies of Bridge-1-regulated transcriptional activation focused on the insulin promoter (Thomas, M. K., et al., supra), the broad distribution of the expression patterns for both p300 and Bridge-1 suggest that these two coregulators regulate a variety of target genes in cellular contexts beyond the endocrine pancreas. The appropriate assembly of multiprotein complexes is essential for the precise regulation of transcriptional activation of complex promoters. In these studies we demonstrate that transcriptional activation by Bridge-1 depends not only on the availability of endogenous p300 but also on structural features of the Bridge-1 PDZ domain that are required for interactions with p300. We propose that Bridge-1 participates in target gene regulation by contributing to multiprotein complexes to couple interactions with p300 and interactions with other transcriptional regulatory proteins (FIG. 21). The observed capacity of Bridge-1 to interact with multiple domains of p300 provides opportunities for multifocal and combinatorial protein interactions with increased complexity and flexibility for the regulation of target genes by Bridge-1.

Rat Bridge-1 is homologous to the human protein PSMD9 (FIG. 27.) that was isolated in a complex with a proteasomal subunit known as TBP-1/Rpt5 known to have transcriptional regulatory properties (Thomas, M. K., et al., supra; Watanabe, T. K., et al., *Genomics* 50:241-250 (1998); DeMartino, G. N., et al., *J. Biol. Chem.* 271:3112-3118 (1996); Ohana, B., et al., *Proc. Natl. Acad. Sci. USA* 90:138-142 (1993); Gonzales, F., et al., *Sci.* 296:548-550 (2002)). It is interesting to note that p300 can participate in similar protein regulatory complexes, as p300 protein expression levels are known to be regulated by the 26S proteasome under certain experimental conditions, including treatment with doxorubicin, sodium butyrate, or inhibitors of PI3 kinase (Poizat, C., et al., *Molec. Cell. Biol.* 20:8643-8654 (2000); Li, Q., et al., *Molec. Endocrinol.* 16:2819-2827 (2002); Chen, J., et al., *Cell. Molec. Life Sci.* 61:1675-1683 (2004)). As a potential modulator of the function of the 26S proteasome, Bridge-1 interactions with p300 could conceivably facilitate the coupling of the intrinsic ubiquitin ligase activity of p300 (Grossman, S. R., et al., *Sci.* 300:342-344 (2003) with proteasomal degradation machinery in the regulation of the expression levels of p300-interacting proteins (Grossman, S. R., et al., *Molec. Cell* 2:405-415 (1998)).

Although multiple interacting proteins for p300 have been identified, we note increasing evidence that the specific composition of coregulator transcriptional complexes is of physiologic and therapeutic relevance. For example, differing biological actions of ligands for nuclear hormone receptors may be mediated by their alteration of the composition of associated coregulatory proteins on target gene promoters (Savkur, R. S., et al., *Vitamins and Hormones* 68:145-183 (2004)). In particular, the therapeutic utility of selective estrogen receptor modulators in directing biological effects to distinct cell types may be directly regulated to differences in coregulator recruitment (Shang, Y. and Brown M., *Sci.* 295:2465-2468 (2002)). Our studies suggest that the regulation of the transcriptional activation of target gene expression by the coactivator Bridge-1 is depends significantly on the availability of p300.

EXAMPLE 18

Materials and Methods for Examples 19 to 22

Yeast interaction trap assays. Semiquantitative yeast two-hybrid interaction trap assays were conducted as previously reported (Golemis et al., 1994; Thomas et al., 1999). A LexA-rat PDX-1 bait fusion protein construct consisting of PDX-1 amino acids 160-283 cloned in the vector pEG202 and an acidic domain-rat Bridge-1 fusion protein construct cloned in the vector pJG4-5 were independently tested for activation of LexA operator-responsive LEU2 or β-galactosidase (lacZ) reporters in yeast. Interactions of E12 with rat Twist and rat inhibitor of differentiation-3 (Id3) proteins were used as positive controls and interactions of Bridge-1 with the human interleukin-1 receptor or *D. melanogaster* bicoid proteins were used as negative controls for the assays (Thomas et al., 1999). Fusion protein interactions were measured independently by growth on leucine dropout plates as a measure of LEU reporter activation or by blue color intensity with growth for 72 hours at 30° C. on X-Gal (5-bromo-4-chloro-3-indoyl-β-D-galactopyranoside) plates as a measure of lacZ reporter activation.

GST protein interaction assays. The glutathione-S-transferase (GST)-Bridge-1 vector was generated by excision of full-length rat Bridge-1 cDNA from the previously reported Gal4-Bridge-1 (pM-Bridge-1) vector (Thomas et al., 1999) with BamHI and EcoRI restriction enzyme digestion and directional cloning into the GST fusion protein expression vector pGEX-5X-1 (Amersham Pharmacia). The GST-PDX-1 expression vector (pGEX-KG-IDX-1) has been described (Miller et al., 1994). GST-PDX-1(1-38) and GST-PDX-1 (1-206) vectors were generated by insertion of premature stop codons in the GST-PDX-1 vector with QuikChange site-directed mutagenesis (Stratagene, La Jolla, Calif.) (Stanojevic et al., 2004). [$^{35}$S]-radiolabeled in vitro translated proteins were synthesized from pET-16B-PDX-1 (rat) and pcDNA3-PDX-1 (human) wild-type and mutant protein expression vectors (Stanojevic et al., 2004) and from the pcDNA3-Bridge-1 protein expression vector (Thomas et al., 1999) with rabbit reticulocyte lysate kits (Promega, Madison, Wis.) according to the manufacturer's protocol. Radiolabeled protein input was normalized by analysis on SDS-polyacrylamide gels and autoradiography. Recombinant GST fusion proteins were generated and GST pull-down protein interaction assays were conducted with glutathione Sepharose 4B beads (Amersham Biosciences, Piscataway, N.J.) as previously reported (Stanojevic et al., 2004). GST fusion protein input was normalized by assessment of recombinant protein yields in serial dilutions by sodium dodecyl sulfate (SDS) polyacrylamide gel electrophoresis.

Cell culture and transfections. BHK and HeLa cells were cultured and transfected with lipofectamine (Invitrogen Life Technologies, Carlsbad, Calif.) (Thomas et al., 1999). Chloramphenicol acetyltransferase (CAT) assays were conducted with fluorescent substrate FAST CAT (Molecular Probes, Eugene, Oreg.) and thin-layer chromatography on silica gel plates (Thomas et al., 1999). Gal4 fusion protein expression vectors (Gal4-Bridge-1 and Gal4-PDX-1), protein expression vectors (pCMV-PDX-1, pcDNA3-E12, and pcDNA3-E47), and promoter enhancer-reporter vectors ((Gal4)$_5$-CAT, (SMS-TAAT1)$_5$-65SMSCAT, and (FarFlat)$_5$-CAT) have been previously described (Miller et al., 1994; Stanojevic et al., 2004; Thomas et al., 1999; Thomas et al., 2001).

EXAMPLE 19

Bridge-1 Interacts with PDX-1

We assessed whether Bridge-1 interacts with PDX-1 in a yeast two-hybrid interaction trap system. A bait construct encoding amino acids 160-283 of rat PDX-1 did not interact with either of the control proteins Twist or Id3. However, the PDX-1 bait consistently interacted with rat Bridge-1 in semiquantitative yeast two-hybrid interaction trap assays as demonstrated by reporter activation both by growth on leucine dropout plates and by intense blue colonies on X-gal plates (Table 1). In contrast rat Bridge-1 did not interact with either of the negative control bait proteins human interleukin-1 receptor or *D. melanogaster* bicoid in these assays (Thomas et al., 1999). Thus the rat Bridge-1 protein interacts with a carboxy-terminal PDX-1 protein fragment in yeast cells.

TABLE 1

Bridge-1 Interacts with PDX-1 in Interaction Trap Assay.

|  | Interaction with PDX-1 Bait |
| --- | --- |
| Twist | − |
| Id3 | − |
| Bridge-1 | ++ |

The symbol "++" indicates growth on leucine dropout plates and intense blue colonies on X-gal plates. The symbol "−" indicates no growth on leucine dropout plates and white colonies on X-gal plates.

As a more direct method to observe the interaction between Bridge-1 and PDX-1, we conducted a series of GST-pull down protein interaction assays with GST-Bridge-1 fusion proteins and [$^{35}$S]-radiolabeled in vitro translated rat PDX-1. In these interaction assays, radiolabeled PDX-1 associated with GST-Bridge-1 preferentially as compared to the GST negative control protein (FIG. 22), independently confirming Bridge-1 and PDX-1 interactions.

EXAMPLE 20

Bridge-1 Directly Interacts with the Amino-Terminal Transcriptional Activation Domain of PDX-1

Figure 23A:
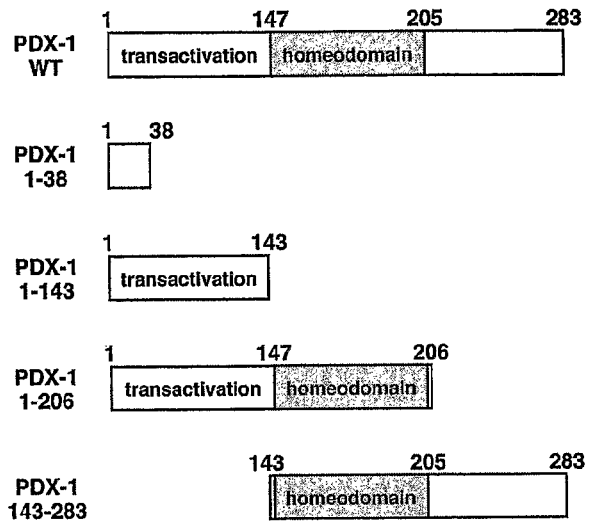

We used the GST-pull down assays to define regions within PDX-1 that are required for interaction with Bridge-1. When GST-Bridge-1 was combined with [$^{35}$S]-radiolabeled in vitro translated rat PDX-1 proteins, strong interactions were observed with full-length PDX-1. Amino-terminal PDX-1 protein fragments encoding amino acids 1-143 and 1-206 had stronger interactions with GST-Bridge-1 than did the full-length PDX-1 protein (FIGS. 23A and B). In contrast, GST-Bridge-1 did not interact with the carboxy-terminal [$^{35}$S]-radiolabeled in vitro translated rat PDX-1 protein fragment encoding amino acids 143-283, despite the interaction observed in yeast between fusion proteins encoding Bridge-1 and rat PDX-1 amino acids 160-283. These data suggest that the amino-terminal domain of PDX-1 extending from amino acids 1-143, known to contain the PDX-1 transcriptional activation domain (Lu et al., 1996; Peers et al., 1994), is both necessary and sufficient for direct Bridge-1 interactions with PDX-1. We found similar results in an independent series of studies in which we combined GST-PDX-1 proteins with [$^{35}$S]-radiolabeled in vitro translated rat Bridge-1 (FIG. 23C). Full-length GST-PDX-1 strongly interacted with radiolabeled Bridge-1, as did the GST-PDX-1 fragment encoding amino acids 1-206. In contrast the GST-PDX-1 (1-38) construct that contains only the penultimate amino-terminal portion of the PDX-1 transactivation domain did not support a strong interaction with radiolabeled Bridge-1.

EXAMPLE 21

Bridge-1 Interacts with Human PDX-1 Proteins

We examined whether the protein interactions that we observed between Bridge-1 and rat PDX-1 also were relevant to the human PDX-1 protein. For these studies we generated a series of [$^{35}$S]-radiolabeled in vitro translated human PDX-1 proteins consisting of wild-type and mutant PDX-1 proteins implicated in conferring susceptibility to the development of diabetes in selected human populations (Hani et al., 1999; Hansen et al., 2000; Macfarlane et al., 1999; Stoffers et al., 1997b; Waeber et al., 2000). The GST-Bridge-1 protein interacted with both wild-type and mutant PDX-1 proteins (FIG. 24). In particular, we observed at least a 2-fold stronger interaction of GST-Bridge-1 with the PDX-1 amino-terminal protein derived from the P63fsdelC mutation associated with MODY4 (Stoffers et al., 1997b) as compared to the wild-type PDX-1 protein, even in the setting of a relatively low amount of protein input in the assay. Because the P63fsdelC mutation introduces a translational frame shift that subsequently results in a premature stop codon, this amino-terminal mutant protein contains amino acids 1-62 of the transcriptional activation domain of native PDX-1, followed by 59 additional frame-shifted amino acids (Stoffers et al., 1998).

EXAMPLE 22

Bridge-1 Augments the Transcriptional Activation of PDX-1

Figure 25A:
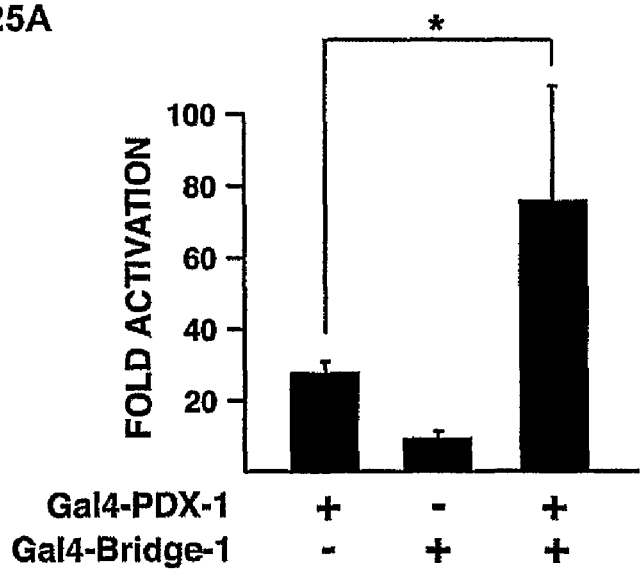

To determine whether the combination of Bridge-1 and PDX-1 alters the transcriptional activation of PDX-1, we conducted cell transfections using multiple approaches. First we transfected constructs encoding Gal4-PDX-1 and Gal4-Bridge-1 fusion proteins to BHK cells and assessed their ability to activate a Gal4-CAT reporter separately and in combination. In this context Gal4-PDX-1 alone activated the transcriptional reporter by 28-fold and Gal4-Bridge-1 alone activated the reporter 9-fold greater than did the empty control Gal4 vector (FIG. 25A). Notably the combination of Gal4-PDX-1 and Gal4-Bridge-1 resulted in a synergistic activation of the Gal4 reporter construct by approximately 76-fold. These data suggest that the combination of Bridge-1 and PDX-1 interacting in close proximity on the same DNA regulatory elements substantially augments transcriptional activation by PDX-1.

Figure 25B:
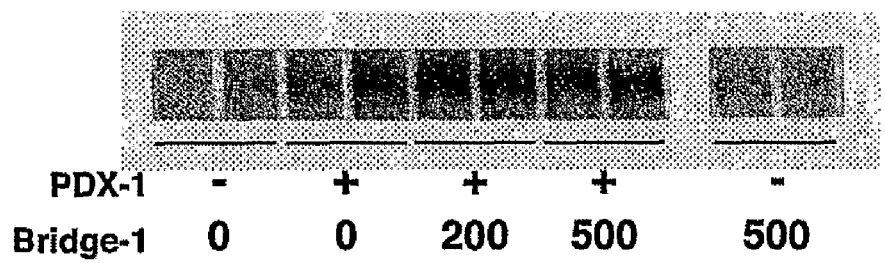

Next we assessed the effect of the dose-dependent addition of Bridge-1 in the context of PDX-1 activation of a multimerized TAAT1 enhancer-CAT reporter construct derived from the rat somatostatin promoter (Miller et al., 1994). On this transcriptional reporter vector, the addition of PDX-1 augmented transcriptional activation (FIG. 25B). The addition of increasing amounts of Bridge-1 expression vector to PDX-1 further increased the reporter activity (FIG. 25B), without changing the level of PDX-1 protein expression as assessed by Western blots (data not shown). Expression of Bridge-1 alone did not activate the somatostatin TAAT1 reporter. Thus in this context, the additional expression of Bridge-1 augmented PDX-1 activation of the target gene regulatory site.

Figure 25C:
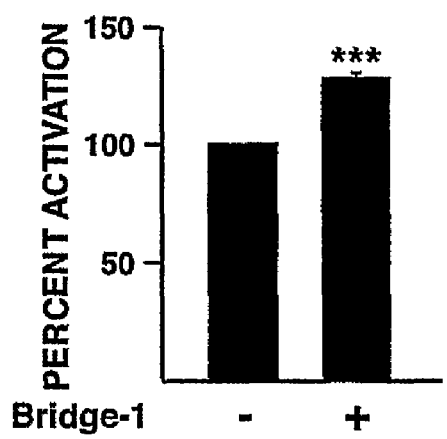

Robust activation of conserved glucose-responsive enhancers in the rat insulin I promoter occurs with the synergistic effect of combining basic helix-loop-helix transcription factors, such as E12 and E47, with homeodomain transcription factors, such as PDX-1 (German et al., 1992; Peers et al., 1994). We assessed the effect of the addition of Bridge-1 on the activation of multimerized rat insulin I promoter FarFlat enhancers in the context of this synergistic activation assay in transfected HeLa cells. Under these experimental conditions, in the absence of the E2A proteins E12 and E47 neither Bridge-1 or PDX-1 alone or in combination substantially activated the FarFlat enhancer. Although no evidence for direct binding of Bridge-1 to FarFlat sequences was found in DNA-binding assays (Thomas et al., 1999), the activation of FarFlat by the combination of PDX-1, E12, and E47 was significantly enhanced by approximately 30 percent with the addition of the Bridge-1 expression vector as compared to the empty vector alone (FIG. 25C).

Discussion

We discovered that the transcriptional coactivator Bridge-1 serves as a protein interaction partner to modify the transcriptional activation functions of the pancreatic homeoprotein PDX-1. We demonstrated a direct interaction between Bridge-1 and an amino-terminal domain within PDX-1. Mapping studies suggest that Bridge-1 interactions occur between amino acids 38 and 143 of PDX-1, within a region known to confer transcriptional activation function to PDX-1 in part via interactions with other coactivators including p300 and CBP (Asahara et al., 1999; Lu et al., 1996; Peers et al., 1994; Qiu et al., 2002; Stanojevic et al., 2004). This finding is supported by the strong interactions we observed between Bridge-1 and the amino-terminal mutant P63fsdelC human PDX-1 protein (FIG. 24). We were surprised that the PDX-1 fragment encoding amino acids 143-283 did not interact directly with Bridge-1 in GST protein interaction assays. This observation suggests that the interactions between Bridge-1 and the carboxy-terminal PDX-1 protein fragment in yeast interaction trap assays may be indirect, reflecting an interaction of unidentified yeast protein complexes with both Bridge-1 and carboxy-terminal domains of PDX-1. Alternatively, post-translational modification of Bridge-1 and/or PDX-1 proteins in yeast cells may differ from those of rabbit reticulocyte lysates from which in vitro translated Bridge-1 and PDX-1 proteins were derived, thereby promoting direct Bridge-1 interactions with a second cryptic protein interaction domain within the carboxy-terminal domain of PDX-1. Regardless of the underlying explanation for the interaction observed in yeast, our data suggest that Bridge-1 participates in multimolecular transcriptional regulatory complexes with PDX-1 via multiple mechanisms.

Figure 23B:
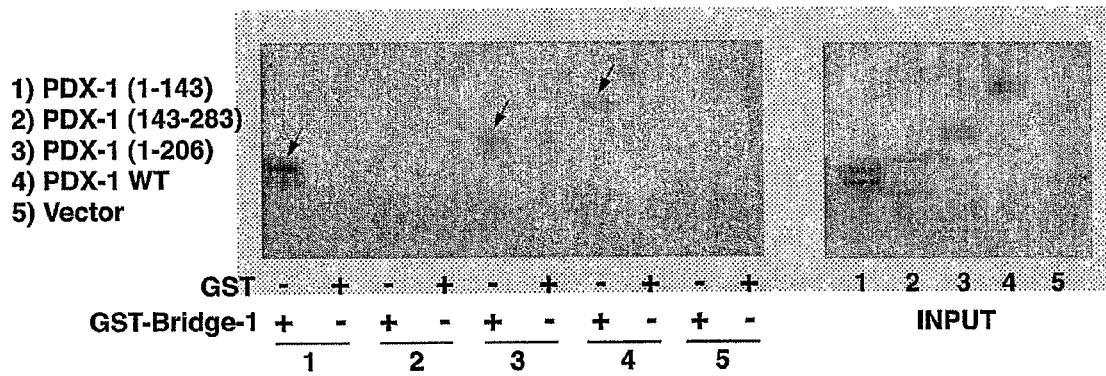
Figure 23C:
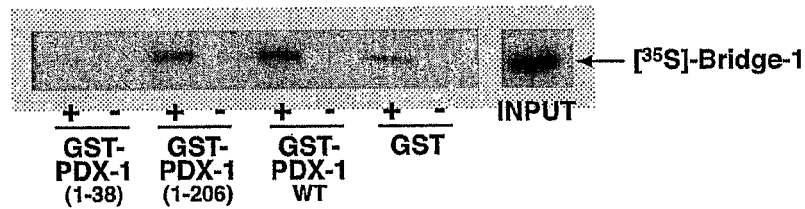

Of note, we frequently generated doublet forms of in vitro translated PDX-1 proteins in rabbit reticulocyte lysates that may represent distinct conformations of PDX-1 proteins as a result of post-translational modifications by phosphorylation, glycosylation, or other processes (FIGS. 22 and 23B). In GST protein interaction assays, GST-Bridge-1 appeared to preferentially interact with the larger of the doublet forms of PDX-1 (FIG. 23B), indicating that direct interactions between Bridge-1 and PDX-1 are likely to be regulated by the protein conformation of PDX-1.

We demonstrated that the combination of Bridge-1 and PDX-1 increased transcriptional activation in three independent systems. In a fusion protein system designed to enhance heterodimeric interactions, related to an approach used in studies of PBX and PDX-1 interactions (Asahara et al., 1999), we found that Bridge-1 and PDX-1 fusion proteins synergistically increased the transcriptional activation of a multimerized reporter construct (FIG. 25A). In assessments of PDX-1 function in the transcriptional activation of key enhancers derived from the well-characterized PDX-1 target genes somatostatin and insulin, we found that the addition of exogenous Bridge-1 increased the activation by PDX-1.

We previously demonstrated that reduced expression of endogenous Bridge-1 substantially decreased the transcriptional activation of the insulin promoter in insulin-expressing cells and that Bridge-1 interactions with E2A proteins, such as E12 or E47, enhanced insulin promoter activation (Thomas et al., 1999). Our additional studies demonstrate that on important glucose-responsive enhancers within the rat insulin I promoter, Bridge-1 is capable of enhancing transcriptional activation via multiple protein-protein interactions, including interactions with PDX-1 (FIG. 26). The cytoplasmic sequestration of the coactivator Bridge-1 by strong interactions with the amino-terminal mutant P63fsdelC human PDX-1 protein may conceivably contribute to the severity of the diabetes phenotype in humans with MODY4 by disrupting insulin gene transcription, in a manner analogous to that proposed for mutant human PDX-1 protein interactions with p300 (Stanojevic et al., 2004).

In summary, we identified an additional coactivator in Bridge-1 that interacts with PDX-1 to modulate its regulation of target gene expression.

EXAMPLE 23

Endogenous Bridge-1 Expression Regulates Insulin Promoter Activation

To determine whether endogenous Bridge-1 contributes to the activation of the insulin promoter in insulin-producing cells, we used the INS-1 clonal β-cell line in a series of transient transfection studies. Bridge-1 antisense cDNA constructs substantially reduced rat insulin I promoter activation in insulin-producing cells in vitro. (FIG. 28A). As an independent method to reduce endogenous Bridge-1 expression, we designed a small interfering duplex RNA (siRNA) complementary to mouse and rat Bridge-1 sequences for use in INS-1 cells transiently transfected with the ~410 rat insulin I promoter. The administration of anti-Bridge-1 siRNA reduced insulin promoter activation by 50% (FIG. 28B), a reduction comparable to that observed by transfection of antisense Bridge-1 cDNA (FIG. 28A). Collectively these data indicate that a substantial component of the transcriptional activation of the insulin promoter in insulin-producing cells is regulated by endogenous levels of Bridge-1. Furthermore they provide us with a second tool in addition to the antisense cDNA construct for the disruption of endogenous Bridge-1 function.

All patents and publications referred to above are hereby entirely and expressly incorporated herein by reference. Various modifications and variations of the described invention will be apparent to those skilled in the art without departing from the scope and spirit of the invention. Although the invention has been described in connection with specific preferred embodiments, it should be understood that the inventions as claimed should not be unduly limited to such specific embodiments. Indeed, various modifications of the described modes for carrying out the invention that are obvious to those skilled in the pertinent art are intended to be within the scope of the claims.

What is claimed is:

1. A method for modulating the mass of pancreatic cells in a subject in need thereof, comprising treating said cells with a compound that activates or inhibits the expression of Bridge-1 protein or activates or inhibits the expression of a Bridge-1 target gene, wherein the treatment of said pancreatic cells results in the modulation of the mass of said pancreatic cells when compared to untreated pancreatic cells.

2. The method of claim 1, wherein said method modulates the mass of pancreatic β-cells or pancreatic α-cells.

3. The method of claim 1, wherein said treating activates the expression of Bridge-1 protein or activates the expression of a Bridge-1 target gene.

4. The method of claim 3, wherein said treating reduces the mass of pancreatic β-cells.

5. The method of claim 3, wherein said treating increases the mass of pancreatic α-cells.

6. The method of claim 3, wherein said compound is Activin A or Trichostatin A.

7. The method of claim 1, wherein said treating inhibits the expression of Bridge-1 protein or inhibits the expression of a Bridge-1 target gene.

8. The method of claim 7, wherein said treating increases the mass of pancreatic β-cells.

9. The method of claim 7, wherein said compound is progesterone.

* * * * *